(12) United States Patent
Nastri et al.

(10) Patent No.: US 12,060,433 B2
(45) Date of Patent: *Aug. 13, 2024

(54) CD73 INHIBITOR AND A2A/A2B ADENOSINE RECEPTOR INHIBITOR COMBINATION THERAPY

(71) Applicant: Incyte Corporation, Wilmington, DE (US)

(72) Inventors: Horacio G. Nastri, West Chester, PA (US); Shaun M. Stewart, Chadds Ford, PA (US); Juan Carlos Almagro, Cambridge, MA (US); Jing Zhou, Boxborough, MA (US); Rebecca A. Buonpane, Wilmington, DE (US); Hui Wang, Hockessin, DE (US); Yingnan Chen, Wilmington, DE (US); Xiaozhao Wang, Mt. Laurel, NJ (US); Peter Niels Carlsen, Claymont, DE (US); Yong Li, Newark, DE (US); Chao Qi, Newark, DE (US); Liangxing Wu, Wilmington, DE (US); Wenqing Yao, Chadds Ford, PA (US); Wenyu Zhu, Media, PA (US); Taisheng Huang, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 295 days.

This patent is subject to a terminal disclaimer.

(21) Appl. No.: 17/138,306

(22) Filed: Dec. 30, 2020

(65) Prior Publication Data
US 2021/0230294 A1 Jul. 29, 2021

Related U.S. Application Data

(60) Provisional application No. 62/956,840, filed on Jan. 3, 2020.

(51) Int. Cl.
| C07K 16/28 | (2006.01) |
| A61K 31/135 | (2006.01) |
| A61K 31/4985 | (2006.01) |
| A61P 35/00 | (2006.01) |
| A61K 39/00 | (2006.01) |

(52) U.S. Cl.
CPC ........ *C07K 16/2896* (2013.01); *A61K 31/135* (2013.01); *A61K 31/4985* (2013.01); *A61P 35/00* (2018.01); *A61K 2039/505* (2013.01)

(58) Field of Classification Search
CPC ............ C07K 16/2896; C07K 2317/21; C07K 2317/24; C07K 2317/33; C07K 2317/34; C07K 2317/565; C07K 2317/76; C07K 2317/92; A61K 31/135; A61K 31/4985; A61K 2039/505; A61K 39/395; A61K 31/519; A61K 45/06; A61P 35/00
See application file for complete search history.

(56) References Cited

U.S. PATENT DOCUMENTS

| 4,399,216 A | 8/1983 | Axel et al. |
| 4,634,665 A | 1/1987 | Axel et al. |
| 5,057,313 A | 10/1991 | Shih et al. |
| 5,156,840 A | 10/1992 | Goers et al. |
| 5,179,017 A | 1/1993 | Axel et al. |
| 5,714,350 A | 2/1998 | Co et al. |
| 5,731,168 A | 3/1998 | Carter et al. |
| 5,849,992 A | 12/1998 | Meade et al. |
| 5,869,046 A | 2/1999 | Presta et al. |
| 6,350,861 B1 | 2/2002 | Co et al. |
| 9,090,697 B2 | 7/2015 | Sim et al. |
| 9,388,249 B2 | 7/2016 | Sugioka et al. |
| 9,605,080 B2 | 3/2017 | Lonberg et al. |
| 9,938,356 B2 | 4/2018 | Hay et al. |
| 10,100,129 B2 | 10/2018 | Lonberg et al. |
| 10,287,362 B2 | 5/2019 | Hay et al. |
| 2004/0142342 A1 | 7/2004 | Barden et al. |
| 2007/0009518 A1 | 1/2007 | Novobrantseva et al. |
| 2011/0300136 A1 | 12/2011 | Benyunes |
| 2016/0129108 A1 | 5/2016 | Sachsenmeier et al. |
| 2018/0009899 A1 | 1/2018 | Griffin et al. |
| 2018/0030144 A1 | 2/2018 | Chanteux et al. |
| 2018/0237536 A1 | 8/2018 | Perrot et al. |
| 2018/0264107 A1 | 9/2018 | Curd et al. |
| 2019/0031766 A1 | 1/2019 | Prinz et al. |

(Continued)

FOREIGN PATENT DOCUMENTS

| CL | 202200515 | 3/2022 |
| EP | 0404097 | 12/1990 |

(Continued)

OTHER PUBLICATIONS

Mariuzza (Annu. Rev. Biophys. Biophys. Chem., 16: 139-159, 1987).*
Allard et al., "Immunosuppressive activities of adenosine in cancer," Current Opinion in Pharmacology, 2016, 29:7-16.
Antonioli et al., "Immunity, inflammation and cancer: a leading role for adenosine," Nature Reviews Cancer, 2013, 13(12):842-857.
Atzrodt et al., "The Renaissance of H/D Exchange," Angew Chem Int Ed., 2007, 46(41):7744-7765.
Berge et al., "Pharmaceutical salts," Journal of Pharmaceutical Science, 1977, 66(2):1-19.
Better et al., "*Escherichia coli* secretion of an active chimeric antibody fragment," Science, 1988, 240:1041-1043.
Better et al., "Expression of engineered antibodies and antibody fragments in microorganisms, " Methods in Enzymology, 1989, 178:476-496.

(Continued)

*Primary Examiner* — Nelson B Moseley, II
(74) *Attorney, Agent, or Firm* — Fish & Richardson P.C.

(57) ABSTRACT

Disclosed are combination therapies comprising administration of a CD73 inhibitor and an adenosine A2A or A2B receptor inhibitor. The disclosed combination therapies are useful in the treatment of diseases related to the activity of adenosine receptors and/or CD73 including, for example, cancer, inflammatory diseases, cardiovascular diseases, and neurodegenerative diseases. Anti-CD73 antibodies and A2A/A2B inhibitors are also disclosed.

39 Claims, 40 Drawing Sheets

Specification includes a Sequence Listing.

(56) References Cited

U.S. PATENT DOCUMENTS

| | | | |
|---|---|---|---|
| 2019/0077873 A1 | 3/2019 | Griffin et al. |
| 2019/0225703 A1 | 7/2019 | Caux et al. |
| 2019/0256598 A1 | 8/2019 | Wang et al. |
| 2019/0292188 A1 | 9/2019 | Wang et al. |
| 2019/0337957 A1 | 11/2019 | Wang et al. |
| 2020/0270244 A1 | 8/2020 | Huang et al. |
| 2021/0061809 A1 | 3/2021 | Han et al. |
| 2021/0230293 A1 | 7/2021 | Nastri et al. |
| 2022/0233529 A1 | 7/2022 | Wang et al. |

FOREIGN PATENT DOCUMENTS

| | | | | |
|---|---|---|---|---|
| WO | WO 93/11161 | 6/1993 | | |
| WO | WO 2001/080884 | 11/2001 | | |
| WO | WO 2004/079013 | 9/2004 | | |
| WO | WO 2005/003175 | 1/2005 | | |
| WO | WO 2005/018572 | 3/2005 | | |
| WO | WO 2011/089004 | 7/2011 | | |
| WO | WO 2014/153424 | 9/2014 | | |
| WO | WO 2016055609 | 4/2016 | | |
| WO | WO 2016/075099 | 5/2016 | | |
| WO | WO 2016/075176 | 5/2016 | | |
| WO | WO 2016/081748 | 5/2016 | | |
| WO | WO 2016131950 | 8/2016 | | |
| WO | WO 2017064043 | 4/2017 | | |
| WO | WO 2017/100670 | 6/2017 | | |
| WO | WO 2017/152085 | 9/2017 | | |
| WO | WO 2018013611 | 1/2018 | | |
| WO | WO 2018/110555 | 6/2018 | | |
| WO | WO 2018/137598 | 8/2018 | | |
| WO | WO 2018/187512 | 10/2018 | | |
| WO | WO 2018/215535 | 11/2018 | | |
| WO | WO 2018/237173 | 12/2018 | | |
| WO | WO 2018237157 | 12/2018 | | |
| WO | WC 2019/173692 | 9/2019 | | |
| WO | WO 2019/168847 | * 9/2019 | ........... | C07D 487/04 |
| WO | WO 2019/170131 | 9/2019 | | |
| WO | WO 2019/173291 | 9/2019 | | |
| WO | WO 2019200256 | 10/2019 | | |
| WO | WO 2019/222677 | * 11/2019 | ........... | C07D 487/04 |
| WO | WO 2019224025 | 11/2019 | | |
| WO | WO 2019/232244 | 12/2019 | | |
| WO | WO 2020/010197 | 1/2020 | | |
| WO | WO 2020097127 | 5/2020 | | |
| WO | WO 2020098599 | 5/2020 | | |
| WO | WO 2020143710 | 7/2020 | | |
| WO | WO 2020143836 | 7/2020 | | |
| WO | WO 2020216697 | 10/2020 | | |
| WO | WO 2020244606 | 12/2020 | | |
| WO | WO 2020253568 | 12/2020 | | |
| WO | WO 2021017892 | 2/2021 | | |
| WO | WO 2021032173 | 2/2021 | | |
| WO | WO 2021044005 | 3/2021 | | |
| WO | WO 2021087463 | 5/2021 | | |
| WO | WO 2021097223 | 5/2021 | | |
| WO | WO 2021127254 | 6/2021 | | |
| WO | WO 2021/138467 | 7/2021 | | |
| WO | WO 2021138498 | 7/2021 | | |
| WO | WO 2021205383 | 10/2021 | | |
| WO | WO 2021213466 | 10/2021 | | |
| WO | WO 2021227306 | 11/2021 | | |
| WO | WO 2021227307 | 11/2021 | | |
| WO | WO 2021241729 | 12/2021 | | |
| WO | WO 2021259199 | 12/2021 | | |

OTHER PUBLICATIONS

Bird et al., "Single chain antibody variable regions," TIBTECH, 1991, 9:132-137.
Blom et al., "Preparative LC-MS Purification: Improved Compound Specific Method Optimization,"J Combi Chem., 2004, 6(6):874-883.
Borrmann, T. et al., "1-alkyl-8-(piperazine-1-sulfonyl)phenylxanthines: development and characterization of adenosine A2B receptor antagonists and a new radioligand with subnanomolar affinity and subtype specificity," J Med Chem., 2009, 52(13):3994-4006.
Bowman et al., "An Exceptionally Potent Inhibitor of Human CD73," Biochem., Aug. 6, 2019, 58(31):3331-3334.
Boyd, "Some practical considerations and applications of the National Cancer Institute in vitro anticancer drug discovery screen," Drug Development Research, 1995, 34:91-109.
Braganhol et al., "Ecto-5'-nucleotidase/CD73 inhibition by quercetin in the human U138MG glioma cell line," Biochim Biophys Acta., 2007, 1770:1352-1359.
Carlsson et al., "Structure-based discovery of A2A adenosine receptor ligands," J Med Chem., 2010, 53:3748-3755.
Carter et al., "High level *Escherichia coli* expression and production of a bivalent humanized antibody fragment," Bio/Technology, 1992, 10:163-167.
Carter et al., "Humanization of an anti-p185HER2 antibody for human cancer therapy," PNAS, 1992, 89:4285-4289.
Co et al., "A humanized antibody specific for the platelet integrin gpIIb/IIIa, " J Immunol., 1994, 152:2968-2976.
Dorai, "Aglycosylated chimeric mouse/human IgG1 antibody retains some effector function, " Hybridoma, 1991, 10(2):211-217.
Friend, "Phase I study of an engineered aglycosylated humanized CD3 antibody in renal transplant rejection," Transplantation, 1999, 68:1632-1637.
GenBank Accession No. NP_002517, "5'-nucleotidase isoform 1 preproprotein [*Homo sapiens*]," Apr. 26, 2021, 3 pages.
GenBank Accession No. NP_035981, "5'-nucleotidase preproprotein [Mus musculus]," May 24, 2021, 3 pages.
Graddis et al., "Designing proteins that work using recombinant technologies," Curr Pharm Biotechnol., 2002, 3:285-297.
Hand et al., "Comparative biological properties of a recombinant chimeric anti-carcinoma mAb and a recombinant aglycosylated variant," Cancer Immunol Immunother., 1992, 35:165-174.
Hasko et al., "Shaping of monocyte and macrophage function by adenosine receptors," Pharmacol. Ther., 2007, 113(2):264-275.
Hay et al., "Targeting CD73 in the tumor microenvironment with MEDI9447," Oncoimmunol., Jul. 11, 2016, 5(8):e1208875.
Hobbs et al., "Interaction of aglycosyl immunoglobulins with the IgG Fc transport receptor from neonatal rat gut: comparison of deglycosylation by tunicamycin treatment and genetic engineering," Mol Immunol., 1992, 29:949-956.
Holliger et al., ""Diabodies": small bivalent and bispecific antibody fragments," Proc Natl Acad Sci USA., 1993, 90:6444-6448.
Hudson et al., "High avidity scFv multimers; diabodies and triabodies," J Immunol Methods, 1999, 231:177-189.
Huston et al., "Protein engineering of antibody binding sites: recovery of specific activity in an anti-digoxin single-chain Fv analogue produced in *Escherichia coli*," Proc Natl Acad Sci USA., 1988, 85:5879-5883.
International Search Report and Written Opinion in International Application No. PCT/US2020/067533, dated Apr. 21, 2021, 20 pages.
International Search Report and Written Opinion in International Application No. PCT/US2020/067576, dated Apr. 28, 2021, 17 pages.
International Preliminary Report on Patentability in International Application No. PCT/US2020/067576, dated Jul. 14, 2022, 10 pages.
International Preliminary Report on Patentability in International Application No. PCT/US2020/067533, dated Jul. 14, 2022, 10 pages.
Isaacs et al., "Therapy with monoclonal antibodies. An in vivo model for the assessment of therapeutic potential," J Immunol., 1992, 148:3062-3071.
Kaufman and Sharp, "Amplification and expression of sequences cotransfected with a modular dihydrofolate reductase complementary dna gene," Mol Biol., 1982, 159(4):601-621.
Kerekes et al., "Aurora kinase inhibitors based on the imidazo[1,2-a]pyrazine core: fluorine and deuterium incorporation improve oral absorption and exposure," *J Med Chem.*, 2011, 54(1):201-210.
Knapp et al., "Crystal structure of the human ecto-5'-nucleotidase (CD73): insights into the regulation of purinergic signaling," Structure, 2012, 20(12):2161-2173.

(56) References Cited

OTHER PUBLICATIONS

Lamoyi, "Preparation of F(ab')2 fragments from mouse IgG of various subclasses," Methods in Enzymology, 1986, 121:652-663.
Leatherbarrow and Dwek, "The effect of aglycosylation on the binding of mouse IgG to *Staphylococcal* protein A," FEBS Lett., Dec. 12, 1983, 164(2):227-230.
Leatherbarrow et al., "Effector functions of a monoclonal aglycosylated mouse IgG2a: binding and activation of complement component C1 and interaction with human monocyte Fc receptor," Mol Immunol., 1985, 22(4):407-415.
Lei et al., "Characterization of the Erwinia carotovora pelB gene and its product pectate lyase," J Bacteriol., 1987, 169:4379-4383.
Livingston et al., "Adenosine, inflammation and asthma—a review," Inflamm Res., 2004, 53(5):171-178.
Matsumoto et al., "Alterations in vasoconstrictor responses to the endothelium-derived contracting factor uridine adenosine tetraphosphate are region specific in DOCA-salt hypertensive rats," Pharmacol Res., 2012, 65:81-90.
Millstein et al., "Hybrid Hybridomas and their use in immunohistochemistry," Nature, 1983, 305:537-539.
Mizushima et al., "pEF-BOS, a powerful mammalian expression vector," Nucleic Acids Res., 1990, 18:5322.
Mulligan et al., "Synthesis of rabbit beta-globin in cultured monkey kidney cells following infection with a SV40 beta-globin recombinant genome," Nature, 1979, 277:108-114.
Niemelä et al., "IFN-alpha induced adenosine production on the endothelium: a mechanism mediated by CD73 (ecto-5'-nucleotidase) up-regulation," J Immunol., 2004, 172:1646-1653.
Nose and Wigzell, "Biological significance of carbohydrate chains on monoclonal antibodies," Immunology, 1983, 80:6632-6636.
Perez de la Lastra et al., "Epitope mapping of 10 monoclonal antibodies against the pig analogue of human membrane cofactor protein (MCP)," Immunol., Apr. 1, 1999, 96(4):663-670.
Pluckthun, "The Pharmacology of Monoclonal Antibodies," New York, 1994, 113:269-315.
Pluckthun et al., "Expression of functional antibody Fv and Fab fragments in *Escherichia coli*, " Methods in Enzymology, 1989, 178:476-496.
Powers et al., "Expression of single-chain Fv-Fc fusions in Pichia pastoris," J Immunol Methods., 2001, 251:123-135.
Raju, "Glycosylation Variations with Expression Systems and Their Impact on Biological Activity of Therapeutic Immunoglobulins, " BioProcess International, Apr. 2003, 44-53.
Remington's Pharmaceutical Sciences, 17th ed., Mack Publishing Company, Easton, Pa., 1985, p. 1418.
Rousseaux et al., "Optimal conditions for the preparation of proteolytic fragments from monoclonal IgG of different rat IgG subclasses," Methods in Enzymology, 1989, 121:663-669.
Ryzhov et al., "Host A2B Adenosine Receptors Promote Carcinoma Growth," Neoplasia, 2008, 10:987-995.
Sachdeva et al., "Adenosine and its receptors as therapeutic targets: An overview," Saudi Pharmaceutical Journal, 2013, 21:245-253.
Sadej et al., "Ecto-5'-Nucleotidase (eN, CD73) is Coexpressed with Metastasis Promoting Antigens in Human Melanoma Cells," Nucleosides Nucleotides Nucleic Acids, 2006, 25:1119-1123.
Salmi and Jalkanen, "Host CD73 impairs anti-tumor immunity," OncoImmunology, 2012, 1:247-248.
Sattin and Rall, "The effect of adenosine and adenine nucleotides on the cyclic adenosine 3', 5'-phosphate content of guinea pig cerebral cortex slices," Mol Pharmacol., 1970, 6:13-23.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem., 2001, 276(9):6591-6604.
Shields et al., "Lack of fucose on human IgG1 N-linked oligosaccharide improves binding to human Fcgamma RIII and antibody-dependent cellular toxicity," J Biol Chem., 2002, 277(30):26733-26740.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem., 2003, 278(5):3466-3473.
Stagg and Smyth, "Extracellular adenosine triphosphate and adenosine in cancer," Oncogene, 2010, 29(39):5346-5358.
Stagg, "The double-edge sword effect of anti-CD73 cancer therapy," OncoImmunology, 2012, 1:217-218.
Tao, "Studies of aglycosylated chimeric mouse-human IgG. Role of carbohydrate in the structure and effector functions mediated by the human IgG constant region.," J Immunol., 1989, 143(8):2595-2601.
Tautenhahn et al., "Purinergic modulation of the excitatory synaptic input onto rat striatal neurons," Neuropharmacology, 2012, 62:1756-1766.
Umana et al., "Engineered glycoforms of an antineuroblastoma IgG1 with optimized antibody-dependent cellular cytotoxic activity," Nat Biotechnol., 1999, 17(2):176-180.
Urlaub and Chasin "Isolation of Chinese hamster cell mutants deficient in dihydrofolate reductase activity," Proc Natl Acad Sci USA., 1980, 77(7):4216-4220.
Walker et al., "Aglycosylation of human IgG1 and IgG3 monoclonal antibodies can eliminate recognition by human cells expressing FγyRI and/or FcγRII receptors," Biochem J., 1989, 259:347-353.
Ward and Ghetie, "The effector functions of immunoglobulins: implications for therapy," Therapeutic Immunology, 1995, 2(2):77-94.
Ward et al., "Binding activities of a repertoire of single immunoglobulin variable domains secreted from *Escherichia coli*," Nature, 1989, 341(6242):544-546.
Wright and Morrison, "Effect of glycosylation on antibody function: implications for genetic engineering, " TIBTECH, 1997, 15(1):26-32.
Xu et al., "Design, synthesis and biological evaluation of deuterated nintedanib for improving pharmacokinetic properties," J Label Compd Radiopharm., 2015, 58(7):308-312.
Zhang, "CD73: a novel target for cancer immunotherapy," 2010, Cancer Res., 2010, 70:6407-6411.
Zhang, "CD73 promotes tumor growth and metastasis," OncoImmunology, 2012, 1:67-17.
Beavis et al., "Targeting the adenosine 2A receptor enhances chimeric antigen receptor T cell efficacy," J. Clin. Investigation, Mar. 2017, 127(3):929-941.
ClinicalTrials.gov [online], "CPI-006 Alone and in Combination With Ciforadenant and With Pembrolizumab for Patients With Advanced Cancers," NCT03454451, last updated Aug. 3, 2022, retrieved on May 31, 2023, retrieved from URL<https://clinicaltrials.gov/ct2/show/NCT03454451>, 19 pages.
DiRenzo et al., "AB928, a Dual Antagonist of the A2aR and A2bR Adenosine Receptors, Relieves Adenosine Mediated Immune Suppression," Poster, Presented at Proceedings of the Fourth CRI-CIMT-EATI-AACR International Cancer Immunotherapy Conference: Translating Science into Survival, New York, NY, Sep. 30-Oct. 3, 2018, 1 page.
GlobeNewswire.com [online], "Corvus Pharmaceuticals Announces Initiation of Phase 1/1b Clinical Trial of Investigational Anti-CD73 Antibody, CPI-006, in Patients with Advanced Cancer," Apr. 26, 2018, retrieved on May 31, 2023, retrieved from URL<https://www.globenewswire.com/news-release/2018/04/26/1488146/0/en/Corvus-Pharmaceuticals-Announces-Initiation-of-Phase-1-1b-Clinical-Trial-of-Investigational-Anti-CD73-Antibody-CPI-006-in-Patients-with-Advanced-Cancer.html>, 6 pages.
Iannone et al., "Blockade of A2b Adenosine Receptor Reduces Tumor Growth and Immune Suppression Mediated by Myeloid-Derived Suppressor Cells in a Mouse Model of Melanoma," Neoplasia, Dec. 2013, 15(12):1400-1409.
Leone et al., "Inhibition of the adenosine A2a receptor modulates expression of T cell coinhibitory receptors and improves effector function for enhanced checkpoint blockade and ACT in murine cancer models," Cancer Immunol. Immunotherapy, Jun. 19, 2018, 67(8):1271-1284.
Lin et al., "Improved affinity of a chicken single-chain antibody to avian infectious bronchitis virus by site-directed mutagenesis of complementarity-determining region H3," African Journal of Biotechnology, Dec. 12, 2011, 10(79):18294-18302.

(56) References Cited

OTHER PUBLICATIONS

McCarthy et al., "Altering the fine specificity of an anti-Legionella single chain antibody by a single amino acid insertion," Journal of Immunological Methods, May 2011, 251(1-2):137-149.

Vigano et al., "Targeting Adenosine in Cancer Immunotherapy to Enhance T-Cell Function," Front. Immunology, Jun. 6, 2019, 10:925, 30 pages.

Willingham et al., "A2AR Antagonism with CPI-444 Induces Antitumor Responses and Augments Efficacy to Anti-PD-(L)1 and Anti-CTLA-4 in Preclinical Models," Cancer Immunol. Research, Oct. 2018, 6(10):1136-1149.

Lee et al., "Abstract #: P484: CB-708, an orally bioavailable small molecule inhibitor of CD73 with immunostimulatory and antitumor activity," Poster, Presented at the Proceedings of 34th Annual Meeting & Pre-Conference Programs of the Society for Immunotherapy of Cancer (SITC): Part 1, National Harbor, MA, Nov. 6-10, 2019; Journal for Immunotherapy of Cancer, Nov. 6, 2019, 7(Suppl. 1):263-264.

\* cited by examiner

FIG. 1A

CL25_hu_10-4 VH
EVQLVQSGAEVKKPGESLKISCKGSGYTFTSYGLSWVRQMPGKGLEWMGEIYPGSG
NTYYNEKFKGQVTISADKSISTAYLQWSSLKASDTAMYYCARYDYLGSSYGFDYWG
AGTTVTVSS (SEQ ID NO:22)
CL25_hu_10-4 VL
DIQMTQSPSSLSASVGDRVTITCKASQDVSTAVAWYQQKPGKAPKLLLYSASYRYS
GVPSRFSGSGSGTDYTLTISSLQPEDFATYYCQQHYNTPYTFGGGTKLEIK (SEQ
ID NO:80)

HzCL25 VH
EVQLVQSGAEVKKPGESLKISCKGSGYTFTSYGLSWVRQMPGKGLEWMGEIYPGSG
NTYYNEKFKGQVTISADKSISTAYLQWSSLKASDTAMYYCARYDYLGSSYGFDYWG
AGTTVTVSS (SEQ ID NO:22)
HzCL25 VL
DIVMTQSPDSLAVSLGERATINCKASQDVSTAVAWYQQKPGQPPKLLIYSASYRYS
GVPDRFSGSGSGTDFTLTISSLQAEDVAVYYCQQHYNTPYTFGGGTKLEIK (SEQ
ID NO:23)

CL25_hu_10-6 VH
EVQLVQSGAEVKKPGESLKISCKGSGYTFTSYGLSWVRQMPGKGLEWMGEIYPGSG
NTYYNEKFKGQVTISADKSISTAYLQWSSLKASDTAMYYCARYDYLGSSYGFDYWG
AGTTVTVSS (SEQ ID NO:22)
CL25_hu_10-6 VL
AIRMTQSPSSFSASTGDRVTITCKASQDVSTAVAWYQQKPGKAPKLLIYSASYRYS
GVPSRFSGSGSGTDFTLTISCLQSEDFATYYCQQHYNTPYTFGGGTKLEIK (SEQ
ID NO:81)

CL25_hu_11-4 VH
QVQLVQSGAEVKKPGASVKVSCKASGYTFTSYGLSWVRQATGQGLEWMGEIYPGSG
NTYYNEKFKGRVTMTANTSISTAYMELSSLRSEDTAVYYCARYDYLGSSYGFDYWG
AGTTVTVSS (SEQ ID NO:82)
CL25_hu_11-4 VL
DIQMTQSPSSLSASVGDRVTITCKASQDVSTAVAWYQQKPGKAPKLLLYSASYRYS
GVPSRFSGSGSGTDYTLTISSLQPEDFATYYCQQHYNTPYTFGGGTKLEIK (SEQ
ID NO:80)

FIG. 1B

CL25_hu_11-5_VH
QVQLVQSGAEVKKPGASVKVSCKASGYTFTSYGLSWVRQATGQGLEWMGEIYPGSG
NTYYNEKFKGRVTMTANTSISTAYMELSSLRSEDTAVYYCARYDYLGSSYGFDYWG
AGTTVTVSS (SEQ ID NO:82)

CL25_hu_11-5 VL
DIVMTQSPDSLAVSLGERATINCKASQDVSTAVAWYQQKPGQPPKLLIYSASYRYS
GVPDRFSGSGSGTDFTLTISSLQAEDVAVYYCQQHYNTPYTFGGGTKLEIK (SEQ
ID NO:23)

CL25_hu_11-6 VH
QVQLVQSGAEVKKPGASVKVSCKASGYTFTSYGLSWVRQATGQGLEWMGEIYPGSG
NTYYNEKFKGRVTMTANTSISTAYMELSSLRSEDTAVYYCARYDYLGSSYGFDYWG
AGTTVTVSS (SEQ ID NO:82)

CL25_hu_11-6 VL
AIRMTQSPSSFSASTGDRVTITCKASQDVSTAVAWYQQKPGKAPKLLIYSASYRYS
GVPSRFSGSGSGTDFTLTISCLQSEDFATYYCQQHYNTPYTFGGGTKLEIK (SEQ
ID NO:81)

CL25_hu_8-4 VH
QVQLVQSGAEVKKPGASVKVSCKASGYTFTSYGLSWVRQATGQGLEWMGEIYPGSG
NTYYNEKFKGRVTMTRNTSISTAYMELSSLRSEDTAVYYCARYDYLGSSYGFDYWG
AGTTVTVSS (SEQ ID NO:83)

CL25_hu_8-4 VL
DIQMTQSPSSLSASVGDRVTITCKASQDVSTAVAWYQQKPGKAPKLLLYSASYRYS
GVPSRFSGSGSGTDYTLTISSLQPEDFATYYCQQHYNTPYTFGGGTKLEIK (SEQ
ID NO:80)

CL25_hu_8-5 VH
QVQLVQSGAEVKKPGASVKVSCKASGYTFTSYGLSWVRQATGQGLEWMGEIYPGSG
NTYYNEKFKGRVTMTRNTSISTAYMELSSLRSEDTAVYYCARYDYLGSSYGFDYWG
AGTTVTVSS (SEQ ID NO:83)

CL25_hu_8-5 VL
DIVMTQSPDSLAVSLGERATINCKASQDVSTAVAWYQQKPGQPPKLLIYSASYRYS
GVPDRFSGSGSGTDFTLTISSLQAEDVAVYYCQQHYNTPYTFGGGTKLEIK (SEQ
ID NO:23)

FIG. 1C

CL25_hu_8-6 VH
QVQLVQSGAEVKKPGASVKVSCKASGYTFTSYGLSWVRQATGQGLEWMGEIYPGSG
NTYYNEKFKGRVTMTRNTSISTAYMELSSLRSEDTAVYYCARYDYLGSSYGFDYWG
AGTTVTVSS (SEQ ID NO:83)

CL25_hu_8-6 VL
AIRMTQSPSSFSASTGDRVTITCKASQDVSTAVAWYQQKPGKAPKLLIYSASYRYS
GVPSRFSGSGSGTDFTLTISCLQSEDFATYYCQQHYNTPYTFGGGTKLEIK (SEQ
ID NO:81)

CL25_hu_9-4 VH
QVQLVQSGAEVKKPGSSVKVSCKASGYTFTSYGLSWVRQAPGQGLEWMGEIYPGSG
NTYYNEKFKGRVTITADESTSTAYMELSSLRSEDTAVYYCARYDYLGSSYGFDYWG
AGTTVTVSS (SEQ ID NO:84)

CL25_hu_9-4 VL
DIQMTQSPSSLSASVGDRVTITCKASQDVSTAVAWYQQKPGKAPKLLLYSASYRYS
GVPSRFSGSGSGTDYLTISSLQPEDFATYYCQQHYNTPYTFGGGTKLEIK (SEQ
ID NO:80)

CL25_hu_9-5 VH
QVQLVQSGAEVKKPGSSVKVSCKASGYTFTSYGLSWVRQAPGQGLEWMGEIYPGSG
NTYYNEKFKGRVTITADESTSTAYMELSSLRSEDTAVYYCARYDYLGSSYGFDYWG
AGTTVTVSS (SEQ ID NO:84)

CL25_hu_9-5 VL
DIVMTQSPDSLAVSLGERATINCKASQDVSTAVAWYQQKPGQPPKLLIYSASYRYS
GVPDRFSGSGSGTDFTLTISSLQAEDVAVYYCQQHYNTPYTFGGGTKLEIK (SEQ
ID NO:23)

CL25_hu_9-6 VH
QVQLVQSGAEVKKPGSSVKVSCKASGYTFTSYGLSWVRQAPGQGLEWMGEIYPGSG
NTYYNEKFKGRVTITADESTSTAYMELSSLRSEDTAVYYCARYDYLGSSYGFDYWG
AGTTVTVSS (SEQ ID NO:84)

CL25_hu_9-6 VL
AIRMTQSPSSFSASTGDRVTITCKASQDVSTAVAWYQQKPGKAPKLLIYSASYRYS
GVPSRFSGSGSGTDFTLTISCLQSEDFATYYCQQHYNTPYTFGGGTKLEIK (SEQ
ID NO:81)

FIG. 1D

```
CL25        QVQLQQSGAELARPGASVKLSCRASGYTFTSYGLSWVKQRTGQGLEWIGEIYPGSGNTYY  60
CL_hu_10-4  EVQLVQSGAEVKKPGESLKISCKGSGYTFTSYGLSWVRQMPGKGLEWMGEIYPGSGNTYY  60
HzCL25      EVQLVQSGAEVKKPGESLKISCKGSGYTFTSYGLSWVRQMPGKGLEWMGEIYPGSGNTYY  60
CL25_hu_10-6 EVQLVQSGAEVKKPGESLKISCKGSGYTFTSYGLSWVRQMPGKGLEWMGEIYPGSGNTYY 60
CL25_hu_9-4 QVQLVQSGAEVKKPGSSVKVSCKASGYTFTSYGLSWVRQAPGQGLEWMGEIYPGSGNTYY  60
CL25_hu_9-5 QVQLVQSGAEVKKPGSSVKVSCKASGYTFTSYGLSWVRQAPGQGLEWMGEIYPGSGNTYY  60
CL25_hu_9-6 QVQLVQSGAEVKKPGSSVKVSCKASGYTFTSYGLSWVRQAPGQGLEWMGEIYPGSGNTYY  60
CL25_hu_11-4 QVQLVQSGAEVKKPGASVKVSCKASGYTFTSYGLSWVRQATGQGLEWMGEIYPGSGNTYY 60
CL25_hu_11-5 QVQLVQSGAEVKKPGASVKVSCKASGYTFTSYGLSWVRQATGQGLEWMGEIYPGSGNTYY 60
CL25_hu_11-6 QVQLVQSGAEVKKPGASVKVSCKASGYTFTSYGLSWVRQATGQGLEWMGEIYPGSGNTYY 60
CL25_hu_8-4 QVQLVQSGAEVKKPGASVKVSCKASGYTFTSYGLSWVRQATGQGLEWMGEIYPGSGNTYY  60
CL25_hu_8-5 QVQLVQSGAEVKKPGASVKVSCKASGYTFTSYGLSWVRQATGQGLEWMGEIYPGSGNTYY  60
CL25_hu_8-6 QVQLVQSGAEVKKPGASVKVSCKASGYTFTSYGLSWVRQATGQGLEWMGEIYPGSGNTYY  60
             :*** *****: :** *:*:**:.************:*  *:****:***********

CL25        NEKFKGKATLTADKSSSTAYMELRSLTSEDSAVYFCARYDYLGSSYGFDYWGQGTTLTVS 120
CL_hu_10-4  NEKFKGQVTISADKSISTAYLQWSSLKASDTAMYYCARYDYLGSSYGFDYWGAGTTVTVS 120
HzCL25      NEKFKGQVTISADKSISTAYLQWSSLKASDTAMYYCARYDYLGSSYGFDYWGAGTTVTVS 120
CL25_hu_10-6 NEKFKGQVTISADKSISTAYLQWSSLKASDTAMYYCARYDYLGSSYGFDYWGAGTTVTVS 120
CL25_hu_9-4 NEKFKGRVTITADESTSTAYMELSSLRSEDTAVYYCARYDYLGSSYGFDYWGAGTTVTVS 120
CL25_hu_9-5 NEKFKGRVTITADESTSTAYMELSSLRSEDTAVYYCARYDYLGSSYGFDYWGAGTTVTVS 120
CL25_hu_9-6 NEKFKGRVTITADESTSTAYMELSSLRSEDTAVYYCARYDYLGSSYGFDYWGAGTTVTVS 120
CL25_hu_11-4 NEKFKGRVTMTANTSISTAYMELSSLRSEDTAVYYCARYDYLGSSYGFDYWGAGTTVTVS 120
CL25_hu_11-5 NEKFKGRVTMTANTSISTAYMELSSLRSEDTAVYYCARYDYLGSSYGFDYWGAGTTVTVS 120
CL25_hu_11-6 NEKFKGRVTMTANTSISTAYMELSSLRSEDTAVYYCARYDYLGSSYGFDYWGAGTTVTVS 120
CL25_hu_8-4 NEKFKGRVTMTRNTSISTAYMELSSLRSEDTAVYYCARYDYLGSSYGFDYWGAGTTVTVS 120
CL25_hu_8-5 NEKFKGRVTMTRNTSISTAYMELSSLRSEDTAVYYCARYDYLGSSYGFDYWGAGTTVTVS 120
CL25_hu_8-6 NEKFKGRVTMTRNTSISTAYMELSSLRSEDTAVYYCARYDYLGSSYGFDYWGAGTTVTVS 120
             ******:.*:: : * ****:: ** :.*;*;*;*****************.***:***

CL25         S 120 (SEQ ID NO:26)
CL_hu_10-4   S 121 (SEQ ID NO:22)
HzCL25       S 121 (SEQ ID NO:22)
CL25_hu_10-6 S 121 (SEQ ID NO:22)
CL25_hu_9-4  S 121 (SEQ ID NO:84)
CL25_hu_9-5  S 121 (SEQ ID NO:84)
CL25_hu_9-6  S 121 (SEQ ID NO:84)
CL25_hu_11-4 S 121 (SEQ ID NO:82)
CL25_hu_11-5 S 121 (SEQ ID NO:82)
CL25_hu_11-6 S 121 (SEQ ID NO:82)
CL25_hu_8-4  S 121 (SEQ ID NO:83)
CL25_hu_8-5  S 121 (SEQ ID NO:83)
CL25_hu_8-6  S 121 (SEQ ID NO:83)
```

FIG. 1E

```
CL25          DIVMTQSHKFMSTSVGDRVSITCKASQDVSTAVAWYQQKPGQSPKLLIYSASYRYNGVPD  60
HzCL25        DIVMTQSPDSLAVSLGERATINCKASQDVSTAVAWYQQKPGQPPKLLIYSASYRYSGVPD  60
CL25_hu_11-5  DIVMTQSPDSLAVSLGERATINCKASQDVSTAVAWYQQKPGQPPKLLIYSASYRYSGVPD  60
CL25_hu_8-5   DIVMTQSPDSLAVSLGERATINCKASQDVSTAVAWYQQKPGQPPKLLIYSASYRYSGVPD  60
CL25_hu_9-5   DIVMTQSPDSLAVSLGERATINCKASQDVSTAVAWYQQKPGQPPKLLIYSASYRYSGVPD  60
CL25_hu_10-4  DIQMTQSPSSLSASVGDRVTITCKASQDVSTAVAWYQQKPGKAPKLLLYSASYRYSGVPS  60
CL25_hu_11-4  DIQMTQSPSSLSASVGDRVTITCKASQDVSTAVAWYQQKPGKAPKLLLYSASYRYSGVPS  60
CL25_hu_8-4   DIQMTQSPSSLSASVGDRVTITCKASQDVSTAVAWYQQKPGKAPKLLLYSASYRYSGVPS  60
CL25_hu_9-4   DIQMTQSPSSLSASVGDRVTITCKASQDVSTAVAWYQQKPGKAPKLLLYSASYRYSGVPS  60
CL25_hu_10-6  AIRMTQSPSSFSASTGDRVTITCKASQDVSTAVAWYQQKPGKAPKLLIYSASYRYSGVPS  60
CL25_hu_11-6  AIRMTQSPSSFSASTGDRVTITCKASQDVSTAVAWYQQKPGKAPKLLIYSASYRYSGVPS  60
CL25_hu_8-6   AIRMTQSPSSFSASTGDRVTITCKASQDVSTAVAWYQQKPGKAPKLLIYSASYRYSGVPS  60
CL25_hu_9-6   AIRMTQSPSSFSASTGDRVTITCKASQDVSTAVAWYQQKPGKAPKLLIYSASYRYSGVPS  60
               * **** . ::.* *;*.:*.********************: ****;*******.***.

CL25          RFTGSGSGTDFTFTISSVQAEDLAVYYCQQHYNTPYTFGGGTKLEIK  107 (SEQ ID NO:27)
HzCL25        RFSGSGSGTDFTLTISSLQAEDVAVYYCQQHYNTPYTFGGGTKLEIK  107 (SEQ ID NO:23)
CL25_hu_11-5  RFSGSGSGTDFTLTISSLQAEDVAVYYCQQHYNTPYTFGGGTKLEIK  107 (SEQ ID NO:23)
CL25_hu_8-5   RFSGSGSGTDFTLTISSLQAEDVAVYYCQQHYNTPYTFGGGTKLEIK  107 (SEQ ID NO:23)
CL25_hu_9-5   RFSGSGSGTDFTLTISSLQAEDVAVYYCQQHYNTPYTFGGGTKLEIK  107 (SEQ ID NO:23)
CL25_hu_10-4  RFSGSGSGTDYTLTISSLQPEDFATYYCQQHYNTPYTFGGGTKLEIK  107 (SEQ ID NO:80)
CL25_hu_11-4  RFSGSGSGTDYTLTISSLQPEDFATYYCQQHYNTPYTFGGGTKLEIK  107 (SEQ ID NO:80)
CL25_hu_8-4   RFSGSGSGTDYTLTISSLQPEDFATYYCQQHYNTPYTFGGGTKLEIK  107 (SEQ ID NO:80)
CL25_hu_9-4   RFSGSGSGTDYTLTISSLQPEDFATYYCQQHYNTPYTFGGGTKLEIK  107 (SEQ ID NO:80)
CL25_hu_10-6  RFSGSGSGTDFTLTISCLQSEDFATYYCQQHYNTPYTFGGGTKLEIK  107 (SEQ ID NO:81)
CL25_hu_11-6  RFSGSGSGTDFTLTISCLQSEDFATYYCQQHYNTPYTFGGGTKLEIK  107 (SEQ ID NO:81)
CL25_hu_8-6   RFSGSGSGTDFTLTISCLQSEDFATYYCQQHYNTPYTFGGGTKLEIK  107 (SEQ ID NO:81)
CL25_hu_9-6   RFSGSGSGTDFTLTISCLQSEDFATYYCQQHYNTPYTFGGGTKLEIK  107 (SEQ ID NO:81)
              **;*******;*;***.;* **.*.********************
```

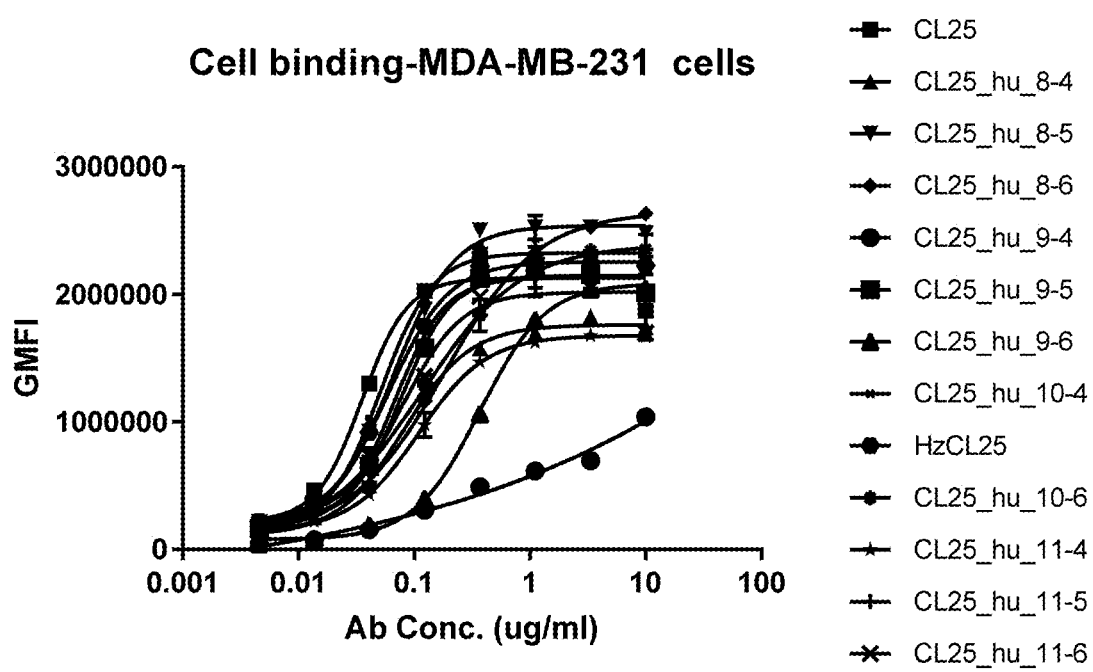

Surface CD73 after 24 hour antibody incubation

Cell binding-MDA-MB-231cells

Cell binding-A375 cells

Cellular CD73 inhibition - A375 cells

Cellular CD73 inhibition - MDA-MB-231 cells

Surface CD73 after 24 hour antibody incubation

FIG. 12A

3-F03_VH_yeast
EVQLVESGGGLVQPGGSLRLSCAASGFTFSSYDMHWVRQAPGKGLEWVAVMSYDGS
NKYYADSVKGRFTISRDNSKNTLYLQMNSLRAEDTAVYYCATEIAAKGDYWGQGTL
VTVSS (SEQ ID NO:77)

3-F03_VL_yeast
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

3-F03_VH
VQLVESGGGLVQPGGSLRLSCAASGFTFSSYDMHWVRQAPGKGLEWVAVMSYDGSN
KYYADSVKGRFTISRDNSKNALYLQMNSLRAEDTAVYYCATEIAAKGDYWGQGTLV
TVSS (SEQ ID NO:60)

3-F03_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

3-F03_411_VH
EVQLVESGGGLVQPGGSLRLSCAASGFTFSSYDMHWVRQAPGKGLEWVAVMSYDGS
NKYYADSVKGRFTISRDNSKNALYLQMNSLRAEDTAVYYCATEIAAKGDYWGQGTL
VTVSS (SEQ ID NO:62)

3-F03_411_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

3-F03_413_VH
EVQLVESGGGLVQPGGSLRLSCAASGFTFSSYDMHWVRQAPGKGLEWVAVMSYEGS
NKYYADSVKGRFTISRDNSKNALYLQMNSLRAEDTAVYYCATEIAAKGDYWGQGTL
VTVSS (SEQ ID NO:63)

3-F03_413_LC
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

FIG. 12B

3-F03_396_VH
EVQLVESGGGLVQPGGSLRLSCAASGFTFSSYDMHWVRQAPGKGLEWVAVMSYDGS
NKYYADSVKGRFTISRDNSKNTLYLQMNSLRAEDTAVYYCATEIAAKGDYWGQGTL
VTVSS (SEQ ID NO:77)

3-F03_396_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

3-F03_408_VH
EVQLVESGGGLVQPGGSLRLSCAASGFTFSSYDMHWVRQAPGKGLEWVAVMSYDGS
NKYYADSVKGRFTISRDNSKNTLYLQMNSLRAEDTAVYYCATEIAAKGDYWGQGTL
VTVSS (SEQ ID NO:77)

3-F03_408_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

3-F03_402_VH
VQLVESGGGLVQPGGSLRLSCAASGFTFSSYDMHWVRQAPGKGLEWVAVMSYDGSN
KYYADSVKGRFTISRDNSKNTLYLQMNSLRAEDTAVYYCATEIAAKGDYWGQGTLV
TVSS (SEQ ID NO:85)

3-F03_402_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

3-F03_384_VH
EVQLVESGGGLVQPGGSLRLSCAASGFTFSSYDMHWVRQAPGKGLEWVAVMSYDGS
NKYYADSVKGRFTISRDNSKNTLYLQMNSLRAEDTAVYYCATEIAAKGDYWGQGTL
VTVSS (SEQ ID NO:77)

3-F03_384_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

FIG. 12C

3-F03_399_VH
EVQLVESGGGLVQPGGSLRLSCAASGFTFSSYDMHWVRQAPGKGLEWVAVMSYDGS
NKYYADSVKGRFTISRDNSKNALYLQMNSLRAEDTAVYYCATEIAAKGDYWGQGTL
VTVSS (SEQ ID NO:62)

3-F03_399_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

3-F03_414_VH
VQLVESGGGLVQPGGSLRLSCAASGFTFSSYDMHWVRQAPGKGLEWVAVMSYDGSN
KYYADSVKGRFTISRDNSKNTLYLQMNSLRAEDTAVYYCATEIAAKGDYWGQGTLV
TVSS (SEQ ID NO:85)

3-F03_414_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

3-F03_390_VH
VQLVESGGGLVQPGGSLRLSCAASGFTFSSYDMHWVRQAPGKGLEWVAVMSYDGSN
KYYADSVKGRFTISRDNSKNTLYLQMNSLRAEDTAVYYCATEIAAKGDYWGQGTLV
TVSS (SEQ ID NO:85)

3-F03_390_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

3-F03_398_VH
EVQLVESGGGLVQPGGSLRLSCAASGFTFSSYDMHWVRQAPGKGLEWVAVMSYEGS
NKYYADSVKGRFTISRDNSKNTLYLQMNSLRAEDTAVYYCATEIAAKGDYWGQGTL
VTVSS (SEQ ID NO:86)

3-F03_398_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

FIG. 12D

3-F03_387_VH
EVQLVESGGGLVQPGGSLRLSCAASGFTFSSYDMHWVRQAPGKGLEWVAVMSYDGS
NKYYADSVKGRFTISRDNSKNALYLQMNSLRAEDTAVYYCATEIAAKGDYWGQGTL
VTVSS (SEQ ID NO:62)

3-F03_387_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

3-F03_386_VH
EVQLVESGGGLVQPGGSLRLSCAASGFTFSSYDMHWVRQAPGKGLEWVAVMSYEGS
NKYYADSVKGRFTISRDNSKNTLYLQMNSLRAEDTAVYYCATEIAAKGDYWGQGTL
VTVSS (SEQ ID NO:86)

3-F03_386_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

3-F03_401_VH
EVQLVESGGGLVQPGGSLRLSCAASGFTFSSYDMHWVRQAPGKGLEWVAVMSYEGS
NKYYADSVKGRFTISRDNSKNALYLQMNSLRAEDTAVYYCATEIAAKGDYWGQGTL
VTVSS (SEQ ID NO:63)

3-F03_401_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

3-F03_410_VH
EVQLVESGGGLVQPGGSLRLSCAASGFTFSSYDMHWVRQAPGKGLEWVAVMSYEGS
NKYYADSVKGRFTISRDNSKNTLYLQMNSLRAEDTAVYYCATEIAAKGDYWGQGTL
VTVSS (SEQ ID NO:86)

3-F03_410_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

FIG. 12E

3-F03_389_VH
EVQLVESGGGLVQPGGSLRLSCAASGFTFSSYDMHWVRQAPGKGLEWVAVMSYEGS
NKYYADSVKGRFTISRDNSKNALYLQMNSLRAEDTAVYYCATEIAAKGDYWGQGTL
VTVSS (SEQ ID NO:63)

3-F03_389_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

3-F03_392_VH
VQLVESGGGLVQPGGSLRLSCAASGFTFSSYDMHWVRQAPGKGLEWVAVMSYEGSN
KYYADSVKGRFTISRDNSKNTLYLQMNSLRAEDTAVYYCATEIAAKGDYWGQGTLV
TVSS (SEQ ID NO:87)

3-F03_392_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

3-F03_404_VH
VQLVESGGGLVQPGGSLRLSCAASGFTFSSYDMHWVRQAPGKGLEWVAVMSYEGSN
KYYADSVKGRFTISRDNSKNTLYLQMNSLRAEDTAVYYCATEIAAKGDYWGQGTLV
TVSS (SEQ ID NO:87)

3-F03_404_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

3-F03_419_VH
VQLVESGGGLVQPGGSLRLSCAASGFTFSSYDMHWVRQAPGKGLEWVAVMSYEGSN
KYYADSVKGRFTISRDNSKNALYLQMNSLRAEDTAVYYCATEIAAKGDYWGQGTLV
TVSS (SEQ ID NO:88)

3-F03_419_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

FIG. 12F

3-F03_416_VH
VQLVESGGGLVQPGGSLRLSCAASGFTFSSYDMHWVRQAPGKGLEWVAVMSYEGSN
KYYADSVKGRFTISRDNSKNTLYLQMNSLRAEDTAVYYCATEIAAKGDYWGQGTLV
TVSS (SEQ ID NO:87)

3-F03_416_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

3-F03_407_VH
VQLVESGGGLVQPGGSLRLSCAASGFTFSSYDMHWVRQAPGKGLEWVAVMSYEGSN
KYYADSVKGRFTISRDNSKNALYLQMNSLRAEDTAVYYCATEIAAKGDYWGQGTLV
TVSS (SEQ ID NO:88)

3-F03_407_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

3-F03_395_VH
VQLVESGGGLVQPGGSLRLSCAASGFTFSSYDMHWVRQAPGKGLEWVAVMSYEGSN
KYYADSVKGRFTISRDNSKNALYLQMNSLRAEDTAVYYCATEIAAKGDYWGQGTLV
TVSS (SEQ ID NO:88)

3-F03_395_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

3-F03_388_VH
EVQLVESGGGLVQPGGSLRLSCAASGFTFSSYDMHWVRQAPGKGLEWVAVMSYSGS
NKYYADSVKGRFTISRDNSKNALYLQMNSLRAEDTAVYYCATEIAAKGDYWGQGTL
VTVSS (SEQ ID NO:69)

3-F03_388_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

FIG. 12G

3-F03_397_VH
EVQLVESGGGLVQPGGSLRLSCAASGFTFSSYDMHWVRQAPGKGLEWVAVMSYSGS
NKYYADSVKGRFTISRDNSKNTLYLQMNSLRAEDTAVYYCATEIAAKGDYWGQGTL
VTVSS (SEQ ID NO:68)

3-F03_397_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

3-F03_385_VH
EVQLVESGGGLVQPGGSLRLSCAASGFTFSSYDMHWVRQAPGKGLEWVAVMSYSGS
NKYYADSVKGRFTISRDNSKNTLYLQMNSLRAEDTAVYYCATEIAAKGDYWGQGTL
VTVSS (SEQ ID NO:68)

3-F03_385_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

3-F03_400_VH
EVQLVESGGGLVQPGGSLRLSCAASGFTFSSYDMHWVRQAPGKGLEWVAVMSYSGS
NKYYADSVKGRFTISRDNSKNALYLQMNSLRAEDTAVYYCATEIAAKGDYWGQGTL
VTVSS (SEQ ID NO:69)

3-F03_400_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

3-F03_409_VH
EVQLVESGGGLVQPGGSLRLSCAASGFTFSSYDMHWVRQAPGKGLEWVAVMSYSGS
NKYYADSVKGRFTISRDNSKNALYLQMNSLRAEDTAVYYCATEIAAKGDYWGQGTL
VTVSS (SEQ ID NO:69)

3-F03_409_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

FIG. 12H

3-F03_403_VH
VQLVESGGGLVQPGGSLRLSCAASGFTFSSYDMHWVRQAPGKGLEWVAVMSYSGSN
KYYADSVKGRFTISRDNSKNTLYLQMNSLRAEDTAVYYCATEIAAKGDYWGQGTLV
TVSS (SEQ ID NO:32)
3-F03_403_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

3-F03_415_VH
VQLVESGGGLVQPGGSLRLSCAASGFTFSSYDMHWVRQAPGKGLEWVAVMSYSGSN
KYYADSVKGRFTISRDNSKNTLYLQMNSLRAEDTAVYYCATEIAAKGDYWGQGTLV
TVSS (SEQ ID NO:32)
3-F03_415_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

3-F03_391_VH
VQLVESGGGLVQPGGSLRLSCAASGFTFSSYDMHWVRQAPGKGLEWVAVMSYSGSN
KYYADSVKGRFTISRDNSKNTLYLQMNSLRAEDTAVYYCATEIAAKGDYWGQGTLV
TVSS (SEQ ID NO:32)
3-F03_391_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

3-F03_406_VH
VQLVESGGGLVQPGGSLRLSCAASGFTFSSYDMHWVRQAPGKGLEWVAVMSYSGSN
KYYADSVKGRFTISRDNSKNALYLQMNSLRAEDTAVYYCATEIAAKGDYWGQGTLV
TVSS (SEQ ID NO:67)
3-F03_406_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

FIG. 12I

3-F03_412_VH
EVQLVESGGGLVQPGGSLRLSCAASGFTFSSYDMHWVRQAPGKGLEWVAVMSYSGS
NKYYADSVKGRFTISRDNSKNALYLQMNSLRAEDTAVYYCATEIAAKGDYWGQGTL
VTVSS (SEQ ID NO:69)

3-F03_412_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

3-F03_394_VH
VQLVESGGGLVQPGGSLRLSCAASGFTFSSYDMHWVRQAPGKGLEWVAVMSYSGSN
KYYADSVKGRFTISRDNSKNALYLQMNSLRAEDTAVYYCATEIAAKGDYWGQGTLV
TVSS (SEQ ID NO:67)

3-F03_394_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

3-F03_418_VH
VQLVESGGGLVQPGGSLRLSCAASGFTFSSYDMHWVRQAPGKGLEWVAVMSYSGSN
KYYADSVKGRFTISRDNSKNALYLQMNSLRAEDTAVYYCATEIAAKGDYWGQGTLV
TVSS (SEQ ID NO:67)

3-F03_418_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

3_F03_417_VH
VQLVESGGGLVQPGGSLRLSCAASGFTFSSYDMHWVRQAPGKGLEWVAVMSYDGSN
KYYADSVKGRFTISRDNSKNALYLQMNSLRAEDTAVYYCATEIAAKGDYWGQGTLV
TVSS (SEQ ID NO:60)

3_F03_417_VL
IQMTQSPSSLSASVGDRVTITCRASQGISNYLAWYQQKPGKAPKLLIYAASTLQSG
VPSRFSGSGSGTDFTLTISSLQPEDFATYYCQQSYSTPHFGQGTRLEIK (SEQ
ID NO:61)

FIG. 12J

3_F03_393_VH
VQLVESGGGLVQPGGSLRLSCAASGFTFSSYDMHWVRQAPGKGLEWVAVMSYDGSN
KYYADSVKGRFTISRDNSKNALYLQMNSLRAEDTAVYYCATEIAAKGDYWGQGTLV
TVSS (SEQ ID NO:60)

3_F03_393_VL
DIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:64)

3_F03_405_VH
VQLVESGGGLVQPGGSLRLSCAASGFTFSSYDMHWVRQAPGKGLEWVAVMSYDGSN
KYYADSVKGRFTISRDNSKNALYLQMNSLRAEDTAVYYCATEIAAKGDYWGQGTLV
TVSS (SEQ ID NO:60)

3_F03_405_VL
AIQMTQSPSSLSASVGDRVTITCRASQGISNYLAWYQQKPGKAPKLLIYAASTLQS
GVPSRFSGSGSGTDFTLTISSLQPEDFATYYCQQSYSTPHFGQGTRLEIK (SEQ
ID NO:65)

FIG. 15

Human IgG1 heavy chain CH1-hinge-CH2-CH3, with N297A mutation
ASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPC
PAPELLGGPSVFLFPPKPKDTLMISRTPEVTCVVVDVSHEDPEVKFNWYVDGVEVH
NAKTKPREEQYASTYRVVSVLTVLHQDWLNGKEYKCKVSNKALPAPIEKTISKAKG
QPREPQVYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPG (SEQ
ID NO:73)

Human IgG1 heavy chain CH1-hinge-CH2-CH3, with N297A mutation with C-terminal lysine
ASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPC
PAPELLGGPSVFLFPPKPKDTLMISRTPEVTCVVVDVSHEDPEVKFNWYVDGVEVH
NAKTKPREEQYASTYRVVSVLTVLHQDWLNGKEYKCKVSNKALPAPIEKTISKAKG
QPREPQVYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK (SEQ
ID NO:75)

Human kappa light chain constant region
RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ
ID NO:74)

FIG. 20A

HzCL25 heavy chain DNA sequence
GAAGTGCAGCTCGTGCAGTCCGGAGCCGAAGTGAAAAAGCCTGGAGAGTCCCTGAAGATC
AGCTGCAAGGGTTCCGGCTATACATTCACCTCCTACGGGCTCAGCTGGGTCAGACAGATG
CCGGGAAAGGGTCTTGAGTGGATGGGAGAGATCTACCCGGGCTCCGGCAACACCTACTAC
AACGAAAAGTTCAAGGGCCAGGTCACCATTTCCGCCGACAAGTCAATCTCCACCGCTTAC
CTCCAATGGTCGAGCCTGAAGGCATCGGATACCGCGATGTACTACTGCGCCCGCTACGAC
TACCTGGGCTCGTCATACGGCTTCGATTACTGGGGGCGGGAACTACCGTGACTGTGTCC
TCCGCCTCCACTAAGGGACCCTCAGTGTTCCCCCTTGCCCCGAGCTCCAAGAGCACTTCG
GGCGGAACCGCTGCCCTGGGTTGCCTCGTGAAGGATTACTTCCCCGAGCCTGTGACCGTG
TCCTGGAACTCCGGGGCCTTGACCAGCGGAGTCCACACCTTCCCGGCCGTGCTGCAATCA
TCCGGTCTGTACAGTCTGTCCTCCGTGGTCACGGTGCCCTCGTCCTCACTGGGGACTCAG
ACTTACATCTGTAACGTGAACCATAAGCCATCGAACACCAAAGTCGACAAACGGGTGGAA
CCTAAGTCATGCGACAAGACCCACACGTGCCCACCTTGCCCCGCCCCGAGCTCCTGGGG
GGGCCGAGCGTGTTCCTCTTCCCGCCGAAACCGAAGGACACCCTGATGATCTCGAGGACT
CCTGAAGTCACTTGCGTGGTCGTGGACGTGTCGCACGAGGACCCCGAAGTCAAGTTCAAT
TGGTACGTGGACGGAGTCGAAGTGCACAACGCTAAGACCAAACCCGCGAGGAGCAGTAC
GCAAGCACCTACCGCGTTGTCAGCGTGCTCACCGTGCTGCATCAGGATTGGCTGAATGGA
AAGGAGTACAAGTGCAAAGTGTCCAACAAGGCCCTGCCTGCACCAATTGAAAAGACCATC
TCCAAGGCCAAGGGCCAGCCCCGGGAGCCCCAAGTCTACACTCTGCCGCCGTCGAGAGAA
GAAATGACCAAGAACCAAGTGTCCCTGACTTGTCTGGTCAAGGGCTTCTATCCTTCGGAC
ATCGCGGTGGAATGGGAGAGCAACGGCCAGCCGGAGAACAATTACAAGACTACGCCACCC
GTGCTGGACTCTGACGGCTCCTTTTTCCTGTATTCCAAGCTCACCGTGGACAAGAGCCGC
TGGCAACAGGGAAACGTGTTCAGCTGCTCCGTGATGCACGAAGCCCTGCACAACCACTAC
ACCCAGAAGTCCCTGAGCTTGTCCCTGGT (SEQ ID NO:89)

HzCL25 light chain DNA sequence
GACATCGTGATGACCCAGTCCCCGGATTCACTCGCGGTGTCTTTGGGGGAGAGGGCAACC
ATTAACTGCAAGGCCTCACAGGATGTGTCCACTGCTGTCGCCTGGTACCAGCAGAAGCCT
GGGCAGCCGCCCAAGCTGCTGATCTACTCGGCCTCCTACCGCTATTCCGGAGTCCCCGAC
CGGTTCTCCGGCTCGGGTTCCGGAACTGATTTCACCCTGACAATTTCGTCGCTGCAAGCC
GAGGACGTGGCCGTGTACTACTGCCAACAGCATTACAACACTCCTTACACTTTTGGTGGC
GGAACTAAGCTCGAGATCAAGCGGACGGTGGCAGCTCCGTCAGTGTTCATCTTCCCTCCA
TCGGACGAACAGCTGAAGTCCGGCACCGCGTCCGTCGTGTGTCTGTTGAACAACTTCTAC
CCGCGGGAAGCCAAGGTCCAGTGGAAAGTCGACAACGCGCTGCAGTCCGGAAATAGCCAG
GAAAGCGTGACCGAACAGGACTCCAAGGACAGCACCTACTCCCTGAGCTCAACCCTGACC
CTGAGCAAGGCCGACTATGAGAAGCACAAAGTGTACGCCTGCGAAGTGACCCACCAAGGC
CTGAGCAGCCCAGTGACCAAGTCCTTCAACCGCGGGGAGTGT (SEQ ID NO:90)

FIG. 20B

3-F03_411 heavy chain DNA sequence

GAAGTGCAGTTGGTGGAGAGCGGGGGCGGACTGGTGCAGCCGGGGGGCTCGCTGCG
GCTGTCCTGCGCCGCGTCCGGTTTCACTTTTTCGAGCTACGACATGCACTGGGTCC
GCCAAGCACCGGGGAAGGGTCTGGAATGGGTGGCCGTGATGTCGTACGACGGCTCC
AACAAGTACTACGCCGACTCCGTGAAGGGACGGTTCACCATCTCCCGCGACAACAG
CAAGAACGCCCTTTACCTCCAAATGAACAGCCTGAGGGCCGAGGACACAGCCGTAT
ACTACTGCGCGACCGAGATCGCCGCCAAGGGGGACTACTGGGGTCAAGGCACTCTG
GTCACCGTGTCCTCCGCCTCCACTAAGGGACCCTCAGTGTTCCCCCTTGCCCCGAG
CTCCAAGAGCACTTCGGGCGGAACCGCTGCCCTGGGTTGCCTCGTGAAGGATTACT
TCCCCGAGCCTGTGACCGTGTCCTGGAACTCCGGGGCCTTGACCAGCGGAGTCCAC
ACCTTCCCGGCCGTGCTGCAATCATCCGGTCTGTACAGTCTGTCCTCCGTGGTCAC
GGTGCCCTCGTCCTCACTGGGGACTCAGACTTACATCTGTAACGTGAACCATAAGC
CATCGAACACCAAAGTCGACAAACGGGTGGAACCTAAGTCATGCGACAAGACCCAC
ACGTGCCCACCTTGCCCCGCCCCCGAGCTCCTGGGGGGCCGAGCGTGTTCCTCTT
CCCGCCGAAACCGAAGGACACCCTGATGATCTCGAGGACTCCTGAAGTCACTTGCG
TGGTCGTGGACGTGTCGCACGAGGACCCCGAAGTCAAGTTCAATTGGTACGTGGAC
GGAGTCGAAGTGCACAACGCTAAGACCAAACCCCGCGAGGAGCAGTACGCAAGCAC
CTACCGCGTTGTCAGCGTGCTCACCGTGCTGCATCAGGATTGGCTGAATGGAAAGG
AGTACAAGTGCAAAGTGTCCAACAAGGCCCTGCCTGCACCAATTGAAAAGACCATC
TCCAAGGCCAAGGGCCAGCCCCGGGAGCCCCAAGTCTACACTCTGCCGCCGTCGAG
AGAAGAAATGACCAAGAACCAAGTGTCCCTGACTTGTCTGGTCAAGGGCTTCTATC
CTTCGGACATCGCGGTGGAATGGGAGAGCAACGGCCAGCCGGAGAACAATTACAAG
ACTACGCCACCCGTGCTGGACTCTGACGGCTCCTTTTTCCTGTATTCCAAGCTCAC
CGTGGACAAGAGCCGCTGGCAACAGGGAAACGTGTTCAGCTGCTCCGTGATGCACG
AAGCCCTGCACAACCACTACACCCAGAAGTCCCTGAGCTTGTCCCTGGT (SEQ
ID NO:91)

FIG. 20C

3-F03_411 and 3-F03_413 light chain DNA sequence
ATCCAGATGACTCAGTCCCCTTCCTCGTTGTCCGCTTCCGTGGGTGATCGGGTCAC
AATCACTTGCCGGGCCAGCCAGGGAATTTCCAACTACCTCGCCTGGTACCAGCAGA
AGCCCGGAAAGGCACCGAAGCTGCTGATCTACGCCGCGTCCACTCTGCAATCCGGA
GTGCCTTCTCGGTTCTCGGGCTCGGGAAGCGGCACCGACTTTACCCTGACCATTAG
CAGCCTGCAGCCCGAGGACTTCGCAACCTACTACTGTCAGCAGTCCTACTCAACCC
CTCACTTCGGACAGGGTACTAGACTCGAGATCAAGAGGACTGTGGCCGCGCCGTCG
GTGTTCATCTTCCCACCCTCGGACGAGCAGCTGAAGTCCGGCACCGCCAGCGTGGT
CTGCCTGCTGAACAACTTCTATCCGCGCGAAGCCAAGGTCCAGTGGAAAGTGGATA
ATGCGCTGCAGAGCGGGAACTCCCAAGAGTCCGTGACGGAACAGGACTCCAAAGAC
TCCACCTACTCACTGTCATCCACCCTGACCCTGTCAAAGGCCGACTACGAGAAGCA
TAAGGTCTACGCCTGCGAAGTGACCCACCAAGGGCTGAGCTCGCCCGTGACCAAGT
CCTTCAACCGGGGCGAATGC (SEQ ID NO:92)

3-F03_413 heavy chain DNA sequence
GAAGTGCAGTTGGTGGAGAGCGGGGGCGGACTGGTGCAGCCGGGGGGCTCGCTGCG
GCTGTCCTGCGCCGCGTCCGGTTTCACTTTTTCGAGCTACGACATGCACTGGGTCC
GCCAAGCACCGGGGAAGGGTCTGGAATGGGTGGCCGTGATGTCGTACGAAGGCTCC
AACAAGTACTACGCCGACTCCGTGAAGGGACGGTTCACCATCTCCCGCGACAACAG
CAAGAACGCCCTTTACCTCCAAATGAACAGCCTGAGGGCCGAGGACACAGCCGTAT
ACTACTGCGCGACCGAGATCGCCGCCAAGGGGGACTACTGGGGTCAAGGCACTCTG
GTCACCGTGTCCTCCGCCTCCACTAAGGGACCCTCAGTGTTCCCCCTTGCCCCGAG
CTCCAAGAGCACTTCGGGCGGAACCGCTGCCCTGGGTTGCCTCGTGAAGGATTACT
TCCCCGAGCCTGTGACCGTGTCCTGGAACTCCGGGGCCTTGACCAGCGGAGTCCAC
ACCTTCCCGGCCGTGCTGCAATCATCCGGTCTGTACAGTCTGTCCTCCGTGGTCAC
GGTGCCCTCGTCCTCACTGGGGACTCAGACTTACATCTGTAACGTGAACCATAAGC
CATCGAACACCAAAGTCGACAAACGGGTGGAACCTAAGTCATGCGACAAGACCCAC
ACGTGCCCACCTTGCCCCGCCCCGAGCTCCTGGGGGGCCGAGCGTGTTCCTCTT
CCCGCCGAAACCGAAGGACACCCTGATGATCTCGAGGACTCCTGAAGTCACTTGCG
TGGTCGTGGACGTGTCGCACGAGGACCCCGAAGTCAAGTTCAATTGGTACGTGGAC
GGAGTCGAAGTGCACAACGCTAAGACCAAACCCCGCGAGGAGCAGTACGCAAGCAC
CTACCGCGTTGTCAGCGTGCTCACCGTGCTGCATCAGGATTGGCTGAATGGAAAGG
AGTACAAGTGCAAAGTGTCCAACAAGGCCCTGCCTGCACCAATTGAAAAGACCATC
TCCAAGGCCAAGGGCCAGCCCCGGGAGCCCAAGTCTACACTCTGCCGCCGTCGAG
AGAAGAAATGACCAAGAACCAAGTGTCCCTGACTTGTCTGGTCAAGGGCTTCTATC
CTTCGGACATCGCGGTGGAATGGGAGAGCAACGGCCAGCCGGAGAACAATTACAAG
ACTACGCCACCCGTGCTGGACTCTGACGGCTCCTTTTTCCTGTATTCCAAGCTCAC
CGTGGACAAGAGCCGCTGGCAACAGGGAAACGTGTTCAGCTGCTCCGTGATGCACG
AAGCCCTGCACAACCACTACACCCAGAAGTCCCTGAGCTTGTCCCCTGGT (SEQ ID NO:93)

CD73 INHIBITOR AND A2A/A2B ADENOSINE RECEPTOR INHIBITOR COMBINATION THERAPY

RELATED APPLICATIONS

This application claims the benefit of U.S. Provisional Application No. 62/956,840, filed Jan. 3, 2020, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 23, 2020, is named 20443-0645001_SL.txt and is 112,058 bytes in size.

TECHNICAL FIELD

Disclosed are combination therapies comprising administration of a CD73 inhibitor and an A2A and/or A2B adenosine receptor inhibitor. The disclosed combination therapies are useful in the treatment of diseases related to the activity of A2A and/or A2B adenosine receptors and/or CD73 including, for example, cancer, inflammatory diseases, cardiovascular diseases, and neurodegenerative diseases. Anti-CD73 inhibitors and A2A/A2B adenosine receptor inhibitors are also disclosed.

BACKGROUND

Cluster of differentiation 73 (CD73) is a glycosyl phosphatidyl inositol- (GPI-) linked membrane protein that catalyzes the conversion of extracellular adenosine monophosphate (AMP) to adenosine. It functions as a homodimer, and can be shed and is active as a soluble protein in circulation. In addition to its enzymatic function, CD73 also is a cellular adhesion molecule and plays a role in regulation of leukocyte trafficking. CD73 levels are known to be upregulated due to tissue injury or hypoxic conditions, and a number of solid tumors have elevated CD73 levels. Upregulation of CD73 within the tumor contributes to the adenosine-rich tumor microenvironment, which has numerous pro-tumor and immuno-suppressive effects.

Adenosine is an extracellular signaling molecule that can modulate immune responses through many immune cell types. Adenosine was first recognized as a physiologic regulator of coronary vascular tone by Drury and Szent-Györgyu (Sachdeva, S. and Gupta, M. Saudi Pharmaceutical Journal, 2013, 21, 245-253), however it was not until 1970 that Sattin and Rall showed that adenosine regulates cell function via occupancy of specific receptors on the cell surface (Sattin, A., and Rall, T. W., 1970. Mol. Pharmacol. 6, 13-23; Hasko´, G., at al., 2007, Pharmacol. Ther. 113, 264-275).

Adenosine plays a vital role in various other physiological functions. It is involved in the synthesis of nucleic acids, when linked to three phosphate groups; it forms ATP, the integral component of the cellular energy system. Adenosine can be generated by the enzymatic breakdown of extracellular ATP, or can be also released from injured neurons and glial cells by passing the damaged plasma membrane (Tautenhahn, M. et al. Neuropharmacology, 2012, 62, 1756-1766). Adenosine produces various pharmacological effects, both in periphery and in the central nervous system, through an action on specific receptors localized on cell membranes (Matsumoto, T. et al. Pharmacol. Res., 2012, 65, 81-90). Alternative pathways for extracellular adenosine generation have been described. These pathways include the production of adenosine from nicotinamide dinucleotide (NAD) instead of ATP by the concerted action of CD38, CD203a and CD73. CD73-independent production of adenosine can also occur by other phosphates such as alkaline phosphatase or prostate-specific phosphatase.

There are four known subtypes of adenosine receptor in humans including A1, A2A, A2B and A3 receptors. A1 and A2A are high affinity receptors, whereas A2B and A3 are low affinity receptors. Adenosine and its agonists can act via one or more of these receptors and can modulate the activity of adenylate cyclase, the enzyme responsible for increasing cyclic AMP (cAMP). The different receptors have differential stimulatory and inhibitory effects on this enzyme. Increased intracellular concentrations of cAMP can suppress the activity of immune and inflammatory cells (Livingston, M. et al., Inflamm. Res., 2004, 53, 171-178).

The A2A adenosine receptor can signal in the periphery and the CNS, with agonists explored as anti-inflammatory drugs and antagonists explored for neurodegenerative diseases (Carlsson, J. et al., J. Med. Chem., 2010, 53, 3748-3755). In most cell types the A2A subtype inhibits intracellular calcium levels whereas the A2B potentiates them. The A2A receptor generally appears to inhibit inflammatory response from immune cells (Borrmann, T. et al., J. Med. Chem., 2009, 52(13), 3994-4006).

A2B receptors are highly expressed in the gastrointestinal tract, bladder, lung and on mast cells (Antonioli, L. et al., Nature Reviews Cancer, 2013, 13, 842-857). The A2B receptor, although structurally closely related to the A2A receptor and able to activate adenylate cyclase, is functionally different. It has been postulated that this subtype may utilize signal transduction systems other than adenylate cyclase (Livingston, M. et al., Inflamm. Res., 2004, 53, 171-178). Among all the adenosine receptors, the A2B adenosine receptor is a low affinity receptor that is thought to remain silent under physiological conditions and to be activated in consequence of increased extracellular adenosine levels (Ryzhov, S. et al. Neoplasia, 2008, 10, 987-995). Activation of A2B adenosine receptor can stimulate adenylate cyclase and phospholipase C through activation of Gs and Gq proteins, respectively. Coupling to mitogen activated protein kinases has also been described (Borrmann, T. et al., J. Med. Chem., 2009, 52(13), 3994-4006).

In the immune system, engagement of adenosine signaling can be a critical regulatory mechanism that protects tissues against excessive immune reactions. Adenosine can negatively modulate immune responses through many immune cell types, including T-cells, natural-killer cells, macrophages, dendritic cells, mast cells and myeloid-derived suppressor cells (Allard, B. et al. Current Opinion in Pharmacology, 2016, 29, 7-16).

In tumors, this pathway is hijacked by the tumor microenvironment and sabotages the antitumor capacity of the immune system, promoting cancer progression. In the tumor micro-environment, adenosine is mainly generated from extracellular ATP by two ectonucleotidases CD39 and CD73. Multiple cell types can generate adenosine by expressing CD39 and CD73. This is the case for tumor cells, T-effector cells, T-regulatory cells, tumor associated macrophages, myeloid derived suppressive cells (MDSCs), endothelial cells, cancer-associated fibroblast (CAFs) and mesenchymal stromal/stem cells (MSCs). Additionally, hypoxia and inflammation, conditions common to the tumor micro-environment induces expression of CD39 and CD73, leading to increased adenosine production. As a result, the adenosine level in solid tumors is higher compared to normal physiological conditions.

A2A are mostly expressed on lymphoid-derived cells, including T-effector cells, T regulatory cells and natural killer (NK) cells. Blocking A2A receptor can prevent downstream immunosuppressive signals that temporarily inactivate T cells. A2B receptors are mainly expressed on monocyte-derived cells including dendritic cells, tumor-associated macrophages, myeloid derived suppressive cells (MDSCs), and mesenchymal stromal/stem cells (MSCs). Blocking A2B receptor in preclinical models can suppress tumor growth, block metastasis, and increase the presentation of tumor antigens.

In terms of safety profile of ADORA2A/ADORA2B (A2A/A2B) blockage, the A2A and A2B receptor knockout (KO) mice are all viable, showing no growth abnormalities and are fertile (Allard, B. et al. Current Opinion in Pharmacology, 2016, 29, 7-16). A2A KO mice displayed increased levels of pro-inflammatory cytokines only upon challenge with lipopolysaccharides (LPS) and no evidence of inflammation at baseline (Antonioli, L. et al., Nature Reviews Cancer, 2013, 13, 842-857). A2B KO mice exhibited normal platelet, red blood, and white blood cell counts but increased inflammation at baseline such as TNF-alpha and IL-6) (Antonioli, L. et al., Nature Reviews Cancer, 2013, 13, 842-857). Further increase in production of TNF-alpha and IL-6 was detected following LPS treatment. A2B KO mice also exhibited increased vascular adhesion molecules that mediate inflammation as well leukocyte adhesion/rolling; enhanced mast-cell activation; increased sensitivity to IgE-mediated anaphylaxis and increased vascular leakage and neutrophil influx under hypoxia (Antonioli, L. et al., Nature Reviews Cancer, 2013, 13, 842-857).

SUMMARY

In a first aspect, the disclosure provides a method for treating a cancer in a human subject in need thereof, comprising administering to the human subject an effective amount of an inhibitor of human CD73 and an inhibitor of A2A adenosine receptor and/or A2B adenosine receptor.

In some embodiments, the (1) the inhibitor of human CD73 comprises:
  (a) an antibody comprising a variable heavy (VH) domain comprising VH complementarity determining region (CDR)1, VH CDR2, and VH CDR3, wherein:
    the VH CDR1 comprises the amino acid sequence GYTFTSYG (SEQ ID NO:1);
    the VH CDR2 comprises the amino acid sequence IYPGSGNT (SEQ ID NO:2); and
    the VH CDR3 comprises the amino acid sequence ARYDYLGSSYGFDY (SEQ ID NO:3); and
  comprising a variable light (VL) domain comprising VL CDR1, VL CDR2, and VL CDR3, wherein:
    the VL CDR1 comprises the amino acid sequence QDVSTA (SEQ ID NO:4);
    the VL CDR2 comprises the amino acid sequence SAS (SEQ ID NO:5); and
    the VL CDR3 comprises the amino acid sequence QQHYNTPYT (SEQ ID NO:6);
  (b) an antibody that binds to human CD73 at an epitope within amino acids 40-53 of SEQ ID NO:70;
  (c) an antibody that binds to human CD73 and competes for binding to human CD73 with an antibody that has a heavy chain comprising the amino acid sequence of SEQ ID NO:24 and a light chain comprising the amino acid sequence of SEQ ID NO:25; or
  (d) an antibody comprising a VH domain comprising VH CDR1, VH CDR2, and VH CDR3, wherein:
    the VH CDR1 comprises the amino acid sequence GFTFSSYD (SEQ ID NO:34);
    the VH CDR2 comprises the amino acid sequence MSYDGSNK (SEQ ID NO:35) or MSYEGSNK (SEQ ID NO:40); and
    the VH CDR3 comprises the amino acid sequence ATEIAAKGDY (SEQ ID NO:36); and an antibody comprising a VL domain comprising VL CDR1, VL CDR2, and VL CDR3, wherein:
    the VL CDR1 comprises the amino acid sequence QGISNY (SEQ ID NO:37);
    the VL CDR2 comprises the amino acid sequence AAS (SEQ ID NO:38); and
    the VL CDR3 comprises the amino acid sequence QQSYSTPH (SEQ ID NO:39);
  (e) an antibody that binds to human CD73 at an epitope within amino acids 386-399 and 470-489 of SEQ ID NO:70;
  (f) an antibody that binds to human CD73 and competes for binding to human CD73 with an antibody that has a heavy chain comprising the amino acid sequence of SEQ ID NO:30 and a light chain comprising the amino acid sequence of SEQ ID NO:31;
  (g) an antibody that binds to human CD73 and competes for binding to human CD73 with an antibody that has a heavy chain comprising the amino acid sequence of SEQ ID NO:33 and a light chain comprising the amino acid sequence of SEQ ID NO:31;
  (h) an antibody selected from the group consisting of 11E1, Medi9447, CPI-006, and BMS-986179; or
  (i) an inhibitor selected from the group consisting of CB-708 and AB680.

In some embodiments, the inhibitor of A2A adenosine receptor and/or A2B adenosine receptor (A2A/A2B) comprises a compound of:
  (a) Formula (I):

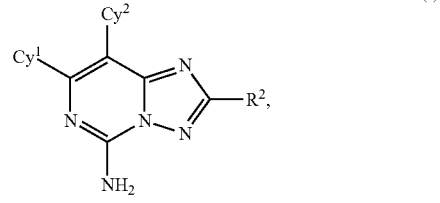

or a pharmaceutically acceptable salt thereof, wherein
$Cy^1$ is phenyl which is substituted by 1 or 2 substituents independently selected from halo and CN;
$Cy^2$ is 5-6 membered heteroaryl or 4-7 membered heterocycloalkyl, wherein the 5-6 membered heteroaryl or 4-7 membered heterocycloalkyl of $Cy^2$ are each optionally substituted with 1, 2, or 3 groups each independently selected from $C_{1-3}$ alkyl, $C_{1-3}$ alkoxy, $NH_2$, $NH(C_{1-3}$ alkyl) and $N(C_{1-3}$ alkyl)$_2$;
$R^2$ is selected from phenyl-$C_{1-3}$ alkyl-, $C_{3-7}$ cycloalkyl-$C_{1-3}$ alkyl-, (5-7 membered heteroaryl)-$C_{1-3}$ alkyl-, (4-7 membered heterocycloalkyl)-$C_{1-3}$ alkyl-, and $OR^{a2}$, wherein the phenyl-$C_{1-3}$ alkyl-, $C_{3-7}$ cycloalkyl-$C_{1-3}$ alkyl-, (5-7 membered heteroaryl)-$C_{1-3}$ alkyl-, and (4-7 membered heterocycloalkyl)-$C_{1-3}$ alkyl- of $R^2$ are each optionally substituted with 1, 2, or 3 independently selected $R^C$ substituents;

$R^{a2}$ is (5-7 membered heteroaryl)-$C_{1-3}$ alkyl- optionally substituted with 1 or 2 independently selected $R^C$ substituents;

each $R^C$ is independently selected from halo, $C_{1-6}$ alkyl, $C_6$ aryl, 5-7 membered heteroaryl, (4-7 membered heterocycloalkyl)-$C_{1-3}$ alkyl-, $OR^{a4}$, and $NR^{c4}R^{d4}$; and each $R^{a4}$, $R^{c4}$, and $R^{d4}$ are independently selected from H and $C_{1-6}$ alkyl;

(b) Formula (II):

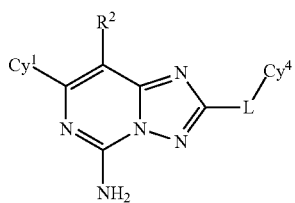

(II)

or a pharmaceutically acceptable salt thereof, wherein
$R^2$ is selected from H and CN;
$Cy^1$ is phenyl which is substituted by 1 or 2 substituents independently selected from halo and CN;
L is $C_{1-3}$ alkylene, wherein said alkylene is optionally substituted with 1, 2, or 3 independently selected $R^{8D}$ substituents;
$Cy^4$ is selected from phenyl, cyclohexyl, pyridyl, pyrrolidinonyl, and imidazolyl, wherein the phenyl, cyclohexyl, pyridyl, pyrrolidinonyl, and imidazolyl are each optionally substituted with 1, 2, or 3 substituents independently selected from $R^{8D}$ and $R^8$;
each $R^8$ is independently selected from halo, $C_{1-6}$ alkyl, $C_{1-6}$ haloalkyl, $C_{2-4}$ alkenyl, $C_{2-4}$ alkynyl, phenyl, $C_{3-7}$ cycloalkyl, 5-6 membered heteroaryl, 4-7 membered heterocycloalkyl, phenyl-$C_{1-3}$ alkyl, $C_{3-7}$ cycloalkyl-$C_{1-3}$ alkyl, (5-6 membered heteroaryl)-$C_{1-3}$ alkyl, and (4-7 membered heterocycloalkyl)-$C_{1-3}$ alkyl, wherein the $C_{1-6}$ alkyl, $C_{2-4}$ alkenyl, $C_{2-4}$ alkynyl, phenyl, $C_{3-7}$ cycloalkyl, 5-6 membered heteroaryl, 4-7 membered heterocycloalkyl, phenyl-$C_{1-3}$ alkyl, $C_{3-7}$ cycloalkyl-$C_{1-3}$ alkyl, (5-6 membered heteroaryl)-$C_{1-3}$ alkyl, and (4-7 membered heterocycloalkyl)-$C_{1-3}$ alkyl of R are each optionally substituted with 1, 2, or 3 independently selected $R^{8A}$ substituents;
each $R^{8A}$ is independently selected from halo, $C_{1-6}$ alkyl, 5-6 membered heteroaryl, 4-7 membered heterocycloalkyl, CN, $OR^{a81}$, and $NR^{c81}R^{d81}$, wherein the $C_{1-3}$ alkyl, 5-6 membered heteroaryl, and 4-7 membered heterocycloalkyl of $R^{8A}$ are each optionally substituted with 1, 2, or 3 independently selected $R^{8B}$ substituents;
each $R^{a81}$, $R^{c81}$, and $R^{d81}$ is independently selected from H, $C_{1-6}$ alkyl, and 4-7 membered heterocycloalkyl, wherein the $C_{1-6}$ alkyl and 4-7 membered heterocycloalkyl of $R^{a81}$, $R^{c81}$, and $R^{d81}$ are each optionally substituted with 1, 2, or 3 independently selected $R^{8B}$ substituents;
each $R^{8B}$ is independently selected from halo and $C_{1-3}$ alkyl; and
each $R^{8D}$ is independently selected from OH, CN, halo, $C_{1-6}$ alkyl, and $C_{1-6}$ haloalkyl;

(c) Formula (III):

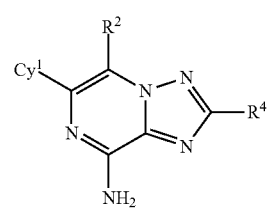

(III)

or a pharmaceutically acceptable salt thereof, wherein
$Cy^1$ is phenyl which is substituted by 1 or 2 substituents independently selected from halo and CN;
$R^2$ is selected from 5-6 membered heteroaryl and 4-7 membered heterocycloalkyl, wherein the 5-6 membered heteroaryl and 4-7 membered heterocycloalkyl of $R^2$ are each optionally substituted with 1, 2, or 3 independently selected $R^{2A}$ substituents;
each $R^{2A}$ is independently selected from D, halo, $C_{1-6}$ alkyl, and $C_{1-6}$ haloalkyl;
$R^4$ is selected from phenyl-$C_{1-3}$ alkyl-, $C_{3-7}$ cycloalkyl-$C_{1-3}$ alkyl-, (5-6 membered heteroaryl)-$C_{1-3}$ alkyl-, and (4-7 membered heterocycloalkyl)-$C_{1-3}$ alkyl wherein the phenyl-$C_{1-3}$ alkyl-, $C_{3-7}$ cycloalkyl-$C_{1-3}$ alkyl-, (5-6 membered heteroaryl)-$C_{1-3}$ alkyl-, and (4-7 membered heterocycloalkyl)-$C_{1-3}$ alkyl- of $R^4$ are each optionally substituted with 1, 2, or 3 independently selected $R^{4A}$ substituents;
each $R^{4A}$ is independently selected from halo, $C_{1-6}$ alkyl, $C_{1-6}$ haloalkyl, CN, $OR^{a41}$, and $NR^{c41}R^{d41}$; and
each $R^{a41}$, $R^{c41}$, and $R^{d41}$ is independently selected from H and $C_{1-6}$ alkyl; or (d) Formula (IV):

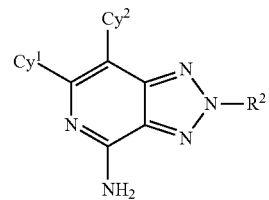

(IV)

or a pharmaceutically acceptable salt thereof, wherein
$Cy^1$ is phenyl which is substituted by 1 or 2 substituents independently selected from halo and CN;
$Cy^2$ is selected from 5-6 membered heteroaryl and 4-7 membered heterocycloalkyl, wherein the 5-6 membered heteroaryl and 4-7 membered heterocycloalkyl of $Cy^2$ are each optionally substituted with 1, 2, or 3 independently selected $R^6$ substituents;
each $R^6$ is independently selected from halo, $C_{1-6}$ alkyl, and $C_{1-6}$ haloalkyl;
$R^2$ is phenyl-$C_{1-3}$ alkyl- or (5-6 membered heteroaryl)-$C_{1-3}$ alkyl-, wherein the phenyl-$C_{1-3}$ alkyl- and (5-6 membered heteroaryl)-$C_{1-3}$ alkyl- of $R^2$ are each optionally substituted with 1, 2, or 3 independently selected $R^{2A}$ substituents; and
each $R^{2A}$ is independently selected from halo, $C_{1-6}$ alkyl, and $C_{1-6}$ haloalkyl.

or a pharmaceutically acceptable salt thereof.

In some embodiments, the inhibitor of human CD73 comprises:

(a) an antibody comprising a variable heavy (VH) domain comprising VH complementarity determining region (CDR)1, VH CDR2, and VH CDR3, wherein:
the VH CDR1 comprises the amino acid sequence GYTFTSYG (SEQ ID NO:1);
the VH CDR2 comprises the amino acid sequence IYPGSGNT (SEQ ID NO:2); and
the VH CDR3 comprises the amino acid sequence ARYDYLGSSYGFDY (SEQ ID NO:3); and
comprising a variable light (VL) domain comprising VL CDR1, VL CDR2, and VL CDR3, wherein:
the VL CDR1 comprises the amino acid sequence QDVSTA (SEQ ID NO:4);
the VL CDR2 comprises the amino acid sequence SAS (SEQ ID NO:5); and
the VL CDR3 comprises the amino acid sequence QQHYNTPYT (SEQ ID NO:6);
(b) an antibody that binds to human CD73 at an epitope within amino acids 40-53 of SEQ ID NO:70;
(c) an antibody that binds to human CD73 and competes for binding to human CD73 with an antibody that has a heavy chain comprising the amino acid sequence of SEQ ID NO:24 and a light chain comprising the amino acid sequence of SEQ ID NO:25; or
(d) an antibody comprising a VH domain comprising VH CDR1, VH CDR2, and VH CDR3, wherein:
the VH CDR1 comprises the amino acid sequence GFTFSSYD (SEQ ID NO:34);
the VH CDR2 comprises the amino acid sequence MSYDGSNK (SEQ ID NO:35) or MSYEGSNK (SEQ ID NO:40); and
the VH CDR3 comprises the amino acid sequence ATEIAAKGDY (SEQ ID NO:36); and
an antibody comprising a VL domain comprising VL CDR1, VL CDR2, and VL CDR3, wherein:
the VL CDR1 comprises the amino acid sequence QGISNY (SEQ ID NO:37);
the VL CDR2 comprises the amino acid sequence AAS (SEQ ID NO:38); and
the VL CDR3 comprises the amino acid sequence QQSYSTPH (SEQ ID NO:39);
(e) an antibody that binds to human CD73 at an epitope within amino acids 386-399 and 470-489 of SEQ ID NO:70;
(f) an antibody that binds to human CD73 and competes for binding to human CD73 with an antibody that has a heavy chain comprising the amino acid sequence of SEQ ID NO:30 and a light chain comprising the amino acid sequence of SEQ ID NO:31;
(g) an antibody that binds to human CD73 and competes for binding to human CD73 with an antibody that has a heavy chain comprising the amino acid sequence of SEQ ID NO:33 and a light chain comprising the amino acid sequence of SEQ ID NO:31;
(h) an antibody selected from the group consisting of 11E1, Medi9447, CPI-006, and BMS-986179; or
(i) an inhibitor selected from the group consisting of CB-708 and AB680; and
the inhibitor of A2A adenosine receptor and/or A2B adenosine receptor (A2A/A2B) comprises a compound of:

(a) Formula (I):

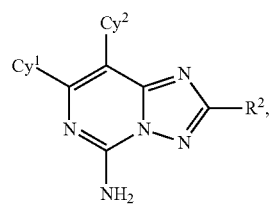

or a pharmaceutically acceptable salt thereof, wherein
$Cy^1$ is phenyl which is substituted by 1 or 2 substituents independently selected from halo and CN;
$Cy^2$ is 5-6 membered heteroaryl or 4-7 membered heterocycloalkyl, wherein the 5-6 membered heteroaryl or 4-7 membered heterocycloalkyl of $Cy^2$ are each optionally substituted with 1, 2, or 3 groups each independently selected from $C_{1-3}$ alkyl, $C_{1-3}$ alkoxy, $NH_2$, $NH(C_{1-3}$ alkyl) and $N(C_{1-3}$ alkyl)$_2$;
$R^2$ is selected from phenyl-$C_{1-3}$ alkyl-, $C_{3-7}$ cycloalkyl-$C_{1-3}$ alkyl-, (5-7 membered heteroaryl)-$C_{1-3}$ alkyl-, (4-7 membered heterocycloalkyl)-$C_{1-3}$ alkyl-, and $OR^{a2}$, wherein the phenyl-$C_{1-3}$ alkyl-, $C_{3-7}$ cycloalkyl-$C_{1-3}$ alkyl-, (5-7 membered heteroaryl)-$C_{1-3}$ alkyl-, and (4-7 membered heterocycloalkyl)-$C_{1-3}$ alkyl- of $R^2$ are each optionally substituted with 1, 2, or 3 independently selected $R^C$ substituents;
$R^{a2}$ is (5-7 membered heteroaryl)-$C_{1-3}$ alkyl- optionally substituted with 1 or 2 independently selected $R^C$ substituents;
each $R^C$ is independently selected from halo, $C_{1-6}$ alkyl, $C_6$ aryl, 5-7 membered heteroaryl, (4-7 membered heterocycloalkyl)-$C_{1-3}$ alkyl-, $OR^{a4}$, and $NR^{c4}R^{d4}$; and
each $R^{a4}$, $R^{c4}$, and $R^{d4}$ are independently selected from H and $C_{1-6}$ alkyl;
(b) Formula (II):

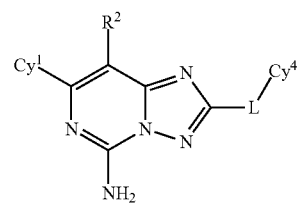

or a pharmaceutically acceptable salt thereof, wherein
$R^2$ is selected from H and CN;
$Cy^1$ is phenyl which is substituted by 1 or 2 substituents independently selected from halo and CN;
L is $C_{1-3}$ alkylene, wherein said alkylene is optionally substituted with 1, 2, or 3 independently selected $R^{8D}$ substituents;
$Cy^4$ is selected from phenyl, cyclohexyl, pyridyl, pyrrolidinonyl, and imidazolyl, wherein the phenyl, cyclohexyl, pyridyl, pyrrolidinonyl, and imidazolyl are each optionally substituted with 1, 2, or 3 substituents independently selected from $R^{8D}$ and $R^8$;
each $R^8$ is independently selected from halo, $C_{1-6}$ alkyl, $C_{1-6}$ haloalkyl, $C_{2-4}$ alkenyl, $C_{2-4}$ alkynyl, phenyl, $C_{3-7}$ cycloalkyl, 5-6 membered heteroaryl, 4-7 membered heterocycloalkyl, phenyl-$C_{1-3}$ alkyl, $C_{3-7}$ cycloalkyl-$C_{1-3}$ alkyl, (5-6 membered heteroaryl)-$C_{1-3}$ alkyl, and (4-7 membered heterocycloalkyl)-$C_{1-3}$ alkyl, wherein the $C_{1-6}$ alkyl, $C_{2-4}$ alkenyl, $C_{2-4}$ alkynyl, phenyl, $C_{3-7}$ cycloalkyl, 5-6 membered heteroaryl, 4-7 membered heterocycloalkyl, phenyl-$C_{1-3}$ alkyl, $C_{3-7}$ cycloalkyl-$C_{1-3}$ alkyl, (5-6 membered heteroaryl)-$C_{1-3}$ alkyl, and (4-7 membered heterocycloalkyl)-$C_{1-3}$ alkyl of $R^8$ are each optionally substituted with 1, 2, or 3 independently selected $R^{8A}$ substituents;

each $R^{8A}$ is independently selected from halo, $C_{1-6}$ alkyl, 5-6 membered heteroaryl, 4-7 membered heterocycloalkyl, CN, $OR^{a81}$, and $NR^{c81}R^{d81}$, wherein the $C_{1-3}$ alkyl, 5-6 membered heteroaryl, and 4-7 membered heterocycloalkyl of $R^{8A}$ are each optionally substituted with 1, 2, or 3 independently selected $R^{8B}$ substituents;

each $R^{a81}$, $R^{c81}$, and $R^{d81}$ is independently selected from H, $C_{1-6}$ alkyl, and 4-7 membered heterocycloalkyl, wherein the $C_{1-6}$ alkyl and 4-7 membered heterocycloalkyl of $R^{a81}$, $R^{c81}$, and $R^{d81}$ are each optionally substituted with 1, 2, or 3 independently selected $R^{8B}$ substituents;

each $R^{8B}$ is independently selected from halo and $C_{1-3}$ alkyl; and each $R^{8D}$ is independently selected from OH, CN, halo, $C_{1-6}$ alkyl, and $C_{1-6}$ haloalkyl;

(c) Formula (III):

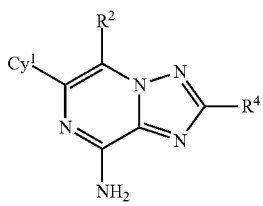

(III)

or a pharmaceutically acceptable salt thereof, wherein
$Cy^1$ is phenyl which is substituted by 1 or 2 substituents independently selected from halo and CN;
$R^2$ is selected from 5-6 membered heteroaryl and 4-7 membered heterocycloalkyl, wherein the 5-6 membered heteroaryl and 4-7 membered heterocycloalkyl of $R^2$ are each optionally substituted with 1, 2, or 3 independently selected $R^{2A}$ substituents;
each $R^{2A}$ is independently selected from D, halo, $C_{1-6}$ alkyl, and $C_{1-6}$ haloalkyl; $R^4$ is selected from phenyl-$C_{1-3}$ alkyl-, $C_{3-7}$ cycloalkyl-$C_{1-3}$ alkyl-, (5-6 membered heteroaryl)-$C_{1-3}$ alkyl-, and (4-7 membered heterocycloalkyl)-$C_{1-3}$ alkyl wherein the phenyl-$C_{1-3}$ alkyl-, $C_{3-7}$ cycloalkyl-$C_{1-3}$ alkyl-, (5-6 membered heteroaryl)-$C_{1-3}$ alkyl-, and (4-7 membered heterocycloalkyl)-$C_{1-3}$ alkyl- of $R^4$ are each optionally substituted with 1, 2, or 3 independently selected $R^{4A}$ substituents;
each $R^{4A}$ is independently selected from halo, $C_{1-6}$ alkyl, $C_{1-6}$ haloalkyl, CN, $OR^{a41}$, and $NR^{c41}R^{d41}$; and
each $R^{a41}$, $R^{c41}$, and $R^{d41}$ is independently selected from H and $C_{1-6}$ alkyl; or (d) Formula (IV):

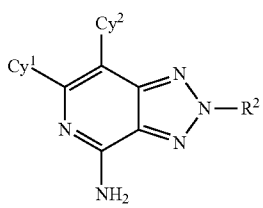

(IV)

or a pharmaceutically acceptable salt thereof, wherein
$Cy^1$ is phenyl which is substituted by 1 or 2 substituents independently selected from halo and CN;
$Cy^2$ is selected from 5-6 membered heteroaryl and 4-7 membered heterocycloalkyl, wherein the 5-6 membered heteroaryl and 4-7 membered heterocycloalkyl of $Cy^2$ are each optionally substituted with 1, 2, or 3 independently selected $R^6$ substituents;
each $R^6$ is independently selected from halo, $C_{1-6}$ alkyl, and $C_{1-6}$ haloalkyl;
$R^2$ is phenyl-$C_{1-3}$ alkyl- or (5-6 membered heteroaryl)-$C_{1-3}$ alkyl-, wherein the phenyl-$C_{1-3}$ alkyl- and (5-6 membered heteroaryl)-$C_{1-3}$ alkyl- of $R^2$ are each optionally substituted with 1, 2, or 3 independently selected $R^{2A}$ substituents; and
each $R^{2A}$ is independently selected from halo, $C_{1-6}$ alkyl, and $C_{1-6}$ haloalkyl.
or a pharmaceutically acceptable salt thereof.

In some embodiments, the inhibitor of A2A/A2B is a compound of Formula (I):

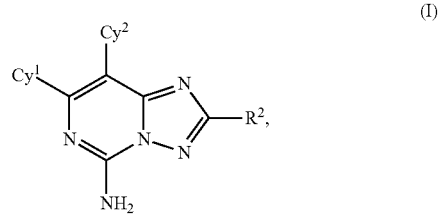

(I)

or a pharmaceutically acceptable salt thereof, wherein
$Cy^1$ is phenyl which is substituted by 1 or 2 substituents independently selected from halo and CN;
$Cy^2$ is 5-6 membered heteroaryl or 4-7 membered heterocycloalkyl, wherein the 5-6 membered heteroaryl or 4-7 membered heterocycloalkyl of $Cy^2$ are each optionally substituted with 1, 2, or 3 groups each independently selected from $C_{1-3}$ alkyl, $C_{1-3}$ alkoxy, $NH_2$, $NH(C_{1-3}$ alkyl) and $N(C_{1-3}$ alkyl$)_2$;
$R^2$ is selected from phenyl-$C_{1-3}$ alkyl-, $C_{3-7}$ cycloalkyl-$C_{1-3}$ alkyl-, (5-7 membered heteroaryl)-$C_{1-3}$ alkyl-, (4-7 membered heterocycloalkyl)-$C_{1-3}$ alkyl-, and $OR^{a2}$, wherein the phenyl-$C_{1-3}$ alkyl-, $C_{3-7}$ cycloalkyl-$C_{1-3}$ alkyl-, (5-7 membered heteroaryl)-$C_{1-3}$ alkyl-, and (4-7 membered heterocycloalkyl)-$C_{1-3}$ alkyl- of $R^2$ are each optionally substituted with 1, 2, or 3 independently selected $R^C$ substituents;
$R^{a2}$ is (5-7 membered heteroaryl)-$C_{1-3}$ alkyl- optionally substituted with 1 or 2 independently selected $R^C$ substituents;
each $R^C$ is independently selected from halo, $C_{1-6}$ alkyl, $C_6$ aryl, 5-7 membered heteroaryl, (4-7 membered heterocycloalkyl)-$C_{1-3}$ alkyl-, $OR^{a4}$, and $NR^{c4}R^{d4}$; and
each $R^{a4}$, $R^{c4}$, and $R^{d4}$ are independently selected from H and $C_{1-6}$ alkyl. In some instances, the inhibitor of A2A/A2B is selected from: 3-(5-Amino-2-(pyridin-2-ylmethyl)-8-(pyrimidin-4-yl)-[1,2,4]triazolo[1,5-c]pyrimidin-7-yl)benzonitrile, or a pharmaceutically acceptable salt thereof, 3-(5-Amino-2-((2,6-difluorophenyl)(hydroxy)methyl)-8-(pyrimidin-4-yl)-[1,2,4]triazolo[1,5-c]pyrimidin-7-yl)benzonitrile, or a pharmaceutically acceptable salt thereof, 3-(5-Amino-2-((5-(pyridin-2-yl)-2H-tetrazol-2-yl)methyl)-8-(pyrimidin-4-yl)-[1,2,4]triazolo[1,5-c]pyrimidin-7-yl) benzonitrile, or a pharmaceutically acceptable salt thereof, 3-(5-Amino-2-((5-(pyridin-2-yl)-1H-tetrazol-1-yl)methyl)-8-(pyrimidin-4-yl)-[1,2,4]triazolo[1,5-c]pyrimidin-7-yl)benzonitrile, or a pharmaceutically acceptable salt thereof, 3-(5-Amino-2-((3-methylpyridin-2-yl)methoxy)-8-(pyrimidin-4-yl)-[1,2,4]triazolo[1,5-c]pyrimidin-7-yl)benzonitrile, or a pharmaceutically acceptable salt thereof, and 3-(2-((5-(1H-Pyrazol-1-yl)-1H-tetrazol-1-yl)methyl)-5-amino-8-(pyrimidin-4-yl)-[1,2,4]triazolo[1,5-c]pyrimidin-7-yl)benzonitrile, or a pharmaceutically acceptable salt thereof.

In some embodiments, the inhibitor of A2A/A2B is a compound of Formula (II):

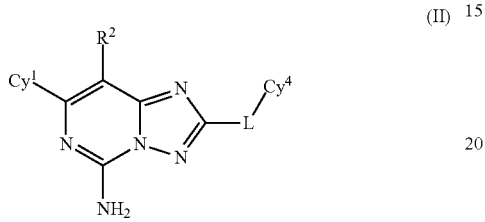

(II)

or a pharmaceutically acceptable salt thereof, wherein
$R^2$ is selected from H and CN;
$Cy^1$ is phenyl which is substituted by 1 or 2 substituents independently selected from halo and CN;
L is $C_{1-3}$ alkylene, wherein said alkylene is optionally substituted with 1, 2, or 3 independently selected $R^{8D}$ substituents;
$Cy^4$ is selected from phenyl, cyclohexyl, pyridyl, pyrrolidinonyl, and imidazolyl, wherein the phenyl, cyclohexyl, pyridyl, pyrrolidinonyl, and imidazolyl are each optionally substituted with 1, 2, or 3 substituents independently selected from $R^{8D}$ and $R^8$;
each $R^8$ is independently selected from halo, $C_{1-6}$ alkyl, $C_{1-6}$ haloalkyl, $C_{2-4}$ alkenyl, $C_{2-4}$ alkynyl, phenyl, $C_{3-7}$ cycloalkyl, 5-6 membered heteroaryl, 4-7 membered heterocycloalkyl, phenyl-$C_{1-3}$ alkyl, $C_{3-7}$ cycloalkyl-$C_{1-3}$ alkyl, (5-6 membered heteroaryl)-$C_{1-3}$ alkyl, and (4-7 membered heterocycloalkyl)-$C_{1-3}$ alkyl, wherein the $C_{1-6}$ alkyl, $C_{2-4}$ alkenyl, $C_{2-4}$ alkynyl, phenyl, $C_{3-7}$ cycloalkyl, 5-6 membered heteroaryl, 4-7 membered heterocycloalkyl, phenyl-$C_{1-3}$ alkyl, $C_{3-7}$ cycloalkyl-$C_{1-3}$ alkyl, (5-6 membered heteroaryl)-$C_{1-3}$ alkyl, and (4-7 membered heterocycloalkyl)-$C_{1-3}$ alkyl of $R^8$ are each optionally substituted with 1, 2, or 3 independently selected $R^{8A}$ substituents;
each $R^{8A}$ is independently selected from halo, $C_{1-6}$ alkyl, 5-6 membered heteroaryl, 4-7 membered heterocycloalkyl, CN, $OR^{a81}$, and $NR^{c81}R^{d81}$, wherein the $C_{1-3}$ alkyl, 5-6 membered heteroaryl, and 4-7 membered heterocycloalkyl of $R^{8A}$ are each optionally substituted with 1, 2, or 3 independently selected $R^{8B}$ substituents;
each $R^{a81}$, $R^{c81}$, and $R^{d81}$ is independently selected from H, $C_{1-6}$ alkyl, and 4-7 membered heterocycloalkyl, wherein the $C_{1-6}$ alkyl and 4-7 membered heterocycloalkyl of $R^{a81}$, $R^{c81}$, and $R^{d81}$ are each optionally substituted with 1, 2, or 3 independently selected $R^{8B}$ substituents; each $R^{8B}$ is independently selected from halo and $C_{1-3}$ alkyl; and
each $R^{8D}$ is independently selected from OH, CN, halo, $C_{1-6}$ alkyl, and $C_{1-6}$ haloalkyl. In some instances, the inhibitor of A2A/A2B is selected from: 3-(5-Amino-2-(hydroxy(phenyl)methyl)-[1,2,4]triazolo[1,5-c]pyrimidin-7-yl)benzonitrile, or a pharmaceutically acceptable salt thereof, 3-(5-Amino-2-((2,6-difluorophenyl)(hydroxy)methyl)-[1,2,4]triazolo[1,5-c]pyrimidin-7-yl)-2-fluorobenzonitrile, or a pharmaceutically acceptable salt thereof, 5-Amino-7-(3-cyano-2-fluorophenyl)-2-((2,6-difluorophenyl)(hydroxy)methyl)-[1,2,4]triazolo[1,5-c]pyrimidine-8-carbonitrile, or a pharmaceutically acceptable salt thereof, and 3-(5-Amino-2-((2-fluoro-6-(((1-methyl-2-oxopyrrolidin-3-yl)amino)methyl)phenyl)(hydroxy)methyl)-[1,2,4]triazolo[1,5-c]pyrimidin-7-yl)-2-fluorobenzonitrile, or a pharmaceutically acceptable salt thereof.

In some embodiments, the inhibitor of A2A/A2B is a compound of Formula (III):

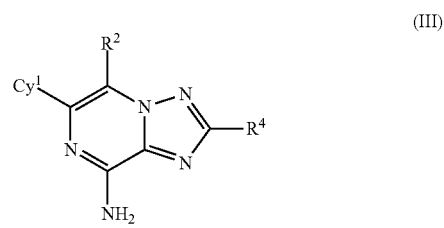

(III)

or a pharmaceutically acceptable salt thereof, wherein
$Cy^1$ is phenyl which is substituted by 1 or 2 substituents independently selected from halo and CN;
$R^2$ is selected from 5-6 membered heteroaryl and 4-7 membered heterocycloalkyl, wherein the 5-6 membered heteroaryl and 4-7 membered heterocycloalkyl of $R^2$ are each optionally substituted with 1, 2, or 3 independently selected $R^{2A}$ substituents;
each $R^{2A}$ is independently selected from D, halo, $C_{1-6}$ alkyl, and $C_{1-6}$ haloalkyl;
$R^4$ is selected from phenyl-$C_{1-3}$ alkyl-, $C_{3-7}$ cycloalkyl-$C_{1-3}$ alkyl-, (5-6 membered heteroaryl)-$C_{1-3}$ alkyl-, and (4-7 membered heterocycloalkyl)-$C_{1-3}$ alkyl wherein the phenyl-$C_{1-3}$ alkyl-, $C_{3-7}$ cycloalkyl-$C_{1-3}$ alkyl-, (5-6 membered heteroaryl)-$C_{1-3}$ alkyl-, and (4-7 membered heterocycloalkyl)-$C_{1-3}$ alkyl- of $R^4$ are each optionally substituted with 1, 2, or 3 independently selected $R^{4A}$ substituents;
each $R^{4A}$ is independently selected from halo, $C_{1-6}$ alkyl, $C_{1-6}$ haloalkyl, CN, $OR^{a41}$, and $NR^{c41}R^{d41}$; and
each $R^{a41}$, $R^{c41}$, and $R^{d41}$ is independently selected from H and $C_{1-6}$ alkyl. In some instances, the inhibitor of A2A/A2B is selected from: 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile; 3-(8-Amino-2-((2,6-difluorophenyl)(hydroxy)methyl)-5-(pyrimidin-4-yl)-[1,2,4]triazolo[1,5-a]pyrazin-6-yl)benzonitrile, or a pharmaceutically acceptable salt thereof, 3-(8-amino-2-(amino(2,6-difluorophenyl)methyl)-5-(4-methyloxazol-5-yl)-[1,2,4]triazolo[1,5-a]pyrazin-6-yl)benzonitrile, or a pharmaceutically acceptable salt thereof, and 3-(8-amino-2-((2,6-difluorophenyl)(hydroxy)methyl)-5-(2,6-dimethylpyridin-4-yl)-[1,2,4]triazolo[1,5-a]pyrazin-6-yl)benzonitrile, or a pharmaceutically acceptable salt thereof.

In some embodiments, the inhibitor of A2A/A2B is a compound of Formula (IV):

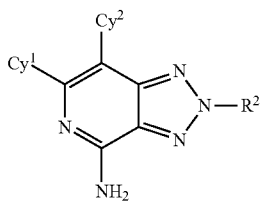

(IV)

or a pharmaceutically acceptable salt thereof, wherein
Cy$^1$ is phenyl which is substituted by 1 or 2 substituents independently selected from halo and CN;
Cy$^2$ is selected from 5-6 membered heteroaryl and 4-7 membered heterocycloalkyl, wherein the 5-6 membered heteroaryl and 4-7 membered heterocycloalkyl of Cy$^2$ are each optionally substituted with 1, 2, or 3 independently selected R$^6$ substituents;
each R$^6$ is independently selected from halo, C$_{1-6}$ alkyl, and C$_{1-6}$ haloalkyl;
R$^2$ is phenyl-C$_{1-3}$ alkyl- or (5-6 membered heteroaryl)-C$_{1-3}$ alkyl-, wherein the phenyl-C$_{1-3}$ alkyl- and (5-6 membered heteroaryl)-C$_{1-3}$ alkyl- of R$^2$ are each optionally substituted with 1, 2, or 3 independently selected R$^{2A}$ substituents; and
each R$^{2A}$ is independently selected from halo, C$_{1-6}$ alkyl, and C$_{1-6}$ haloalkyl.
or a pharmaceutically acceptable salt thereof. In some instances, the inhibitor of A2A/A2B is selected from: 3-(4-amino-2-(pyridin-2-ylmethyl)-7-(pyrimidin-4-yl)-2H-[1,2,3]triazolo[4,5-c]pyridin-6-yl)benzonitrile, or a pharmaceutically acceptable salt thereof, 3-(4-amino-2-((3-fluoropyridin-2-yl)methyl)-7-(pyrimidin-4-yl)-2H-[1,2,3]triazolo[4,5-c]pyridin-6-yl)benzonitrile, or a pharmaceutically acceptable salt thereof, 3-(4-amino-2-((3-fluoropyridin-2-yl)methyl)-7-(pyridin-4-yl)-2H-[1,2,3]triazolo[4,5-c]pyridin-6-yl)benzonitrile, or a pharmaceutically acceptable salt thereof, and 3-(4-amino-7-(1-methyl-1H-pyrazol-5-yl)-2-(pyridin-2-ylmethyl)-2H-[1,2,3]triazolo[4,5-c]pyridin-6-yl)-2-fluorobenzonitrile, or a pharmaceutically acceptable salt thereof.

In some embodiments, the inhibitor of A2A/A2B is 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile, or a pharmaceutically acceptable salt thereof.

In some embodiments, the inhibitor of A2A/A2B is 3-(5-Amino-2-((5-(pyridin-2-yl)-2H-tetrazol-2-yl)methyl)-8-(pyrimidin-4-yl)-[1,2,4]triazolo[1,5-c]pyrimidin-7-yl)benzonitrile, or a pharmaceutically acceptable salt thereof.

In some embodiments, the inhibitor of A2A/A2B is 3-(5-Amino-2-((5-(pyridin-2-yl)-1H-tetrazol-1-yl)methyl)-8-(pyrimidin-4-yl)-[1,2,4]triazolo[1,5-c]pyrimidin-7-yl)benzonitrile, or a pharmaceutically acceptable salt thereof.

In some embodiments, the inhibitor of human CD73 comprises an antibody comprising:
 a VH domain comprising VH CDR1, VH CDR2, and VH CDR3, wherein:
  the VH CDR1 comprises the amino acid sequence GYTFTSYG (SEQ ID NO:1);
  the VH CDR2 comprises the amino acid sequence IYPGSGNT (SEQ ID NO:2); and
  the VH CDR3 comprises the amino acid sequence ARYDYLGSSYGFDY (SEQ ID NO:3); and
 a VL domain comprising VL CDR1, VL CDR2, and VL CDR3, wherein:
  the VL CDR1 comprises the amino acid sequence QDVSTA (SEQ ID NO:4);
  the VL CDR2 comprises the amino acid sequence SAS (SEQ ID NO:5); and
  the VL CDR3 comprises the amino acid sequence QQHYNTPYT (SEQ ID NO:6).

In some embodiments, the inhibitor of human CD73 comprises an antibody that binds to human CD73 at an epitope within amino acids 40-53 of SEQ ID NO:70.

In some embodiments, the inhibitor of human CD73 comprises an antibody that binds to human CD73 and competes for binding to human CD73 with an antibody that has a heavy chain comprising the amino acid sequence of SEQ ID NO:24 and a light chain comprising the amino acid sequence of SEQ ID NO:25.

In some embodiments, the inhibitor of human CD73 comprises an antibody comprising:
 a VH domain comprising VH CDR1, VH CDR2, and VH CDR3, wherein:
  the VH CDR1 comprises the amino acid sequence GFTFSSYD (SEQ ID NO:34);
  the VH CDR2 comprises the amino acid sequence MSYDGSNK (SEQ ID NO:35) or MSYEGSNK (SEQ ID NO:40); and
  the VH CDR3 comprises the amino acid sequence ATEIAAKGDY (SEQ ID NO:36); and
 a VL domain comprising VL CDR1, VL CDR2, and VL CDR3, wherein:
  the VL CDR1 comprises the amino acid sequence QGISNY (SEQ ID NO:37);
  the VL CDR2 comprises the amino acid sequence AAS (SEQ ID NO:38); and
  the VL CDR3 comprises the amino acid sequence QQSYSTPH (SEQ ID NO:39).

In some embodiments, the inhibitor of human CD73 comprises an antibody that binds to human CD73 at an epitope within amino acids 386-399 and 470-489 of SEQ ID NO:70.

In some embodiments, the inhibitor of human CD73 comprises an antibody that binds to human CD73 and competes for binding to human CD73 with an antibody that has a heavy chain comprising the amino acid sequence of SEQ ID NO:30 and a light chain comprising the amino acid sequence of SEQ ID NO:31.

In some embodiments, the inhibitor of human CD73 comprises an antibody that binds to human CD73 and competes for binding to human CD73 with an antibody that has a heavy chain comprising the amino acid sequence of SEQ ID NO:33 and a light chain comprising the amino acid sequence of SEQ ID NO:31.

In some embodiments, the inhibitor of human CD73 comprises an antibody selected from the group consisting of 11E1, Medi9447, CPI-006, and BMS-986179.

In some embodiments, the inhibitor of human CD73 is selected from the group consisting of CB-708 and AB680.

In some embodiments, the inhibitor of human CD73 comprises an antibody comprising a VH domain comprising the amino acid sequence set forth in SEQ ID NO:22 and a VL domain comprising the amino acid sequence set forth in SEQ ID NO:23, and the inhibitor of A2A/A2B comprises 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile.

In some embodiments, the inhibitor of human CD73 comprises an antibody comprising a heavy chain and a light chain, and wherein the heavy chain comprises the amino acid sequence set forth in SEQ ID NO:24 and the light chain comprises the amino acid sequence set forth in SEQ ID NO:25, and the inhibitor of A2A/A2B comprises 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile.

In some embodiments, the inhibitor of human CD73 comprises an antibody comprising a VH domain comprising the amino acid sequence set forth in SEQ ID NO:62 and a VL domain comprising the amino acid sequence set forth in SEQ ID NO:61, and the inhibitor of A2A/A2B comprises 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile.

In some embodiments, the inhibitor of human CD73 comprises an antibody comprising a heavy chain and a light chain, and wherein the heavy chain comprises the amino acid sequence set forth in SEQ ID NO:30 and the light chain comprises the amino acid sequence set forth in SEQ ID NO:31, and the inhibitor of A2A/A2B comprises 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile.

In some embodiments, the inhibitor of human CD73 comprises an antibody comprising a VH domain comprising the amino acid sequence set forth in SEQ ID NO:63 and a VL domain comprising the amino acid sequence set forth in SEQ ID NO:61, and the inhibitor of A2A/A2B comprises 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile.

In some embodiments, the inhibitor of human CD73 comprises an antibody comprising a heavy chain and a light chain, and wherein the heavy chain comprises the amino acid sequence set forth in SEQ ID NO:33 and the light chain comprises the amino acid sequence set forth in SEQ ID NO:31, and the inhibitor of A2A/A2B comprises 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile.

In a second aspect, the disclosure provides a method for treating a cancer in a human subject in need thereof, comprising administering to the human subject an effective amount of an antibody that binds to human CD73 and an inhibitor of A2A adenosine receptor and/or A2B adenosine receptor, wherein the antibody:
(a) comprises a VH domain comprising VH CDR1, VH CDR2, and VH CDR3, wherein:
the VH CDR1 comprises the amino acid sequence GYTFTSYG (SEQ ID NO:1);
the VH CDR2 comprises the amino acid sequence IYPGSGNT (SEQ ID NO:2); and
the VH CDR3 comprises the amino acid sequence ARYDYLGSSYGFDY (SEQ ID NO:3); and
comprises a VL domain comprising VL CDR1, VL CDR2, and VL CDR3, wherein:
the VL CDR1 comprises the amino acid sequence QDVSTA (SEQ ID NO:4);
the VL CDR2 comprises the amino acid sequence SAS (SEQ ID NO:5); and
the VL CDR3 comprises the amino acid sequence QQHYNTPYT (SEQ ID NO:6);
(b) binds to human CD73 at an epitope within amino acids 40-53 of SEQ ID NO:70;
(c) binds to human CD73 and competes for binding to human CD73 with an antibody that has a heavy chain comprising the amino acid sequence of SEQ ID NO:24 and a light chain comprising the amino acid sequence of SEQ ID NO:25;
(d) comprises a VH domain comprising VH CDR1, VH CDR2, and VH CDR3, wherein:
the VH CDR1 comprises the amino acid sequence GFTFSSYD (SEQ ID NO:34);
the VH CDR2 comprises the amino acid sequence MSYDGSNK (SEQ ID NO:35) or MSYEGSNK (SEQ ID NO:40); and
the VH CDR3 comprises the amino acid sequence ATEIAAKGDY (SEQ ID NO:36); and
wherein the antibody comprises a VL domain comprising VL CDR1, VL CDR2, and VL CDR3, wherein:
the VL CDR1 comprises the amino acid sequence QGISNY (SEQ ID NO:37);
the VL CDR2 comprises the amino acid sequence AAS (SEQ ID NO:38); and
the VL CDR3 comprises the amino acid sequence QQSYSTPH (SEQ ID NO:39);
(e) binds to human CD73 at an epitope within amino acids 386-399 and 470-489 of SEQ ID NO:70;
(f) binds to human CD73 and competes for binding to human CD73 with an antibody that has a heavy chain comprising the amino acid sequence of SEQ ID NO:30 and a light chain comprising the amino acid sequence of SEQ ID NO:31; or
(g) binds to human CD73 and competes for binding to human CD73 with an antibody that has a heavy chain comprising the amino acid sequence of SEQ ID NO:33 and a light chain comprising the amino acid sequence of SEQ ID NO:31.

In some embodiments, the antibody comprises a VH domain comprising VH CDR1, VH CDR2, and VH CDR3, wherein:
the VH CDR1 comprises the amino acid sequence GYTFTSYG (SEQ ID NO:1);
the VH CDR2 comprises the amino acid sequence IYPGSGNT (SEQ ID NO:2); and
the VH CDR3 comprises the amino acid sequence ARYDYLGSSYGFDY (SEQ ID NO:3); and
wherein the antibody comprises a VL domain comprising VL CDR1, VL CDR2, and VL CDR3, wherein:
the VL CDR1 comprises the amino acid sequence QDVSTA (SEQ ID NO:4);
the VL CDR2 comprises the amino acid sequence SAS (SEQ ID NO:5); and
the VL CDR3 comprises the amino acid sequence QQHYNTPYT (SEQ ID NO:6). In some instances, the VH domain comprises the amino acid sequence set forth in SEQ ID NO:22. In some instances, the antibody comprises a heavy chain and wherein the heavy chain comprises the amino acid sequence set forth in SEQ ID NO:24. In some instances, the VL domain comprises the amino acid sequence set forth in SEQ ID NO:23. In some instances, the antibody comprises a light chain and wherein the light chain comprises the amino acid sequence set forth in SEQ ID NO:25. In some instances, the VH domain is at least 80% identical to the amino acid sequence set forth in SEQ ID NO:22 and the VL domain is at least 80% identical to the amino acid sequence set forth in SEQ ID NO:23. In some instances, the VH domain comprises the amino acid sequence set forth in SEQ ID NO:22 and the VL domain comprises the amino acid sequence set forth in SEQ ID NO:23. In some instances, the antibody comprises a heavy chain and a light chain, and wherein the heavy chain comprises the amino acid sequence set forth in SEQ ID NO:24 and the light chain comprises the amino acid sequence set forth in SEQ ID NO:25.

In some embodiments, the antibody binds to human CD73 at an epitope within amino acids 40-53 of SEQ ID NO:70.

In some embodiments, the antibody binds to human CD73 and competes for binding to human CD73 with an antibody that has a heavy chain comprising the amino acid sequence of SEQ ID NO:24 and a light chain comprising the amino acid sequence of SEQ ID NO:25.

In some embodiments, the antibody comprises a VH domain comprising VH CDR1, VH CDR2, and VH CDR3, wherein:
  the VH CDR1 comprises the amino acid sequence GFTFSSYD (SEQ ID NO:34);
  the VH CDR2 comprises the amino acid sequence MSYDGSNK (SEQ ID NO:35) or MSYEGSNK (SEQ ID NO:40); and
  the VH CDR3 comprises the amino acid sequence ATEIAAKGDY (SEQ ID NO:36); and
  wherein the antibody comprises a VL domain comprising VL CDR1, VL CDR2, and VL CDR3, wherein:
  the VL CDR1 comprises the amino acid sequence QGISNY (SEQ ID NO:37);
  the VL CDR2 comprises the amino acid sequence AAS (SEQ ID NO:38); and
  the VL CDR3 comprises the amino acid sequence QQSYSTPH (SEQ ID NO:39).

In some embodiments, the antibody comprises a VH domain comprising VH CDR1, VH CDR2, and VH CDR3, wherein:
  the VH CDR1 comprises the amino acid sequence GFTFSSYD (SEQ ID NO:34);
  the VH CDR2 comprises the amino acid sequence MSYDGSNK (SEQ ID NO:35);
  the VH CDR3 comprises the amino acid sequence ATEIAAKGDY (SEQ ID NO:36); and
  wherein the antibody comprises a VL domain comprising VL CDR1, VL CDR2, and VL CDR3, wherein:
  the VL CDR1 comprises the amino acid sequence QGISNY (SEQ ID NO:37);
  the VL CDR2 comprises the amino acid sequence AAS (SEQ ID NO:38); and
  the VL CDR3 comprises the amino acid sequence QQSYSTPH (SEQ ID NO:39). In some instances, the VH domain comprises the amino acid sequence set forth in SEQ ID NO: 62. In some instances, the antibody comprises a heavy chain and wherein the heavy chain comprises the amino acid sequence set forth in SEQ ID NO:30. In some instances, the VL domain comprises the amino acid sequence set forth in SEQ ID NO: 61. In some instances, the antibody comprises a light chain and wherein the light chain comprises the amino acid sequence set forth in SEQ ID NO: 31. In some instances, the VH domain is at least 80% identical to the amino acid sequence set forth in SEQ ID NO: 62 and the VL domain is at least 80% identical to the amino acid sequence set forth in SEQ ID NO: 61. In some instances, the VH domain comprises the amino acid sequence set forth in SEQ ID NO: 62 and the VL domain comprises the amino acid sequence set forth in SEQ ID NO: 61. In some instances, the antibody comprises a heavy chain and a light chain, and wherein the heavy chain comprises the amino acid sequence set forth in SEQ ID NO: 30 and the light chain comprises the amino acid sequence set forth in SEQ ID NO: 31.

In some embodiments, the antibody comprises a VH domain comprising VH CDR1, VH CDR2, and VH CDR3, wherein:
  the VH CDR1 comprises the amino acid sequence GFTFSSYD (SEQ ID NO:34);
  the VH CDR2 comprises the amino acid sequence MSYEGSNK (SEQ ID NO:40);
  the VH CDR3 comprises the amino acid sequence ATEIAAKGDY (SEQ ID NO:36); and
  wherein the antibody comprises a VL domain comprising VL CDR1, VL CDR2, and VL CDR3, wherein:
  the VL CDR1 comprises the amino acid sequence QGISNY (SEQ ID NO:37);
  the VL CDR2 comprises the amino acid sequence AAS (SEQ ID NO:38); and
  the VL CDR3 comprises the amino acid sequence QQSYSTPH (SEQ ID NO:39). In some instances, the VH domain comprises the amino acid sequence set forth in SEQ ID NO: 63. In some instances, the antibody comprises a heavy chain and wherein the heavy chain comprises the amino acid sequence set forth in SEQ ID NO:33. In some instances, the VL domain comprises the amino acid sequence set forth in SEQ ID NO: 61. In some instances, the antibody comprises a light chain and wherein the light chain comprises the amino acid sequence set forth in SEQ ID NO: 31. In some instances, the VH domain is at least 80% identical to the amino acid sequence set forth in SEQ ID NO: 63 and the VL domain is at least 80% identical to the amino acid sequence set forth in SEQ ID NO: 61. In some instances, the VH domain comprises the amino acid sequence set forth in SEQ ID NO: 63 and the VL domain comprises the amino acid sequence set forth in SEQ ID NO: 61. In some instances, the antibody comprises a heavy chain and a light chain, and wherein the heavy chain comprises the amino acid sequence set forth in SEQ ID NO: 33 and the light chain comprises the amino acid sequence set forth in SEQ ID NO: 31.

In some embodiments, the antibody binds to human CD73 at an epitope within amino acids 386-399 and 470-489 of SEQ ID NO:70.

In some embodiments, the antibody binds to human CD73 and competes for binding to human CD73 with an antibody that has a heavy chain comprising the amino acid sequence of SEQ ID NO:30 and a light chain comprising the amino acid sequence of SEQ ID NO:31.

In some embodiments, the antibody binds to human CD73 and competes for binding to human CD73 with an antibody that has a heavy chain comprising the amino acid sequence of SEQ ID NO:33 and a light chain comprising the amino acid sequence of SEQ ID NO:31.

In some embodiments, the inhibitor is selected from the group consisting of 7-(5-methylfuran-2-yl)-3-[[6-[[(3S)-oxolan-3-yl]oxymethyl]pyridin-2-yl]methyl]triazolo[4,5-d]pyrimidin-5-amine; 3-(5-Amino-2-((5-(pyridin-2-yl)-2H-tetrazol-2-yl)methyl)-8-(pyrimidin-4-yl)-[1,2,4]triazolo[1,5-c]pyrimidin-7-yl)benzonitrile; 3-[2-Amino-6-[1-[[6-(2-hydroxypropan-2-yl)pyridin-2-yl]methyl]triazol-4-yl]pyrimidin-4-yl]-2-methylbenzonitrile; 6-(2-Chloro-6-methylpyridin-4-yl)-5-(4-fluorophenyl)-1,2,4-triazin-3-amine, 5-Bromo-2,6-di(1H-pyrazol-1-yl)pyrimidin-4-amine; and EOS100850.

In some embodiments, the inhibitor is selected from the group consisting of 7-(5-methylfuran-2-yl)-3-[[6-[[(3S)-oxolan-3-yl]oxymethyl]pyridin-2-yl]methyl]triazolo[4,5-d]pyrimidin-5-amine; 3-(5-Amino-2-((5-(pyridin-2-yl)-1H- tetrazol-1-yl)methyl)-8-(pyrimidin-4-yl)-[1,2,4]triazolo[1,5-c]pyrimidin-7-yl)benzonitrile; 3-[2-Amino-6-[1-[[6-(2-hydroxypropan-2-yl)pyridin-2-yl]methyl]triazol-4-yl]pyrimidin-4-yl]-2-methylbenzonitrile; 6-(2-Chloro-6-methylpyridin-4-yl)-5-(4-fluorophenyl)-1,2,4-triazin-3-amine, 5-Bromo-2,6-di(1H-pyrazol-1-yl)pyrimidin-4-amine; and EOS100850.

In some embodiments of the foregoing methods, the cancer has a high adenosine signature. In some embodiments of the foregoing methods, the cancer is head and neck cancer, colorectal cancer, lung cancer, melanoma, ovarian, bladder, liver cancer, or renal cell carcinoma.

BRIEF DESCRIPTION OF THE DRAWINGS

FIG. 1A shows the heavy chain variable domain (VH) and light chain variable domain (VL) amino acid sequences for humanized CL25 antibodies CL_hu10-4, HzCL25, CL25_hu_10-6, and CL25_hu_11-4.

FIG. 1B shows the VH and VL amino acid sequences for humanized CL25 antibodies CL25_hu_11-5, CL25_hu_11-6, CL25_hu_8-4, and CL25_hu_8-5.

FIG. 1C shows the VH and VL amino acid sequences for humanized CL25 antibodies CL25_hu_8-6, CL25_hu_9-4, CL25_hu_9-5, and CL25_hu_9-6.

FIG. 1D shows an alignment of the VH for CL25 and humanized CL25 antibodies. CDRs according to the IMGT definition are underlined.

FIG. 1E shows an alignment of the VL for CL25 and humanized CL25 antibodies. CDRs according to the IMGT definition are underlined.

FIG. 2A is a graph depicting the cell binding (measured by geometric mean fluorescence intensity [GMFI]) for the indicated antibodies at the indicated concentrations on MDA-MB-231 cells.

FIGS. 12A-12J show the VH and VL amino acid sequences of 3-F03 and exemplary 3-F03 variants.

FIG. 15 shows exemplary amino acid sequences of a human IgG1 heavy chain CH1-hinge-CH2-CH3 with an N297A mutation (SEQ ID NO:73), a human IgG1 heavy chain CH1-hinge-CH2-CH3 with an N297A mutation with C-terminal lysine (SEQ ID NO:75), and a human kappa light chain constant region (SEQ ID NO:74).

FIG. 20A shows the DNA sequences encoding the HzCL25 heavy chain and light chain.

FIG. 20B shows the DNA sequence encoding the 3-F03_411 heavy chain.

FIG. 20C shows the DNA sequences encoding the 3-F03_411 and 3-F03_413 light chain and 3-F03_413 heavy chain.

DETAILED DESCRIPTION

Figure 2B:
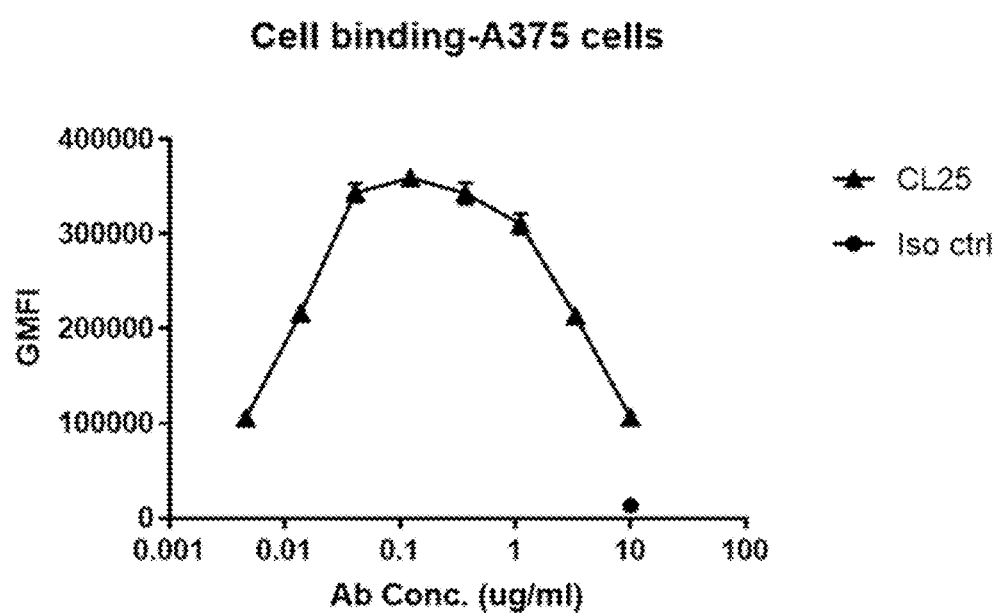
FIG. 2B is a graph depicting the cell binding (measured by GMFI) for CL25 or isotype control (iso ctrl) at the indicated concentrations on A375 cells.

Provided herein are combination therapies comprising administration of a CD73 inhibitor and an A2A and/or A2B adenosine receptor inhibitor. The disclosed combination therapies are useful in the treatment of diseases related to the activity of A2A and/or A2B adenosine receptors and/or CD73 including, for example, cancer, inflammatory diseases, cardiovascular diseases, and neurodegenerative diseases. CD73 inhibitors and A2A/A2B adenosine receptor inhibitors are also disclosed.

CD73

CD73 (also known as "5'-nucleotidase" and "ecto-5'-nucleotidase") is a dimeric enzyme (EC:3.1.3.5) that functions as a homodimer bound by a GPI linkage to the external face of the plasma membrane. CD73 can be shed and is active as a soluble protein in circulation. CD73 catalyzes the conversion of extracellular AMP to adenosine. CD73 enzymatic activity requires substrate binding in the open CD73 conformation. After the substrate binding, CD73 goes through a large conformational change from open to closed conformation to convert AMP to adenosine (see, e.g., Knapp et al., 2012, Structure, 20(12):2161-73). CD73 also functions as a cellular adhesion molecule and plays a role in regulation of leukocyte trafficking.

CD73 enzymatic activity plays a role in the promotion and metastasis of cancer (see, e.g., Stagg and Smyth, 2010, Oncogene, 29:5346-5358; Salmi and Jalkanen, 2012, OncoImmunology, 1:247-248, 2012; Stagg, 2012, OncoImmunology, 1:217-218; Zhang, 2012, OncoImmunology, 167-70). Overexpression of CD73 in cancer cells impairs adaptive antitumor immune responses, enhancing tumor growth and metastasis (see, e.g., Niemela et al., 2004, J. Immunol., 172:1646-1653; Sadej et al., 2006, Nucleosides Nucleotides Nucleic Acids, 25:1119-1123; Braganhol et al., 2007, Biochim. Biophys. Acta., 1770:1352-1359; Zhang, 2010, Cancer Res., 70:6407-6411; Zhang, 2012, OncoImmunology, 1:67-70).

An exemplary amino acid sequence of the mature human CD73 protein (amino acids 27-549 of GenBank Accession No. NP_002517) is:

(SEQ ID NO: 70)
WELTILHTNDVHSRLEQTSEDSSKCVNASRCMGGVARLFTKVQQIRRAEP

NVLLLDAGDQYQGTIWFTVYKGAEVAHFMNALRYDAMALGNHEFDNGVEG

LIEPLLKEAKFPILSANIKAKGPLASQISGLYLPYKVLPVGDEVVGIVGY

TSKETPFLSNPGTNLVFEDEITALQPEVDKLKTLNVNKIIALGHSGFEMD

KLIAQKVRGVDVVVGGHSNTFLYTGNPPSKEVPAGKYPFIVTSDDGRKVP

VVQAYAFGKYLGYLKIEFDERGNVISSHGNPILLNSSIPEDPSIKADINK

WRIKLDNYSTQELGKTIVYLDGSSQSCRFRECNMGNLICDAMINNNLRHT

-continued
DEMFWNHVSMCILNGGGIRSPIDERNNGTITWENLAAVLPFGGTFDLVQL

KGSTLKKAFEHSVHRYGQSTGEFLQVGGIHVVYDLSRKPGDRVVKLDVLC

TKCRVPSYDPLKMDEVYKVILPNFLANGGDGFQMIKDELLRHDSGDQDIN

VVSTYISKMKVIYPAVEGRIKFS.

An exemplary amino acid sequence of the mature murine CD73 protein (amino acids 29-551 of GenBank Accession No. NP_035981) is:

(SEQ ID NO: 71)
WELTILHTNDVHSRLEQTSDDSTKCLNASLCVGGVARLFTKVQQIRKEEP

NVLFLDAGDQYQGTIWFTVYKGLEVAHFMNILGYDAMALGNHEFDNGVEG

LIDPLLRNVKFPILSANIKARGPLAHQISGLFLPSKVLSVGGEVVGIVGY

TSKETPFLSNPGTNLVFEDEISALQPEVDKLKTLNVNKIIALGHSGFEMD

KLIAQKVRGVDIVVGGHSNTFLYTGNPPSKEVPAGKYPFIVTADDGRQVP

VVQAYAFGKYLGYLKVEFDDKGNVITSYGNPILLNSSIPEDATIKADINQ

WRIKLDNYSTQELGRTIVYLDGSTQTCRFRECNMGNLICDAMINNNLRHP

DEMFWNHVSMCIVNGGGIRSPIDEKNNGTITWENLAAVLPFGGTFDLVQL

KGSTLKKAFEHSVHRYGQSTGEFLQVGGIHVVYDINRKPWNRVVQLEVLC

TKCRVPIYEPLEMDKVYKVTLPSYLANGGDGFQMIKDELLKHDSGDQDIS

VVSEYISKMKVVYPAVEGRIKFS.

An exemplary amino acid sequence of the mature cynomolgus CD73 protein is:

(SEQ ID NO: 72)
WELTILHTNDVHSRLEQTSEDSSKCVNASRCMGGVARLFTKVQQIRRAEP

NVLLLDAGDQYQGTIWFTVYKGAEVAHEMNALRYDAMALGNHEFDNGVEG

LIEPLLKEAKFPILSANIKAKGPLASQISGLYLPYKVLPVGDEVVGIVGY

TSKETPFLSNPGTNLVFEDEITALQPEVDKLKTLNVNKIIALGHSGFETD

KLIAQKVRGVDVVVGGHSNTFLYTGNPPSKEVPAGKYPFIVTSDDGRKVP

VVQAYAFGKYLGYLKIEFDERGNVISSHGNPILLNSSIPEDPSIKADINK

WRIKLDNYSTQELGKTIVYLDGSSQSCRFRECNMGNLICDAMINNNLRHA

DEMFWNHVSMCILNGGGIRSPIDERNNGTITWENLAAVLPFGGTFDLVQL

KGSTLKKAFEHSVHRYGQSTGEFLQVGGIHVVYDLSRKPGDRVVKLDVLC

TKCRVPSYDPLKMDEIYKVILPNFLANGGDGFQMIKDELLRHDSGDQDIN

VVSTYISKMKVIYPAVEGRIKFS.

Anti-CD73 Antibodies

This disclosure provides anti-CD73 antibodies that are useful in combination with an A2A and/or A2B adenosine receptor inhibitor in treating diseases, e.g., cancer. These anti-CD73 antibodies can bind human CD73.

In some instances, these antibodies bind human CD73 and cynomolgus CD73. In some instances, these antibodies bind human CD73 and cynomolgus CD73 and do not bind murine CD73. Such anti-CD73 antibodies include the sequences of an anti-CD73 monoclonal antibody, CL25, and a humanized version thereof, HzCL25, which humanized version thereof binds with high affinity to both human and cynomolgus CD73, and has undetectable binding to mouse CD73.

In some instances, these antibodies bind human CD73, cynomolgus CD73, and murine CD73. Such anti-CD73 antibodies includes the sequences of a human anti-CD73 monoclonal antibody, 3-F03, which binds with high affinity to the open conformation of each of human, cynomolgus, and murine CD73.

Antibody HzCL25

Antibody HzCL25 is a humanized IgG1/kappa monoclonal antibody with alanine at position Asparagine-297 (N297, according to EU numbering) of the heavy chain constant region to reduce effector function. It specifically binds human and cynomolgus CD73 with high affinity ($K_D \leq 0.5$ nM) and has low effector functionality.

HzCL25 was constructed from a chimeric version of the CL25 antibody. The CL25 murine heavy chain variable domain (VH) and light chain variable domain (VL) were obtained from a mouse immunized with recombinant human CD73 (SEQ ID NO:70) comprising a HIS-tag. Antibody sequences of the B cells were determined and the murine heavy chain variable domain (VH) (SEQ ID NO:26) and light chain variable domain (VL) (SEQ ID NO:27) were expressed as chimeras with human IgG1 Fc (heavy chain constant region comprising the amino acid sequence of SEQ ID NO:73 and kappa light chain constant region comprising the amino acid sequence of SEQ ID NO:74). Table 1, below, shows the amino acid sequences of the CL25 complementarity determining regions (CDRs) according to IMGT, Chothia, AbM, Kabat, and Contact numbering. Table 1, below, also shows the amino acid sequences of the CL25 mature VH and VL.

TABLE 1

CL25 CDRs, VH, and VL

|  | IMGT | Chothia | AbM | Kabat | Contact |
|---|---|---|---|---|---|
| VH CDR1 | GYTFTSYG (SEQ ID NO: 1) | GYTFTSY (SEQ ID NO: 7) | GYTFTSYGLS (SEQ ID NO: 12) | SYGLS (SEQ ID NO: 14) | TSYGLS (SEQ ID NO: 16) |
| VH CDR2 | IYPGSGNT (SEQ ID NO: 2) | YPGSGN (SEQ ID NO: 8) | EIYPGSGNTY (SEQ ID NO: 13) | EIYPGSGNTYY NEKFKG (SEQ ID NO: 15) | WIGEIYPGSGN TY (SEQ ID NO: 28) |
| VH CDR3 | ARYDYLGSSY GFDY (SEQ ID NO: 3) | YDYLGSSYGFD Y (SEQ ID NO: 9) | YDYLGSSYGFD Y (SEQ ID NO: 9) | YDYLGSSYGFD Y (SEQ ID NO: 9) | ARYDYLGSSY GFD (SEQ ID NO: 18) |
| VL CDR1 | QDVSTA (SEQ ID NO: 4) | KASQDVSTAV A (SEQ ID NO: 10) | KASQDVSTAV A (SEQ ID NO: 10) | KASQDVSTAV A (SEQ ID NO: 10) | STAVAWY (SEQ ID NO: 19) |
| VL CDR2 | SAS (SEQ ID NO: 5) | SASYRYN (SEQ ID NO: 29) | SASYRYN (SEQ ID NO: 29) | SASYRYN (SEQ ID NO: 29) | LLIYSASYRY (SEQ ID NO: 20) |
| VL CDR3 | QQHYNTPYT (SEQ ID NO: 6) | QQHYNTPYT (SEQ ID NO: 6) | QQHYNTPYT (SEQ ID NO: 6) | QQHYNTPYT (SEQ ID NO: 6) | QQHYNTPY (SEQ ID NO: 21) |
| VH | QVQLQQSGAELARPGASVKLSCRASGYTFTSYGLSWVKQRTGQGLEWIGEIYPGSGNTYYNE KFKGKATLTADKSSSTAYMELRSLTSEDSAVYFCARYDYLGSSYGFDYWGQGTTLTVSS (SEQ ID NO: 26) | | | | |
| VL | DIVMTQSHKFMSTSVGDRVSITCKASQDVSTAVAWYQQKPGQSPKLLIYSASYRYNGVPDRF TGSGSGTDFTFTISSVQAEDLAVYYCQQHYNTPYTFGGGTKLEIK (SEQ ID NO: 27) | | | | |

To construct HzCL25, the CL25 VH and VL sequences were aligned to a database of human VH and VK genes. The CDRs (Table 1) from the murine CL25 antibody were grafted into human VH and VK genes.

Table 2, below, shows the amino acid sequences of the HzCL25 CDRs according to IMGT, Chothia, AbM, Kabat, and Contact numbering. Table 2, below, also shows the amino acid sequences of the HzCL25 mature VH, VL, heavy chain, and light chain.

TABLE 2

Amino acid sequences of HzCL25 CDRs, VH, VL, heavy chain, and light chain

|  | IMGT | Chothia | AbM | Kabat | Contact |
|---|---|---|---|---|---|
| VH CDR1 | GYTFTSYG (SEQ ID NO: 1) | GYTFTSY (SEQ ID NO: 7) | GYTFTSYGLS (SEQ ID NO: 12) | SYGLS (SEQ ID NO: 14) | TSYGLS (SEQ ID NO: 16) |
| VH CDR2 | IYPGSGNT (SEQ ID NO: 2) | YPGSGN (SEQ ID NO: 8) | EIYPGSGNTY (SEQ ID NO: 13) | EIYPGSGNTYY NEKFKG (SEQ ID NO: 15) | WMGEIYPGSG NTY (SEQ ID NO: 17) |
| VH CDR3 | ARYDYLGSSY GFDY (SEQ ID NO: 3) | YDYLGSSYGFD Y (SEQ ID NO: 9) | YDYLGSSYGFD Y (SEQ ID NO: 9) | YDYLGSSYGFD Y (SEQ ID NO: 9) | ARYDYLGSSY GFD (SEQ ID NO: 18) |

TABLE 2-continued

Amino acid sequences of HzCL25 CDRs, VH, VL, heavy chain, and light chain

|  | IMGT | Chothia | AbM | Kabat | Contact |
|---|---|---|---|---|---|
| VL CDR1 | QDVSTA (SEQ ID NO: 4) | KASQDVSTAVA (SEQ ID NO: 10) | KASQDVSTAVA (SEQ ID NO: 10) | KASQDVSTAVA (SEQ ID NO: 10) | STAVAWY (SEQ ID NO: 19) |
| VL CDR2 | SAS (SEQ ID NO: 5) | SASYRYS (SEQ ID NO: 11) | SASYRYS (SEQ ID NO: 11) | SASYRYS (SEQ ID NO: 11) | LLIYSASYRY (SEQ ID NO: 20) |
| VL CDR3 | QQHYNTPYT (SEQ ID NO: 6) | QQHYNTPYT (SEQ ID NO: 6) | QQHYNTPYT (SEQ ID NO: 6) | QQHYNTPYT (SEQ ID NO: 6) | QQHYNTPY (SEQ ID NO: 21) |
| VH | EVQLVQSGAEVKKPGESLKISCKGSGYTFTSYGLSWVRQMPGKGLEWMGEIYPGSGNTYYNEKFKGQVTISADKSISTAYLQWSSLKASDTAMYYCARYDYLGSSYGFDYWGAGTTVTVSS (SEQ ID NO: 22) | | | | |
| VL | DIVMTQSPDSLAVSLGERATINCKASQDVSTAVAWYQQKPGQPPKLLIYSASYRYSGVPDRFSGSGSGTDFTLTISSLQAEDVAVYYCQQHYNTPYTFGGGTKLEIK (SEQ ID NO: 23) | | | | |
| Heavy Chain | EVQLVQSGAEVKKPGESLKISCKGSGYTFTSYGLSWVRQMPGKGLEWMGEIYPGSGNTYYNEKFKGQVTISADKSISTAYLQWSSLKASDTAMYYCARYDYLGSSYGFDYWGAGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG (SEQ ID NO: 24) | | | | |
| Light Chain | DIVMTQSPDSLAVSLGERATINCKASQDVSTAVAWYQQKPGQPPKLLIYSASYRYSGVPDRFSGSGSGTDFTLTISSLQAEDVAVYYCQQHYNTPYTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 25) | | | | |

The anti-CD73 antibodies can encompass the VH CDR1, VH CDR2, and VH CDR3 and the VL CDR1, VL CDR2, and VL CDR3 of HzCL25 or CL25. In some instances, the anti-CD73 antibody comprises a VH comprising VH CDR1, VH CDR2, and VH CDR3 of HzCL25 (see Table 2). In some instances, the anti-CD73 antibody comprises a VL comprising VL CDR1, VL CDR2, and VL CDR3 of HzCL25 (see Table 2). In some instances, the anti-CD73 antibody comprises a VH comprising VH CDR1, VH CDR2, and VH CDR3 of HzCL25 (see Table 2) and a VL comprising VL CDR1, VL CDR2, and VL CDR3 of HzCL25 (see Table 2). In some instances, the anti-CD73 antibody comprises a VH comprising VH CDR1, VH CDR2, and VH CDR3 of CL25 (see Table 1). In some instances, the anti-CD73 antibody comprises a VL comprising VL CDR1, VL CDR2, and VL CDR3 of CL25 (see Table 1). In some instances, the anti-CD73 antibody comprises a VH comprising VH CDR1, VH CDR2, and VH CDR3 of CL25 (see Table 1) and a VL comprising VL CDR1, VL CDR2, and VL CDR3 of CL25 (see Table 1). In some instances, the anti-CD73 antibodies can have, e.g., 1, 2, or 3 substitutions within one or more (i.e., 1, 2, 3, 4, 5, or 6) of the six CDRs of HzCL25 or CL25. In some instances, the antibodies (i) inhibit cellular CD73 (e.g., at least 10%; at least 20%, at least 30%, at least 40%, at least 50%, at least 60%, at least 70%, at least 80%, at least 90%, at least 95%, at least 97%, at least 99%, or 100% reduction in cellular CD73 activity as compared to an isotype control as determined by, e.g., the assay described in Example 3); and/or (ii) inhibit soluble CD73 (e.g., at least 10%; at least 20%, at least 30%, at least 40%, at least 50%, at least 60%, at least 70%, at least 80%, at least 90%, at least 95%, at least 97%, at least 99%, or 100% reduction in soluble CD73 activity as compared to an isotype control as determined by, e.g., the assay described in Example 4); and/or (iii) bind human or cynomolgus monkey CD73 in the open conformation with high affinity (e.g., $K_D \leq 0.5$ nM) but do not significantly bind CD73 in the open conformation from mice (e.g., as determined by the binding assay described in Example 5); and/or (iv) bind human or cynomolgus monkey CD73 in the closed conformation with high affinity (e.g., $K_D \leq 0.5$ nM) but do not significantly bind CD73 in the closed conformation from mice; and/or (v) bind to an epitope within amino acids 40-53 of SEQ ID NO:70 (i.e., within TKVQQIRRAEPNVL (SEQ ID NO:76)) (e.g., as determined by the binding assay described in Example 5); and/or (vi) reduce AMP-mediated suppression of T cell proliferation (e.g., at least 10%; at least 20%, at least 30%, at least 40%, at least 50%, at least 60%, at least 70%, at least 80%, at least 90%, at least 95%, at least 97%, at least 99%, or 100% reduction in T cell proliferation as compared to an isotype control as determined by, e.g., the assay described in Example 16); and/or (vii) decreases levels of cell surface CD73 (e.g., on cancer cells, e.g., on melanoma cancer cells, e.g., by at least 10%; at least 20%, at least 30%, at least 40%, at least 50%, at least 60%, at least 70%, at least 80%, at least 90%, at least 95%, at least 97%, at least 99%, or 100% as compared to an isotype control); and/or (viii) reduce tumor growth (e.g., melanoma tumors, e.g., by at least 10%; at least 20%, at least 30%, at least 40%, at least 50%, at least 60%, at least 70%, at least 80%, at least 90%, at least 95%, at least 97%, at least 99%, or 100% as compared to an isotype control as determined by, e.g., the assay described in Example 17); and/or (ix) reduce free surface CD73 on cells (e.g., cancer cells, e.g., melanoma cancer cancers, e.g., by at least 10%; at least 20%, at least 30%, at least 40%, at least 50%, at least 60%, at least 70%, at least 80%, at least 90%, at least 95%, at least 97%, at least 99%, or 100% as compared to an isotype control).

The anti-CD73 antibodies can comprise the VH CDR1, VH CDR2, and VH CDR3 of HzCL25 or CL25 according to the IMGT definition, or an alternate CDR definition such as, but not limited to, the Kabat definition, the Chothia definition, the AbM CDR definition, or the contact definition. These anti-CD73 antibodies may include zero, one, two, or three substitutions in VH CDR1 and/or VH CDR2 and/or VH CDR3 of HzCL25 or CL25. In some embodiments, the anti-CD73 antibodies further comprise the VL CDR1, VL CDR2, and VL CDR3 of HzCL25 or CL25 according to the IMGT definition, or an alternate CDR definition such as, but not limited to, the Kabat definition, the Chothia definition, the AbM CDR definition, or the contact definition. These anti-CD73 antibodies may include zero, one, two, or three substitutions in VL CDR1 and/or VL CDR2 and/or VL CDR3 of HzCL25 or CL25. In some instances, the anti-CD73 antibody comprises a VH comprising the VH CDR1, VH CDR2, and VH CDR3 set forth in SEQ ID NOs: 1, 2, and 3, respectively, and a VL comprising the VL CDR1, VL CDR2, and VL CDR3 set forth in SEQ ID NOs: 4, 5, and 6, respectively. In some instances, the anti-CD73 antibody comprises a VH comprising the VH CDR1, VH CDR2, and VH CDR3 set forth in SEQ ID NOs: 7, 8, and 9, respectively, and a VL comprising the VL CDR1, VL CDR2, and VL CDR3 set forth in SEQ ID NOs: 10, 11, and 6, respectively. In some instances, the anti-CD73 antibody comprises a VH comprising the VH CDR1, VH CDR2, and VH CDR3 set forth in SEQ ID NOs: 12, 13, and 9, respectively, and a VL comprising the VL CDR1, VL CDR2, and VL CDR3 set forth in SEQ ID NOs: 10, 11, and 6, respectively. In some instances, the anti-CD73 antibody comprises a VH comprising the VH CDR1, VH CDR2, and VH CDR3 set forth in SEQ ID NOs: 14, 15, and 9, respectively, and a VL comprising the VL CDR1, VL CDR2, and VL CDR3 set forth in SEQ ID NOs: 10, 11, and 6, respectively. In some instances, the anti-CD73 antibody comprises a VH comprising the VH CDR1, VH CDR2, and VH CDR3 set forth in SEQ ID NOs: 16, 17, and 18, respectively, and a VL comprising the VL CDR1, VL CDR2, and VL CDR3 set forth in SEQ ID NOs: 19, 20, and 21, respectively. In some instances, the anti-CD73 antibody comprises a VH comprising the VH CDR1, VH CDR2, and VH CDR3 set forth in SEQ ID NOs: 7, 8, and 9, respectively, and a VL comprising the VL CDR1, VL CDR2, and VL CDR3 set forth in SEQ ID NOs: 10, 29, and 6, respectively. In some instances, the anti-CD73 antibody comprises a VH comprising the VH CDR1, VH CDR2, and VH CDR3 set forth in SEQ ID NOs: 12, 13, and 9, respectively, and a VL comprising the VL CDR1, VL CDR2, and VL CDR3 set forth in SEQ ID NOs: 10, 29, and 6, respectively. In some instances, the anti-CD73 antibody comprises a VH comprising the VH CDR1, VH CDR2, and VH CDR3 set forth in SEQ ID NOs: 14, 15, and 9, respectively, and a VL comprising the VL CDR1, VL CDR2, and VL CDR3 set forth in SEQ ID NOs: 10, 29, and 6, respectively. In some instances, the anti-CD73 antibody comprises a VH comprising the VH CDR1, VH CDR2, and VH CDR3 set forth in SEQ ID NOs: 16, 28, and 18, respectively, and a VL comprising the VL CDR1, VL CDR2, and VL CDR3 set forth in SEQ ID NOs: 19, 20, and 21, respectively. In some instances these antibodies (i) inhibit cellular CD73 (e.g., at least 10%; at least 20%, at least 30%, at least 40%, at least 50%, at least 60%, at least 70%, at least 80%, at least 90%, at least 95%, at least 97%, at least 99%, or 100% reduction in cellular CD73 activity as compared to an isotype control as determined by, e.g., the assay described in Example 3); and/or (ii) inhibit soluble CD73 (e.g., at least 10%; at least 20%, at least 30%, at least 40%, at least 50%, at least 60%, at least 70%, at least 80%, at least 90%, at least 95%, at least 97%, at least 99%, or 100% reduction in soluble CD73 activity as compared to an isotype control as determined by, e.g., the assay described in Example 4); and/or (iii) bind human or cynomolgus monkey CD73 in the open conformation with high affinity (e.g., $K_D \leq 0.5$ nM) but do not significantly bind CD73 in the open conformation from mice (e.g., as determined by the binding assay described in Example 5); and/or (iv) bind human or cynomolgus monkey CD73 in the closed conformation with high affinity (e.g., $K_D \leq 0.5$ nM) but do not significantly bind CD73 in the closed conformation from mice; and/or (v) bind to an epitope within amino acids 40-53 of SEQ ID NO:70 (i.e., within TKVQQIRRAEPNVL (SEQ ID NO:76)) (e.g., as determined by the binding assay described in Example 5); and/or (vi) reduce AMP-mediated suppression of T cell proliferation (e.g., at least 10%; at least 20%, at least 30%, at least 40%, at least 50%, at least 60%, at least 70%, at least 80%, at least 90%, at least 95%, at least 97%, at least 99%, or 100% reduction in T cell proliferation as compared to an isotype control as determined by, e.g., the assay described in Example 16); and/or (vii) decreases levels of cell surface CD73 (e.g., on cancer cells, e.g., on melanoma cancer cells, e.g., by at least 10%; at least 20%, at least 30%, at least 40%, at least 50%, at least 60%, at least 70%, at least 80%, at least 90%, at least 95%, at least 97%, at least 99%, or 100% as compared to an isotype control); and/or (viii) reduce tumor growth (e.g., melanoma tumors, e.g., by at least 10%; at least 20%, at least 30%, at least 40%, at least 50%, at least 60%, at least 70%, at least 80%, at least 90%, at least 95%, at least 97%, at least 99%, or 100% as compared to an isotype control as determined by, e.g., the assay described in Example 17); and/or (ix) reduce free surface CD73 on cells (e.g., cancer cells, e.g., melanoma cancer cancers, e.g., by at least 10%; at least 20%, at least 30%, at least 40%, at least 50%, at least 60%, at least 70%, at least 80%, at least 90%, at least 95%, at least 97%, at least 99%, or 100% as compared to an isotype control).

In certain embodiments, the anti-CD73 antibodies comprise an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:22, 26, and 82-84. In certain embodiments, the anti-CD73 antibodies comprise a VH comprising the VH CDR1, VH CDR2, and VH CDR3 of HzCL25 (see Table 1, e.g., according to the IMGT definition, i.e., the amino acid sequences set forth in SEQ ID NOs: 1-3, respectively), wherein the VH comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:22, 26, and 82-84. In some embodiments, the anti-CD73 antibodies comprise an amino acid sequence having one or more (e.g., 1, 2, 3, 4, 5, 6, 7, 8, 9, 10) amino acid substitutions, additions, and/or deletions relative to the amino acid sequence set forth in SEQ ID NO:24. In some embodiments, the anti-CD73 antibodies comprise a heavy chain comprising the VH CDR1, VH CDR2, and VH CDR3 of HzCL25 (see Table 1, e.g., according to the IMGT definition, i.e., the amino acid sequences set forth in SEQ ID NOs: 1-3, respectively), wherein the heavy chain comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO:24. In certain embodiments, the anti-CD73 antibodies comprise an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:23, 27, 80, and 81. In certain embodiments, the anti-CD73 antibodies comprise a VL comprising the VL CDR1, VL CDR2, and VL CDR3 of HzCL25 (see Table 1, e.g., according to the IMGT definition, i.e., the amino acid sequences set forth in SEQ ID NOs: 4-6, respectively), wherein the VL comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:23, 27, 80, and 81. In some embodiments, the anti-CD73 antibodies comprise an amino acid sequence having one or more (e.g., 1, 2, 3, 4, 5, 6, 7, 8, 9, 10) amino acid substitutions, additions, and/or deletions relative to the amino acid sequence set forth in SEQ ID NO:25. In some embodiments, the anti-CD73 antibodies comprise a light chain comprising the VL CDR1, VL CDR2, and VL CDR3 of HzCL25 (see Table 1, e.g., according to the IMGT definition, i.e., the amino acid sequences set forth in SEQ ID NOs: 4-6, respectively), wherein the light chain comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO:25. In certain embodiments, the anti-CD73 antibodies comprise: (i) an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:22, 26, and 82-84; and (ii) an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:23, 27, 80, and 81. In certain embodiments, the anti-CD73 antibodies comprise: (i) a VH comprising the VH CDR1, VH CDR2, and VH CDR3 of HzCL25 (see Table 1, e.g., according to the IMGT definition, i.e., the amino acid sequences set forth in SEQ ID NOs: 1-3, respectively), wherein the VH comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:22, 26, and 82-84; and (ii) a VL comprising the VL CDR1, VL CDR2, and VL CDR3 of HzCL25 (see Table 1, e.g., according to the IMGT definition, i.e., the amino acid sequences set forth in SEQ ID NOs: 4-6, respectively), wherein the VL comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:23, 27, 80, and 81. In some embodiments, the anti-CD73 antibodies comprise: (i) an amino acid sequence having one or more (e.g., 1, 2, 3, 4, 5, 6, 7, 8, 9, 10) amino acid substitutions, additions, and/or deletions relative to the amino acid sequence set forth in SEQ ID NOs:24; and (ii) an amino acid sequence having one or more (e.g., 1, 2, 3, 4, 5, 6, 7, 8, 9, 10) amino acid substitutions, additions, and/or deletions relative to the amino acid sequence set forth in SEQ ID NOs:25. In some embodiments, the anti-CD73 antibodies comprise: (i) a heavy chain comprising the VH CDR1, VH CDR2, and VH CDR3 of HzCL25 (see Table 1, e.g., according to the IMGT definition, i.e., the amino acid sequences set forth in SEQ ID NOs: 1-3, respectively), wherein the heavy chain comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO:24; and (ii) a light chain comprising the VL CDR1, VL CDR2, and VL CDR3 of HzCL25 (see Table 1, e.g., according to the IMGT definition, i.e., the amino acid sequences set forth in SEQ ID NOs: 4-6, respectively), wherein the light chain comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO:25.

In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH set forth in any one of SEQ ID NOs: 22, 26, and 82-84. In certain embodiments, the anti-CD73 antibodies comprise a VH comprising the VH CDR1, VH CDR2, and VH CDR3 of HzCL25 (see Table 1, e.g., according to the IMGT definition, i.e., the amino acid sequences set forth in SEQ ID NOs: 1-3, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH set forth in any one of SEQ ID NOs: 22, 26, and 82-84. In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL set forth in any one of SEQ ID NOs: 23, 27, 80, and 81. In certain embodiments, the anti-CD73 antibodies comprise a VL comprising the VL CDR1, VL CDR2, and VL CDR3 of HzCL25 (see Table 1, e.g., according to the IMGT definition, i.e., the amino acid sequences set forth in SEQ ID NOs: 4-6, respectively), wherein the VL comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL set forth in any one of SEQ ID NOs: 23, 27, 80, and 81. In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH set forth in any one of SEQ ID NOs: 22, 26, and 82-84 and an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL set forth in SEQ ID NO: 23, 27, 80, and 81. In certain embodiments, the anti-CD73 antibodies comprise: (i) a VH comprising the VH CDR1, VH CDR2, and VH CDR3 of HzCL25 (see Table 1, e.g., according to the IMGT definition, i.e., the amino acid sequences set forth in SEQ ID NOs: 1-3, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH set forth in any one of SEQ ID NOs: 22, 26, and 82-84, and (ii) a VL comprising the VL CDR1, VL CDR2, and VL CDR3 of HzCL25 (see Table 1, e.g., according to the IMGT definition, i.e., the amino acid sequences set forth in SEQ ID NOs: 4-6, respectively), wherein the VL comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL set forth in any one of SEQ ID NOs: 23, 27, 80, and 81.

In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of HzCL25 (i.e., the amino acid sequence set forth in SEQ ID NO:22). In certain embodiments, the anti-CD73 antibodies comprise a VH comprising the VH CDR1, VH CDR2, and VH CDR3 of HzCL25 (see Table 1, e.g., according to the IMGT definition, i.e., the amino acid sequences set forth in SEQ ID NOs: 1-3, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of HzCL25 (i.e., the amino acid sequence set forth in SEQ ID NO:22). In certain embodiments, the anti-CD73 antibodies comprise a VH comprising the amino acid sequence set forth in SEQ ID NO:22. In some embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the heavy chain of HzCL25 (i.e., the amino acid sequence set forth in SEQ ID NO:24). In some embodiments, the anti-CD73 antibodies comprise a heavy chain comprising a VH comprising the VH CDR1, VH CDR2, and VH CDR3 of HzCL25 (see Table 1, e.g., according to the IMGT definition, i.e., the amino acid sequences set forth in SEQ ID NOs: 1-3, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of HzCL25 (i.e., the amino acid sequence set forth in SEQ ID NO:22), wherein the heavy chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the heavy chain of HzCL25 (i.e., the amino acid sequence set forth in SEQ ID NO:24). In certain embodiments, the anti-CD73 antibodies comprise a heavy chain comprising the amino acid sequence set forth in SEQ ID NO:24. In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL of HzCL25 (i.e., the amino acid sequence set forth in SEQ ID NO:23). In certain embodiments, the anti-CD73 antibodies comprise a VL comprising the VL CDR1, VL CDR2, and VL CDR3 of HzCL25 (see Table 1, e.g., according to the IMGT definition, i.e., the amino acid sequences set forth in SEQ ID NOs: 4-6, respectively), wherein the VL comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL of HzCL25 (i.e., the amino acid sequence set forth in SEQ ID NO:23). In certain embodiments, the anti-CD73 antibodies comprise a VL comprising the amino acid sequence set forth in SEQ ID NO:23. In some embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the light chain of HzCL25 (i.e., the amino acid sequence set forth in SEQ ID NO:25). In some embodiments, the anti-CD73 antibodies comprise a light chain comprising a VL comprising the VL CDR1, VL CDR2, and VL CDR3 of HzCL25 (see Table 1, e.g., according to the IMGT definition, i.e., the amino acid sequences set forth in SEQ ID NOs: 4-6, respectively), wherein the VL comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL of HzCL25 (i.e., the amino acid sequence set forth in SEQ ID NO:23), wherein the light chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the light chain of HzCL25 (i.e., the amino acid sequence set forth in SEQ ID NO:25). In certain embodiments, the anti-CD73 antibodies comprise a light chain comprising the amino acid sequence set forth in SEQ ID NO:25. In certain embodiments, the anti-CD73 antibodies comprise: (i) an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of HzCL25 (i.e., the amino acid sequence set forth in SEQ ID NO:22); and (ii) an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL of HzCL25 (i.e., the amino acid sequence set forth in SEQ ID NO:23). In certain embodiments, the anti-CD73 antibodies comprise: (i) a VH comprising the VH CDR1, VH CDR2, and VH CDR3 of HzCL25 (see Table 1, e.g., according to the IMGT definition, i.e., the amino acid sequences set forth in SEQ ID NOs: 1-3, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of HzCL25 (i.e., the amino acid sequence set forth in SEQ ID NO:22), and (ii) a VL comprising the VL CDR1, VL CDR2, and VL CDR3 of HzCL25 (see Table 1, e.g., according to the IMGT definition, i.e., the amino acid sequences set forth in SEQ ID NOs: 4-6, respectively), wherein the VL comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL of HzCL25 (i.e., the amino acid sequence set forth in SEQ ID NO:23). In certain embodiments, the anti-CD73 antibodies comprise: a VH comprising the amino acid sequence set forth in SEQ ID NO:22, and (ii) a VL comprising the amino acid sequence set forth in SEQ ID NO:23. In some embodiments, the anti-CD73 antibodies comprise: (i) an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the heavy chain of HzCL25 (i.e., the amino acid sequence set forth in SEQ ID NO:24); and (ii) an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the light chain of HzCL25 (i.e., the amino acid sequence set forth in SEQ ID NO:25). In some embodiments, the anti-CD73 antibodies comprise: (i) a heavy chain comprising a VH comprising the VH CDR1, VH CDR2, and VH CDR3 of HzCL25 (see Table 1, e.g., according to the IMGT definition, i.e., the amino acid sequences set forth in SEQ ID NOs: 1-3, respectively), wherein the heavy chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the heavy chain of HzCL25 (i.e., the amino acid sequence set forth in SEQ ID NO:24), and (ii) a light chain comprising a VL comprising the VL CDR1, VL CDR2, and VL CDR3 of HzCL25 (see Table 1, e.g., according to the IMGT definition, i.e., the amino acid sequences set forth in SEQ ID NOs: 4-6, respectively), wherein the light chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the light chain of HzCL25 (i.e., the amino acid sequence set forth in SEQ ID NO:25). In some embodiments, the anti-CD73 antibodies comprise: (i) a heavy chain comprising the amino acid sequence set forth in SEQ ID NO:24, and (ii) a light chain comprising the amino acid sequence set forth in SEQ ID NO:25.

The CD73-binding epitope of HzCL25 is within the amino acid sequence TKVQQIRRAEPNVL (SEQ ID NO:76) (i.e., amino acids 40-53 of the amino acid sequence set forth in SEQ ID NO:70). This disclosure features antibodies that bind to CD73 within the sequence TKVQQIRRAEPNVL (SEQ ID NO:76). This disclosure features antibodies that bind to the same epitope as HzCL25. This disclosure also features antibodies that competitively inhibit binding of HzCL25 to human CD73.

In some embodiments, the VH of HzCL25 is linked to a heavy chain constant region comprising a CH1 domain and a hinge region. In some embodiments, the VH of HzCL25 is linked to a heavy chain constant region comprising a CH3 domain. In some embodiments, the CH3 domain lacks the C-terminal lysine (K) amino acid residue. In some embodiments, the CH3 domain contains the C-terminal lysine (K) amino acid residue. In certain embodiments, the VH of HzCL25 is linked to a heavy chain constant region comprising a CH1 domain, hinge region, CH2 domain, and CH3 domain from human IgG1. In some embodiments, the CH3 domain from human IgG1 lacks the C-terminal lysine (K) amino acid residue. In some embodiments, the CH3 domain from human IgG1 contains the C-terminal lysine (K) amino acid residue. In certain embodiments such an antibody contains one or more additional mutations in the heavy chain constant region that increase the stability of the antibody. In certain embodiments, the heavy chain constant region includes substitutions that modify the properties of the antibody (e.g., decrease Fc receptor binding, increase or decrease antibody glycosylation, decrease binding to C1q). In certain embodiments, the heavy chain constant region includes an alanine at position Asparagine-297 (N297, according to EU numbering) of the heavy chain constant region to reduce effector function.

In certain embodiments, the anti-CD73 antibody is an IgG antibody. In one embodiment, the antibody is an IgG1 antibody. In one embodiment, the antibody is an IgG4 antibody. In another embodiment, the antibody is an IgG2 antibody. In certain embodiments, the anti-CD73 antibody comprises a heavy chain constant region lacking one or more lysine (K) amino acid residues relative to a wild type heavy chain constant region. For example, in certain embodiments, the antibody comprises heavy chain constant region lacking the C-terminal lysine (K) amino acid residue of the CH3 domain of the heavy chain constant region. In certain embodiments, the anti-CD73 antibody comprises a heavy chain constant region having the amino acid sequence set forth in SEQ ID NO:73. In certain embodiments, the anti-CD73 antibody comprises a heavy chain constant region having the amino acid sequence set forth in SEQ ID NO:75. In certain embodiments, the anti-CD73 antibody comprises a light chain constant region having the amino acid sequence set forth in SEQ ID NO:74. In certain embodiments, the anti-CD73 antibody comprises a heavy chain constant region having the amino acid sequence set forth in SEQ ID NO:73 and a light chain constant region having the amino acid sequence set forth in SEQ ID NO:74. In certain embodiments, the anti-CD73 antibody comprises a heavy chain constant region having the amino acid sequence set forth in SEQ ID NO:75 and a light chain constant region having the amino acid sequence set forth in SEQ ID NO:74.

Antibody 3-F03

Antibody 3-F03 is a human IgG1/kappa monoclonal antibody with alanine at position Asparagine-297 (N297, according to EU numbering) of the heavy chain constant region to reduce effector function. 3-F03 specifically binds human, cynomolgus, and murine CD73 with high affinity ($K_D \leq 2$ nM) and has low effector functionality.

3-F03 was engineered from sequences obtained by multiple selection rounds of single donor library. scFv cassettes from this pool were then recombined into a yeast display vector library, which was subjected to FACs selection with murine CD73 (SEQ ID NO:71). The amino acid sequences of the yeast 3-F03 scFv cassette are set forth in SEQ ID NOs:77 and 65, respectively:

```
                                      (SEQ ID NO: 77)
EVQLVESGGGLVQPGGSLRLSCAASGFTFSSYDMHWVRQAPGKGLEWVAV

MSYDGSNKYYADSVKGRFTISRDNSKNTLYLQMNSLRAEDTAVYYCATEI

AAKGDYWGQGTLVTVSS;
and
                                      (SEQ ID NO: 65)
AIQMTQSPSSLSASVGDRVTITCRASQGISNYLAWYQQKPGKAPKLLIYA

ASTLQSGVPSRFSGSGSGTDFTLTISSLQPEDFATYYCQQSYSTPHFGQG

TRLEIK.
```

To construct the 3-F03 antibody, the yeast 3-F03VH and VL were modified as follows and cloned into a human IgG1/kappa scaffold. For the VH, the N-terminal glutamate (E) of yeast 3-F03 VH (SEQ ID NO:77) was removed and the threonine (T) at Kabat position H77 of SEQ ID NO:77 (i.e., position 78 of SEQ ID NO:77) was substituted with an alanine (A). For the VL, the N-terminal alanine (A) of SEQ ID NO:65 was removed. The resulting full-length human 3-F03 antibody contains the VH and VL set forth in the amino acid sequences of SEQ ID NOs:60 and 61, respectively. The resulting full-length human 3-F03 antibody is referred to herein as "3-F03". Table 3, below, shows the amino acid sequences of the 3-F03 CDRs according to IMGT, Chothia, AbM, Kabat, and Contact numbering. Table 3, below, also shows the amino acid sequences of the 3-F03 mature VH, VL, heavy chain, and light chain.

contains an N-terminal glutamate (E) that is lacking in 3-F03 and (ii) does not include the C-terminal lysine present in 3-F03. Table 4, below, shows the amino acid sequences of the 3-F03_411 mature VH, VL, heavy chain and light chain. 3-F03_413 is identical to 3-F03_411, except that it contains a glutamate (E) at VH Kabat position H53 (position 54 of SEQ ID NO:60) instead of an aspartic acid (D). Table 5, below, shows the amino acid sequences of the 3-F03_413 CDRs according to IMGT, Chothia, AbM, Kabat, and Contact numbering. Table 5, below, also shows the amino acid sequences of the 3-F03_413 mature VH, VL, heavy chain, and light chain. Additional variants are described in the Examples below (see FIG. 12A-FIG. 12J).

TABLE 3

Amino acid sequences of 3-F03 CDRs, VH, and VL

| | IMGT | Chothia | AbM | Kabat | Contact |
|---|---|---|---|---|---|
| VH CDR1 | GFTFSSYD (SEQ ID NO: 34) | GFTFSSY (SEQ ID NO: 41) | GFTFSSYDMH (SEQ ID NO: 46) | SYDMH (SEQ ID NO: 49) | SSYDMH (SEQ ID NO: 53) |
| VH CDR2 | MSYDGSNK (SEQ ID NO: 35) | SYDGSN (SEQ ID NO: 42) | VMSYDGSNKY (SEQ ID NO: 47) | VMSYDGSNKYYADSVKG (SEQ ID NO: 50) | WVAVMSYDGSNKY (SEQ ID NO: 54) |
| VH CDR3 | ATEIAAKGDY (SEQ ID NO: 36) | EIAAKGDY (SEQ ID NO: 52) | EIAAKGDY (SEQ ID NO: 52) | EIAAKGDY (SEQ ID NO: 52) | ATEIAAKGD (SEQ ID NO: 56) |
| VL CDR1 | QGISNY (SEQ ID NO: 37) | RASQGISNYLA (SEQ ID NO: 44) | RASQGISNYLA (SEQ ID NO: 44) | RASQGISNYLA (SEQ ID NO: 44) | SNYLAWY (SEQ ID NO: 57) |
| VL CDR2 | AAS (SEQ ID NO: 38) | AASTLQS (SEQ ID NO: 45) | AASTLQS (SEQ ID NO: 45) | AASTLQS (SEQ ID NO: 45) | LLIYAASTLQ (SEQ ID NO: 58) |
| VL CDR3 | QQSYSTPH (SEQ ID NO: 39) | QQSYSTPH (SEQ ID NO: 39) | QQSYSTPH (SEQ ID NO: 39) | QQSYSTPH (SEQ ID NO: 39) | QQSYSTP (SEQ ID NO: 59) |

| VH | VQLVESGGGLVQPGGSLRLSCAASGFTFSSYDMHWVRQAPGKGLEWVAVMSYDGSNKYYA DSVKGRFTISRDNSKNALYLQMNSLRAEDTAVYYCATEIAAKGDYWGQGTLVTVSS (SEQ ID NO: 60) |
|---|---|
| VL | IQMTQSPSSLSASVGDRVTITCRASQGISNYLAWYQQKPGKAPKLLIYAASTLQSGVPSRFSGS GSGTDFTLTISSLQPEDFATYYCQQSYSTPHFGQGTRLEIK (SEQ ID NO: 61) |
| HC | VQLVESGGGLVQPGGSLRLSCAASGFTFSSYDMHWVRQAPGKGLEWVAVMSYDGSNKYYA DSVKGRFTISRDNSKNALYLQMNSLRAEDTAVYYCATEIAAKGDYWGQGTLVTVSSASTKG PSVFPLAPSSKSTSGGTAALGCLVKDYFPEPVTVSWNSGALTSGVHTFPAVLQSSGLYSLSSV VTVPSSSLGTQTYICNVNHKPSNTKVDKRVEPKSCDKTHTCPPCPAPELLGGPSVFLFPPKPKD TLMISRTPEVTCVVVDVSHEDPEVKFNWYVDGVEVHNAKTKPREEQYASTYRVVSVLTVLH QDWLNGKEYKCKVSNKALPAPIEKTISKAKGQPREPQVYTLPPSREEMTKNQVSLTCLVKGF YPSDIAVEWESNGQPENNYKTTPPVLDSDGSFFLYSKLTVDKSRWQQGNVFSCSVMHEALHN HYTQKSLSLSPGK (SEQ ID NO: 66) |
| LC | IQMTQSPSSLSASVGDRVTITCRASQGISNYLAWYQQKPGKAPKLLIYAASTLQSGVPSRFSGS GSGTDFTLTISSLQPEDFATYYCQQSYSTPHFGQGTRLEIKRTVAAPSVFIFPPSDEQLKSGTAS VVCLLNNFYPREAKVQWKVDNALQSGNSQESVTEQDSKDSTYSLSSTLTLSKADYEKHKVY ACEVTHQGLSSPVTKSFNRGEC (SEQ ID NO: 31) |

Variants of 3-F03 are also described herein. 3-F03_411 is identical to 3-F03, except that the 3-F03_411 heavy chain (i)

TABLE 4

Amino acid sequences of 3-F03 411 HC and LC

| | SEQUENCE |
|---|---|
| VH | EVQLVESGGGLVQPGGSLRLSCAASGFTFSSYDMHWVRQAPGKGLEWVAVMSYDGSNKYY ADSVKGRFTISRDNSKNALYLQMNSLRAEDTAVYYCATEIAAKGDYWGQGTLVTVSS (SEQ ID NO: 62) |

TABLE 4-continued

Amino acid sequences of 3-F03_411 HC and LC

| | SEQUENCE |
|---|---|
| VL | IQMTQSPSSLSASVGDRVTITCRASQGISNYLAWYQQKPGKAPKLLIYAASTLQSGVPSRFSGS<br>GSGTDFTLTISSLQPEDFATYYCQQSYSTPHFGQGTRLEIK (SEQ ID NO: 61) |
| Heavy<br>Chain | EVQLVESGGGLVQPGGSLRLSCAASGFTFSSYDMHWVRQAPGKGLEWVAVMSYDGSNKYY<br>ADSVKGRFTISRDNSKNALYLQMNSLRAEDTAVYYCATEIAAKGDYWGQGTLVTVSSASTK<br>GPSVFPLAPSSKSTSGGTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPAPELLGGPSVFLFPPKPK<br>DTLMISRTPEVTCVVVDVSHEDPEVKFNWYVDGVEVHNAKTKPREEQYASTYRVVSVLTVL<br>HQDWLNGKEYKCKVSNKALPAPIEKTISKAKGQPREPQVYTLPPSREEMTKNQVSLTCLVKG<br>FYPSDIAVEWESNGQPENNYKTTPPVLDSDGSFFLYSKLTVDKSRWQQGNVFSCSVMHEALH<br>NHYTQKSLSLSPG (SEQ ID NO: 30) |
| Light<br>Chain | IQMTQSPSSLSASVGDRVTITCRASQGISNYLAWYQQKPGKAPKLLIYAASTLQSGVPSRFSGS<br>GSGTDFTLTISSLQPEDFATYYCQQSYSTPHFGQGTRLEIKRTVAAPSVFIFPPSDEQLKSGTAS<br>VVCLLNNFYPREAKVQWKVDNALQSGNSQESVTEQDSKDSTYSLSSTLTLSKADYEKHKVY<br>ACEVTHQGLSSPVTKSFNRGEC (SEQ ID NO: 31) |

TABLE 5

Amino acid sequences of 3-F03_413 CDRs, VH, VL, HC, LC

| | IMGT | Chothia | AbM | Kabat | Contact |
|---|---|---|---|---|---|
| VH CDR1 | GFTFSSYD (SEQ ID NO: 34) | GFTFSSY (SEQ ID NO: 41) | GFTFSSYDMH (SEQ ID NO: 46) | SYDMH (SEQ ID NO: 49) | SSYDMH (SEQ ID NO: 53) |
| VH CDR2 | MSYEGSNK (SEQ ID NO: 40) | SYEGSN (SEQ ID NO: 43) | VMSYEGSNKY (SEQ ID NO: 48) | VMSYEGSNKYYADSVKG (SEQ ID NO: 51) | WVAVMSYEGSNKY (SEQ ID NO: 55) |
| VH CDR3 | ATEIAAKGDY (SEQ ID NO: 36) | EIAAKGDY (SEQ ID NO: 52) | EIAAKGDY (SEQ ID NO: 52) | EIAAKGDY (SEQ ID NO: 52) | ATEIAAKGD (SEQ ID NO: 56) |
| VL CDR1 | QGISNY (SEQ ID NO: 37) | RASQGISNYLA (SEQ ID NO: 44) | RASQGISNYLA (SEQ ID NO: 44) | RASQGISNYLA (SEQ ID NO: 44) | SNYLAWY (SEQ ID NO: 57) |
| VL CDR2 | AAS (SEQ ID NO: 38) | AASTLQS (SEQ ID NO: 45) | AASTLQS (SEQ ID NO: 45) | AASTLQS (SEQ ID NO: 45) | LLIYAASTLQ (SEQ ID NO: 58) |
| VL CDR3 | QQSYSTPH (SEQ ID NO: 39) | QQSYSTPH (SEQ ID NO: 39) | QQSYSTPH (SEQ ID NO: 39) | QQSYSTPH (SEQ ID NO: 39) | QQSYSTP (SEQ ID NO: 59) |
| VH | EVQLVESGGGLVQPGGSLRLSCAASGFTFSSYDMHWVRQAPGKGLEWVAVMSYEGSNKYY<br>ADSVKGRFTISRDNSKNALYLQMNSLRAEDTAVYYCATEIAAKGDYWGQGTLVTVSS (SEQ ID NO: 63) | | | | |
| VL | IQMTQSPSSLSASVGDRVTITCRASQGISNYLAWYQQKPGKAPKLLIYAASTLQSGVPSRFSGS<br>GSGTDFTLTISSLQPEDFATYYCQQSYSTPHFGQGTRLEIK (SEQ ID NO: 61) | | | | |
| HC | EVQLVESGGGLVQPGGSLRLSCAASGFTFSSYDMHWVRQAPGKGLEWVAVMSYEGSNKYY<br>ADSVKGRFTISRDNSKNALYLQMNSLRAEDTAVYYCATEIAAKGDYWGQGTLVTVSSASTK<br>GPSVFPLAPSSKSTSGGTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPAPELLGGPSVFLFPPKPK<br>DTLMISRTPEVTCVVVDVSHEDPEVKFNWYVDGVEVHNAKTKPREEQYASTYRVVSVLTVL<br>HQDWLNGKEYKCKVSNKALPAPIEKTISKAKGQPREPQVYTLPPSREEMTKNQVSLTCLVKG<br>FYPSDIAVEWESNGQPENNYKTTPPVLDSDGSFFLYSKLTVDKSRWQQGNVFSCSVMHEALH<br>NHYTQKSLSLSPG (SEQ ID NO: 33) | | | | |
| LC | IQMTQSPSSLSASVGDRVTITCRASQGISNYLAWYQQKPGKAPKLLIYAASTLQSGVPSRFSGS<br>GSGTDFTLTISSLQPEDFATYYCQQSYSTPHFGQGTRLEIKRTVAAPSVFIFPPSDEQLKSGTAS<br>VVCLLNNFYPREAKVQWKVDNALQSGNSQESVTEQDSKDSTYSLSSTLTLSKADYEKHKVY<br>ACEVTHQGLSSPVTKSFNRGEC (SEQ ID NO: 31) | | | | |

The anti-CD73 antibodies can encompass the VH CDR1, VH CDR2, and VH CDR3 and the VL CDR1, VL CDR2, and VL CDR3 of 3-1F03 or 3-103413. In some instances, the anti-CD73 antibody comprises a VH comprising VH CDR1, VH CDR2, and VH CDR3 of 3-F03 (see Table 3). In some instances, the anti-CD73 antibody comprises a VL comprising VL CDR1, VL CDR2, and VL CDR3 of 3-1F03 (see Table 3). In some instances, the anti-CD73 antibody comprises a VH comprising VH CDR1, VH CDR2, and VH CDR3 of 3-103 (see Table 3) and a VL comprising VL CDR1, VL CDR2, and VL CDR3 of 3-1F03 (see Table 3). In some instances, the anti-CD73 antibody comprises a VH comprising VH CDR1, VH CDR2, and VH CDR3 of 3-103413 (see Table 5). In some instances, the anti-CD73 antibody comprises a VL comprising VL CDR1, VL CDR2, and VL CDR3 of 3-103413 (see Table 5). In some instances, the anti-CD73 antibody comprises a VH comprising VH CDR1, VH CDR2, and VH CDR3 of 3-103413 (see Table 5) and a VL comprising VL CDR1, VL CDR2, and VL CDR3 of 3-103413 (see Table 5). In some instances, the anti-CD73 antibodies can have, e.g., 1, 2, or 3 substitutions within one or more (i.e., 1, 2, 3, 4, 5, or 6) of the six CDRs of 3-F03 or 3-F03_413. In some instances, these antibodies (i) inhibit cellular CD73 (e.g., at least 10%; at least 20%, at least 30%, at least 40%, at least 50%, at least 60%, at least 70%, at least 80%, at least 90%, at least 95%, at least 97%, at least 99%, or 100% reduction in cellular CD73 activity as compared to an isotype control as determined by, e.g., the assay described in Example 10); and/or (ii) inhibit soluble CD73 (e.g., at least 10%; at least 20%, at least 30%, at least 40%, at least 50%, at least 60%, at least 70%, at least 80%, at least 90%, at least 95%, at least 97%, at least 99%, or 100% reduction in soluble CD73 activity as compared to an isotype control as determined by, e.g., the assay described in Example 11); and/or (iii) bind human, cynomolgus monkey, or murine CD73 in the open conformation with high affinity (e.g., $K_D \leq 2$ nM) (e.g., as determined by the binding assay described in Example 12); and/or (iv) do not bind human, cynomolgus monkey, or murine CD73 in the closed conformation; and/or (v) bind to an epitope within amino acids 386-399 of SEQ ID NO:70 (i.e., within AAVLPFGGTFDLVQ (SEQ ID NO:78) amino acids 470-489 of SEQ ID NO:70 (i.e., within ILPNFLANGGDGFQMIKDEL (SEQ ID NO:79)) (e.g., as determined by the binding assay described in Example 12); and/or (vi) reduce AMP-mediated suppression of T cell proliferation (e.g., at least 10%; at least 20%, at least 30%, at least 40%, at least 50%, at least 60%, at least 70%, at least 80%, at least 90%, at least 95%, at least 97%, at least 99%, or 100% reduction in T cell proliferation as compared to an isotype control as determined by, e.g., the assay described in Example 16); and/or (vii) decreases levels of cell surface CD73 (e.g., on cancer cells, e.g., on melanoma cancer cells, e.g., by at least 10%; at least 20%, at least 30%, at least 40%, at least 50%, at least 60%, at least 70%, at least 80%, at least 90%, at least 95%, at least 97%, at least 99%, or 100% as compared to an isotype control); and/or (viii) reduce tumor growth (e.g., melanoma tumors, e.g., by at least 10%; at least 20%, at least 30%, at least 40%, at least 50%, at least 60%, at least 70%, at least 80%, at least 90%, at least 95%, at least 97%, at least 99%, or 100% as compared to an isotype control as determined by, e.g., the assay described in Example 17).

The anti-CD73 antibodies can comprise the VH CDR1, VH CDR2, and VH CDR3 of 3-F03 or 3-F03_413 according to the IMGT definition, or an alternate CDR definition such as, but not limited to, the Kabat definition, the Chothia definition, the AbM CDR definition, or the contact definition. These anti-CD73 antibodies may include zero, one, two, or three substitutions in VH CDR1 and/or VH CDR2 and/or VH CDR3 of 3-F03 or 3-F03_413. In some embodiments, the anti-CD73 antibodies further comprise the VL CDR1, VL CDR2, and VL CDR3 of 3-F03 or 3-F03_413 according to the IMGT definition, or an alternate CDR definition such as, but not limited to, the Kabat definition, the Chothia definition, the AbM CDR definition, or the contact definition. These anti-CD73 antibodies may include zero, one, two, or three substitutions in VL CDR1 and/or VL CDR2 and/or VL CDR3 of 3-F03 or 3-F03_413. In some instances, the anti-CD73 antibody comprises a VH comprising the VH CDR1, VH CDR2, and VH CDR3 set forth in SEQ ID NOs: 34, 35, and 36, respectively, and a VL comprising the VL CDR1, VL CDR2, and VL CDR3 set forth in SEQ ID NOs: 37, 38, and 39, respectively. In some instances, the anti-CD73 antibody comprises a VH comprising the VH CDR1, VH CDR2, and VH CDR3 set forth in SEQ ID NOs: 41, 42, and 52, respectively, and a VL comprising the VL CDR1, VL CDR2, and VL CDR3 set forth in SEQ ID NOs: 44, 45, and 39, respectively. In some instances, the anti-CD73 antibody comprises a VH comprising the VH CDR1, VH CDR2, and VH CDR3 set forth in SEQ ID NOs: 46, 47, and 52, respectively, and a VL comprising the VL CDR1, VL CDR2, and VL CDR3 set forth in SEQ ID NOs: 44, 45, and 39, respectively. In some instances, the anti-CD73 antibody comprises a VH comprising the VH CDR1, VH CDR2, and VH CDR3 set forth in SEQ ID NOs: 49, 50, and 52, respectively, and a VL comprising the VL CDR1, VL CDR2, and VL CDR3 set forth in SEQ ID NOs: 44, 45, and 39, respectively. In some instances, the anti-CD73 antibody comprises a VH comprising the VH CDR1, VH CDR2, and VH CDR3 set forth in SEQ ID NOs: 53, 54, and 56, respectively, and a VL comprising the VL CDR1, VL CDR2, and VL CDR3 set forth in SEQ ID NOs: 57, 58, and 59, respectively. In some instances, the anti-CD73 antibody comprises a VH comprising the VH CDR1, VH CDR2, and VH CDR3 set forth in SEQ ID NOs: 34, 40, and 36, respectively, and a VL comprising the VL CDR1, VL CDR2, and VL CDR3 set forth in SEQ ID NOs: 37, 38, and 39, respectively. In some instances, the anti-CD73 antibody comprises a VH comprising the VH CDR1, VH CDR2, and VH CDR3 set forth in SEQ ID NOs: 41, 43, and 52, respectively, and a VL comprising the VL CDR1, VL CDR2, and VL CDR3 set forth in SEQ ID NOs: 44, 45, and 39, respectively. In some instances, the anti-CD73 antibody comprises a VH comprising the VH CDR1, VH CDR2, and VH CDR3 set forth in SEQ ID NOs: 46, 48, and 52, respectively, and a VL comprising the VL CDR1, VL CDR2, and VL CDR3 set forth in SEQ ID NOs: 44, 45, and 39, respectively. In some instances, the anti-CD73 antibody comprises a VH comprising the VH CDR1, VH CDR2, and VH CDR3 set forth in SEQ ID NOs: 49, 51, and 52, respectively, and a VL comprising the VL CDR1, VL CDR2, and VL CDR3 set forth in SEQ ID NOs: 44, 45, and 39, respectively. In some instances, the anti-CD73 antibody comprises a VH comprising the VH CDR1, VH CDR2, and VH CDR3 set forth in SEQ ID NOs: 53, 55, and 56, respectively, and a VL comprising the VL CDR1, VL CDR2, and VL CDR3 set forth in SEQ ID NOs: 57, 58, and 59, respectively. In some instances, these antibodies (i) inhibit cellular CD73 (e.g., at least 10%; at least 20%, at least 30%, at least 40%, at least 50%, at least 60%, at least 70%, at least 80%, at least 90%, at least 95%, at least 97%, at least 99%, or 100% reduction in cellular CD73 activity as compared to an isotype control as determined by, e.g., the assay described in Example 10); and/or (ii) inhibit soluble CD73 (e.g., at least 10%; at least 20%, at least 30%, at least 40%, at least 50%, at least 60%, at least 70%, at least 80%, at least 90%, at least 95%, at least 97%, at least 99%, or 100% reduction in soluble CD73 activity as compared to an isotype control as determined by, e.g., the assay described in Example 11); and/or (iii) bind human, cynomolgus monkey, or murine CD73 in the open conformation with high affinity (e.g., $K_D \leq 2$ nM) (e.g., as determined by the binding assay described in Example 12); and/or (iv) do not bind human, cynomolgus monkey, or murine CD73 in the closed conformation; and/or (v) bind to an epitope within amino acids 386-399 of SEQ ID NO:70 (i.e., within AAVLPFGGTFDLVQ (SEQ ID NO:78) amino acids 470-489 of SEQ ID NO:70 (i.e., within ILPNFLANGGDGFQMIKDEL (SEQ ID NO:79)) (e.g., as determined by the binding assay described in Example 12); and/or (vi) reduce AMP-mediated suppression of T cell proliferation (e.g., at least 10%; at least 20%, at least 30%, at least 40%, at least 50%, at least 60%, at least 70%, at least 80%, at least 90%, at least 95%, at least 97%, at least 99%, or 100% reduction in T cell proliferation as compared to an isotype control as determined by, e.g., the assay described in Example 16); and/or (vii) decreases levels of cell surface CD73 (e.g., on cancer cells, e.g., on melanoma cancer cells, e.g., by at least 10%; at least 20%, at least 30%, at least 40%, at least 50%, at least 60%, at least 70%, at least 80%, at least 90%, at least 95%, at least 97%, at least 99%, or 100% as compared to an isotype control); and/or (viii) reduce tumor growth (e.g., melanoma tumors, e.g., by at least 10%; at least 20%, at least 30%, at least 40%, at least 50%, at least 60%, at least 70%, at least 80%, at least 90%, at least 95%, at least 97%, at least 99%, or 100% as compared to an isotype control as determined by, e.g., the assay described in Example 17).

In certain embodiments, the anti-CD73 antibodies comprise an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs: 32, 60, 62, 63, 67-69, 77, and 85-88. In certain embodiments, the anti-CD73 antibodies comprise a VH comprising the VH CDR1, VH CDR2, and VH CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs: 34-36, respectively, or SEQ ID NOs:34, 40 and 36, respectively), wherein the VH comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs: 32, 60, 62, 63, 67-69, 77, and 85-88. In some embodiments, the anti-CD73 antibodies comprise an amino acid sequence having one or more (e.g., 1, 2, 3, 4, 5, 6, 7, 8, 9, 10) amino acid substitutions, additions, and/or deletions relative to the amino acid sequence set forth in SEQ ID NO: 30, 33, and 66. In some embodiments, the anti-CD73 antibodies comprise a heavy chain comprising the VH CDR1, VH CDR2, and VH CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs:34-36, respectively, or SEQ ID NOs:34, 40, and 36, respectively), wherein the heavy chain comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO: 30, 33, and 66. In certain embodiments, the anti-CD73 antibodies comprise an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs: 61, 64, and 65. In certain embodiments, the anti-CD73 antibodies comprise a VL comprising the VL CDR1, VL CDR2, and VL CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs: 37-39, respectively), wherein the VL comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs: 61, 64, and 65. In some embodiments, the anti-CD73 antibodies comprise an amino acid sequence having one or more (e.g., 1, 2, 3, 4, 5, 6, 7, 8, 9, 10) amino acid substitutions, additions, and/or deletions relative to the amino acid sequence set forth in SEQ ID NO: 31. In some embodiments, the anti-CD73 antibodies comprise a light chain comprising the VL CDR1, VL CDR2, and VL CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs:37-39, respectively), wherein the light chain comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO: 31. In certain embodiments, the anti-CD73 antibodies comprise: (i) an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs: 32, 60, 62, 63, 67-69, 77, and 85-88; and (ii) an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs: 61, 64, and 65. In certain embodiments, the anti-CD73 antibodies comprise: (i) a VH comprising the VH CDR1, VH CDR2, and VH CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs:34-36, respectively, or SEQ ID NOs: 34, 40, and 36, respectively), wherein the VH comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs: 32, 60, 62, 63, 67-69, 77, and 85-88; and (ii) a VL comprising the VL CDR1, VL CDR2, and VL CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs: 37-39, respectively), wherein the VL comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs: 61, 64, and 65. In some embodiments, the anti-CD73 antibodies comprise: (i) an amino acid sequence having one or more (e.g., 1, 2, 3, 4, 5, 6, 7, 8, 9, 10) amino acid substitutions, additions, and/or deletions relative to the amino acid sequence set forth in SEQ ID NOs: 30, 33, and 66; and (ii) an amino acid sequence having one or more (e.g., 1, 2, 3, 4, 5, 6, 7, 8, 9, 10) amino acid substitutions, additions, and/or deletions relative to the amino acid sequence set forth in SEQ ID NO: 31. In some embodiments, the anti-CD73 antibodies comprise: (i) a heavy chain comprising the VH CDR1, VH CDR2, and VH CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs: 34-36, respectively, or SEQ ID NOs:34, 40, and 36, respectively), wherein the heavy chain comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO: 30, 33, and 66; and (ii) a light chain comprising the VL CDR1, VL CDR2, and VL CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs:37-39, respectively), wherein the light chain comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO: 31.

In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH set forth in any one of SEQ ID NOs: 32, 60, 62, 63, 67-69, 77, and 85-88. In certain embodiments, the anti-CD73 antibodies comprise a VH comprising the VH CDR1, VH CDR2, and VH CDR3 of 3-F03 or a variant thereof (e.g., 3-F03_411 or 3-F03413) (see, e.g., Table 3 and Table 5, e.g., according to the IMGT definition, e.g., the amino acid sequences set forth in SEQ ID NOs:34-36, respectively, or SEQ ID NOs:34, 40, and 36, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH set forth in any one of SEQ ID NOs: 32, 60, 62, 63, 67-69, 77, and 85-88. In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL set forth in any one of SEQ ID NOs: 61, 64, and 65. In certain embodiments, the anti-CD73 antibodies comprise a VL comprising the VL CDR1, VL CDR2, and VL CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs:37-39, respectively), wherein the VL comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL set forth in any one of SEQ ID NOs: 61, 64, and 65. In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH set forth in any one of SEQ ID NOs: 32, 60, 62, 63, 67-69, 77, and 85-88 and an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL set forth in SEQ ID NO: 61, 64, and 65. In certain embodiments, the anti-CD73 antibodies comprise: (i) a VH comprising the VH CDR1, VH CDR2, and VH CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs:34-36, respectively, or SEQ ID NOs: 34, 40, and 36, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH set forth in any one of SEQ ID NOs: 32, 60, 62, 63, 67-69, 77, and 85-88, and (ii) a VL comprising the VL CDR1, VL CDR2, and VL CDR3 of 3-F03 or a variant thereof (e.g., 3-F03_411 or 3-F03_413) (see, e.g., Table 3 and Table 5, e.g., according to the IMGT definition, e.g., the amino acid sequences set forth in SEQ ID NOs:37-39, respectively), wherein the VL comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL set forth in any one of SEQ ID NOs: 61, 64, and 65.

In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of 3-F03_411 or 3-F03_413 (i.e., the amino acid sequence set forth in SEQ ID NO:62 or 63, respectively). In certain embodiments, the anti-CD73 antibodies comprise a VH comprising the VH CDR1, VH CDR2, and VH CDR3 of 3-F03411 (see Table 3, e.g., according to the IMGT definition, i.e., the amino acid sequences set forth in SEQ ID NOs: 34-36, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of 3-F03_411 (i.e., the amino acid sequence set forth in SEQ ID NO:62). In certain embodiments, the anti-CD73 antibodies comprise a VH comprising the VH CDR1, VH CDR2, and VH CDR3 of 3-F03413 (see Table 5, e.g., according to the IMGT definition, i.e., the amino acid sequences set forth in SEQ ID NOs: 34, 40, and 36, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of 3-F03_411 (i.e., the amino acid sequence set forth in SEQ ID NO:63). In some embodiments, the anti-CD73 antibodies comprise a VH comprising the amino acid sequence set forth in SEQ ID NO:62. In some embodiments, the anti-CD73 antibodies comprise a VH comprising the amino acid sequence set forth in SEQ ID NO:63. In some embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the heavy chain of 3-F03_411 or 3-F03_F13 (i.e., the amino acid sequence set forth in SEQ ID NO:30 or 33, respectively). In some embodiments, the anti-CD73 antibodies comprise a heavy chain comprising a VH comprising the VH CDR1, VH CDR2, and VH CDR3 of 3-F03_411 (see Table 3, e.g., according to the IMGT definition, i.e., the amino acid sequences set forth in SEQ ID NOs: 34-36, respectively), wherein the heavy chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the heavy chain of 3-F03_411 (i.e., the amino acid sequence set forth in SEQ ID NO:30). In some embodiments, the anti-CD73 antibodies comprise a heavy chain comprising a VH comprising the VH CDR1, VH CDR2, and VH CDR3 of 3-F03413 (see Table 5, e.g., according to the IMGT definition, i.e., the amino acid sequences set forth in SEQ ID NOs: 34, 40, and 36, respectively), wherein the heavy chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the heavy chain of 3-F03_413 (i.e., the amino acid sequence set forth in SEQ ID NO:33). In some embodiments, the anti-CD73 antibodies comprise a heavy chain comprising the amino acid sequence set forth in SEQ ID NO:30. In some embodiments, the anti-CD73 antibodies comprise a heavy chain comprising the amino acid sequence set forth in SEQ ID NO:33. In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL of 3-F03_411 or 3-F03413 (i.e., the amino acid sequence set forth in SEQ ID NO:61). In certain embodiments, the anti-CD73 antibodies comprise a VL comprising the VL CDR1, VL CDR2, and VL CDR3 of 3-F03_411 or 3-F03_413 (see Table 3, e.g., according to the IMGT definition, i.e., the amino acid sequences set forth in SEQ ID NOs: 37-39, respectively), wherein the VL comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL of 3-F03_411 or 3-F03_413 (i.e., the amino acid sequence set forth in SEQ ID NO:61). In some embodiments, the anti-CD73 antibodies comprise a VL comprising the amino acid sequence set forth in SEQ ID NO:61. In some embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the light chain of 3-F03_411 or 3-F03_413 (i.e., the amino acid sequence set forth in SEQ ID NO:31). In some embodiments, the anti-CD73 antibodies comprise a light chain comprising a VL comprising the VL CDR1, VL CDR2, and VL CDR3 of 3-F03_411 or 3-F03_413 (see Table 5, e.g., according to the IMGT definition, i.e., the amino acid sequences set forth in SEQ ID NOs: 37-39, respectively), wherein the light chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the light chain of 3-F03_411 or 3-F03_413 (i.e., the amino acid sequence set forth in SEQ ID NO:31). In some embodiments, the anti-CD73 antibodies comprise a light chain comprising the amino acid sequence set forth in SEQ ID NO:31. In certain embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of 3-F03_411 or 3-F03_413 (i.e., the amino acid sequence set forth in SEQ ID NO:62 or 63, respectively) and an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL of 3-F03_411 or 3-F03_413 (i.e., the amino acid sequence set forth in SEQ ID NO:61). In certain embodiments, the anti-CD73 antibodies comprise: (i) a VH comprising the VH CDR1, VH CDR2, and VH CDR3 of 3-F03411 (see Table 3, e.g., according to the IMGT definition, i.e., the amino acid sequences set forth in SEQ ID NOs: 34-36, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of 3-F03 (i.e., the amino acid sequence set forth in SEQ ID NO:62), and (ii) a VL comprising the VL CDR1, VL CDR2, and VL CDR3 of 3-F03_411 (see Table 3, e.g., according to the IMGT definition, i.e., the amino acid sequences set forth in SEQ ID NOs: 37-39, respectively), wherein the VL comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL of 3-F03 (i.e., the amino acid sequence set forth in SEQ ID NO:61). In certain embodiments, the anti-CD73 antibodies comprise: (i) a VH comprising the VH CDR1, VH CDR2, and VH CDR3 of 3-F03_413 (see Table 5, e.g., according to the IMGT definition, i.e., the amino acid sequences set forth in SEQ ID NOs: 34, 40, and 36, respectively), wherein the VH comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VH of 3-F03_413 (i.e., the amino acid sequence set forth in SEQ ID NO:63), and (ii) a VL comprising the VL CDR1, VL CDR2, and VL CDR3 of 3-F03_413 (see Table 5, e.g., according to the IMGT definition, i.e., the amino acid sequences set forth in SEQ ID NOs: 37-39, respectively), wherein the VL comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the VL of 3-F03_413 (i.e., the amino acid sequence set forth in SEQ ID NO:61). In some embodiments, the anti-CD73 antibody comprises: (i) a VH comprising the amino acid sequence set forth in SEQ ID NO:62; and (ii) a VL comprising the amino acid sequence set forth in SEQ ID NO:61. In some embodiments, the anti-CD73 antibody comprises: (i) a VH comprising the amino acid sequence set forth in SEQ ID NO:63; and (ii) a VL comprising the amino acid sequence set forth in SEQ ID NO:61. In some embodiments, the anti-CD73 antibodies comprise an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the heavy chain of 3-F03_411 or 3-F03_413 (i.e., the amino acid sequence set forth in SEQ ID NO:30 or 33) and an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the light chain of 3-F03_411 or 3-F03413 (i.e., the amino acid sequence set forth in SEQ ID NO:31). In some embodiments, the anti-CD73 antibodies comprise: (i) a heavy chain comprising the a VH comprising the VH CDR1, VH CDR2, and VH CDR3 of 3-F03_411 (see Table 3, e.g., according to the IMGT definition, i.e., the amino acid sequences set forth in SEQ ID NOs: 34-36, respectively), wherein the heavy chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the heavy chain of 3-F03_411 (i.e., the amino acid sequence set forth in SEQ ID NO:30), and (ii) a light chain comprising a VL comprising the VL CDR1, VL CDR2, and VL CDR3 of 3-F03_411 (see Table 3, e.g., according to the IMGT definition, i.e., the amino acid sequences set forth in SEQ ID NOs: 37-39, respectively), wherein the light chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the light chain of 3-F03 (i.e., the amino acid sequence set forth in SEQ ID NO:31). In some embodiments, the anti-CD73 antibodies comprise: (i) a heavy chain comprising the a VH comprising the VH CDR1, VH CDR2, and VH CDR3 of 3-F03413 (see Table 5, e.g., according to the IMGT definition, i.e., the amino acid sequences set forth in SEQ ID NOs: 34, 40, and 36, respectively), wherein the heavy chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the heavy chain of 3-F03 (i.e., the amino acid sequence set forth in SEQ ID NO:33), and (ii) a light chain comprising a VL comprising the VL CDR1, VL CDR2, and VL CDR3 of 3-F03_413 (see Table 5, e.g., according to the IMGT definition, i.e., the amino acid sequences set forth in SEQ ID NOs: 37-39, respectively), wherein the light chain comprises an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the light chain of 3-F03_413 (i.e., the amino acid sequence set forth in SEQ ID NO:31). In some embodiments, the anti-CD73 antibody comprises: (i) a heavy chain comprising the amino acid sequence set forth in SEQ ID NO:30; and (ii) a light chain comprising the amino acid sequence set forth in SEQ ID NO:31. In some embodiments, the anti-CD73 antibody comprises: (i) a heavy chain comprising the amino acid sequence set forth in SEQ ID NO:33; and (ii) a light chain comprising the amino acid sequence set forth in SEQ ID NO:31.

The CD73-binding epitope of 3-F03 (and variants thereof, e.g., 3-F03_411 and 3-F03_413) contains AAVLPFGGTFDLVQ (SEQ ID NO:78) (i.e., amino acids 386-399 of the amino acid sequence set forth in SEQ ID NO:70) and ILPNFLANGGDGFQMIKDEL (SEQ ID NO:79) (i.e., amino acids 470-489 of the amino acid sequence set forth in SEQ ID NO:70). This disclosure features antibodies that bind to CD73 an epitope within AAVLPFGGTFDLVQ (SEQ ID NO:78) and ILPNFLANGGDGFQMIKDEL (SEQ ID NO:79). This disclosure features antibodies that bind to the same epitope as 3-F03 (or a variant thereof, e.g., 3-F03_411 or 3-F03_413). This disclosure also features antibodies that competitively inhibit binding of 3-F03 (or a variant thereof, e.g., 3-F03_411 or 3-F03_413) to human CD73.

In some embodiments, the VH of 3-F03 (or a variant thereof, e.g., 3-F03_411 or 3-F03_413) is linked to a heavy chain constant region comprising a CH1 domain and a hinge region. In some embodiments, the VH of 3-F03 (or a variant thereof, e.g., 3-F03_411 or 3-F03_413) is linked to a heavy chain constant region comprising a CH3 domain. In some embodiments, the CH3 domain lacks the C-terminal lysine (K) amino acid residue. In some embodiments, the CH3 domain contains the C-terminal lysine (K) amino acid residue. In certain embodiments, the VH of 3-F03 (or a variant thereof, e.g., 3-F03_411 or 3-F03413) is linked to a heavy chain constant region comprising a CH1 domain, hinge region, CH2 domain, and CH3 domain from human IgG1. In some embodiments, the CH3 domain from human IgG1 lacks the C-terminal lysine (K) amino acid residue. In some embodiments, the CH3 domain from human IgG1 contains the C-terminal lysine (K) amino acid residue. In certain embodiments such an antibody contains one or more additional mutations in the heavy chain constant region that increase the stability of the antibody. In certain embodiments, the heavy chain constant region includes substitutions that modify the properties of the antibody (e.g., decrease Fc receptor binding, increase or decrease antibody glycosylation, decrease binding to C1q). In certain embodiments, the heavy chain constant region includes an alanine (A) at position Asparagine-297 (N297, according to EU numbering) of the heavy chain constant region to reduce effector function.

In certain embodiments, the anti-CD73 antibody is an IgG antibody. In one embodiment, the antibody is an IgG1 antibody. In one embodiment, the antibody is an IgG4 antibody. In another embodiment, the antibody is an IgG2 antibody. In certain embodiments, the anti-CD73 antibody comprises a heavy chain constant region lacking one or more lysine (K) amino acid residues relative to a wild type heavy chain constant region. For example, in certain embodiments, the antibody comprises heavy chain constant region lacking the C-terminal lysine (K) amino acid residue of the CH3 domain of the heavy chain constant region. In certain embodiments, the anti-CD73 antibody comprises a heavy chain constant region having the amino acid sequence set forth in SEQ ID NO:73. In certain embodiments, the anti-CD73 antibody comprises a heavy chain constant region having the amino acid sequence set forth in SEQ ID NO:75. In certain embodiments, the anti-CD73 antibody comprises a light chain constant region having the amino acid sequence set forth in SEQ ID NO:74. In certain embodiments, the anti-CD73 antibody comprises a heavy chain constant region having the amino acid sequence set forth in SEQ ID NO:73 and a light chain constant region having the amino acid sequence set forth in SEQ ID NO:74. In certain embodiments, the anti-CD73 antibody comprises a heavy chain constant region having the amino acid sequence set forth in SEQ ID NO:75 and a light chain constant region having the amino acid sequence set forth in SEQ ID NO:74.

Additional Anti-CD73 Antibodies and Inhibitors

This disclosure provides additional anti-CD73 antibodies and CD73 inhibitors that are useful in combination with an A2A and/or A2B adenosine receptor inhibitor in treating diseases, e.g., cancer.

Other anti-CD73 antibodies useful in combination with an inhibitor of A2A and/or A2B adenosine receptor in the methods described herein are known in the art. See, e.g., U.S. Pat. Nos. 9,090,697, 9,388,249, 9,605,080, 9,938,356, 10,100,129, and 10,287,362, US Patent Application Publication Nos. 2004/0142342, 2007/0009518, 2011/0300136, 2018/0009899, 2018/0030144, 2018/0237536, 2018/0264107, 2019/0031766, 2019/0225703, 2019/0077873, and 2019/0256598, and international patent application publication nos. WO 2004/079013, WO 2011/089004, WO 2014/153424, WO 2017/100670, WO 2001/080884, WO 2018/110555, WO 2018/137598, WO 2018/187512, WO 2018/215535, WO 2018/237173, WO 2019/170131, WO 2019/173692, and WO 2019/173291, each of which is incorporated by reference herein in its entirety.

In some instances, the anti-CD73 antibody comprises a VH comprising a VH CDR1, a VH CDR2, and a VH CDR3 of a VH comprising the amino acid sequence EIQLQQSG-PELVKPGASVKVSCKASGYAFTSYN-MYWVKQSHGKSLEWIGYIDPYNG GTSYN-QKFKGKATLTVDKSSSTAYMHLNSLTSEDSAVYYCAR-GYGNYKAWFAYW GQGTLVTVSA (SEQ ID NO:100), and a VL comprising a VL CDR1, a VL CDR2, and a VL CDR3 of a VL comprising the amino acid sequence DAVMTQTPKFLLVSAGDRVTITCK-ASQSVTNDVAWYQQKPGQSPKLLIYYASNRYT GVPDRFTGSGYGTDFTFTISTVQAEDLAVYFCQQD-YSSLTFGAGTKLELK (SEQ ID NO:101). In some instances, the anti-CD73 antibody comprises a VH comprising the amino acid sequence set forth in SEQ ID NO:100 and a VL comprising the amino acid sequence set forth in SEQ ID NO:101. In some instances, the anti-CD73 antibody is 11E1 (see US patent application publication no. 2018/0237536, which is incorporated by reference herein in its entirety). In some instances, the anti-CD73 antibody comprises a heavy chain comprising the amino acid sequence set forth in SEQ ID NO:102. In some instances, the anti-CD73 antibody comprises a light chain comprising the amino acid sequence set forth in SEQ ID NO:103. In some instances, the anti-CD73 antibody comprises a heavy chain comprising the amino acid sequence set forth in SEQ ID NO:102 and a light chain comprising the amino acid sequence set forth in SEQ ID NO:103.

In some instances, the anti-CD73 antibody comprises a VH comprising a VH CDR1, a VH CDR2, and a VH CDR3 of a VH comprising the amino acid sequence EVQLLESGGGLVQPGGSLRLSCAASGFTFSSYAY-SWVRQAPGKGLEWVSAISGSGGR TYY-ADSVKGRFTISRDNSKNTLYLQMNSLRAEDTAVYY-CARLGYGRVDEWGRGTL VTVSS (SEQ ID NO:96), and a VL comprising a VL CDR1, a VL CDR2, and a VL CDR3 of a VL comprising the amino acid sequence QSVLTQPP-SASGTPGQRVTISCSGSLSNI-GRNPVNWYQQLPGTAPKLLIYLDNLRLSG VPDRFSGSKSGTSASLAISGLQSEDEADYYCATWDD-SHPGWTFGGGTKLTVL (SEQ ID NO:97). In some instances, the anti-CD73 antibody comprises a VH comprising the amino acid sequence set forth in SEQ ID NO:96 and a VL comprising the amino acid sequence set forth in SEQ ID NO:97. In some instances, the anti-CD73 antibody is Medi9447 (see U.S. Pat. No. 10,287,362, which is incorporated by reference herein in its entirety). In some instances, the anti-CD73 antibody comprises a heavy chain comprising the amino acid sequence set forth in SEQ ID NO:98. In some instances, the anti-CD73 antibody comprises a light chain comprising the amino acid sequence set forth in SEQ ID NO:99. In some instances, the anti-CD73 antibody comprises a heavy chain comprising the amino acid sequence set forth in SEQ ID NO:98 and a light chain comprising the amino acid sequence set forth in SEQ ID NO:99.

In some instances, the CD73 inhibitor is CPI-006 (Corvus; see US Patent Application Publication No. US 2018/0009899 A1 and international patent application publication no. WO 2017/100670 A1, each of which is incorporated by reference herein in its entirety).

In some instances, the CD73 inhibitor is CB-708 SM (Calithera).

In some instances, the CD73 inhibitor is AB680 (Arcus).

In some instances, the CD73 inhibitor is BMS-986179 (BMS).

Antibody Fragments

In some instances, the anti-CD73 antibody is an antibody fragment. Fragments of the antibodies described herein (e.g., Fab, Fab', F(ab')$_2$, Facb, and Fv) may be prepared by proteolytic digestion of intact antibodies. For example, antibody fragments can be obtained by treating the whole antibody with an enzyme such as papain, pepsin, or plasmin. Papain digestion of whole antibodies produces F(ab)$_2$ or Fab fragments; pepsin digestion of whole antibodies yields F(ab')$_2$ or Fab'; and plasmin digestion of whole antibodies yields Facb fragments.

Alternatively, antibody fragments can be produced recombinantly. For example, nucleic acids encoding the antibody fragments of interest can be constructed, introduced into an expression vector, and expressed in suitable host cells. See, e.g., Co, M. S. et al., J. Immunol., 152:2968-2976 (1994); Better, M. and Horwitz, A. H., Methods in Enzymology, 178:476-496 (1989); Plueckthun, A. and Skerra, A., Methods in Enzymology, 178:476-496 (1989); Lamoyi, E., Methods in Enzymology, 121:652-663 (1989); Rousseaux, J. et al., Methods in Enzymology, (1989)121: 663-669 (1989); and Bird, R. E. et al., TIBTECH, 9:132-137 (1991)). Antibody fragments can be expressed in and secreted from E. coli, thus allowing the facile production of large amounts of these fragments. Antibody fragments can be isolated from the antibody phage libraries. Alternatively, Fab'-SH fragments can be directly recovered from E. coli and chemically coupled to form F(ab)$_2$ fragments (Carter et al., Bio/Technology, 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046.

Minibodies

In some instances, the anti-CD73 antibody is a minibody. Minibodies of anti-CD73 antibodies include diabodies, single chain (scFv), and single-chain (Fv)$_2$ (sc(Fv)$_2$).

A "diabody" is a bivalent minibody constructed by gene fusion (see, e.g., Holliger, P. et al., Proc. Natl. Acad. Sci. U.S.A., 90:6444-6448 (1993); EP 404,097; WO 93/11161). Diabodies are dimers composed of two polypeptide chains. The VL and VH domain of each polypeptide chain of the diabody are bound by linkers. The number of amino acid residues that constitute a linker can be between 2 to 12 residues (e.g., 3-10 residues or five or about five residues). The linkers of the polypeptides in a diabody are typically too short to allow the VL and VH to bind to each other. Thus, the VL and VH encoded in the same polypeptide chain cannot form a single-chain variable region fragment, but instead form a dimer with a different single-chain variable region fragment. As a result, a diabody has two antigen-binding sites.

An scFv is a single-chain polypeptide antibody obtained by linking the VH and VL with a linker (see, e.g., Huston et al., Proc. Natl. Acad. Sci. U.S.A., 85:5879-5883 (1988); and Plickthun, "The Pharmacology of Monoclonal Antibodies" Vol. 113, Ed Resenburg and Moore, Springer Verlag, New York, pp. 269-315, (1994)). The order of VHs and VLs to be linked is not particularly limited, and they may be arranged in any order. Examples of arrangements include: [VH] linker [VL]; or [VL] linker [VH]. The heavy chain variable domain and light chain variable domain in an scFv may be derived from any anti-CD73 antibody described herein.

An sc(Fv)$_2$ is a minibody in which two VHs and two VLs are linked by a linker to form a single chain (Hudson, et al., J. Immunol. Methods, (1999)231: 177-189 (1999)). An sc(Fv)$_2$ can be prepared, for example, by connecting scFvs with a linker. The sc(Fv)$_2$ of the present invention include antibodies preferably in which two VHs and two VLs are arranged in the order of: VH, VL, VH, and VL ([VH] linker [VL] linker [VH] linker [VL]), beginning from the N terminus of a single-chain polypeptide; however the order of the two VHs and two VLs is not limited to the above arrangement, and they may be arranged in any order.

Bispecific Antibodies

In some instances, the anti-CD73 antibody is a bispecific antibody. Bispecific antibodies are antibodies that have binding specificities for at least two different epitopes. Exemplary bispecific antibodies may bind to two different epitopes of the CD73 protein. Other such antibodies may combine a CD73 binding site with a binding site for another protein. Bispecific antibodies can be prepared as full length antibodies or low molecular weight forms thereof (e.g., F(ab')$_2$ bispecific antibodies, sc(Fv)$_2$ bispecific antibodies, diabody bispecific antibodies).

Traditional production of full length bispecific antibodies is based on the co-expression of two immunoglobulin heavy chain-light chain pairs, where the two chains have different specificities (Millstein et al., Nature, 305:537-539 (1983)). In a different approach, antibody variable domains with the desired binding specificities are fused to immunoglobulin constant domain sequences. DNAs encoding the immunoglobulin heavy chain fusions and, if desired, the immunoglobulin light chain, are inserted into separate expression vectors, and are co-transfected into a suitable host cell. This provides for greater flexibility in adjusting the proportions of the three polypeptide fragments. It is, however, possible to insert the coding sequences for two or all three polypeptide chains into a single expression vector when the expression of at least two polypeptide chains in equal ratios results in high yields.

According to another approach described in U.S. Pat. No. 5,731,168, the interface between a pair of antibody molecules can be engineered to maximize the percentage of heterodimers that are recovered from recombinant cell culture. The preferred interface comprises at least a part of the CH3 domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods.

The "diabody" technology provides an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites.

Multivalent Antibodies

In some instances, the anti-CD73 antibody is a multivalent antibody. A multivalent antibody may be internalized (and/or catabolized) faster than a bivalent antibody by a cell expressing an antigen to which the antibodies bind. The antibodies describe herein can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. An exemplary dimerization domain comprises (or consists of) an Fc region or a hinge region. A multivalent antibody can comprise (or consist of) three to about eight (e.g., four) antigen binding sites. The multivalent antibody optionally comprises at least one polypeptide chain (e.g., at least two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is a polypeptide chain of an Fc region, X1 and X2 represent an amino acid or peptide spacer, and n is 0 or 1.

Conjugated Antibodies

In some instances, the anti-CD73 antibody is a conjugated antibody. The antibodies disclosed herein may be conjugated antibodies, which are bound to various molecules including macromolecular substances such as polymers (e.g., polyethylene glycol (PEG), polyethylenimine (PEI) modified with PEG (PEI-PEG), polyglutamic acid (PGA) (N-(2-Hydroxypropyl) methacrylamide (HPMA) copolymers), hyaluronic acid, radioactive materials (e.g. $^{90}$Y, $^{131}$I), fluorescent substances, luminescent substances, haptens, enzymes, metal chelates, drugs, and toxins (e.g., calcheamicin, Pseudomonas exotoxin A, ricin (e.g. deglycosylated ricin A chain)).

In one embodiment, to improve the cytotoxic actions of anti-CD73 antibodies and consequently their therapeutic effectiveness, the antibodies are conjugated with highly toxic substances, including radioisotopes and cytotoxic agents. These conjugates can deliver a toxic load selectively to the target site (i.e., cells expressing the antigen recognized by the antibody) while cells that are not recognized by the antibody are spared. In order to minimize toxicity, conjugates are generally engineered based on molecules with a short serum half-life (thus, the use of murine sequences, and IgG3 or IgG4 isotypes).

In certain embodiments, an anti-CD73 antibody is modified with a moiety that improves its stabilization and/or retention in circulation, e.g., in blood, serum, or other tissues, e.g., by at least 1.5, 2, 5, 10, or 50 fold. For example, the anti-CD73 antibody can be associated with (e.g., conjugated to) a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used. For example, the anti-CD73 antibody can be conjugated to a water soluble polymer, e.g., a hydrophilic polyvinyl polymer, e.g., polyvinylalcohol or polyvinylpyrrolidone. Examples of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene; polymethacrylates; carbomers; and branched or unbranched polysaccharides.

The above-described conjugated antibodies can be prepared by performing chemical modifications on the antibodies, respectively, or the lower molecular weight forms thereof described herein. Methods for modifying antibodies are well known in the art (e.g., U.S. Pat. Nos. 5,057,313 and 5,156,840).

Methods of Producing Antibodies

Antibodies may be produced in bacterial or eukaryotic cells. Some antibodies, e.g., Fabs, can be produced in bacterial cells, e.g., *E. coli* cells. Antibodies can also be produced in eukaryotic cells such as transformed cell lines (e.g., CHO, 293E, COS). In addition, antibodies (e.g., scFvs) can be expressed in a yeast cell such as *Pichia* (see, e.g., Powers et al., J Immunol Methods. 251:123-35 (2001)), *Hanseula*, or *Saccharomyces*. To produce the antibody of interest, a polynucleotide encoding the antibody is constructed, introduced into an expression vector, and then expressed in suitable host cells. Standard molecular biology techniques are used to prepare the recombinant expression vector, transfect the host cells, select for transformants, culture the host cells and recover the antibody.

If the antibody is to be expressed in bacterial cells (e.g., *E. coli*), the expression vector should have characteristics that permit amplification of the vector in the bacterial cells. Additionally, when *E. coli* such as JM109, DH5α, HB101, or XL1-Blue is used as a host, the vector must have a promoter, for example, a lacZ promoter (Ward et al., 341: 544-546 (1989), araB promoter (Better et al., Science, 240:1041-1043 (1988)), or T7 promoter that can allow efficient expression in *E. coli*. Examples of such vectors include, for example, M13-series vectors, pUC-series vectors, pBR322, pBluescript, pCR-Script, pGEX-5X-1 (Pharmacia), "QIAexpress system" (QIAGEN), pEGFP, and pET (when this expression vector is used, the host is preferably BL21 expressing T7 RNA polymerase). The expression vector may contain a signal sequence for antibody secretion. For production into the periplasm of *E. coli*, the pelB signal sequence (Lei et al., J. Bacteriol., 169:4379 (1987)) may be used as the signal sequence for antibody secretion. For bacterial expression, calcium chloride methods or electroporation methods may be used to introduce the expression vector into the bacterial cell.

If the antibody is to be expressed in animal cells such as CHO, COS, and NIH3T3 cells, the expression vector includes a promoter necessary for expression in these cells, for example, an SV40 promoter (Mulligan et al., Nature, 277:108 (1979)), MMLV-LTR promoter, EF1α promoter (Mizushima et al., Nucleic Acids Res., 18:5322 (1990)), or CMV promoter. In addition to the nucleic acid sequence encoding the immunoglobulin or domain thereof, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin, or methotrexate, on a host cell into which the vector has been introduced. Examples of vectors with selectable markers include pMAM, pDR2, pBK-RSV, pBK-CMV, pOPRSV, and pOP13.

In one embodiment, antibodies are produced in mammalian cells. Exemplary mammalian host cells for expressing an antibody include Chinese Hamster Ovary (CHO cells) (including dhfr-CHO cells, described in Urlaub and Chasin (1980) Proc. Natl. Acad. Sci. USA 77:4216-4220, used with a DHFR selectable marker, e.g., as described in Kaufman and Sharp (1982) Mol. Biol. 159:601 621), human embryonic kidney 293 cells (e.g., 293, 293E, 293T), COS cells, NIH3T3 cells, lymphocytic cell lines, e.g., NS0 myeloma cells and SP2 cells, and a cell from a transgenic animal, e.g., a transgenic mammal. For example, the cell is a mammary epithelial cell.

In an exemplary system for antibody expression, a recombinant expression vector encoding both the antibody heavy chain and the antibody light chain of an anti-CD73 antibody (e.g., CL25, HzCL25, 3-F03, 3-F03_411, or 3-F03_413) is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and the antibody is recovered from the culture medium.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly. Animals are also provided comprising one or more of the nucleic acids described herein.

The antibodies of the present disclosure can be isolated from inside or outside (such as medium) of the host cell and purified as substantially pure and homogenous antibodies. Methods for isolation and purification commonly used for antibody purification may be used for the isolation and purification of antibodies, and are not limited to any particular method. Antibodies may be isolated and purified by appropriately selecting and combining, for example, column chromatography, filtration, ultrafiltration, salting out, solvent precipitation, solvent extraction, distillation, immunoprecipitation, SDS-polyacrylamide gel electrophoresis, isoelectric focusing, dialysis, and recrystallization. Chromatography includes, for example, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., Cold Spring Harbor Laboratory Press, 1996). Chromatography can be carried out using liquid phase chromatography such as HPLC and FPLC. Columns used for affinity chromatography include protein A column and protein G column. Examples of columns using protein A column include Hyper D, POROS, and Sepharose FF (GE Healthcare Biosciences). The present disclosure also includes antibodies that are highly purified using these purification methods.

Polynucleotides, Expression Vectors, and Cells

The disclosure also provides polynucleotides and vectors encoding an anti-CD73 antibody or portion thereof (e.g., VH, VL, HC, or LC) described herein. The polynucleotides of the disclosure can be in the form of RNA or in the form of DNA. In some instances, the polynucleotide is DNA. In some instances, the polynucleotide is complementary DNA (cDNA). In some instances, the polynucleotide is RNA.

In some instances, the polynucleotide encodes a VH comprising the VH CDR1, VH CDR2, and VH CDR3 of any antibody described herein (see, e.g., Tables 1, 2, 3, and 5). In some instances, the polynucleotide encodes a VL comprising the VL CDR1, VL CDR2, and VL CDR3 of any antibody described herein (see, e.g., Tables 1, 2, 3, and 5). In some instances, the polynucleotide encodes a heavy chain comprising a VH comprising the VH CDR1, VH CDR2, and VH CDR3 of any antibody described herein (see, e.g., Tables 1, 2, 3, and 5). In some instances, the polynucleotide encodes a light chain comprising a VL comprising the VL CDR1, VL CDR2, and VL CDR3 of any antibody described herein (see, e.g., Tables 1, 2, 3, and 5). In some instances, the polynucleotide is operably linked to a promoter.

In some instances, the polynucleotide comprises: (i) a first nucleic acid sequence encoding a first polypeptide, wherein the first polypeptide comprises a VH comprising the VH CDR1, VH CDR2, and VH CDR3 of any antibody described herein (see, e.g., Tables 1, 2, 3, and 5); and (ii) a second nucleic acid sequence encoding a second polypeptide, wherein the second polypeptide comprises a VL comprising the VL CDR1, VL CDR2, and VL CDR3 of any antibody described herein (see, e.g., Tables 1, 2, 3, and 5). In some instances, the polynucleotide comprises: (i) a first nucleic acid sequence encoding a first polypeptide, wherein the first polypeptide comprises a heavy chain comprising a VH comprising the VH CDR1, VH CDR2, and VH CDR3 of any antibody described herein (see, e.g., Tables 1, 2, 3, and 5); and (ii) a second nucleic acid sequence encoding a second polypeptide, wherein the second polypeptide comprises a light chain comprising a VL comprising the VL CDR1, VL CDR2, and VL CDR3 of any antibody described herein (see, e.g., Tables 1, 2, 3, and 5). In some instances, the first nucleic acid is operably linked to a first promoter and the second nucleic acid is operably linked to a second promoter.

In some instances, the polynucleotide encodes the VH of CL25 or a variant thereof (e.g., a humanized version thereof, e.g., HzCL25). In some instances, the polynucleotide encodes a polypeptide comprising an amino acid sequence having at least 80%, at least 85%, at least 90%, at least 95%, at least 97%, or 100% identity to the amino acid sequence set forth in any one of SEQ ID NOs:22, 26, and 82-84. In some instances, the polynucleotide encodes a polypeptide comprising an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:22, 26, and 82-84. In some instances, the polynucleotide encodes a polypeptide comprising the amino acid sequence set forth in any one of SEQ ID NOs:22, 26, and 82-84. In some instances, the polynucleotide encodes a polypeptide comprising the amino acid sequence set forth in SEQ ID NO:22. In some instances, the polynucleotide is operably linked to a promoter.

In some instances, the polynucleotide encodes the VL of CL25 or a variant thereof (e.g., a humanized version thereof, e.g., HzCL25). In some instances, the polynucleotide encodes a polypeptide comprising an amino acid sequence having at least 80%, at least 85%, at least 90%, at least 95%, at least 97%, or 100% identity to the amino acid sequence set forth in any one of SEQ ID NOs:23, 27, 80, and 81. In some instances, the polynucleotide encodes a polypeptide comprising an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NO:23, 27, 80, and 81. In some instances, the polynucleotide encodes a polypeptide comprising the amino acid sequence set forth in any one of SEQ ID NOs:23, 27, 80, and 81. In some instances, the polynucleotide encodes a polypeptide comprising the amino acid sequence set forth in SEQ ID NO:23. In some instances, the polynucleotide is operably linked to a promoter.

In some instances, the polynucleotide comprises: (i) a first nucleic acid encoding a first polypeptide, wherein the first polypeptide comprises the VH of CL25 or a variant thereof (e.g., a humanized version thereof, e.g., HzCL25); and (ii) a second nucleic acid encoding a second polypeptide, wherein the second polypeptide comprises the VL of CL25 or a variant thereof (e.g., a humanized version thereof, e.g., HzCL25). In some instances, the polynucleotide comprises: (i) a first nucleic acid sequence encoding a first polypeptide, wherein the first polypeptide comprises an amino acid sequence having at least 80%, at least 85%, at least 90%, at least 95%, at least 97%, or 100% identity to the amino acid sequence set forth in any one of SEQ ID NOs:22, 26, and 82-84, and (ii) a second nucleic acid sequence encoding a second polypeptide, wherein the second polypeptide comprises an amino acid sequence having at least 80%, at least 85%, at least 90%, at least 95%, at least 97%, or 100% identity to the amino acid sequence set forth in any one of SEQ ID NOs:23, 27, 80, and 81. In some instances, the polynucleotide comprises: (i) a first nucleic acid sequence encoding a first polypeptide, wherein the first polypeptide comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:22, 26, and 82-84; and (ii) a second nucleic acid sequence encoding a second polypeptide, wherein the second polypeptide comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:23, 27, 80, and 81. In some instances, the first nucleic acid encodes the amino acid sequence set forth in any one of SEQ ID NOs:22, 26, and 82-84 and the second nucleic acid encodes the amino acid sequence set forth in any one of SEQ ID NOs:23, 27, 80, and 81. In some instances, the first nucleic acid encodes the amino acid sequence set forth in SEQ ID NO:22 and the second nucleic acid encodes the amino acid sequence set forth in SEQ ID NO:23. In some instances, the first nucleic acid is operably linked to a first promoter and the second nucleic acid is operably linked to a second promoter.

In some instances, the polynucleotide encodes the heavy chain of CL25 or a variant thereof (e.g., a humanized version thereof, e.g., HzCL25). In some instances, the polynucleotide encodes a polypeptide comprising an amino acid sequence having at least 80%, at least 85%, at least 90%, at least 95%, at least 97%, or 100% identity to the amino acid sequence set forth in SEQ ID NO:24. In some instances, the polynucleotide encodes a polypeptide comprising an amino acid sequence having one or more (e.g., 1, 2, 3, 4, 5, 6, 7, 8, 9, 10) amino acid substitutions, additions, and/or deletions relative to the amino acid sequence set forth in SEQ ID NO:24. In some instances, the polynucleotide encodes a polypeptide comprising the amino acid sequence set forth in SEQ ID NO:24. In some instances, the polynucleotide comprises the sequence set forth in SEQ ID NO:89. In some instances, the polynucleotide is operably linked to a promoter.

In some instances, the polynucleotide encodes the light chain of CL25 or a variant thereof (e.g., a humanized version thereof, e.g., HzCL25). In some instances, the polynucleotide encodes a polypeptide comprising an amino acid sequence having at least 80%, at least 85%, at least 90%, at least 95%, at least 97%, or 100% identity to the amino acid sequence set forth in SEQ ID NO:25. In some instances, the polynucleotide encodes a polypeptide comprising an amino acid sequence having one or more (e.g., 1, 2, 3, 4, 5, 6, 7, 8, 9, 10) amino acid substitutions, additions, and/or deletions relative to the amino acid sequence set forth in SEQ ID NO:25. In some instances, the polynucleotide encodes a polypeptide comprising the amino acid sequence set forth in SEQ ID NO:25. In some instances, the polynucleotide comprises the sequence set forth in SEQ ID NO:90. In some instances, the polynucleotide is operably linked to a promoter.

In some instances, the polynucleotide encodes the heavy chain of CL25 or a variant thereof (e.g., a humanized version thereof, e.g., HzCL25) and the light chain of CL25 or a variant thereof (e.g., a humanized version thereof, e.g., HzCL25). In some instances, the polynucleotide comprises: (i) a first nucleic acid encoding a first polypeptide, wherein the first polypeptide comprises an amino acid sequence having at least 80%, at least 85%, at least 90%, at least 95%, at least 97%, or 100% identity to the amino acid sequence set forth in SEQ ID NO:24, and (ii) a second nucleic acid encoding a second polypeptide, wherein the second polypeptide comprises an amino acid sequence having at least 80%, at least 85%, at least 90%, at least 95%, at least 97%, or 100% identity to the amino acid sequence set forth in SEQ ID NO:25. In some instances, the polynucleotide comprises: (i) a first nucleic acid encoding a first polypeptide, wherein the first polypeptide comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO:24, and (ii) a second nucleic acid encoding a second polypeptide, wherein the second polypeptide comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO:25. In some instances, the polynucleotide comprises: (i) a first nucleic acid encoding a first polypeptide, wherein the first polypeptide comprises the amino acid sequence set forth in SEQ ID NO:24, and (ii) a second nucleic acid encoding a second polypeptide, wherein the second polypeptide comprises the amino acid sequence set forth in SEQ ID NO:25. In some instances, the polynucleotide comprises: (i) a first nucleic acid comprising the sequence set forth in SEQ ID NO:89, and (ii) a second nucleic acid comprising the sequence set forth in SEQ ID NO:90. In some instances, the first nucleic acid is operably linked to a first promoter and the second nucleic acid is operably linked to a second promoter.

In some instances, the polynucleotide encodes the VH of 3-F03 or a variant thereof (e.g., 3-F03_411 or 3-F03_413). In some instances, the polynucleotide encodes a polypeptide comprising an amino acid sequence having at least 80%, at least 85%, at least 90%, at least 95%, at least 97%, or 100% identity to the amino acid sequence set forth in any one of SEQ ID NOs: 32, 60, 62, 63, 67-69, 77, and 85-88. In some instances, the polynucleotide encodes a polypeptide comprising an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs: 32, 60, 62, 63, 67-69, 77, and 85-88. In some instances, the polynucleotide encodes a polypeptide comprising the amino acid sequence set forth in any one of SEQ ID NOs: 32, 60, 62, 63, 67-69, 77, and 85-88. In some instances, the polynucleotide encodes a polypeptide comprising the amino acid sequence set forth in SEQ ID NO:62. In some instances, the polynucleotide encodes a polypeptide comprising the amino acid sequence set forth in SEQ ID NO:63. In some instances, the polynucleotide is operably linked to a promoter.

In some instances, the polynucleotide encodes the VL of 3-F03 or a variant thereof (e.g., 3-F03_411 or 3-F03_413). In some instances, the polynucleotide encodes a polypeptide comprising an amino acid sequence having at least 80%, at least 85%, at least 90%, at least 95%, at least 97%, or 100% identity to the amino acid sequence set forth in any one of SEQ ID NOs:61, 64, and 65. In some instances, the polynucleotide encodes a polypeptide comprising an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NO: 61, 64, and 65. In some instances, the polynucleotide encodes a polypeptide comprising the amino acid sequence set forth in any one of SEQ ID NOs: 61, 64, and 65. In some instances, the polynucleotide encodes a polypeptide comprising the amino acid sequence set forth in SEQ ID NO:61. In some instances, the polynucleotide is operably linked to a promoter.

In some instances, the polynucleotide comprises: (i) a first nucleic acid encoding a first polypeptide, wherein the first polypeptide comprises the VH of 3-F03 or a variant thereof (e.g., 3-F03_411 or 3-F03_413); and (ii) a second nucleic acid encoding a second polypeptide, wherein the second polypeptide comprises the VL of 3-F03 or a variant thereof (e.g., 3-F03_411 or 3-F03_413). In some instances, the polynucleotide comprises: (i) a first nucleic acid sequence encoding a first polypeptide, wherein the first polypeptide comprises an amino acid sequence having at least 80%, at least 85%, at least 90%, at least 95%, at least 97%, or 100% identity to the amino acid sequence set forth in any one of SEQ ID NOs: 32, 60, 62, 63, 67-69, 77, and 85-88, and (ii) a second nucleic acid sequence encoding a second polypeptide, wherein the second polypeptide comprises an amino acid sequence having at least 80%, at least 85%, at least 90%, at least 95%, at least 97%, or 100% identity to the amino acid sequence set forth in any one of SEQ ID NOs:61, 64, and 65. In some instances, the polynucleotide comprises: (i) a first nucleic acid sequence encoding a first polypeptide, wherein the first polypeptide comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs: 32, 60, 62, 63, 67-69, 77, and 85-88; and (ii) a second nucleic acid sequence encoding a second polypeptide, wherein the second polypeptide comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NOs:61, 64, and 65. In some instances, the first nucleic acid encodes the amino acid sequence set forth in any one of SEQ ID NOs: 32, 60, 62, 63, 67-69, 77, and 85-88 and the second nucleic acid encodes the amino acid sequence set forth in any one of SEQ ID NOs:61, 64, and 65. In some instances, the first nucleic acid encodes the amino acid sequence set forth in SEQ ID NO:62 and the second nucleic acid encodes the amino acid sequence set forth in SEQ ID NO:61. In some instances, the first nucleic acid encodes the amino acid sequence set forth in SEQ ID NO:63 and the second nucleic acid encodes the amino acid sequence set forth in SEQ ID NO:61. In some instances, the first nucleic acid is operably linked to a first promoter and the second nucleic acid is operably linked to a second promoter.

In some instances, the polynucleotide encodes the heavy chain of 3-F03 or a variant thereof (e.g., 3-F03_411 or 3-F03_413). In some instances, the polynucleotide encodes a polypeptide comprising an amino acid sequence having at least 80%, at least 85%, at least 90%, at least 95%, at least 97%, or 100% identity to the amino acid sequence set forth in any one of SEQ ID NO:30, 33, and 66. In some instances, the polynucleotide encodes a polypeptide comprising an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NO: 30, 33, and 66. In some instances, the polynucleotide encodes a polypeptide comprising the amino acid sequence set forth in any one of SEQ ID NO: 30, 33, and 66. In some instances, the polynucleotide encodes a polypeptide comprising the amino acid sequence set forth in SEQ ID NO:30. In some instances, the polynucleotide encodes a polypeptide comprising the amino acid sequence set forth in SEQ ID NO:33. In some instances, the polynucleotide comprises the sequence set forth in SEQ ID NO:91. In some instances, the polynucleotide comprises the sequence set forth in SEQ ID NO:93. In some instances, the polynucleotide is operably linked to a promoter.

In some instances, the polynucleotide encodes the light chain of 3-F03 or a variant thereof (e.g., 3-F03_411 or 3-F03_413). In some instances, the polynucleotide encodes a polypeptide comprising an amino acid sequence having at least 80%, at least 85%, at least 90%, at least 95%, at least 97%, or 100% identity to the amino acid sequence set forth in SEQ ID NO:31. In some instances, the polynucleotide encodes a polypeptide comprising an amino acid sequence having one or more (e.g., 1, 2, 3, 4, 5, 6, 7, 8, 9, 10) amino acid substitutions, additions, and/or deletions relative to the amino acid sequence set forth in SEQ ID NO: 31. In some instances, the polynucleotide encodes a polypeptide comprising the amino acid sequence set forth in SEQ ID NO: 31. In some instances, the polynucleotide encodes a polypeptide comprising the amino acid sequence set forth in SEQ ID NO:31. In some instances, the polynucleotide comprises the sequence set forth in SEQ ID NO:92. In some instances, the polynucleotide is operably linked to a promoter.

In some instances, the polynucleotide encodes the heavy chain of 3-F03 or a variant thereof (e.g., 3-F03_411 or 3-F03_413) and the light chain of 3-F03 or a variant thereof (e.g., 3-F03_411 or 3-F03_413). In some instances, the polynucleotide comprises: (i) a first nucleic acid encoding a first polypeptide, wherein the first polypeptide comprises an amino acid sequence having at least 80%, at least 85%, at least 90%, at least 95%, at least 97%, or 100% identity to the amino acid sequence set forth in any one of SEQ ID NO: 30, 33, and 66, and (ii) a second nucleic acid encoding a second polypeptide, wherein the second polypeptide comprises an amino acid sequence having at least 80%, at least 85%, at least 90%, at least 95%, at least 97%, or 100% identity to the amino acid sequence set forth in SEQ ID NO: 31. In some instances, the polynucleotide comprises: (i) a first nucleic acid encoding a first polypeptide, wherein the first polypeptide comprises an amino acid sequence having one or more (e.g., 1, 2, 3, 4, 5, 6, 7, 8, 9, 10) amino acid substitutions, additions, and/or deletions relative to the amino acid sequence set forth in any one of SEQ ID NO: 30, 33, and 66, and (ii) a second nucleic acid encoding a second polypeptide, wherein the second polypeptide comprises an amino acid sequence having one or more (e.g., 1, 2, 3, 4, 5, 6, 7, 8, 9, 10) amino acid substitutions, additions, and/or deletions relative to the amino acid sequence set forth in SEQ ID NO: 31. In some instances, the polynucleotide comprises: (i) a first nucleic acid encoding a first polypeptide, wherein the first polypeptide comprises the amino acid sequence set forth in any one of SEQ ID NO: 30, 33, and 66, and (ii) a second nucleic acid encoding a second polypeptide, wherein the second polypeptide comprises the amino acid sequence set forth in SEQ ID NO: 31. In some instances, the polynucleotide comprises: (i) a first nucleic acid encoding a first polypeptide, wherein the first polypeptide comprises the amino acid sequence set forth in SEQ ID NO:30, and (ii) a second nucleic acid encoding a second polypeptide, wherein the second polypeptide comprises the amino acid sequence set forth in SEQ ID NO:31. In some instances, the polynucleotide comprises: (i) a first nucleic acid encoding a first polypeptide, wherein the first polypeptide comprises the amino acid sequence set forth in SEQ ID NO:33, and (ii) a second nucleic acid encoding a second polypeptide, wherein the second polypeptide comprises the amino acid sequence set forth in SEQ ID NO:31. In some instances, the polynucleotide comprises: (i) a first nucleic acid comprising the sequence set forth in SEQ ID NO:91, and (ii) a second nucleic acid comprising the sequence set forth in SEQ ID NO:92. In some instances, the polynucleotide comprises: (i) a first nucleic acid comprising the sequence set forth in SEQ ID NO:93, and (ii) a second nucleic acid comprising the sequence set forth in SEQ ID NO:92. In some instances, the first nucleic acid is operably linked to a first promoter and the second nucleic acid is operably linked to a second promoter.

In some embodiments, a polynucleotide described herein is isolated.

Also provided herein are expression vectors encoding the anti-CD73 antibodies or portions thereof (e.g., VH, VL, HC, and/or LC) described herein. Also provided herein are expression vectors comprising one or more polynucleotides described herein. Various types of expression vectors are known in the art and described herein (e.g., see the section "Methods of Producing Antibodies" above).

Also provided herein are cells comprising the anti-CD73 antibodies described herein. Also provided herein are cells comprising one or more polynucleotides described herein. Also provided herein are cells comprising one or more expression vectors described herein. Various types of cells are known in the art and described herein (e.g., see the section "Methods of Producing Antibodies" above).

Anti-CD73 Antibodies with Altered Glycosylation

Different glycoforms can profoundly affect the properties of a therapeutic, including pharmacokinetics, pharmacodynamics, receptor-interaction and tissue-specific targeting (Graddis et al., 2002, Curr Pharm Biotechnol. 3: 285-297). In particular, for antibodies, the oligosaccharide structure can affect properties relevant to protease resistance, the serum half-life of the antibody mediated by the FcRn receptor, phagocytosis and antibody feedback, in addition to effector functions of the antibody (e.g., binding to the complement complex C1, which induces CDC, and binding to FcγR receptors, which are responsible for modulating the ADCC pathway) (Nose and Wigzell, 1983; Leatherbarrow and Dwek, 1983; Leatherbarrow et al., 1985; Walker et al., 1989; Carter et al., 1992, PNAS, 89: 4285-4289).

Accordingly, another means of modulating effector function of antibodies includes altering glycosylation of the antibody constant region. Altered glycosylation includes, for example, a decrease or increase in the number of glycosylated residues, a change in the pattern or location of glycosylated residues, as well as a change in sugar structure(s). The oligosaccharides found on human IgGs affects their degree of effector function (Raju, T. S. BioProcess International April 2003. 44-53); the microheterogeneity of human IgG oligosaccharides can affect biological functions such as CDC and ADCC, binding to various Fc receptors, and binding to C1q protein (Wright A. & Morrison SL. TIBTECH 1997, 15 26-32; Shields et al. J Biol Chem. 2001276(9):6591-604; Shields et al. J Biol Chem. 2002; 277(30):26733-40; Shinkawa et al. J Biol Chem. 2003 278(5):3466-73; Umana et al. Nat Biotechnol. 1999 February; 17(2): 176-80). For example, the ability of IgG to bind C1q and activate the complement cascade may depend on the presence, absence or modification of the carbohydrate moiety positioned between the two CH2 domains (which is normally anchored at Asn297) (Ward and Ghetie, Therapeutic Immunology 2:77-94 (1995). Thus, in some instances, the anti-CD73 antibody contains an Asn297 Ala substitution relative to a wild type constant region.

Glycosylation sites in an Fc-containing polypeptide, for example an antibody such as an IgG antibody, may be identified by standard techniques. The identification of the glycosylation site can be experimental or based on sequence analysis or modeling data. Consensus motifs, that is, the amino acid sequence recognized by various glycosyl transferases, have been described. For example, the consensus motif for an N-linked glycosylation motif is frequently NXT or NXS, where X can be any amino acid except proline. Several algorithms for locating a potential glycosylation motif have also been described. Accordingly, to identify potential glycosylation sites within an antibody or Fc-containing fragment, the sequence of the antibody is examined, for example, by using publicly available databases such as the website provided by the Center for Biological Sequence Analysis (see NetNGlyc services for predicting N-linked glycosylation sites and NetOGlyc services for predicting O-linked glycosylation sites).

In vivo studies have confirmed the reduction in the effector function of aglycosyl antibodies. For example, an aglycosyl anti-CD8 antibody is incapable of depleting CD8-bearing cells in mice (Isaacs, 1992 J. Immunol. 148: 3062) and an aglycosyl anti-CD3 antibody does not induce cytokine release syndrome in mice or humans (Boyd, 1995 supra; Friend, 1999 Transplantation 68:1632). Aglycosylated forms of the anti-CD73 antibody also have reduced effector function.

Importantly, while removal of the glycans in the CH2 domain appears to have a significant effect on effector function, other functional and physical properties of the antibody remain unaltered. Specifically, it has been shown that removal of the glycans had little to no effect on serum half-life and binding to antigen (Nose, 1983 supra; Tao, 1989 supra; Dorai, 1991 supra; Hand, 1992 supra; Hobbs, 1992 Mol. Immunol. 29:949).

The anti-CD73 antibodies of the present invention may be modified or altered to elicit increased or decreased effector function(s) (compared to a second CD73-specific antibody). Methods for altering glycosylation sites of antibodies are described, e.g., in U.S. Pat. Nos. 6,350,861 and 5,714,350, WO 05/18572 and WO 05/03175; these methods can be used to produce anti-CD73 antibodies of the present invention with altered, reduced, or no glycosylation.

A2A/A2B Adenosine Receptor

A2A adenosine receptor is a high affinity receptor, whereas A2B is a low affinity receptor. Adenosine and its agonists can act via one or both of these receptors and can modulate the activity of adenylate cyclase, the enzyme responsible for increasing cyclic AMP (cAMP). The different receptors have differential stimulatory and inhibitory effects on this enzyme. Increased intracellular concentrations of cAMP can suppress the activity of immune and inflammatory cells.

The A2A adenosine receptor can signal in the periphery and the CNS, with agonists explored as anti-inflammatory drugs and antagonists explored for neurodegenerative diseases. In most cell types the A2A subtype inhibits intracellular calcium levels whereas the A2B potentiates them. The A2A receptor generally appears to inhibit inflammatory response from immune cells. A2A are mostly expressed on lymphoid-derived cells, including T-effector cells, T regulatory cells and nature killing cells.

A2B adenosine receptor is a low affinity receptor. A2B receptors are highly expressed in the gastrointestinal tract, bladder, lung and on mast cells. The A2B receptor, although structurally closely related to the A2A receptor and able to activate adenylate cyclase, is functionally different. It has been postulated that this subtype may utilize signal transduction systems other than adenylate cyclase. Among all the adenosine receptors, the A2B adenosine receptor is a low affinity receptor that is thought to remain silent under physiological conditions and to be activated in consequence of increased extracellular adenosine levels. Activation of A2B adenosine receptor can stimulate adenylate cyclase and phospholipase C through activation of Gs and Gq proteins, respectively. Coupling to mitogen activated protein kinases has also been described. A2B receptors are mainly expressed on monocyte-derived cells including dendritic cells, tumor-associated macrophages, myeloid derived suppressive cells (MDSCs), and mesenchymal stromal/stem cells (MSCs).

An exemplary amino acid sequence of human A2A adenosine receptor protein (GenBank Accession No. NP_001265428) is:

```
                                            (SEQ ID NO: 94)
MPIMGSSVYITVELAIAVLAILGNVLVCWAVWLNSNLQNVTNYFVVSLAA

ADIAVGVLAIPFAITISTGFCAACHGCLFIACFVLVLTQSSIFSLLAIAI

DRYIAIRIPLRYNGLVTGTRAKGIIAICWVLSFAIGLTPMLGWNNCGQPK

EGKNHSQGCGEGQVACLFEDVVPMNYMVYFNFFACVLVPLLLMLGVYLRI

FLAARRQLKQMESQPLPGERARSTLQKEVHAAKSLAIIVGLFALCWLPLH

IINCFTFFCPDCSHAPLWLMYLAIVLSHTNSVVNPFIYAYRIREFRQTFR

KIIRSHVLRQQEPFKAAGTSARVLAAHGSDGEQVSLRLNGHPPGVWANGS

APHPERRPNGYALGLVSGGSAQESQGNTGLPDVELLSHELKGVCPEPPGL

DDPLAQDGAGVS.
```

An exemplary amino acid sequence of human A2B adenosine receptor protein (GenBank Accession No. NP_000667) is:

(SEQ ID NO: 95)
MLLETQDALYVALELVIAALSVAGNVLVCAAVGTANTLQTPTNYELVSLA

AADVAVGLFAIPFAITISLGFCTDFYGCLFLACFVLVLTQSSIFSLLAVA

VDRYLAICVPLRYKSLVTGTRARGVIAVLWVLAFGIGLTPFLGWNSKDSA

TNNCTEPWDGTTNESCCLVKCLFENVVPMSYMVYENFFGCVLPPLLIMLV

IYIKIFLVACRQLQRTELMDHSRTTLQREIHAAKSLAMIVGIFALCWLPV

HAVNCVTLFQPAQGKNKPKWAMNMAILLSHANSVVNPIVYAYRNRDFRYT

FHKIISRYLLCQADVKSGNGQAGVQPALGVGL.

A2A/A2B Adenosine Receptor Inhibitors

In some embodiments, the inhibitor of A2A/A2B is a compound selected from Table 6, or a pharmaceutically acceptable salt thereof.

TABLE 6

| Comp. No. | Name | Structure |
|---|---|---|
| 1 | 3-(5-Amino-2-(pyridin-2-ylmethyl)-8-(pyrimidin-4-yl)-[1,2,4]triazolo[1,5-c]pyrimidin-7-yl)benzonitrile | 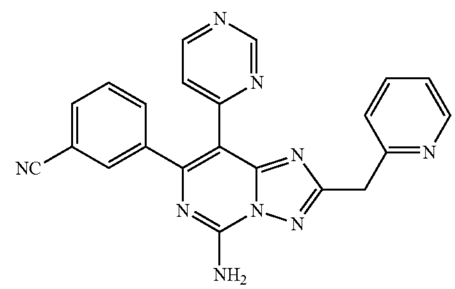 [SMILES: N#Cc1cccc(-c2nc(N)n3nc(Cc4ccccn4)nc3c2-c2ccncn2)c1] |
| 2 | 3-(5-Amino-2-((2,6-difluorophenyl)(hydroxy)methyl)-8-(pyrimidin-4-yl)-[1,2,4]triazolo[1,5-c]pyrimidin-7-yl)benzonitrile | 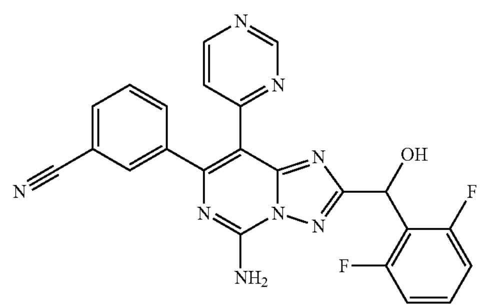 [SMILES: N#Cc1cccc(-c2nc(N)n3nc(C(O)c4c(F)cccc4F)nc3c2-c2ccncn2)c1] |
| 3A | 3-(5-amino-2-((5-(pyridin-2-yl)-2H-tetrazol-2-yl)methyl)-8-(pyrimidin-4-yl)-[1,2,4]triazolo[1,5-c]pyrimidin-7-yl)benzonitrile | 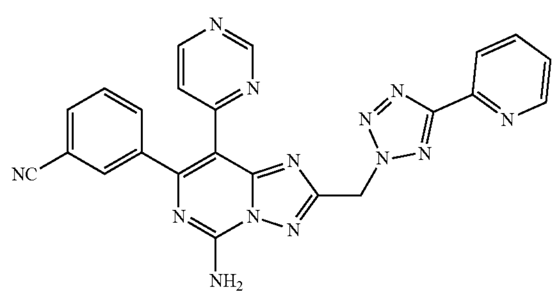 [SMILES: N#Cc1cccc(-c2nc(N)n3nc(Cn4nnc(-c5ccccn5)n4)nc3c2-c2ccncn2)c1] |
| 3B | 3-(5-Amino-2-((5-(pyridin-2-yl)-1H-tetrazol-1-yl)methyl)-8-(pyrimidin-4-yl)-[1,2,4]triazolo[1,5-c]pyrimidin-7-yl)benzonitrile | 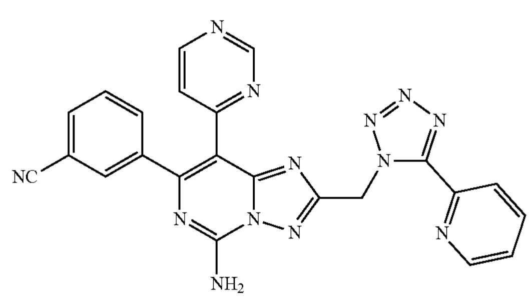 [SMILES: N#Cc1cccc(-c2nc(N)n3nc(Cn4nnnc4-c4ccccn4)nc3c2-c2ccncn2)c1] |

TABLE 6-continued

| Comp. No. | Name |
|---|---|
| 4 | 3-(5-Amino-2-((3-methylpyridin-2-yl)methoxy)-8-(pyrimidin-4-yl)-[1,2,4]triazolo[1,5-c]pyrimidin-7-yl)benzonitrile |
| 5 | 3-(5-Amino-2-(hydroxy(phenyl)methyl)-[1,2,4]triazolo[1,5-c]pyrimidin-7-yl)benzonitrile |
| 6 | 3-(5-Amino-2-((2,6-difluorophenyl)(hydroxy)methyl)-[1,2,4]triazolo[1,5-c]pyrimidin-7-yl)-2-fluorobenzonitrile |
| 7 | 5-Amino-7-(3-cyano-2-fluorophenyl)-2-((2,6-difluorophenyl)(hydroxy)methyl)-[1,2,4]triazolo[1,5-c]pyrimidine-8-carbonitrile |
| 8 | 3-(5-Amino-2-((2-fluoro-6-(((1-methyl-2-oxopyrrolidin-3-yl)amino)methyl)phenyl)(hydroxy)methyl)-[1,2,4]triazolo[1,5-c]pyrimidin-7-yl)-2-fluorobenzonitrile |
| 9 | 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile |

TABLE 6-continued

| Comp. No. | Name | Structure |
|---|---|---|
| 10 | 3-(8-Amino-2-((2,6-difluorophenyl)(hydroxy)methyl)-5-(pyrimidin-4-yl)-[1,2,4]triazolo[1,5-a]pyrazin-6-yl)benzonitrile | 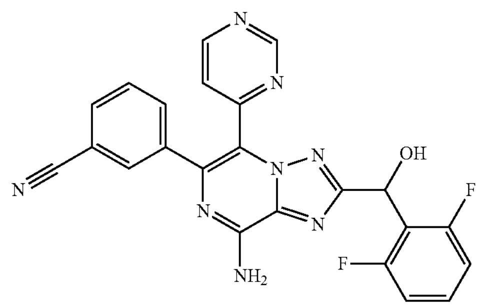 [SMILES: N#Cc1cccc(-c2nc(N)c3nc(C(O)c4c(F)cccc4F)nn3c2-c2ccncn2)c1] |
| 11 | 3-(8-amino-2-(amino(2,6-difluorophenyl)methyl)-5-(4-methyloxazol-5-yl)-[1,2,4]triazolo[1,5-a]pyrazin-6-yl)benzonitrile | 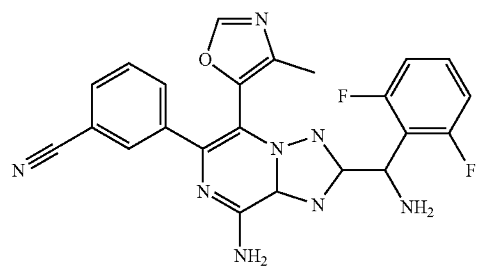 [SMILES: Cc1ncoc1C1=C(c2cccc(C#N)c2)N=C(N)C2NC(C(N)c3c(F)cccc3F)NN12] |
| 12 | 3-(8-amino-2-((2,6-difluorophenyl)(hydroxy)methyl)-5-(2,6-dimethylpyridin-4-yl)-[1,2,4]triazolo[1,5-a]pyrazin-6-yl)benzonitrile | 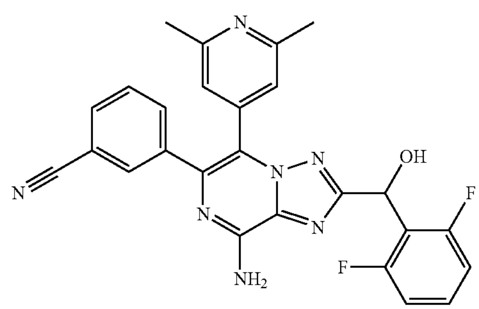 [SMILES: Cc1cc(-c2c(-c3cccc(C#N)c3)nc(N)c3nc(C(O)c4c(F)cccc4F)nn23)cc(C)n1] |
| 13 | 3-(4-amino-2-(pyridin-2-ylmethyl)-7-(pyrimidin-4-yl)-2H-[1,2,3]triazolo[4,5-c]pyridin-6-yl)benzonitrile | 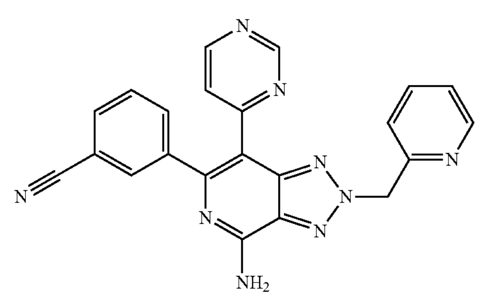 |
| 14 | 3-(4-amino-2-((3-fluoropyridin-2-yl)methyl)-7-(pyrimidin-4-yl)-2H-[1,2,3]triazolo[4,5-c]pyridin-6-yl)benzonitrile | 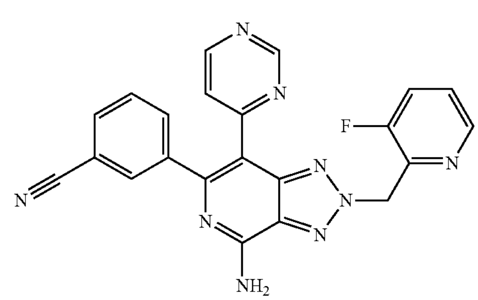 |

TABLE 6-continued

| Comp. No. | Name | Structure |
|---|---|---|
| 15 | 3-(4-amino-2-((3-fluoropyridin-2-yl)methyl)-7-(pyridin-4-yl)-2H-[1,2,3]triazolo[4,5-c]pyridin-6-yl)benzonitrile | 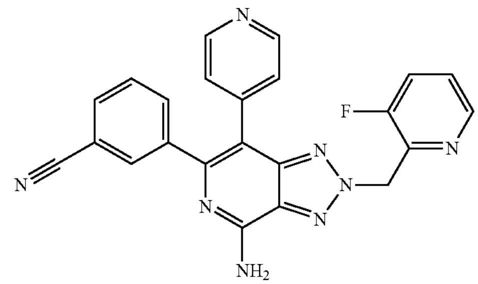 |
| 16 | 3-(4-amino-7-(1-methyl-1H-pyrazol-5-yl)-2-(pyridin-2-ylmethyl)-2H-[1,2,3]triazolo[4,5-c]pyridin-6-yl)-2-fluorobenzonitrile | 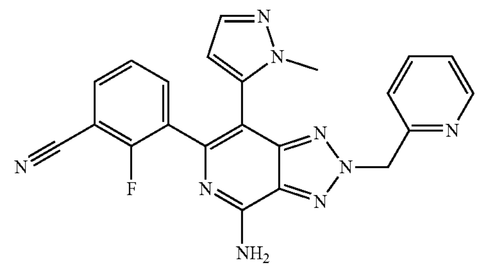 [SMILES: Cn1nccc1-c1c(-c2cccc(C#N)c2F)nc(N)c2nn(Cc3ccccn3)nc12] |
| 17 | 7-(1-((5-Chloropyridin-3-yl)methyl)-1H-pyrazol-4-yl)-3-methyl-9-pentyl-6,9-dihydro-5H-pyrrolo[3,2-d][1,2,4]triazolo[4,3-a]pyrimidin-5-one | 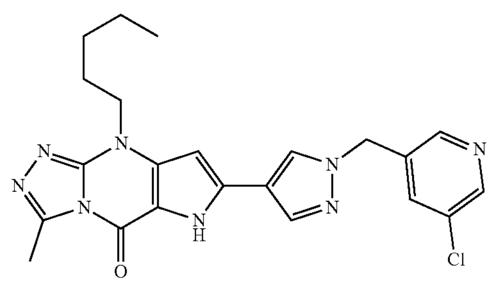 [SMILES: CCCCCn1c2cc(-c3cnn(Cc4cncc(Cl)c4)c3)[nH]c2c(=O)n2c(C)nnc12] |
| 18 | 3-Methyl-7-(1-((5-methylpyridin-3-yl)methyl)-1H-pyrazol-4-yl)-9-pentyl-6,9-dihydro-5H-pyrrolo[3,2-d][1,2,4]triazolo[4,3-a]pyrimidin-5-one | 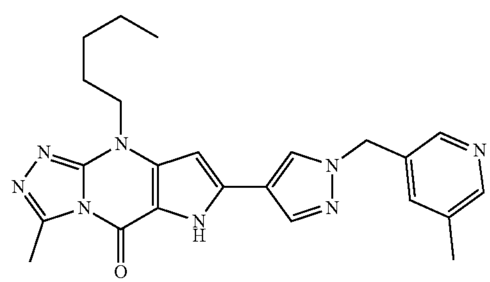 [SMILES: CCCCCn1c2cc(-c3cnn(Cc4cncc(C)c4)c3)[nH]c2c(=O)n2c(C)nnc12] |
| 19 | 3-Methyl-9-pentyl-7-(1-(thieno[3,2-b]pyridin-6-ylmethyl)-1H-pyrazol-4-yl)-6,9-dihydro-5H-pyrrolo[3,2-d][1,2,4]triazolo[4,3-a]pyrimidin-5-one | 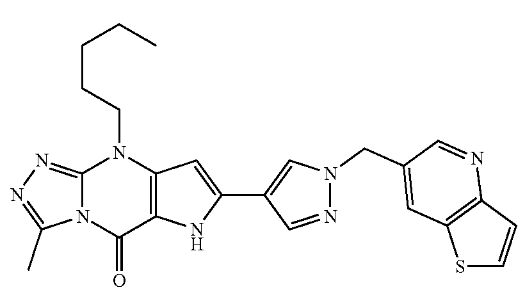 [SMILES: CCCCCn1c2cc(-c3cnn(Cc4cnc5ccsc5c4)c3)[nH]c2c(=O)n2c(C)nnc12] |

TABLE 6-continued

| Comp. No. | Name | Structure |
|---|---|---|
| 20 | 7-(1-((2-(2-(Dimethylamino)acetyl)-1,2,3,4-tetrahydroisoquinolin-6-yl)methyl)-1H-pyrazol-4-yl)-3-methyl-9-pentyl-6,9-dihydro-5H-pyrrolo[3,2-d][1,2,4]triazolo [4,3-a]pyrimidin-5-one | 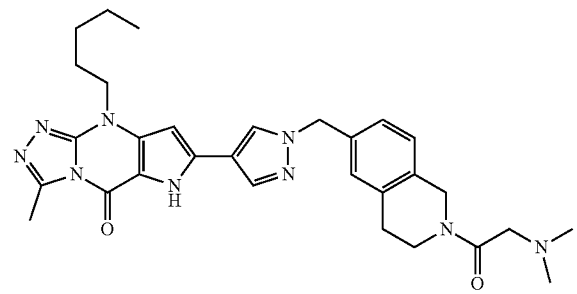 [SMILES: CCCCCn1c2cc(-c3cnn(Cc4ccc5c(c4)CCN(C(=O)CN(C)C)C5)c3)[nH]c2c(=O)n2c(C)nnc12] |
| 21A | 3-(2-((5-(1H-Pyrazol-1-yl)-2H-tetrazol-2-yl)methyl)-5-amino-8-(pyrimidin-4-yl)-[1,2,4]triazolo[1,5-c]pyrimidin-7-yl)benzonitrile | 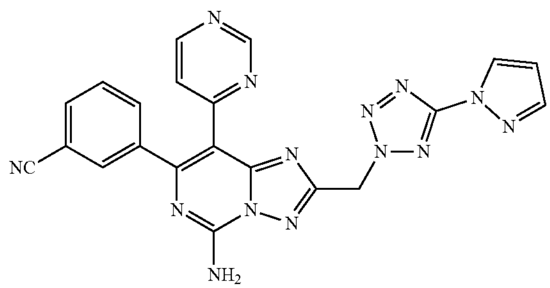 [SMILES: N#Cc1cccc(-c2nc(N)n3nc(Cn4nnc(-n5cccn5)n4)nc3c2-c2ccncn2)c1] |
| 21B | 3-(2-((5-(1H-Pyrazol-1-yl)-1H-tetrazol-1-yl)methyl)-5-amino-8-(pyrimidin-4-yl)-[1,2,4]triazolo[1,5-c]pyrimidin-7-yl)benzonitrile | 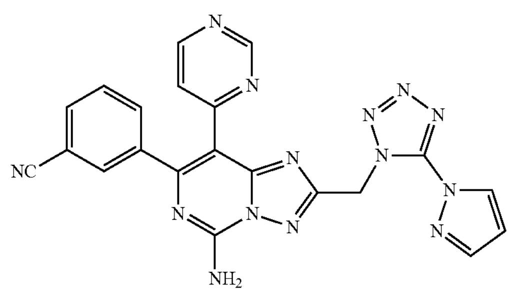 [SMILES: N#Cc1cccc(-c2nc(N)n3nc(Cn4nnnc4-n4cccn4)nc3c2-c2ccncn2)c1] |

In some embodiments, the inhibitor of A2A/A2B is a compound of Formula (I):

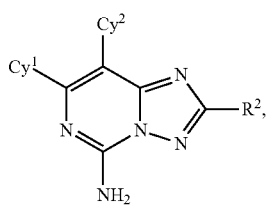

or a pharmaceutically acceptable salt thereof, wherein
$Cy^1$ is phenyl which is substituted by 1 or 2 substituents independently selected from halo and CN;
$Cy^2$ is 5-6 membered heteroaryl or 4-7 membered heterocycloalkyl, wherein the 5-6 membered heteroaryl or 4-7 membered heterocycloalkyl of $Cy^2$ are each optionally substituted with 1, 2, or 3 groups each independently selected from $C_{1-3}$ alkyl, $C_{1-3}$ alkoxy, $NH_2$, $NH(C_{1-3}$ alkyl) and $N(C_{1-3}$ alkyl)$_2$;
$R^2$ is selected from phenyl-$C_{1-3}$ alkyl-, $C_{3-7}$ cycloalkyl-$C_{1-3}$ alkyl-, (5-7 membered heteroaryl)-$C_{1-3}$ alkyl-, (4-7 membered heterocycloalkyl)-$C_{1-3}$ alkyl-, and $OR^{a2}$, wherein the phenyl-$C_{1-3}$ alkyl-, $C_{3-7}$ cycloalkyl-$C_{1-3}$ alkyl-, (5-7 membered heteroaryl)-$C_{1-3}$ alkyl-, and (4-7 membered heterocycloalkyl)-$C_{1-3}$ alkyl- of $R^2$ are each optionally substituted with 1, 2, or 3 independently selected $R^C$ substituents;
$R^{a2}$ is (5-7 membered heteroaryl)-$C_{1-3}$ alkyl- optionally substituted with 1 or 2 independently selected $R^C$ substituents;
each $R^C$ is independently selected from halo, $C_{1-6}$ alkyl, $C_6$ aryl, 5-7 membered heteroaryl, (4-7 membered heterocycloalkyl)-$C_{1-3}$ alkyl-, $OR^{a4}$, and $NR^{c4}R^{d4}$; and
each $R^{a4}$, $R^{c4}$, and $R^{d4}$ are independently selected from H and $C_{1-6}$ alkyl.

In some embodiments of the compound of Formula (I), $Cy^2$ is pyrimidinyl.

In some embodiments of the compound of Formula (I), $R^2$ is selected from pyridin-2-ylmethyl, (2,6-difluorophenyl)(hydroxy)methyl, (5-(pyridin-2-yl)-1H-tetrazol-1-yl)methyl, (3-methylpyridin-2-yl)methoxy, and (5-(1H-Pyrazol-1-yl)-1H-tetrazol-1-yl)methyl.

In some embodiments, the compound of Formula (I), or a pharmaceutically acceptable salt thereof, is 3-(5-Amino-2-(pyridin-2-ylmethyl)-8-(pyrimidin-4-yl)-[1,2,4]triazolo[1,5-c]pyrimidin-7-yl)benzonitrile, or a pharmaceutically acceptable salt thereof (see Compound 1, Table 6).

In some embodiments, the compound of Formula (I), or a pharmaceutically acceptable salt thereof, is 3-(5-Amino-2-

((2,6-difluorophenyl)(hydroxy)methyl)-8-(pyrimidin-4-yl)-[1,2,4]triazolo[1,5-c]pyrimidin-7-yl)benzonitrile, or a pharmaceutically acceptable salt thereof (see Compound 2, Table 6).

In some embodiments, the compound of Formula (I), or a pharmaceutically acceptable salt thereof, is 3-(5-Amino-2-((5-(pyridin-2-yl)-2H-tetrazol-2-yl)methyl)-8-(pyrimidin-4-yl)-[1,2,4]triazolo[1,5-c]pyrimidin-7-yl)benzonitrile, or a pharmaceutically acceptable salt thereof (see Compound 3A, Table 6).

In some embodiments, the compound of Formula (I), or a pharmaceutically acceptable salt thereof, is 3-(5-Amino-2-((5-(pyridin-2-yl)-1H-tetrazol-1-yl)methyl)-8-(pyrimidin-4-yl)-[1,2,4]triazolo[1,5-c]pyrimidin-7-yl)benzonitrile, or a pharmaceutically acceptable salt thereof (see Compound 3B, Table 6).

In some embodiments, the compound of Formula (I), or a pharmaceutically acceptable salt thereof, is 3-(5-Amino-2-((3-methylpyridin-2-yl)methoxy)-8-(pyrimidin-4-yl)-[1,2,4]triazolo[1,5-c]pyrimidin-7-yl)benzonitrile, or a pharmaceutically acceptable salt thereof (see Compound 4, Table 6).

In some embodiments, the compound of Formula (I), or a pharmaceutically acceptable salt thereof, is 3-(2-((5-(1H-Pyrazol-1-yl)-2H-tetrazol-2-yl)methyl)-5-amino-8-(pyrimidin-4-yl)-[1,2,4]triazolo[1,5-c]pyrimidin-7-yl)benzonitrile, or a pharmaceutically acceptable salt thereof (see Compound 21A, Table 6).

In some embodiments, the compound of Formula (I), or a pharmaceutically acceptable salt thereof, is 3-(2-((5-(1H-Pyrazol-1-yl)-1H-tetrazol-1-yl)methyl)-5-amino-8-(pyrimidin-4-yl)-[1,2,4]triazolo[1,5-c]pyrimidin-7-yl)benzonitrile, or a pharmaceutically acceptable salt thereof (see Compound 21B, Table 6).

The synthesis and characterization of compounds of Formula (I) can be found in WO2019/168847 and U.S. 62/891,685, both of which are hereby incorporated by reference in their entireties.

In some embodiments, the inhibitor of A2A/A2B is a compound of Formula (II):

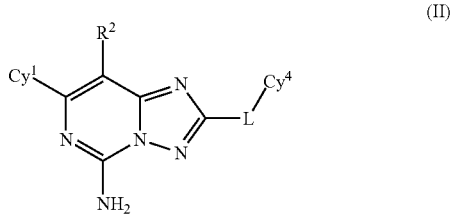

(II)

or a pharmaceutically acceptable salt thereof, wherein
$R^2$ is selected from H and CN;
$Cy^1$ is phenyl which is substituted by 1 or 2 substituents independently selected from halo and CN;
L is $C_{1-3}$ alkylene, wherein said alkylene is optionally substituted with 1, 2, or 3 independently selected $R^{8D}$ substituents;
$Cy^4$ is selected from phenyl, cyclohexyl, pyridyl, pyrrolidinonyl, and imidazolyl, wherein the phenyl, cyclohexyl, pyridyl, pyrrolidinonyl, and imidazolyl are each optionally substituted with 1, 2, or 3 substituents independently selected from $R^{8D}$ and $R^8$;
$R^8$ is independently selected from halo, $C_{1-6}$ alkyl, $C_{1-6}$ haloalkyl, $C_{2-4}$ alkenyl, $C_{2-4}$ alkynyl, phenyl, $C_{3-7}$ cycloalkyl, 5-6 membered heteroaryl, 4-7 membered heterocycloalkyl, phenyl-$C_{1-3}$ alkyl, $C_{3-7}$ cycloalkyl-$C_{1-3}$ alkyl, (5-6 membered heteroaryl)-$C_{1-3}$ alkyl, and (4-7 membered heterocycloalkyl)-$C_{1-3}$ alkyl, wherein the $C_{1-6}$ alkyl, $C_{2-4}$ alkenyl, $C_{2-4}$ alkynyl, phenyl, $C_{3-7}$ cycloalkyl, 5-6 membered heteroaryl, 4-7 membered heterocycloalkyl, phenyl-$C_{1-3}$ alkyl, $C_{3-7}$ cycloalkyl-$C_{1-3}$ alkyl, (5-6 membered heteroaryl)-$C_{1-3}$ alkyl, and (4-7 membered heterocycloalkyl)-$C_{1-3}$ alkyl of $R^8$ are each optionally substituted with 1, 2, or 3 independently selected $R^{8A}$ substituents;
each $R^{8A}$ is independently selected from halo, $C_{1-6}$ alkyl, 5-6 membered heteroaryl, 4-7 membered heterocycloalkyl, CN, $OR^{a81}$, and $NR^{c81}R^{d81}$, wherein the $C_{1-3}$ alkyl, 5-6 membered heteroaryl, and 4-7 membered heterocycloalkyl of $R^{8A}$ are each optionally substituted with 1, 2, or 3 independently selected $R^{8B}$ substituents;
each $R^{a81}$, $R^{c81}$, and $R^{d81}$ is independently selected from H, $C_{1-6}$ alkyl, and 4-7 membered heterocycloalkyl, wherein the $C_{1-6}$ alkyl and 4-7 membered heterocycloalkyl of $R^{a81}$, $R^{c81}$, and $R^{d81}$ are each optionally substituted with 1, 2, or 3 independently selected $R^{8B}$ substituents;
each $R^{8B}$ is independently selected from halo and $C_{1-3}$ alkyl; and
$R^{8D}$ is independently selected from OH, CN, halo, $C_{1-6}$ alkyl, and $C_{1-6}$ haloalkyl.

In some embodiments, the compound of Formula (II), or a pharmaceutically acceptable salt thereof, is 3-(5-Amino-2-(hydroxy(phenyl)methyl)-[1,2,4]triazolo[1,5-c]pyrimidin-7-yl)benzonitrile, or a pharmaceutically acceptable salt thereof (see Compound 5, Table 6).

In some embodiments, the compound of Formula (II), or a pharmaceutically acceptable salt thereof, is 3-(5-Amino-2-((2,6-difluorophenyl)(hydroxy)methyl)-[1,2,4]triazolo[1,5-c]pyrimidin-7-yl)-2-fluorobenzonitrile, or a pharmaceutically acceptable salt thereof (see Compound 6, Table 6).

In some embodiments, the compound of Formula (II), or a pharmaceutically acceptable salt thereof, is 5-Amino-7-(3-cyano-2-fluorophenyl)-2-((2,6-difluorophenyl)(hydroxy)methyl)-[1,2,4]triazolo[1,5-c]pyrimidine-8-carbonitrile, or a pharmaceutically acceptable salt thereof (see Compound 7, Table 6).

In some embodiments, the compound of Formula (II), or a pharmaceutically acceptable salt thereof, is 3-(5-Amino-2-((2-fluoro-6-(((1-methyl-2-oxopyrrolidin-3-yl)amino)methyl)phenyl)(hydroxy)methyl)-[1,2,4]triazolo[1,5-c]pyrimidin-7-yl)-2-fluorobenzonitrile, or a pharmaceutically acceptable salt thereof (see Compound 8, Table 6).

The synthesis and characterization of compounds of Formula (II) can be found in WO2019/222677, which is hereby incorporated by reference in its entirety.

In some embodiments, the inhibitor of A2A/A2B is a compound of Formula (III):

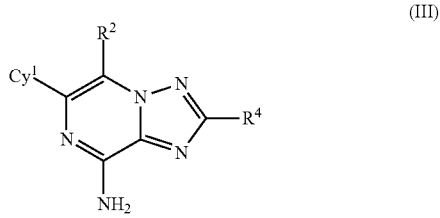

(III)

or a pharmaceutically acceptable salt thereof, wherein
$Cy^1$ is phenyl which is substituted by 1 or 2 substituents independently selected from halo and CN;

$R^2$ is selected from 5-6 membered heteroaryl and 4-7 membered heterocycloalkyl, wherein the 5-6 membered heteroaryl and 4-7 membered heterocycloalkyl of $R^2$ are each optionally substituted with 1, 2, or 3 independently selected $R^{2A}$ substituents;

each $R^{2A}$ is independently selected from D, halo, $C_{1-6}$ alkyl, and $C_{1-6}$ haloalkyl;

$R^4$ is selected from phenyl-$C_{1-3}$ alkyl-, $C_{3-7}$ cycloalkyl-$C_{1-3}$ alkyl-, (5-6 membered heteroaryl)-$C_{1-3}$ alkyl-, and (4-7 membered heterocycloalkyl)-$C_{1-3}$ alkyl wherein the phenyl-$C_{1-3}$ alkyl-, $C_{3-7}$ cycloalkyl-$C_{1-3}$ alkyl-, (5-6 membered heteroaryl)-$C_{1-3}$ alkyl-, and (4-7 membered heterocycloalkyl)-$C_{1-3}$ alkyl- of $R^4$ are each optionally substituted with 1, 2, or 3 independently selected $R^{4A}$ substituents;

each $R^{4A}$ is independently selected from halo, $C_{1-6}$ alkyl, $C_{1-6}$ haloalkyl, CN, $OR^{a41}$, and $NR^{c41}R^{d41}$; and each $R^{a41}$, $R^{c41}$, and $R^{d41}$ is independently selected from H and $C_{1-6}$ alkyl.

In some embodiments, the compound of Formula (III), or a pharmaceutically acceptable salt thereof, is 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile, or a pharmaceutically acceptable salt thereof (see Compound 9, Table 6).

In some embodiments, the compound of Formula (III), or a pharmaceutically acceptable salt thereof, is 3-(8-Amino-2-((2,6-difluorophenyl)(hydroxy)methyl)-5-(pyrimidin-4-yl)-[1,2,4]triazolo[1,5-a]pyrazin-6-yl)benzonitrile, or a pharmaceutically acceptable salt thereof (See Compound 10, Table 6).

In some embodiments, the compound of Formula (III), or a pharmaceutically acceptable salt thereof, is 3-(8-amino-2-(amino(2,6-difluorophenyl)methyl)-5-(4-methyloxazol-5-yl)-[1,2,4]triazolo[1,5-a]pyrazin-6-yl)benzonitrile, or a pharmaceutically acceptable salt thereof (see Compound 11, Table 6).

In some embodiments, the compound of Formula (III), or a pharmaceutically acceptable salt thereof, is 3-(8-amino-2-((2,6-difluorophenyl)(hydroxy)methyl)-5-(2,6-dimethylpyridin-4-yl)-[1,2,4]triazolo[1,5-a]pyrazin-6-yl)benzonitrile, or a pharmaceutically acceptable salt thereof (see Compound 12, Table 6).

The synthesis and characterization of compounds of Formula (III) can be found in PCT/US2019/040496, which is hereby incorporated by reference in its entirety.

In some embodiments, the inhibitor of A2A/A2B is a compound of Formula (I):

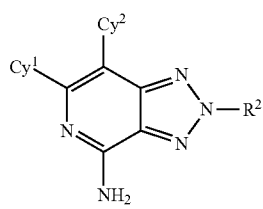

(IV)

or a pharmaceutically acceptable salt thereof, wherein
$Cy^1$ is phenyl which is substituted by 1 or 2 substituents independently selected from halo and CN;
$Cy^2$ is selected from 5-6 membered heteroaryl and 4-7 membered heterocycloalkyl, wherein the 5-6 membered heteroaryl and 4-7 membered heterocycloalkyl of $Cy^2$ are each optionally substituted with 1, 2, or 3 independently selected $R^6$ substituents;

each $R^6$ is independently selected from halo, $C_{1-6}$ alkyl, and $C_{1-6}$ haloalkyl;

$R^2$ is phenyl-$C_{1-3}$ alkyl- or (5-6 membered heteroaryl)-$C_{1-3}$ alkyl-, wherein the phenyl-$C_{1-3}$ alkyl- and (5-6 membered heteroaryl)-$C_{1-3}$ alkyl- of $R^2$ are each optionally substituted with 1, 2, or 3 independently selected $R^{2A}$ substituents; and each $R^{2A}$ is independently selected from halo, $C_{1-6}$ alkyl, and $C_{1-6}$ haloalkyl.

In some embodiments, the compound of Formula (IV), or a pharmaceutically acceptable salt thereof, is 3-(4-amino-2-(pyridin-2-ylmethyl)-7-(pyrimidin-4-yl)-2H-[1,2,3]triazolo[4,5-c]pyridin-6-yl)benzonitrile, or a pharmaceutically acceptable salt thereof (see Compound 13, Table 6).

In some embodiments, the compound of Formula (IV), or a pharmaceutically acceptable salt thereof, is 3-(4-amino-2-((3-fluoropyridin-2-yl)methyl)-7-(pyrimidin-4-yl)-2H-[1,2,3]triazolo[4,5-c]pyridin-6-yl)benzonitrile, or a pharmaceutically acceptable salt thereof (see Compound 14, Table 6).

In some embodiments, the compound of Formula (IV), or a pharmaceutically acceptable salt thereof, is 3-(4-amino-2-((3-fluoropyridin-2-yl)methyl)-7-(pyridin-4-yl)-2H-[1,2,3]triazolo[4,5-c]pyridin-6-yl)benzonitrile, or a pharmaceutically acceptable salt thereof (see Compound 15, Table 6).

In come embodiments, the compound of Formula (IV), or a pharmaceutically acceptable salt thereof, is 3-(4-amino-7-(1-methyl-1H-pyrazol-5-yl)-2-(pyridin-2-ylmethyl)-2H-[1,2,3]triazolo[4,5-c]pyridin-6-yl)-2-fluorobenzonitrile, or a pharmaceutically acceptable salt thereof (see Compound 16, Table 6).

The synthesis and characterization of compounds of Formula (IV) can be found in U.S. 62/798,180, which is hereby incorporated by reference in its entirety.

In some embodiments, the inhibitor of A2A/A2B is a compound of Formula (V):

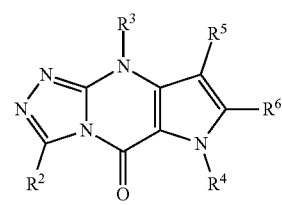

(V)

or a pharmaceutically acceptable salt thereof, wherein
$R^2$ is selected from H, D, halo, $C_{1-6}$ alkyl and $C_{1-6}$ haloalkyl;
$R^3$ is selected from H and $C_{1-6}$ alkyl;
$R^4$ is selected from H and $C_{1-6}$ alkyl;
$R^5$ is selected from H, halo, CN, $C_{1-6}$ alkyl;
$R^6$ is selected from phenyl, $C_{3-7}$ cycloalkyl, 5-7 membered heteroaryl, and 4-7 membered heterocycloalkyl wherein said phenyl, $C_{3-7}$ cycloalkyl, 5-7 membered heteroaryl, and 4-7 membered heterocycloalkyl of $R^6$ are optionally substituted by 1, 2, or 3 independently selected $R^A$ substituents;

each $R^A$ is independently selected from (5-10 membered heteroaryl)-$C_{1-3}$ alkyl- and (4-10 membered heterocycloalkyl)-$C_{1-3}$ alkyl-, wherein the (5-10 membered heteroaryl)-$C_{1-3}$ alkyl- and (4-10 membered heterocycloalkyl)-$C_{1-3}$ alkyl- of $R^A$ are each optionally substituted with 1 or 2 independently selected $R^B$ substituents;

each $R^B$ is independently selected from halo, $C_{1-6}$ alkyl, and $C(O)R^{b26}$;

$R^{b26}$ is independently selected from H and $C_{1-3}$ alkyl, wherein the $C_{1-3}$ alkyl of $R^{b26}$ is optionally substituted with 1 or 2 independently selected $R^C$ substituents each $R^C$ is independently selected from halo, $C_{1-6}$ alkyl, CN, $OR^{a36}$, and $NR^{c36}R^{d36}$; and each $R^{a36}$, $R^{c36}$, and $R^{d36}$ is independently selected from H and $C_{1-6}$ alkyl.

In some embodiments, the compound of Formula (V), or a pharmaceutically acceptable salt thereof, is 7-(1-((5-Chloropyridin-3-yl)methyl)-1H-pyrazol-4-yl)-3-methyl-9-pentyl-6,9-dihydro-5H-pyrrolo[3,2-d][1,2,4]triazolo[4,3-a]pyrimidin-5-one, or a pharmaceutically acceptable salt thereof (see Compound 17, Table 6).

In some embodiments, the compound of Formula (V), or a pharmaceutically acceptable salt thereof, is 3-Methyl-7-(1-((5-methylpyridin-3-yl)methyl)-1H-pyrazol-4-yl)-9-pentyl-6,9-dihydro-5H-pyrrolo[3,2-d][1,2,4]triazolo[4,3-a]pyrimidin-5-one, or a pharmaceutically acceptable salt thereof (see Compound 18, Table 6).

In some embodiments, the compound of Formula (V), or a pharmaceutically acceptable salt thereof, is 3-Methyl-9-pentyl-7-(1-(thieno[3,2-b]pyridin-6-ylmethyl)-1H-pyrazol-4-yl)-6,9-dihydro-5H-pyrrolo[3,2-d][1,2,4]triazolo[4,3-a]pyrimidin-5-one, or a pharmaceutically acceptable salt thereof (see Compound 19, Table 6).

In some embodiments, the compound of Formula (V), or a pharmaceutically acceptable salt thereof, is 7-(1-((2-(2-(Dimethylamino)acetyl)-1,2,3,4-tetrahydroisoquinolin-6-yl)methyl)-1H-pyrazol-4-yl)-3-methyl-9-pentyl-6,9-dihydro-5H-pyrrolo[3,2-d][1,2,4]triazolo[4,3-a]pyrimidin-5-one, or a pharmaceutically acceptable salt thereof (see Compound 20, Table 6).

The synthesis and characterization of compounds of Formula (V) can be found in US-2019-0337957, which is hereby incorporated by reference in its entirety.

As used herein, "about" when referring to a measurable value such as an amount, a dosage, a temporal duration, and the like, is meant to encompass variations of ±10%. In certain embodiments, "about" can include variations of ±5%, ±1%, or ±0.1% from the specified value and any variations there between, as such variations are appropriate to perform the disclosed methods.

In some embodiments, the compound disclosed herein is the (S)-enantiomer of the compound, or a pharmaceutically acceptable salt thereof. In some embodiments, the compound is the (R)-enantiomer of the compound, or a pharmaceutically acceptable salt thereof.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

As used herein, the phrase "each 'variable' is independently selected from" means substantially the same as wherein "at each occurrence 'variable' is selected from."

Throughout the definitions, the term "$C_{n-m}$" indicates a range which includes the endpoints, wherein n and m are integers and indicate the number of carbons. Examples include $C_{1-3}$, $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (iPr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ alkoxy", employed alone or in combination with other terms, refers to a group of formula-O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 5 to 10 carbon atoms. In some embodiments, the aryl group is phenyl or naphthyl. In some embodiments, the aryl is phenyl (i.e., $C_6$ aryl).

As used herein, "halo" or "halogen" refers to F, Cl, Br, or I. In some embodiments, a halo is F, Cl, or Br. In some embodiments, a halo is F or Cl. In some embodiments, a halo is F. In some embodiments, a halo is Cl.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. Example haloalkyl groups include $CF_3$, $C_2F_5$, $CHF_2$, $CH_2F$, $CCl_3$, $CHCl_2$, $C_2Cl_5$ and the like.

As used herein, "cycloalkyl" refers to non-aromatic cyclic hydrocarbons including cyclized alkyl and alkenyl groups. Cycloalkyl groups can include mono- or polycyclic (e.g., having 2 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons (i.e., $C_{3-10}$). In some embodiments, the cycloalkyl is a $C_{3-10}$ monocyclic or bicyclic cycloalkyl. In some embodiments, the cycloalkyl is a $C_{3-7}$ monocyclic cycloalkyl. In some embodiments, the cycloalkyl is a $C_{4-7}$ monocyclic cycloalkyl. In some embodiments, the cycloalkyl is a $C_{4-10}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1] heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic (e.g., having 2 fused rings) aromatic heterocycle having at least one heteroatom ring member selected from N, O, S and B. In some embodiments, the heteroaryl ring has 1, 2, 3, or 4 heteroatom ring members independently selected from N, O, S and B. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from N, O, S, and B. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-6 monocyclic heteroaryl having 1 or 2 heteroatom ring members independently selected from N, O, S, and B. In some embodiments, the heteroaryl is a 5-6 monocyclic heteroaryl having 1 or 2 heteroatom ring members independently selected from N, O, and S. In some embodiments, the heteroaryl group contains 3 to 10, 4 to 10, 5 to 10, 5 to 7, 3 to 7, or 5 to 6 ring-forming atoms. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, thienyl (or thiophenyl), furyl (or furanyl), pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl and 1,2-dihydro-1,2-azaborine, pyridinyl, pyrimidinyl, pyrazinyl, pyridazinyl, azolyl, triazolyl, thiadiazolyl, quinolinyl, isoquinolinyl, indolyl, benzothiophenyl, benzofuranyl, benzisoxazolyl, imidazo[1,2-b]thiazolyl, purinyl, triazinyl, thieno[3,2-b]pyridinyl, imidazo[1,2-a]pyridinyl, 1,5-naphthyridinyl, 1H-pyrazolo[4,3-b]pyridinyl, triazolo[4,3-a] pyridinyl, 1H-pyrrolo[3,2-b]pyridinyl, 1H-pyrrolo[2,3-b] pyridinyl, pyrazolo[1,5-a]pyridinyl, indazolyl, and the like.

As used herein, "heterocycloalkyl" refers to monocyclic or polycyclic heterocycles having at least one non-aromatic ring (saturated or partially unsaturated ring), wherein one or more of the ring-forming carbon atoms of the heterocycloalkyl is replaced by a heteroatom selected from N, O, S, and B, and wherein the ring-forming carbon atoms and heteroatoms of a heterocycloalkyl group can be optionally substituted by one or more oxo or sulfido (e.g., C(O), S(O), C(S), or $S(O)_2$, etc.). When a ring-forming carbon atom or heteroatom of a heterocycloalkyl group is optionally substituted by one or more oxo or sulfide, the O or S of said group is in addition to the number of ring-forming atoms specified herein (e.g., a 1-methyl-6-oxo-1,6-dihydropyridazin-3-yl is a 6-membered heterocycloalkyl group, wherein a ring-forming carbon atom is substituted with an oxo group, and wherein the 6-membered heterocycloalkyl group is further substituted with a methyl group). Heterocycloalkyl groups include monocyclic and polycyclic (e.g., having 2 fused rings) systems. Included in heterocycloalkyl are monocyclic and polycyclic 3 to 10, 4 to 10, 5 to 10, 4 to 7, 5 to 7, or 5 to 6 membered heterocycloalkyl groups. Heterocycloalkyl groups can also include spirocycles and bridged rings (e.g., a 5 to 10 membered bridged biheterocycloalkyl ring having one or more of the ring-forming carbon atoms replaced by a heteroatom independently selected from N, O, S, and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring.

In some embodiments, the heterocycloalkyl group contains 3 to 10 ring-forming atoms, 4 to 10 ring-forming atoms, 3 to 7 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom. In some embodiments, the heterocycloalkyl is a monocyclic 4-6 membered heterocycloalkyl having 1 or 2 heteroatoms independently selected from N, O, S and B and having one or more oxidized ring members. In some embodiments, the heterocycloalkyl is a monocyclic or bicyclic 5-10 membered heterocycloalkyl having 1, 2, 3, or 4 heteroatoms independently selected from N, O, S, and B and having one or more oxidized ring members. In some embodiments, the heterocycloalkyl is a monocyclic or bicyclic 5 to 10 membered heterocycloalkyl having 1, 2, 3, or 4 heteroatoms independently selected from N, O, and S and having one or more oxidized ring members. In some embodiments, the heterocycloalkyl is a monocyclic 5 to 6 membered heterocycloalkyl having 1, 2, 3, or 4 heteroatoms independently selected from N, O, and S and having one or more oxidized ring members.

Example heterocycloalkyl groups include pyrrolidin-2-one (or 2-oxopyrrolidinyl), 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, 1,2,3,4-tetrahydroisoquinoline, benzazapene, azabicyclo[3.1.0]hexanyl, diazabicyclo[3.1.0]hexanyl, oxobicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo [3.2.1]octanyl, oxobicyclo[2.2.2]octanyl, azabicyclo[2.2.2] octanyl, azaadamantanyl, diazaadamantanyl, oxo-adamantanyl, azaspiro[3.3]heptanyl, diazaspiro[3.3] heptanyl, oxo-azaspiro[3.3]heptanyl, azaspiro[3.4]octanyl, diazaspiro[3.4]octanyl, oxo-azaspiro[3.4]octanyl, azaspiro [2.5]octanyl, diazaspiro[2.5]octanyl, azaspiro[4.4]nonanyl, diazaspiro[4.4]nonanyl, oxo-azaspiro[4.4]nonanyl, azaspiro[4.5]decanyl, diazaspiro[4.5]decanyl, diazaspiro[4.4]nonanyl, oxo-diazaspiro[4.4]nonanyl, oxo-dihydropyridazinyl, oxo-2,6-diazaspiro[3.4]octanyl, oxohexahydropyrrolo[1,2-a]pyrazinyl, 3-oxopiperazinyl, oxo-pyrrolidinyl, oxo-pyridinyl and the like. For example, heterocycloalkyl groups include the following groups (with and without N-methyl substitution):

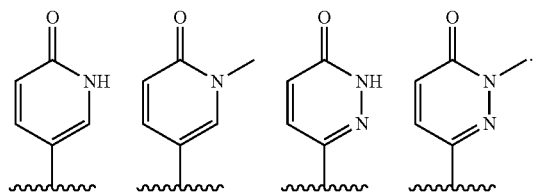

As used herein, "$C_{o-p}$ cycloalkyl-$C_{n-m}$ alkyl-" refers to a group of formula cycloalkyl-alkylene-, wherein the cycloalkyl has o to p carbon atoms and the alkylene linking group has n to m carbon atoms.

As used herein "$C_{o-p}$ aryl-$C_{n-m}$ alkyl-" refers to a group of formula aryl-alkylene-, wherein the aryl has o to p carbon atoms and the alkylene linking group has n to m carbon atoms.

As used herein, "heteroaryl-$C_{n-m}$ alkyl-" refers to a group of formula heteroaryl-alkylene-, wherein alkylene linking group has n to m carbon atoms.

As used herein "heterocycloalkyl-$C_{n-m}$ alkyl-" refers to a group of formula heterocycloalkyl-alkylene-, wherein alkylene linking group has n to m carbon atoms.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl or sulfonyl group.

As used herein, the term "independently selected from" means that each occurrence of a variable or substituent are independently selected at each occurrence from the applicable list.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. The Formulas (e.g., Formula (I), (II), etc.) provided herein include stereoisomers of the compounds.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Compounds described herein, including salts thereof, can be prepared using known organic synthesis techniques and can be synthesized according to any of numerous possible synthetic routes.

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" Karl F. Blom, et al. *J. Combi. Chem.* 2004, 6(6), 874-883, which is incorporated herein by reference in its entirety) and normal phase silica chromatography.

The compounds described herein can modulate activity of one or more of various G-protein coupled receptors (GPCRs) including, for example, A2A/A2B. The term "modulate" is meant to refer to an ability to increase or decrease the activity of one or more members of the A2A/A2B family. Accordingly, the compounds described herein can be used in methods of modulating A2A/A2B by contacting the A2A/A2B with any one or more of the compounds or compositions described herein. In some embodiments, compounds of the present invention can act as inhibitors of one or both of A2A and A2B. In further embodiments, the compounds described herein can be used to modulate activity of A2A/A2B in an individual in need of modulation of the receptor by administering a modulating amount of a compound described herein, or a pharmaceutically acceptable salt thereof. In some embodiments, modulating is inhibiting.

Given that cancer cell growth and survival is impacted by multiple signaling pathways, the present invention is useful for treating disease states characterized by drug resistant mutants. In addition, different GPCR inhibitors, exhibiting different preferences in the GPCRs which they modulate the activities of, may be used in combination. This approach could prove highly efficient in treating disease states by targeting multiple signaling pathways, reduce the likelihood of drug-resistance arising in a cell, and reduce the toxicity of treatments for disease.

GPCRs to which the present compounds bind and/or modulate (e.g., inhibit) include any member of the A2A/A2B family.

In some embodiments, more than one compound described herein is used to inhibit the activity of one GPCR (e.g., A2A).

In some embodiments, more than one compound described herein is used to inhibit more than one GPCR, such as at least two GPCRs (e.g., A2A and A2B).

In some embodiments, one or more of the compounds is used in combination with another GPCR antagonist to inhibit the activity of one GPCR (e.g., A2A or A2B).

The inhibitors of A2A/A2B described herein can be selective. By "selective" is meant that the compound binds to or inhibits a GPCR with greater affinity or potency, respectively, compared to at least one other GPCR. In some embodiments, the compounds described herein are selective inhibitors of A2A or A2B. In some embodiments, the compounds described herein are selective inhibitors of A2A (e.g., over A2B). In some embodiments, the compounds described herein are selective inhibitors of A2B (e.g., over A2A). In some embodiments, selectivity can be at least about 2-fold, 5-fold, 10-fold, at least about 20-fold, at least about 50-fold, at least about 100-fold, at least about 200-fold, at least about 500-fold or at least about 1000-fold. Selectivity can be measured by methods routine in the art. In some embodiments, selectivity can be tested at the biochemical affinity against each GPCR. In some embodiments, the selectivity of compounds described herein can be determined by cellular assays associated with particular A2A/A2B activity.

As used herein, the term "contacting" refers to the bringing together of indicated moieties in an in vitro system or an in vivo system. For example, "contacting" A2A/A2B with a compound described herein includes the administration of a compound of the present invention to an individual or patient, such as a human, having a A2A/A2B, as well as, for example, introducing a compound described herein into a sample containing a cellular or purified preparation containing the A2A/A2B.

Additional Inhibitors of A2A and/or A2B Adenosine Receptor

Other inhibitors of A2A and/or A2B adenosine receptor useful in combination with an inhibitor of CD73 in the methods described herein are known in the art.

In some instances, the inhibitor of A2A and/or A2B adenosine receptor is CPI-444 (also referred to herein as "Compound B"; 7-(5-methylfuran-2-yl)-3-[[6-[[(3S)-oxolan-3-yl]oxymethyl]pyridin-2-yl]methyl]triazolo[4,5-d]pyrimidin-5-amine).

In some instances, the inhibitor of A2A and/or A2B adenosine receptor is AB928 (3-[2-Amino-6-[1-[[6-(2-hydroxypropan-2-yl)pyridin-2-yl]methyl]triazol-4-yl]pyrimidin-4-yl]-2-methylbenzonitrile).

In some instances, the inhibitor of A2A and/or A2B adenosine receptor is AZD4635 (6-(2-Chloro-6-methylpyridin-4-yl)-5-(4-fluorophenyl)-1,2,4-triazin-3-amine).

In some instances, the inhibitor of A2A and/or A2B adenosine receptor is NIR-178 (5-Bromo-2,6-di(1H-pyrazol-1-yl)pyrimidin-4-amine).

In some instances, the inhibitor of A2A and/or A2B adenosine receptor is EOS100850.

In some instances, the inhibitor of A2A and/or A2B adenosine receptor is a compound, pharmaceutically acceptable salt thereof, or stereoisomer thereof described in US patent application publication no. 2019/0292188, which is incorporated by reference herein in its entirety. In some instances, the inhibitor of A2A and/or A2B adenosine receptor comprises or consists of

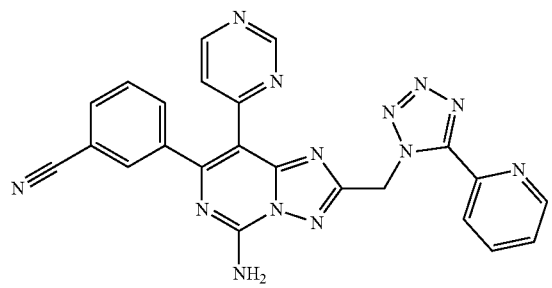 [SMILES: N#Cc1cccc(-c2nc(N)n3nc(Cn4nnnc4-c4ccccn4)nc3c2-c2ccncn2)c1]

(3-(5-Amino-2-((5-(pyridin-2-yl)-1H-tetrazol-1-yl)methyl)-8-(pyrimidin-4-yl)-[1,2,4]triazolo[1,5-c]pyrimidin-7-yl)benzonitrile), or a pharmaceutically acceptable salt thereof or a stereoisomer thereof.

In some instances, the inhibitor of A2A and/or A2B adenosine receptor comprises or consists of

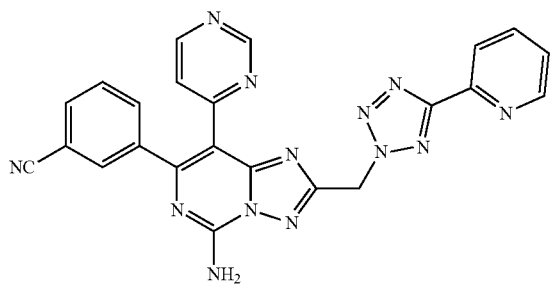 [SMILES: N#Cc1cccc(-c2nc(N)n3nc(Cn4nnc(-c5ccccn5)n4)nc3c2-c2ccncn2)c1]

(3-(5-Amino-2-((5-(pyridin-2-yl)-2H-tetrazol-2-yl)methyl)-8-(pyrimidin-4-yl)-[1,2,4]triazolo[1,5-c]pyrimidin-7-yl)benzonitrile), or a pharmaceutically acceptable salt thereof or a stereoisomer thereof.

Labeled Agents and Assay Methods

Another aspect of the present disclosure relates to labeled agents (i.e., labeled inhibitors of CD73 and inhibitors of A2A and/or A2B adenosine receptor) of the disclosure (radio-labeled, fluorescent-labeled, etc.) that would be useful not only in imaging techniques but also in assays, both in vitro and in vivo, for localizing and quantitating CD73 or A2A and/or A2B receptors in tissue samples, including human, and for identifying CD73 or A2A and/or A2B antagonists by inhibition binding of a labeled compound. Substitution of one or more of the atoms of the compounds of the present disclosure can also be useful in generating differentiated ADME (Adsorption, Distribution, Metabolism and Excretion.) Accordingly, the present disclosure includes adenosine receptor (e.g., A2A and/or A2B) assays that contain such labeled or substituted compounds.

The present disclosure further includes isotopically-labeled agents of the disclosure. An "isotopically" or "radiolabeled" agent is an agent of the disclosure where one or more atoms are replaced or substituted by an atom having an atomic mass or mass number different from the atomic mass or mass number typically found in nature (i.e., naturally occurring). Suitable radionuclides that may be incorporated in agents of the present disclosure include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$C, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —$CD_3$ being substituted for —$CH_3$). In some embodiments, alkyl groups in any of the disclosed Formulas, e.g., Formula (I), can be perdeuterated.

One or more constituent atoms of the agents presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as —$CD_3$ being substituted for —$CH_3$). In some embodiments, the agent includes two or more deuterium atoms. In some embodiments, the agent includes 1-2, 1-3, 1-4, 1-5, or 1-6 deuterium atoms. In some embodiments, all of the hydrogen atoms in an agent can be replaced or substituted by deuterium atoms.

In some embodiments, 1, 2, 3, 4, 5, 6, 7, or 8 hydrogen atoms, attached to carbon atoms of any "alkyl", "alkenyl", "alkynyl", "aryl", "phenyl", "cycloalkyl", "heterocycloalkyl", or "heteroaryl" substituents or "—$C_{1-6}$ alkyl-", "alkylene", "alkenylene" and "alkynylene" linking groups, as described herein, are each optionally replaced by a deuterium atom.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled agents can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. *J. Label Compd. Radiopharm.* 2015, 58, 308-312). In particular, substitution at one or more metabolism sites may afford one or more of the therapeutic advantages.

The radionuclide that is incorporated in the instant radio-labeled agents will depend on the specific application of that radio-labeled agent. For example, for in vitro adenosine receptor labeling and competition assays, agents that incorporate $^3$H, $^{14}$C, $^{82}$Br, $^{125}$I, $^{131}$I or $^{35}$S can be useful. For radio-imaging applications $^{11}$C, $^{18}$F, $^{125}$I, $^{123}$I, $^{124}$I, $^{131}$I, $^{75}$Br, $^{76}$Br or $^{77}$Br can be useful.

It is understood that a "radio-labeled" or "labeled agent" is an agent that has incorporated at least one radionuclide. In some embodiments, the radionuclide is selected from the group consisting of $^3$H, $^{14}$C, $^{125}$I, $^{35}$S and $^{82}$Br.

The present disclosure can further include synthetic methods for incorporating radio-isotopes into agents of the disclosure. Synthetic methods for incorporating radio-isotopes into organic compounds and antibodies are well known in the art, and an ordinary skill in the art will readily recognize the methods applicable for the compounds and antibodies of disclosure.

A labeled agent of the disclosure can be used in a screening assay to identify/evaluate agents. For example, a newly synthesized or identified agent (i.e., test agent) which is labeled can be evaluated for its ability to bind an adenosine receptor or CD73 by monitoring its concentration variation when contacting with the adenosine receptor or CD73, respectively, through tracking of the labeling. For example, a test agent (labeled) can be evaluated for its ability to reduce binding of another agent which is known to bind to an adenosine receptor or CD73 (i.e., standard agent). Accordingly, the ability of a test agent to compete with the standard agent for binding to the adenosine receptor or CD73 directly correlates to its binding affinity. Conversely, in some other screening assays, the standard agent is labeled and test agents are unlabeled. Accordingly, the concentration of the labeled standard agent is monitored in order to evaluate the competition between the standard agent and the test agent, and the relative binding affinity of the test agent is thus ascertained.

Combination Therapy and Indications

The CD73 inhibitors of the present disclosure can modulate the activity of CD73. Accordingly, the CD73 inhibitors described herein can be used in methods of inhibiting CD73 by contacting CD73 with any one or more of the antibodies or compositions thereof described herein. Likewise, the A2A and/or A2B inhibitors of the present disclosure can modulate the activity of A2A and/or A2B adenosine receptor. Accordingly, the A2A and/or A2B adenosine receptor inhibitors, salts or stereoisomers described herein can be used in methods of inhibiting A2A and/or A2B adenosine receptor by contacting A2A and/or A2B adenosine receptor, respectively with any one or more of the A2A and/or A2B adenosine receptor inhibitors or compositions thereof described herein. CD73 inhibitors of the present disclosure and inhibitors of A2A and/or A2B adenosine receptor of the present disclosure can function synergistically, e.g., to treat a disease or disorder, e.g., cancer. Accordingly, the CD73 inhibitors described herein can be used in combination with the inhibitors of A2A and/or A2B adenosine receptor described herein in methods of inhibiting CD73 and A2A and/or A2B adenosine receptor by contacting CD73 with any one or more of the CD73 inhibitors or compositions thereof described herein and contacting A2A and/or A2B adenosine receptor with any one or more of the inhibitors of A2A and/or A2B adenosine receptor or compositions thereof described herein.

In some embodiments, the CD73 inhibitors and A2A and/or A2B adenosine receptor inhibitors can be used in combination in methods of inhibiting: (i) activity of CD73 in an individual/patient in need of the inhibition, and (ii) activity of A2A and/or A2B adenosine receptor in an individual/patient in need of the inhibition, by administering an effective amount of a CD73 inhibitor described herein and an inhibitor of A2A and/or A2B adenosine receptor described herein. In some embodiments, modulating is inhibiting. In some embodiments, the contacting is in vivo. In some embodiments, the contacting is ex vivo or in vitro.

Another aspect of the present disclosure pertains to methods of treating a CD73- and/or A2A and/or A2B adenosine receptor-associated disease or disorder in an individual (e.g., patient) by administering to the individual in need of such treatment a therapeutically effective amount or dose of one or more CD73 inhibitors of the present disclosure or a pharmaceutical composition thereof and a therapeutically effective amount or dose of one or more inhibitors of A2A and/or A2B adenosine receptor of the present disclosure or a pharmaceutical composition thereof. A CD73-associated disease or disorder can include any disease, disorder or condition that is directly or indirectly linked to expression or activity of CD73, including overexpression and/or abnormal activity levels. An A2A and/or A2B adenosine receptor-associated disease or disorder can include any disease, disorder or condition that is directly or indirectly linked to expression or activity of A2A and/or A2B adenosine receptor, including overexpression and/or abnormal activity levels. A CD73- and/or A2A and/or A2B adenosine receptor-associated disease or disorder can include any disease, disorder or condition that is directly or indirectly linked to expression or activity of CD73 and/or A2A and/or A2B adenosine receptor, including overexpression and/or abnormal activity levels of CD73 and/or A2A and/or A2B adenosine receptor.

Another aspect of the present disclosure pertains to methods of treating a disease or disorder (e.g., cancer) in an individual (e.g., patient) by administering to the individual in need of such treatment a therapeutically effective amount or dose of one or more inhibitors of CD73 of the present disclosure or a pharmaceutical composition thereof and a therapeutically effective amount or dose of one or more inhibitors of A2A and/or A2B adenosine receptor of the present disclosure or a pharmaceutical composition thereof, wherein the disease or disorder has a high adenosine signature. Methods of determining that a disease or disorder has a high adenosine signature are known in the art. For instance, gene expression analysis of tumor tissue may be performed using a defined panel of adenosine-responsive genes.

The CD73 inhibitors and inhibitors of A2A and/or A2B adenosine receptor of the present disclosure are useful in combination in the treatment of diseases related to the activity of CD73 and/or A2A and/or A2B adenosine receptor including, for example, cancer, inflammatory diseases, cardiovascular diseases, neurodegenerative diseases, immunomodulatory disorders, central nerve system diseases, and diabetes.

In some embodiments, the inhibitor of human CD73 comprises:
(a) an antibody comprising a variable heavy (VH) domain comprising VH complementarity determining region (CDR)1, VH CDR2, and VH CDR3, wherein:
the VH CDR1 comprises the amino acid sequence GYTFTSYG (SEQ ID NO:1);
the VH CDR2 comprises the amino acid sequence IYPGSGNT (SEQ ID NO:2); and
the VH CDR3 comprises the amino acid sequence ARYDYLGSSYGFDY (SEQ ID NO:3); and
comprising a variable light (VL) domain comprising VL CDR1, VL CDR2, and VL CDR3, wherein:
the VL CDR1 comprises the amino acid sequence QDVSTA (SEQ ID NO:4);
the VL CDR2 comprises the amino acid sequence SAS (SEQ ID NO:5); and
the VL CDR3 comprises the amino acid sequence QQHYNTPYT (SEQ ID NO:6);
(b) an antibody that binds to human CD73 at an epitope within amino acids 40-53 of SEQ ID NO:70;
(c) an antibody that binds to human CD73 and competes for binding to human CD73 with an antibody that has a heavy chain comprising the amino acid sequence of SEQ ID NO:24 and a light chain comprising the amino acid sequence of SEQ ID NO:25; or
(d) an antibody comprising a VH domain comprising VH CDR1, VH CDR2, and VH CDR3, wherein:
the VH CDR1 comprises the amino acid sequence GFTFSSYD (SEQ ID NO:34);
the VH CDR2 comprises the amino acid sequence MSYDGSNK (SEQ ID NO:35) or MSYEGSNK (SEQ ID NO:40); and
the VH CDR3 comprises the amino acid sequence ATEIAAKGDY (SEQ ID NO:36); and
an antibody comprising a VL domain comprising VL CDR1, VL CDR2, and VL CDR3, wherein:
the VL CDR1 comprises the amino acid sequence QGISNY (SEQ ID NO:37);
the VL CDR2 comprises the amino acid sequence AAS (SEQ ID NO:38); and
the VL CDR3 comprises the amino acid sequence QQSYSTPH (SEQ ID NO:39);
(e) an antibody that binds to human CD73 at an epitope within amino acids 386-399 and 470-489 of SEQ ID NO:70;
(f) an antibody that binds to human CD73 and competes for binding to human CD73 with an antibody that has a heavy chain comprising the amino acid sequence of SEQ ID NO:30 and a light chain comprising the amino acid sequence of SEQ ID NO:31;
(g) an antibody that binds to human CD73 and competes for binding to human CD73 with an antibody that has a heavy chain comprising the amino acid sequence of SEQ ID NO:33 and a light chain comprising the amino acid sequence of SEQ ID NO:31;
(h) an antibody selected from the group consisting of 11E1, Medi9447, CPI-006, and BMS-986179; or
(i) an inhibitor selected from the group consisting of CB-708 and AB680.

In some embodiments, the inhibitor of A2A adenosine receptor and/or A2B adenosine receptor (A2A/A2B) comprises a compound of:

(a) Formula (I):

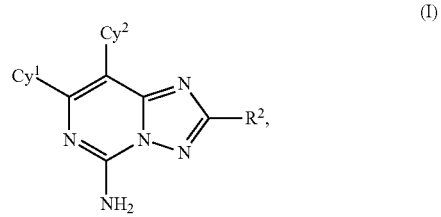

or a pharmaceutically acceptable salt thereof, wherein
$Cy^1$ is phenyl which is substituted by 1 or 2 substituents independently selected from halo and CN;
$Cy^2$ is 5-6 membered heteroaryl or 4-7 membered heterocycloalkyl, wherein the 5-6 membered heteroaryl or 4-7 membered heterocycloalkyl of $Cy^2$ are each optionally substituted with 1, 2, or 3 groups each independently selected from $C_{1-3}$ alkyl, $C_{1-3}$ alkoxy, $NH_2$, $NH(C_{1-3}$ alkyl) and $N(C_{1-3}$ alkyl$)_2$;
$R^2$ is selected from phenyl-$C_{1-3}$ alkyl-, $C_{3-7}$ cycloalkyl-$C_{1-3}$ alkyl-, (5-7 membered heteroaryl)-$C_{1-3}$ alkyl-, (4-7 membered heterocycloalkyl)-$C_{1-3}$ alkyl-, and $OR^{a2}$, wherein the phenyl-$C_{1-3}$ alkyl-, $C_{3-7}$ cycloalkyl-$C_{1-3}$ alkyl-, (5-7 membered heteroaryl)-$C_{1-3}$ alkyl-, and (4-7 membered heterocycloalkyl)-$C_{1-3}$ alkyl- of $R^2$ are each optionally substituted with 1, 2, or 3 independently selected $R^C$ substituents;
$R^{a2}$ is (5-7 membered heteroaryl)-$C_{1-3}$ alkyl- optionally substituted with 1 or 2 independently selected $R^C$ substituents;
each $R^C$ is independently selected from halo, $C_{1-6}$ alkyl, $C_6$ aryl, 5-7 membered heteroaryl, (4-7 membered heterocycloalkyl)-$C_{1-3}$ alkyl-, $OR^{a4}$, and $NR^{c4}R^{d4}$; and
each $R^{a4}$, $R^{c4}$, and $R^{d4}$ are independently selected from H and $C_{1-6}$ alkyl;

(b) Formula (II):

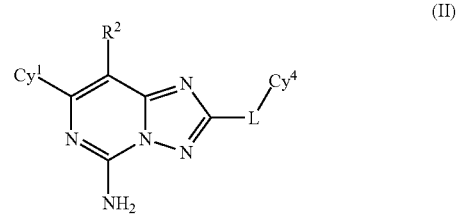

or a pharmaceutically acceptable salt thereof, wherein
$R^2$ is selected from H and CN;
$Cy^1$ is phenyl which is substituted by 1 or 2 substituents independently selected from halo and CN;
L is $C_{1-3}$ alkylene, wherein said alkylene is optionally substituted with 1, 2, or 3 independently selected $R^{8D}$ substituents;
$Cy^4$ is selected from phenyl, cyclohexyl, pyridyl, pyrrolidinonyl, and imidazolyl, wherein the phenyl, cyclohexyl, pyridyl, pyrrolidinonyl, and imidazolyl are each optionally substituted with 1, 2, or 3 substituents independently selected from $R^{8D}$ and $R^8$;
each $R^8$ is independently selected from halo, $C_{1-6}$ alkyl, $C_{1-6}$ haloalkyl, $C_{2-4}$ alkenyl, $C_{2-4}$ alkynyl, phenyl, $C_{3-7}$ cycloalkyl, 5-6 membered heteroaryl, 4-7 membered heterocycloalkyl, phenyl-$C_{1-3}$ alkyl, cycloalkyl-$C_{1-3}$ alkyl, (5-6 membered heteroaryl)-$C_{1-3}$ alkyl, and (4-7 membered heterocycloalkyl)-$C_{1-3}$ alkyl, wherein the C$_{1-6}$ alkyl, C$_{2-4}$ alkenyl, C$_{2-4}$ alkynyl, phenyl, C$_{3-7}$ cycloalkyl, 5-6 membered heteroaryl, 4-7 membered heterocycloalkyl, phenyl-C$_{1-3}$ alkyl, C$_{3-7}$ cycloalkyl-C$_{1-3}$ alkyl, (5-6 membered heteroaryl)-C$_{1-3}$ alkyl, and (4-7 membered heterocycloalkyl)-C$_{1-3}$ alkyl of R$^8$ are each optionally substituted with 1, 2, or 3 independently selected R$^{8A}$ substituents;

each R$^{8A}$ is independently selected from halo, C$_{1-6}$ alkyl, 5-6 membered heteroaryl, 4-7 membered heterocycloalkyl, CN, OR$^{a81}$, and NR$^{c81}$R$^{d81}$, wherein the C$_{1-3}$ alkyl, 5-6 membered heteroaryl, and 4-7 membered heterocycloalkyl of R$^{8A}$ are each optionally substituted with 1, 2, or 3 independently selected R$^{8B}$ substituents;

each R$^{a81}$, R$^{c81}$, and R$^{d81}$ is independently selected from H, C$_{1-6}$ alkyl, and 4-7 membered heterocycloalkyl, wherein the C$_{1-6}$ alkyl and 4-7 membered heterocycloalkyl of R$^{a81}$, R$^{c81}$, and R$^{d81}$ are each optionally substituted with 1, 2, or 3 independently selected R$^{8B}$ substituents;

each R$^{8B}$ is independently selected from halo and C$_{1-3}$ alkyl; and each R$^{8D}$ is independently selected from OH, CN, halo, C$_{1-6}$ alkyl, and C$_{1-6}$ haloalkyl;

(c) Formula (III):

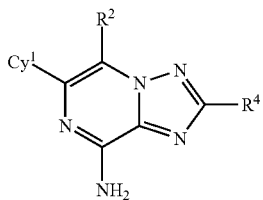

or a pharmaceutically acceptable salt thereof, wherein

Cy$^1$ is phenyl which is substituted by 1 or 2 substituents independently selected from halo and CN;

R$^2$ is selected from 5-6 membered heteroaryl and 4-7 membered heterocycloalkyl, wherein the 5-6 membered heteroaryl and 4-7 membered heterocycloalkyl of R$^2$ are each optionally substituted with 1, 2, or 3 independently selected R$^{2A}$ substituents;

each R$^{2A}$ is independently selected from D, halo, C$_{1-6}$ alkyl, and C$_{1-6}$ haloalkyl;

R$^4$ is selected from phenyl-C$_{1-3}$ alkyl-, C$_{3-7}$ cycloalkyl-C$_{1-3}$ alkyl-, (5-6 membered heteroaryl)-C$_{1-3}$ alkyl-, and (4-7 membered heterocycloalkyl)-C$_{1-3}$ alkyl wherein the phenyl-C$_{1-3}$ alkyl-, C$_{3-7}$ cycloalkyl-C$_{1-3}$ alkyl-, (5-6 membered heteroaryl)-C$_{1-3}$ alkyl-, and (4-7 membered heterocycloalkyl)-C$_{1-3}$ alkyl- of R$^4$ are each optionally substituted with 1, 2, or 3 independently selected R$^{4A}$ substituents;

each R$^{4A}$ is independently selected from halo, C$_{1-6}$ alkyl, C$_{1-6}$ haloalkyl, CN, OR$^{a41}$, and NR$^{c41}$R$^{d41}$; and each R$^{a41}$, R$^{c41}$, and R$^{d41}$ is independently selected from H and C$_{1-6}$ alkyl; or (d) Formula (IV):

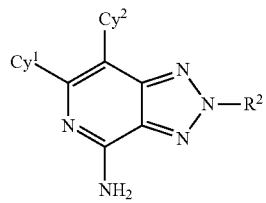

or a pharmaceutically acceptable salt thereof, wherein

Cy$^1$ is phenyl which is substituted by 1 or 2 substituents independently selected from halo and CN;

Cy$^2$ is selected from 5-6 membered heteroaryl and 4-7 membered heterocycloalkyl, wherein the 5-6 membered heteroaryl and 4-7 membered heterocycloalkyl of Cy$^2$ are each optionally substituted with 1, 2, or 3 independently selected R$^6$ substituents;

each R$^6$ is independently selected from halo, C$_{1-6}$ alkyl, and C$_{1-6}$ haloalkyl;

R$^2$ is phenyl-C$_{1-3}$ alkyl- or (5-6 membered heteroaryl)-C$_{1-3}$ alkyl-, wherein the phenyl-C$_{1-3}$ alkyl- and (5-6 membered heteroaryl)-C$_{1-3}$ alkyl- of R$^2$ are each optionally substituted with 1, 2, or 3 independently selected R$^{2A}$ substituents; and each R$^{2A}$ is independently selected from halo, C$_{1-6}$ alkyl, and C$_{1-6}$ haloalkyl.

or a pharmaceutically acceptable salt thereof.

In some embodiments, the inhibitor of human CD73 comprises:

(a) an antibody comprising a variable heavy (VH) domain comprising VH complementarity determining region (CDR)1, VH CDR2, and VH CDR3, wherein:
the VH CDR1 comprises the amino acid sequence GYTFTSYG (SEQ ID NO:1);
the VH CDR2 comprises the amino acid sequence IYPGSGNT (SEQ ID NO:2); and
the VH CDR3 comprises the amino acid sequence ARYDYLGSSYGFDY (SEQ ID NO:3); and
comprising a variable light (VL) domain comprising VL CDR1, VL CDR2, and VL CDR3, wherein:
the VL CDR1 comprises the amino acid sequence QDVSTA (SEQ ID NO:4);
the VL CDR2 comprises the amino acid sequence SAS (SEQ ID NO:5); and
the VL CDR3 comprises the amino acid sequence QQHYNTPYT (SEQ ID NO:6);

(b) an antibody that binds to human CD73 at an epitope within amino acids 40-53 of SEQ ID NO:70;

(c) an antibody that binds to human CD73 and competes for binding to human CD73 with an antibody that has a heavy chain comprising the amino acid sequence of SEQ ID NO:24 and a light chain comprising the amino acid sequence of SEQ ID NO:25; or (d) an antibody comprising a VH domain comprising VH CDR1, VH CDR2, and VH CDR3, wherein:
the VH CDR1 comprises the amino acid sequence GFTFSSYD (SEQ ID NO:34);
the VH CDR2 comprises the amino acid sequence MSYDGSNK (SEQ ID NO:35) or MSYEGSNK (SEQ ID NO:40); and
the VH CDR3 comprises the amino acid sequence ATEIAAKGDY (SEQ ID NO:36); and an antibody comprising a VL domain comprising VL CDR1, VL CDR2, and VL CDR3, wherein:

the VL CDR1 comprises the amino acid sequence QGISNY (SEQ ID NO:37);

the VL CDR2 comprises the amino acid sequence AAS (SEQ ID NO:38); and the VL CDR3 comprises the amino acid sequence QQSYSTPH (SEQ ID NO:39);

(e) an antibody that binds to human CD73 at an epitope within amino acids 386-399 and 470-489 of SEQ ID NO:70;

(f) an antibody that binds to human CD73 and competes for binding to human CD73 with an antibody that has a heavy chain comprising the amino acid sequence of SEQ ID NO:30 and a light chain comprising the amino acid sequence of SEQ ID NO:31;

(g) an antibody that binds to human CD73 and competes for binding to human CD73 with an antibody that has a heavy chain comprising the amino acid sequence of SEQ ID NO:33 and a light chain comprising the amino acid sequence of SEQ ID NO:31;

(h) an antibody selected from the group consisting of 11E1, Medi9447, CPI-006, and BMS-986179; or (i) an inhibitor selected from the group consisting of CB-708 and AB680; and the inhibitor of A2A adenosine receptor and/or A2B adenosine receptor (A2A/A2B) comprises a compound of:

(a) Formula (I):

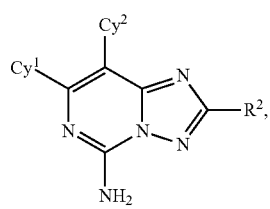

or a pharmaceutically acceptable salt thereof, wherein $Cy^1$ is phenyl which is substituted by 1 or 2 substituents independently selected from halo and CN;

$Cy^2$ is 5-6 membered heteroaryl or 4-7 membered heterocycloalkyl, wherein the 5-6 membered heteroaryl or 4-7 membered heterocycloalkyl of $Cy^2$ are each optionally substituted with 1, 2, or 3 groups each independently selected from $C_{1-3}$ alkyl, $C_{1-3}$ alkoxy, $NH_2$, $NH(C_{1-3}$ alkyl) and $N(C_{1-3}$ alkyl)$_2$;

$R^2$ is selected from phenyl-$C_{1-3}$ alkyl-, $C_{3-7}$ cycloalkyl-$C_{1-3}$ alkyl-, (5-7 membered heteroaryl)-$C_{1-3}$ alkyl-, (4-7 membered heterocycloalkyl)-$C_{1-3}$ alkyl-, and $OR^{a2}$, wherein the phenyl-$C_{1-3}$ alkyl-, $C_{3-7}$ cycloalkyl-$C_{1-3}$ alkyl-, (5-7 membered heteroaryl)-$C_{1-3}$ alkyl-, and (4-7 membered heterocycloalkyl)-$C_{1-3}$ alkyl- of $R^2$ are each optionally substituted with 1, 2, or 3 independently selected $R^C$ substituents;

$R^{a2}$ is (5-7 membered heteroaryl)-$C_{1-3}$ alkyl- optionally substituted with 1 or 2 independently selected $R^C$ substituents;

each $R^C$ is independently selected from halo, $C_{1-6}$ alkyl, $C_6$ aryl, 5-7 membered heteroaryl, (4-7 membered heterocycloalkyl)-$C_{1-3}$ alkyl-, $OR^{a4}$, and $NR^{c4}R^{d4}$; and each $R^{a4}$, $R^{c4}$, and $R^{d4}$ are independently selected from H and $C_{1-6}$ alkyl;

(b) Formula (II):

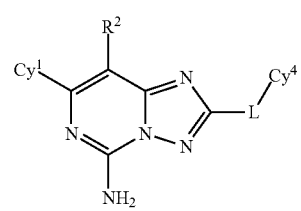

or a pharmaceutically acceptable salt thereof, wherein $R^2$ is selected from H and CN;

$Cy^1$ is phenyl which is substituted by 1 or 2 substituents independently selected from halo and CN;

L is $C_{1-3}$ alkylene, wherein said alkylene is optionally substituted with 1, 2, or 3 independently selected $R^{8D}$ substituents;

$Cy^4$ is selected from phenyl, cyclohexyl, pyridyl, pyrrolidinonyl, and imidazolyl, wherein the phenyl, cyclohexyl, pyridyl, pyrrolidinonyl, and imidazolyl are each optionally substituted with 1, 2, or 3 substituents independently selected from $R^{8D}$ and $R^8$;

each $R^8$ is independently selected from halo, $C_{1-6}$ alkyl, $C_{1-6}$ haloalkyl, $C_{2-4}$ alkenyl, $C_{2-4}$ alkynyl, phenyl, $C_{3-7}$ cycloalkyl, 5-6 membered heteroaryl, 4-7 membered heterocycloalkyl, phenyl-$C_{1-3}$ alkyl, $C_{3-7}$ cycloalkyl-$C_{1-3}$ alkyl, (5-6 membered heteroaryl)-$C_{1-3}$ alkyl, and (4-7 membered heterocycloalkyl)-$C_{1-3}$ alkyl, wherein the $C_{1-6}$ alkyl, $C_{2-4}$ alkenyl, $C_{2-4}$ alkynyl, phenyl, $C_{3-7}$ cycloalkyl, 5-6 membered heteroaryl, 4-7 membered heterocycloalkyl, phenyl-$C_{1-3}$ alkyl, $C_{3-7}$ cycloalkyl-$C_{1-3}$ alkyl, (5-6 membered heteroaryl)-$C_{1-3}$ alkyl, and (4-7 membered heterocycloalkyl)-$C_{1-3}$ alkyl of R are each optionally substituted with 1, 2, or 3 independently selected $R^{8A}$ substituents;

each $R^{8A}$ is independently selected from halo, $C_{1-6}$ alkyl, 5-6 membered heteroaryl, 4-7 membered heterocycloalkyl, CN, $OR^{a81}$, and $NR^{c81}R^{d81}$, wherein the $C_{1-3}$ alkyl, 5-6 membered heteroaryl, and 4-7 membered heterocycloalkyl of $R^{8A}$ are each optionally substituted with 1, 2, or 3 independently selected $R^{8B}$ substituents;

each $R^{a81}$, $R^{c81}$, and $R^{d81}$ is independently selected from H, $C_{1-6}$ alkyl, and 4-7 membered heterocycloalkyl, wherein the $C_{1-6}$ alkyl and 4-7 membered heterocycloalkyl of $R^{a81}$, $R^{c81}$, and $R^{d81}$ are each optionally substituted with 1, 2, or 3 independently selected $R^{8B}$ substituents;

each $R^{8B}$ is independently selected from halo and $C_{1-3}$ alkyl; and each $R^{8D}$ is independently selected from OH, CN, halo, $C_{1-6}$ alkyl, and $C_{1-6}$ haloalkyl;

(c) Formula (III):

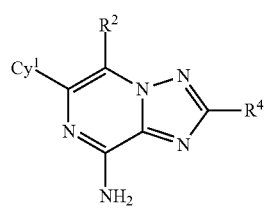

or a pharmaceutically acceptable salt thereof, wherein
Cy$^1$ is phenyl which is substituted by 1 or 2 substituents independently selected from halo and CN;
R$^2$ is selected from 5-6 membered heteroaryl and 4-7 membered heterocycloalkyl, wherein the 5-6 membered heteroaryl and 4-7 membered heterocycloalkyl of R$^2$ are each optionally substituted with 1, 2, or 3 independently selected R$^{2A}$ substituents;
each R$^{2A}$ is independently selected from D, halo, C$_{1-6}$ alkyl, and C$_{1-6}$ haloalkyl;
R$^4$ is selected from phenyl-C$_{1-3}$ alkyl-, C$_{3-7}$ cycloalkyl-C$_{1-3}$ alkyl-, (5-6 membered heteroaryl)-C$_{1-3}$ alkyl-, and (4-7 membered heterocycloalkyl)-C$_{1-3}$ alkyl wherein the phenyl-C$_{1-3}$ alkyl-, C$_{3-7}$ cycloalkyl-C$_{1-3}$ alkyl-, (5-6 membered heteroaryl)-C$_{1-3}$ alkyl-, and (4-7 membered heterocycloalkyl)-C$_{1-3}$ alkyl- of R$^4$ are each optionally substituted with 1, 2, or 3 independently selected R$^{4A}$ substituents;
each R$^{4A}$ is independently selected from halo, C$_{1-6}$ alkyl, C$_{1-6}$ haloalkyl, CN, OR$^{a41}$, and NR$^{c41}$R$^{d41}$; and
each R$^{a41}$, R$^{c41}$, and R$^{d41}$ is independently selected from H and C$_{1-6}$ alkyl; or
(d) Formula (IV):

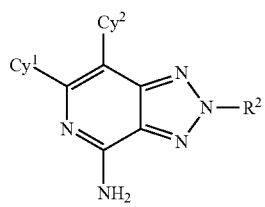

(IV)

or a pharmaceutically acceptable salt thereof, wherein
Cy$^1$ is phenyl which is substituted by 1 or 2 substituents independently selected from halo and CN;
Cy$^2$ is selected from 5-6 membered heteroaryl and 4-7 membered heterocycloalkyl, wherein the 5-6 membered heteroaryl and 4-7 membered heterocycloalkyl of Cy$^2$ are each optionally substituted with 1, 2, or 3 independently selected R$^6$ substituents;
each R$^6$ is independently selected from halo, C$_{1-6}$ alkyl, and C$_{1-6}$ haloalkyl;
R$^2$ is phenyl-C$_{1-3}$ alkyl- or (5-6 membered heteroaryl)-C$_{1-3}$ alkyl-, wherein the phenyl-C$_{1-3}$ alkyl- and (5-6 membered heteroaryl)-C$_{1-3}$ alkyl- of R$^2$ are each optionally substituted with 1, 2, or 3 independently selected R$^{2A}$ substituents; and
each R$^{2A}$ is independently selected from halo, C$_{1-6}$ alkyl, and C$_{1-6}$ haloalkyl.
or a pharmaceutically acceptable salt thereof.

In some embodiments, the CD73 inhibitor comprises an antibody comprising a VH domain comprising the amino acid sequence set forth in SEQ ID NO:22 and a VL domain comprising the amino acid sequence set forth in SEQ ID NO:23, and the inhibitor of A2a and/or A2B adenosine receptor comprises the compound 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile.

In some embodiments, the CD73 inhibitor comprises an antibody comprising a heavy chain comprising the amino acid sequence set forth in SEQ ID NO:24 and a light chain comprising the amino acid sequence set forth in SEQ ID NO:25, and the inhibitor of A2a and/or A2B adenosine receptor comprises the compound 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile.

In some embodiments, the CD73 inhibitor comprises an antibody comprising a VH domain comprising the amino acid sequence set forth in SEQ ID NO:62 and a VL domain comprising the amino acid sequence set forth in SEQ ID NO:61, and the inhibitor of A2a and/or A2B adenosine receptor comprises the compound 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile.

In some embodiments, the CD73 inhibitor comprises an antibody comprising a heavy chain comprising the amino acid sequence set forth in SEQ ID NO:30 and a light chain comprising the amino acid sequence set forth in SEQ ID NO:31, and the inhibitor of A2a and/or A2B adenosine receptor comprises the compound 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile.

In some embodiments, the CD73 inhibitor comprises an antibody comprising a VH domain comprising the amino acid sequence set forth in SEQ ID NO:63 and a VL domain comprising the amino acid sequence set forth in SEQ ID NO:61, and the inhibitor of A2a and/or A2B adenosine receptor comprises the compound 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile.

In some embodiments, the CD73 inhibitor comprises an antibody comprising a heavy chain comprising the amino acid sequence set forth in SEQ ID NO:33 and a light chain comprising the amino acid sequence set forth in SEQ ID NO:31, and the inhibitor of A2a and/or A2B adenosine receptor comprises the compound 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile.

Based on the compelling roles of CD73 and A2A and/or A2B adenosine receptor in multiple immunosuppressive mechanisms, combination therapy can boost the immune system to suppress tumor progression. CD73 inhibitors and inhibitors of A2A and/or A2B adenosine receptor can be used in combination to treat, optionally in further combination with other therapies, bladder cancer, lung cancer (e.g., non-small cell lung cancer (NSCLC), lung metastasis), melanoma (e.g., metastatic melanoma), breast cancer, cervical cancer, ovarian cancer, colorectal cancer, pancreatic cancer, esophageal cancer, prostate cancer, kidney cancer, skin cancer, thyroid cancer, liver cancer (e.g., hepatocellular carcinoma), uterine cancer, head and neck cancer (e.g., head and neck squamous cell carcinoma), and renal cell carcinoma. In some embodiments, the prostate cancer is metastatic castrate-resistant prostate carcinoma (mCRPC). In some embodiments, the colorectal cancer is colorectal carcinoma (CRC).

In some embodiments, the disease or disorder is lung cancer (e.g., non-small cell lung cancer), melanoma, pancreatic cancer, breast cancer, head and neck squamous cell carcinoma, prostate cancer, liver cancer, color cancer, endometrial cancer, bladder cancer, skin cancer, cancer of the uterus, renal cancer, gastric cancer, or sarcoma. In some embodiments, the sarcoma is Askin's tumor, sarcoma botryoides, chondrosarcoma, Ewing's sarcoma, malignant hemangioendothelioma, malignant schwannoma, osteosarcoma, alveolar soft part sarcoma, angiosarcoma, cystosarcoma phyllodes, dermatofibrosarcoma protuberans, desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, malignant peripheral nerve sheath tumor (MPNST), neurofibrosarcoma, rhabdomyosarcoma, synovial sarcoma, or undifferentiated pleomorphic sarcoma.

In some embodiments, the disease or disorder is head and neck cancer (e.g., head and neck squamous cell carcinoma), colorectal cancer, lung cancer (e.g., non-small cell lung cancer (NSCLC)), melanoma, ovarian, bladder, liver cancer (e.g., hepatocellular carcinoma), or renal cell carcinoma.

In some embodiments, the disease or disorder is mesothelioma or adrenocarcinoma. In some embodiments, the disease or disorder is mesothelioma. In some embodiments, the disease or disorder is adrenocarcinoma.

MDSC (myeloid-derived suppressor cells) are a heterogenous group of immune cells from the myeloid lineage (a family of cells that originate from bone marrow stem cells). MDSCs strongly expand in pathological situations such as chronic infections and cancer, as a result of an altered haematopoiesis. MDSCs are discriminated from other myeloid cell types in which they possess strong immunosuppressive activities rather than immunostimulatory properties. Similar to other myeloid cells, MDSCs interact with other immune cell types including T cells, dendritic cells, macrophages and natural killer cells to regulate their functions. In some embodiments, the compounds, etc. described herein can be used in methods related to cancer tissue (e.g., tumors) with high infiltration of MDSCs, including Solid tumors with high basal level of macrophage and/or MDSC infiltration.

In some embodiments, the CD73 inhibitors and inhibitors of A2A and/or A2B adenosine receptor of the disclosure can be used in combination in treating pulmonary inflammation, including bleomycin-induced pulmonary fibrosis and injury related to adenosine deaminase deficiency.

In some embodiments, the CD73 inhibitors and inhibitors of A2A and/or A2B adenosine receptor of the disclosure can be used in combination as a treatment for inflammatory disease such as allergic reactions (e.g., CD73- and/or A2A and/or A2B adenosine receptor-dependent allergic reactions) and other CD73- and/or A2A and/or A2B adenosine receptor-immune reactions. Further inflammatory diseases that can be treated by combination of the CD73 inhibitors and A2A and/or A2B adenosine receptor inhibitors of the disclosure include respiratory disorders, sepsis, reperfusion injury, and thrombosis.

In some embodiments, the CD73 inhibitors and A2A and/or A2B adenosine receptor inhibitors of the disclosure can be used in combination as a treatment for cardiovascular disease such as coronary artery disease (myocardial infarction, angina pectoris, heart failure), cerebrovascular disease (stroke, transient ischemic attack), peripheral artery disease, and aortic atherosclerosis and aneurysm. Atherosclerosis is an underlying etiologic factor in many types of cardiovascular disease. Atherosclerosis begins in adolescence with fatty streaks, which progress to plaques in adulthood and finally results in thrombotic events that cause occlusion of vessels leading to clinically significant morbidity and mortality.

In some embodiments, the CD73 inhibitors and A2A and/or A2B adenosine receptor inhibitors of the disclosure can be used in combination as a treatment for disorders in motor activity; deficiency caused by degeneration of the striatonigral dopamine system; and Parkinson's disease; some of the motivational symptoms of depression.

In some embodiments, the CD73 inhibitors and A2A and/or A2B adenosine receptor inhibitors of the disclosure can be used in combination as a treatment for diabetes and related disorders, such as insulin resistance. Diabetes affects the production of adenosine and the expression of A2B adenosine receptors (A2BRs) that stimulate IL-6 and CRP production, insulin resistance, and the association between A2BR gene single-nucleotide polymorphisms (ADORA2B SNPs) and inflammatory markers. The increased A2BR signaling in diabetes may increase insulin resistance in part by elevating pro-inflammatory mediators. Selective CD73 inhibitors may be useful to treat insulin resistance.

The terms "individual" or "patient" or "subject", used interchangeably, refer to any animal, including mammals, preferably mice, rats, other rodents, rabbits, dogs, cats, swine, cattle, sheep, horses, or primates, and most preferably humans (i.e., a human subject).

The phrase "therapeutically effective amount" refers to the amount of active antibody or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the CD73 inhibitors and A2A and/or A2B adenosine receptor inhibitors of the disclosure are useful in combination in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Pharmaceutical Compositions

The CD73 inhibitors and inhibitors of A2A and/or A2B adenosine receptor described herein can be formulated as pharmaceutical compositions for administration to a subject, e.g., to treat a disorder described herein. In some instances, the pharmaceutical composition comprises a CD73 inhibitor as a single agent. In some instances, the pharmaceutical composition comprises an inhibitor of A2A and/or A2B adenosine receptor as a single agent. In some instances, the pharmaceutical composition comprises a CD73 inhibitor and an inhibitor of A2A and/or A2B adenosine receptor.

Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or abase addition salt (see e.g., Berge, S. M., et al. (1977) J. Pharm. Sci. 66:1-19).

Pharmaceutical formulation is a well-established art, and is further described, e.g., in Gennaro (ed.), Remington: The Science and Practice of Pharmacy, 20th ed., Lippincott, Williams & Wilkins (2000) (ISBN: 0683306472); Ansel et al., Pharmaceutical Dosage Forms and Drug Delivery Systems, 7th Ed., Lippincott Williams & Wilkins Publishers (1999) (ISBN: 0683305727); and Kibbe (ed.), Handbook of Pharmaceutical Excipients American Pharmaceutical Association, 3rd ed. (2000) (ISBN: 091733096X).

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form can depend on the intended mode of administration and therapeutic application. Typically compositions for the agents described herein are in the form of injectable or infusible solutions.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze drying that yield a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the CD73 inhibitor and/or inhibitor of A2A and/or A2B adenosine receptor may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, ed., Marcel Dekker, Inc., New York (1978).

Administration

The CD73 inhibitor and inhibitor of A2A and/or A2B adenosine receptor can be administered to a subject, e.g., a subject in need thereof, for example, a human subject, by a variety of methods. In some instances, the CD73 inhibitor and the inhibitor of A2A and/or A2B adenosine receptor are administered to the subject by the same route. In some instances, the CD73 inhibitor and the inhibitor of A2A and/or A2B adenosine receptor are administered to the subject by different routes. For many applications, the route of administration is one of: intravenous injection or infusion (IV), subcutaneous injection (SC), intraperitoneally (IP), or intramuscular injection. It is also possible to use intraarticular delivery. Other modes of parenteral administration can also be used. Examples of such modes include: intraarterial, intrathecal, intracapsular, intraorbital, intracardiac, intradermal, transtracheal, subcuticular, intraarticular, subcapsular, subarachnoid, intraspinal, and epidural and intrasternal injection. In some cases, administration can be oral.

The route and/or mode of administration of the CD73 inhibitor or inhibitor of A2A and/or A2B adenosine receptor can also be tailored for the individual case, e.g., by monitoring the subject, e.g., using tomographic imaging, e.g., to visualize a tumor.

Each of the CD73 inhibitor and the inhibitor of A2A and/or A2B adenosine receptor can be administered as a fixed dose, or in a mg/kg patient weight dose. The dose can also be chosen to reduce or avoid production of antibodies against the CD73 inhibitor or inhibitor of A2A and/or A2B adenosine receptor. Dosage regimens are adjusted to provide the desired response, e.g., a therapeutic response or a combinatorial therapeutic effect. Generally, doses of the CD73 inhibitor and of the inhibitor of A2A and/or A2B adenosine receptor can be used in order to provide a subject with the agent in bioavailable quantities.

Dosage unit form or "fixed dose" or "flat dose" as used herein refers to physically discrete units suited as unitary dosages for the subjects to be treated; each unit contains a predetermined quantity of active compound calculated to produce the desired therapeutic effect in association with the required pharmaceutical carrier and optionally in association with the other agent. Single or multiple dosages may be given. Alternatively, or in addition, the antibody and/or inhibitor may be administered via continuous infusion.

The following are examples of the practice of the invention. They are not to be construed as limiting the scope of the invention in any way.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art can develop equivalent means or reactants without the exercise of inventive capacity and without departing from the scope of the invention.

Example A: Activity of A2A/A2B Inhibitors

I. A2A Tag-Lite® HTRF Assay

Assays were conducted in black low volume 384-well polystyrene plates (Greiner 784076-25) in a final volume of 10 µL. Test compounds were first serially diluted in DMSO and 100 nl added to the plate wells before the addition of other reaction components. The final concentration of DMSO was 1%. Tag-Lite® Adenosine A2A labeled cells (CisBio C1TT1A2A) were diluted 1:5 into Tag-lite buffer (CisBio LABMED) and spun 1200 g for 5 mins. The pellet was resuspended at a volume 10.4× the initial cell suspension volume in Tag-lite buffer, and Adenosine A2A Receptor Red antagonist fluorescent ligand (CisBio L0058RED) added at 12.5 nM final concentration. 10 ul of the cell and ligand mix was added to the assay wells and incubated at room temperature for 45 minutes before reading on a PHERAstar FS plate reader (BMG Labtech) with HTRF 337/620/665 optical module. Percent binding of the fluorescent ligand was calculated; where 100 nM of A2A antagonist control ZM 241385 (Tocris 1036) displaces the ligand 100% and 1% DMSO has 0% displacement. The % binding data versus the log of the inhibitor concentration was fitted to a one-site competitive binding model (GraphPad Prism version 7.02) where the ligand constant=12.5 nM and the ligand Kd=1.85 nM. The $K_i$ data obtained via this method are shown in Table 7.

II. Adenosine A2B Receptor Cyclic AMP GS Assay

Stably transfected HEK-293 cells expressing the human adenosine A2B receptor (Perkin Elmer) were maintained in MEM culture medium with 10% FBS and 100 µg/ml Geneticin (Life Technologies). 18 to 24 hours prior to assay, geneticin was removed from culture. The cisbio cAMP-GS Dynamic kit utilizing the FRET (Fluorescence Resonance Energy Transfer) technology was used to measure cAMP accumulation in the cells. Compounds of the present disclosure at an appropriate concentration were mixed with 10000 cells/well in white 96 well half area plates (Perkin Elmer) for 30 min at RT gently shaking. Agonist, NECA (R&D Technologies) at 12 nM was added to each well for 60 min at RT gently shaking. Detection reagents, d2-labeled cAMP (acceptor) and anti-cAMP cryptate (donor) were added to each well for 60 min at RT gently shaking. Plates were read on Pherastar (BMG Labtech), fluorescence ratio 665/620 was calculated and $EC_{50}$ determination was performed by fitting the curve of percent of control versus the log of the compound concentration using GraphPad Prism. The $EC_{50}$ data obtained via this method are shown in Table 7.

TABLE 7

The $A_{2A}\_K_i$ data (Example A(I)) and $A_{2B}\_cAMP\_EC_{50}$ data (Example A(II)) are provided below.

| Comp. No. | $A_{2A}\_K_i$ (nM) | $A_{2B}\_cAMP\_EC_{50}$ (nM) |
|---|---|---|
| 1 | † | † |
| 2 | † | † |
| 3 | † | † |
| 4 | † | † |
| 5 | † | † |
| 6 | † | † |
| 7 | † | † |
| 8 | † | †† |
| 9 | † | † |
| 10 | † | † |
| 11 | † | † |
| 12 | † | †† |
| 13 | † | † |
| 14 | † | † |
| 15 | † | † |
| 16 | † | † |
| 17 | † | †† |
| 18 | † | † |
| 19 | † | † |
| 20 | † | † |
| 21 | † | † |

† indicates $A_{2A}\_K_i$ or $A_{2B}\_cAMP\_EC_{50} \leq 10$ nM,

†† indicates $A_{2A}\_K_i$ or $A_{2B}\_cAMP\_EC_{50} > 10$ nM but $\leq 100$ nM, ††† indicates $A_{2A}\_K_i$ or $A_{2B}\_cAMP\_EC_{50} > 100$ nM but $\leq 1$ µM, †††† indicates $A_{2A}\_K_i$ or $A_{2B}\_CAMP\_EC_{50}$ is greater than 1 µM.

Example A1: Synthesis of 3-(5-Amino-2-(pyridin-2-ylmethyl)-8-(pyrimidin-4-yl)-[1,2,4]triazolo[1,5-c]pyrimidin-7-yl)benzonitrile (Compound 1)

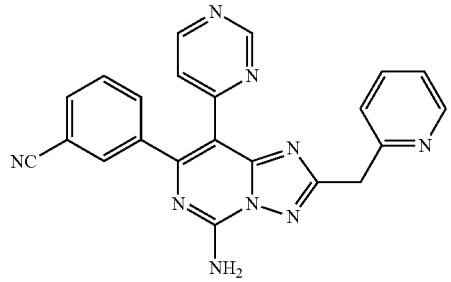 [SMILES: N#Cc1cccc(-c2nc(N)n3nc(Cc4ccccn4)nc3c2-c2ccncn2)c1]

Step 1:
3-(2-Amino-6-chloropyrimidin-4-yl)benzonitrile

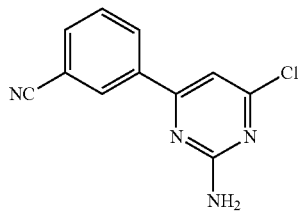

A mixture of 4,6-dichloropyrimidin-2-amine (2.5 g, 15.2 mmol), (3-cyanophenyl)boronic acid (2.02 g, 13.7 mmol), tetrakis(triphenylphosphine)palladium(0) (1.06 g, 0.92 mmol) and sodium carbonate (3.23 g, 30.5 mmol) in 1,4-dioxane (60 mL), and water (5 mL) was degassed with nitrogen, then the resulting mixture was heated and stirred at 60° C. for two days. After cooled to room temperature (r.t.), the mixture was concentrated, diluted with water, and extracted with DCM (30 mL×3). The combined organic layers were dried over $MgSO_4$, filtered, and concentrated. The resulting residue was purified by flash chromatography on a silica gel column eluting with 8% EtOAc in dichloromethane to afford the desired product. LCMS calculated for $C_{11}H_8ClN_4$ (M+H)$^+$: 231.0. Found: 231.0.

Step 2: 2-(Pyridin-2-yl)acetohydrazide

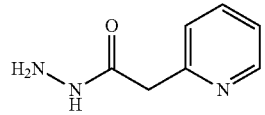

Hydrazine (4.15 mL, 132 mmol) was added to a ethanol (66 mL) solution of methyl 2-(pyridin-2-yl)acetate (10 g, 66.2 mmol) at r.t. The mixture was heated and stirred at 85° C. for 4 h, and then cooled to r.t. White solid was formed upon standing, which was collected via filtration and used in next step without further purification. LCMS calculated for $C_7H_{10}N_3O$ (M+H)$^+$: 152.1. Found: 152.0.

Step 3: 3-(5-Amino-2-(pyridin-2-ylmethyl)-[1,2,4]triazolo[1,5-c]pyrimidin-7-yl)benzonitrile

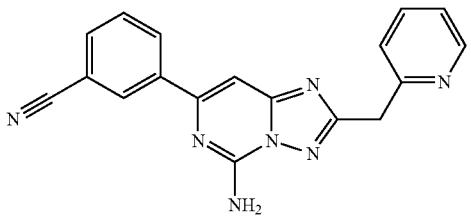 [SMILES: N#Cc1cccc(-c2cc3nc(Cc4ccccn4)nn3c(N)n2)c1]

2-(pyridin-2-yl)acetohydrazide (2.62 g, 17.34 mmol) was added to a ethanol (35 mL) solution of 3-(2-amino-6-chloropyrimidin-4-yl)benzonitrile (4.00 g, 17.34 mmol) at r.t. After being heated and stirred at reflux for 2 h, the reaction mixture was cooled to r.t., and concentrated. The resulting residue was taken into N,O-bis(trimethylsilyl)acetamide (20 mL) and stirred at 120° C. for 7 h. The mixture was then cooled to r.t., poured onto ice, and allowed to stir at r.t. for 1 h. The resulting solid was collected by filtration, and taken into 20 mL of 1 N HCl solution. The resulting mixture was stirred at r.t. for 1 h, filtered, and the aqueous layer was neutralized by addition of saturated NaHCO$_3$ solution. The resulting precipitate was collected by filtration, and dried to obtain the desired product as a brown solid. LCMS calculated for $C_{18}H_{14}N_7$ (M+H)$^+$: 328.1; found 328.1.

Step 4: 3-(5-Amino-8-bromo-2-(pyridin-2-ylmethyl)-[1,2,4]triazolo[1,5-c]pyrimidin-7-yl)benzonitrile

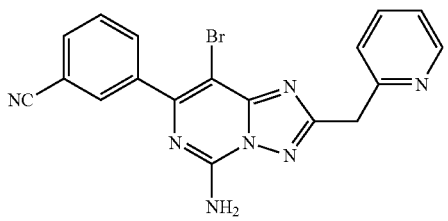 [SMILES: N#Cc1cccc(-c2nc(N)n3nc(Cc4ccccn4)nc3c2Br)c1]

To a mixture of 3-(5-amino-2-(pyridin-2-ylmethyl)-[1,2,4]triazolo[1,5-c]pyrimidin-7-yl)benzonitrile (2 g, 6.11 mmol) in DMF (12 mL) at −30° C. was added NBS (1.09 g, 6.11 mmol) portion-wise. The reaction mixture was allowed to slowly warm to 0° C., resulting a homogenous solution. After stirring at 0° C. for 1 h, the reaction mixture was diluted with saturated NaHCO$_3$ solution and the resulting solid was collected by filtration. The solid was then purified by flash chromatography on a silica gel column eluting with 0 to 10% MeOH in DCM to afford the desired product. LCMS calculated for $C_{18}H_{13}BrN_7$ (M+H)$^+$: 406.0; found 406.0.

Step 5: 3-(5-Amino-2-(pyridin-2-ylmethyl)-8-(pyrimidin-4-yl)-[1,2,4]triazolo[1,5-c]pyrimidin-7-yl)benzonitrile Pd(Ph$_3$P)$_4$ (284 mg, 0.246 mmol) was added to a mixture of 4-(tributylstannyl)pyrimidine (1090 mg, 2.95 mmol), 3-(5-amino-8-bromo-2-(pyridin-2-ylmethyl)-[1,2,4]triazolo[1,5-c]pyrimidin-7-yl)benzonitrile (1000 mg, 2.46 mmol), and copper(I) chloride (244 mg, 2.46 mmol) in 1,4-dioxane (12 mL). The reaction mixture was purged with N$_2$ and stirred at 80° C. for 7 h. The resulting mixture was cooled to r.t., concentrated, diluted with DCM (50 mL) and washed with saturated NH$_4$OH solution. The organic layer was dried over Na$_2$SO$_4$, concentrated, and purified by preparative LC-MS (pH 2, acetonitrile/water with TFA) to afford the product as a TFA salt. LCMS calculated for $C_{22}H_{16}N_9$ (M+H)$^+$: 406.2; found 406.2. $^1$H NMR (500 MHz, DMSO) δ 8.95 (s, 1H), 8.83 (d, J=5.3 Hz, 1H), 8.59 (d, J=5.1 Hz, 1H), 7.96 (m, 1H), 7.88 (d, J=5.1 Hz, 1H), 7.82 (d, J=7.6 Hz, 1H), 7.76 (s, 1H), 7.60-7.53 (m, 2H), 7.53-7.48 (m, 1H), 7.48-7.42 (m, 1H), 4.49 (s, 2H).

Example A2: Synthesis of 3-(5-Amino-2-((2,6-difluorophenyl)(hydroxy)methyl)-8-(pyrimidin-4-yl)-[1,2,4]triazolo[1,5-c]pyrimidin-7-yl)benzonitrile (Compound 2)

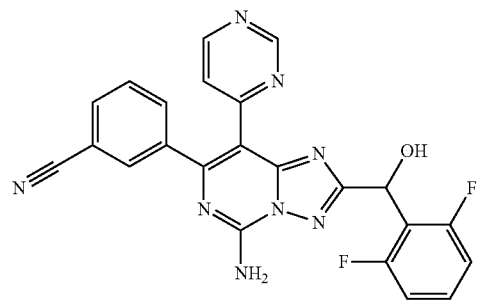 [SMILES: N#Cc1cccc(-c2nc(N)n3nc(C(O)c4c(F)cccc4F)nc3c2-c2ccncn2)c1]

Step 1: Methyl 2-(2,6-difluorophenyl)-2-hydroxyacetate

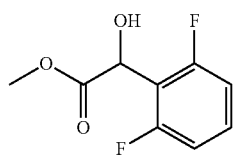

Concentrated sulfuric acid (1.42 mL, 27 mmol) was added to a methanol (45 mL) solution of 2,6-difluoromandelic acid (5 g, 27 mmol) at 0° C. The mixture was stirred at r.t. for 4 h before being concentrated. To the resulting slurry was added saturated NaHCO$_3$ solution (30 mL). The resulting mixture was extracted with DCM (3×20 mL). The combined organic layers were washed with water, dried over Mg$_2$SO$_4$, filtered, and concentrated to afford the crude product, which was used in the next step without further purification. LC-MS calculated for $C_{11}H_{12}F_2NO_3$ (M+H+MeCN)$^+$: m/z=244.1; found 244.2.

Step 2: 3-(5-Amino-2-((2,6-difluorophenyl)(hydroxy)methyl)-8-(pyrimidin-4-yl)-[1,2,4]triazolo[1,5-c]pyrimidin-7-yl)benzonitrile This compound was prepared using similar procedures as described for Example A1, with methyl 2-(2,6-difluorophenyl)-2-hydroxyacetate replacing methyl 2-(pyridin-2-yl)acetate in Step 2. The two enantiomers were separated by chiral SFC using a Phenomenex Lux Cellulose-1 column (21.2×250 mm, 5 m particle size) eluting with an isocratic mobile phase 25% MeOH in $CO_2$ with a flow rate of 80 mL/minute. Peak 1 was isolated, and further purified by prep-LCMS (pH=2, MeCN/water with TFA) to give the desired product as a TFA salt. LC-MS calculated for $C_{23}H_{15}F_2N_8O$ (M+H)$^+$: m/z=457.1; found 457.1. $^1$H NMR (500 MHz, DMSO) δ 8.94 (d, J=1.3 Hz, 1H), 8.81 (d, J=5.2 Hz, 1H), 7.85 (dd, J=5.3, 1.4 Hz, 1H), 7.81 (dt, J=7.4, 1.5 Hz, 1H), 7.76 (t, J=1.7 Hz, 1H), 7.55 (dt, J=7.8, 1.5 Hz, 1H), 7.49 (t, J=7.8 Hz, 1H), 7.44 (tt, J=8.4, 6.4 Hz, 1H), 7.09 (t, J=8.3 Hz, 2H), 6.27 (s, 1H).

Example A3: Synthesis of 3-(5-Amino-2-((5-(pyridin-2-yl)-2H-tetrazol-2-yl)methyl)-8-(pyrimidin-4-yl)-[1,2,4]triazolo[1,5-c]pyrimidin-7-yl)benzonitrile (Compound 3A) and 3-(5-Amino-2-((5-(pyridin-2-yl)-1H-tetrazol-1-yl)methyl)-8-(pyrimidin-4-yl)-[1,2,4]triazolo[1,5-c]pyrimidin-7-yl)benzonitrile (Compound 3B)

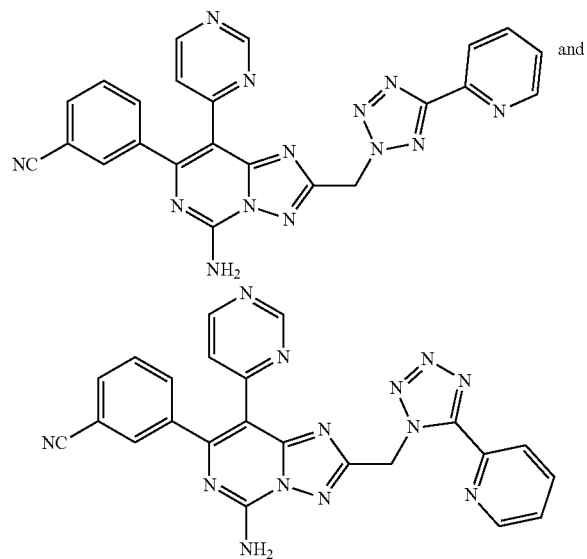

Step 1: 3-(5-Amino-2-(hydroxymethyl)-[1,2,4]triazolo[1,5-c]pyrimidin-7-yl)benzonitrile 2-Hydroxyacetohydrazide (2.34 g, 26.01 mmol) was added to a ethanol (35 mL) solution of 3-(2-amino-6-chloropyrimidin-4-yl)benzonitrile (4.00 g, 17.34 mmol) (Example A1, Step 1) at r.t. After being heated and stirred at reflux for 2 h, the reaction mixture was cooled to r.t., and concentrated. The resulting residue was taken into N,O-bis(trimethylsilyl)acetamide (20 mL) and stirred at 120° C. for 7 h. The mixture was then cooled to r.t., poured onto ice, and allowed to stir at r.t. for 1 h. The resulting solid was collected by filtration, and taken into 20 mL of 1 N HCl solution. The resulting mixture was stirred at r.t. for 1 h, filtered, and the aqueous layer was neutralized by addition of saturated $NaHCO_3$ solution. The resulting precipitate was collected by filtration, and dried to obtain the desired product as a brown solid. LCMS calculated for C13H11N6O (M+H)+: 267.1; found 267.1.

Step 2: 3-(5-Amino-8-bromo-2-(hydroxymethyl)-[1,2,4]triazolo[1,5-c]pyrimidin-7-yl)benzonitrile To a mixture of 3-(5-amino-2-(hydroxymethyl)-[1,2,4]triazolo[1,5-c]pyrimidin-7-yl)benzonitrile (1.0 g, 3.76 mmol) in DMF (12 mL) at −30° C. was added NBS (0.67 g, 3.76 mmol) portion-wise. The reaction mixture was allowed to slowly warm to 0° C., resulting a homogenous solution. After stirring at 0° C. for 1 h, the reaction mixture was diluted with saturated $NaHCO_3$ solution and the desired product was collected by filtration and dried. LCMS calculated for C13H10BrN6O (M+H)+: 345.0; found 345.0.

Step 3: 3-(5-Amino-2-(hydroxymethyl)-8-(pyrimidin-4-yl)-[1,2,4]triazolo[1,5-c]pyrimidin-7-yl)benzonitrile Tetrakis(triphenylphosphine)palladium(0) (0.067 g, 0.058 mmol) was added to a mixture of 4-(tributylstannyl)pyrimidine (0.321 g, 0.869 mmol), 3-(5-amino-8-bromo-2-(hydroxymethyl)-[1,2,4]triazolo[1,5-c]pyrimidin-7-yl)benzonitrile (0.20 g, 0.579 mmol), CsF (0.176 g, 1.159 mmol), and copper(I)iodide (0.022 g, 0.116 mmol) in 1,4-dioxane (5.0 mL). The reaction mixture was purged with N2 and stirred at 80° C. for 7 h. The resulting mixture was cooled to r.t., concentrated and purified by flash column chromatography eluting with 0% to 10% methanol in DCM to afford the product. LC-MS calculated for C17H13N8O (M+H)+: 345.1; found 345.1.

Step 4: 3-(5-Amino-2-(chloromethyl)-8-(pyrimidin-4-yl)-[1,2,4]triazolo[1,5-c]pyrimidin-7-yl)benzonitrile

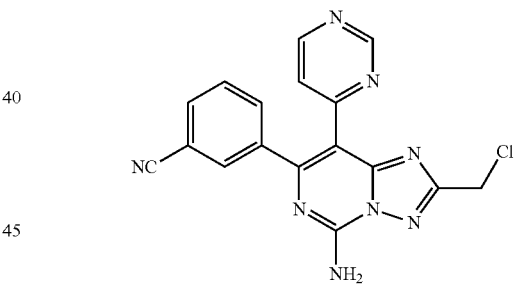

To a mixture of 3-(5-amino-2-(hydroxymethyl)-8-(pyrimidin-4-yl)-[1,2,4]triazolo[1,5-c]pyrimidin-7-yl)benzonitrile (0.1 g, 0.290 mmol) in Acetonitrile (10 ml) was added thionyl chloride (0.212 ml, 2.90 mmol) at r.t. The reaction mixture was stirred at r.t. for 5 h, concentrated, and purified by flash chromatography eluting with 0% to 5% methanol in DCM to afford the product. LC-MS calculated for $C_{17}H_{12}ClN_8$ (M+H)$^+$: 363.1; found 363.1.

Step 5: Mixture of 3-(5-amino-2-((5-(pyridin-2-yl)-2H-tetrazol-2-yl)methyl)-8-(pyrimidin-4-yl)-[1,2,4]triazolo[1,5-c]pyrimidin-7-yl)benzonitrile (Compound 3A) and 3-(5-Amino-2-((5-(pyridin-2-yl)-1H-tetrazol-1-yl)methyl)-8-(pyrimidin-4-yl)-[1,2,4]triazolo[1,5-c]pyrimidin-7-yl)benzonitrile (Compound 3B)

A mixture of 3-(5-amino-2-(chloromethyl)-8-(pyrimidin-4-yl)-[1,2,4]triazolo[1,5-c]pyrimidin-7-yl)benzonitrile (10 mg, 0.028 mmol), 2-(1H-tetrazol-5-yl)pyridine (8.1 mg, 0.055 mmol) and Cs$_2$CO$_3$ (20.7 mg, 0.064 mmol) in DMF (1 mL) was stirred at 100° C. for 10 min. The reaction mixture was then cooled to r.t., diluted with methanol (4 mL), and purified by preparative LC-MS (pH 2, acetonitrile/water with TFA) to afford the product as a TFA salt. LCMS calculated for C$_{23}$H$_{16}$N$_{13}$ (M+H)$^+$: 474.2; found 474.2.

Compound 3A: $^1$H NMR (500 MHz, DMSO) δ 8.99 (d, J=1.4 Hz, 1H), 8.85 (d, J=5.3 Hz, 1H), 8.80-8.71 (m, 1H), 8.71-8.39 (b, 2H), 8.18 (d, J=7.7, 1.1 Hz, 1H), 8.04 (t, J=7.8, 1.8 Hz, 1H), 7.85 (m, 2H), 7.80-7.76 (m, 1H), 7.62-7.55 (m, 2H), 7.53 (t, J=7.8 Hz, 1H), 6.39 (s, 2H).

Example A4: Synthesis of 3-(5-Amino-2-((3-methylpyridin-2-yl)methoxy)-8-(pyrimidin-4-yl)-[1,2,4]triazolo[1,5-c]pyrimidin-7-yl)benzonitrile (Compound 4)

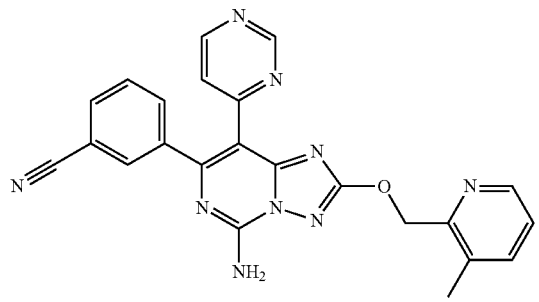 [SMILES: Cc1cccnc1COc1nc2c(-c3ccncn3)c(-c3cccc(C#N)c3)nc(N)n2n1]

Step 1: 6-Chloro-N$^2$,N$^2$-bis(4-methoxybenzyl)pyrimidine-2,4-diamine

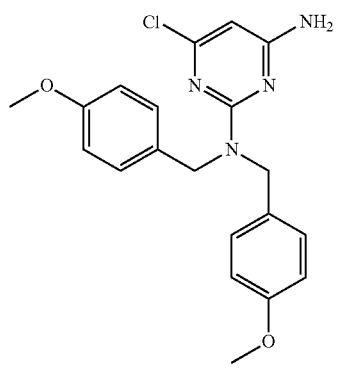 [SMILES: COc1ccc(CN(Cc2ccc(OC)cc2)c2nc(N)cc(Cl)n2)cc1]

To a solution of 2,6-dichloropyrimidin-4-amine (5.0 g, 31 mmol) in 2-propanol (31 mL) was added N,N-diisopropylethylamine (6.4 ml, 37 mmol) and bis(4-methoxybenzyl)amine (7.9 g, 31 mmol). The resulting solution was stirred at 100° C. for 16 h, cooled to r.t., diluted with water (100 mL), and extracted with EtOAc (100 mL). The organic layer was washed with water and brine, dried over anhydrous sodium sulfate, and concentrated to yield the crude product, which was used in the next step without further purification. LC-MS calculated for C$_{20}$H$_{22}$ClN$_4$O$_2$ (M+H)$^+$. 385.1; found 385.1.

Step 2: 7-Chloro-N$^5$,N$^5$-bis(4-methoxybenzyl)-[1,2,4]triazolo[1,5-c]pyrimidine-2,5-diamine

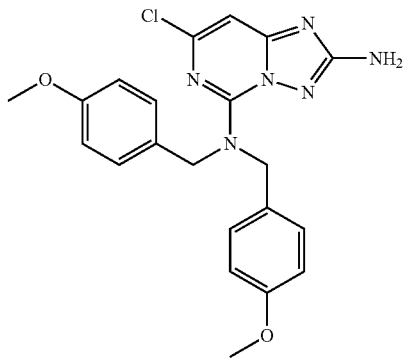 [SMILES: COc1ccc(CN(Cc2ccc(OC)cc2)c2nc(Cl)cc3nc(N)nn23)cc1]

O-ethyl carbonisothiocyanatidate (3.1 mL, 26 mmol) was added to a 1,4-dioxane (5.0 mL) solution of 6-chloro-N$^2$,N$^2$-bis(4-methoxybenzyl)pyrimidine-2,4-diamine (1.0 g, 2.6 mmol) at r.t. The reaction mixture was then stirred at 90° C. overnight, cooled to r.t., and concentrated. The resulting material was dissolved in methanol (12 mL) and ethanol (12 mL), and N,N-diisopropylethylamine (0.91 mL, 5.2 mmol) was added, followed by hydroxylamine hydrochoride (0.54 g, 7.8 mmol). The reaction mixture was stirred at 45° C. for 2 h, cooled to r.t., and concentrated. The resulting material was taken into EtOAc, washed with water, dried over anhydrous sodium sulfate, and concentrated. The crude material was then purified by silica gel chromatography eluting with 0% to 50% EtOAc in hexanes to afford the product. LC-MS calculated for C$_{21}$H$_{22}$ClN$_6$O$_2$ (M+H)$^+$: 425.1; found 425.2.

Step 3: 3-(2-Amino-5-(bis(4-methoxybenzyl)amino)-[1,2,4]triazolo[1,5-c]pyrimidin-7-yl)benzonitrile

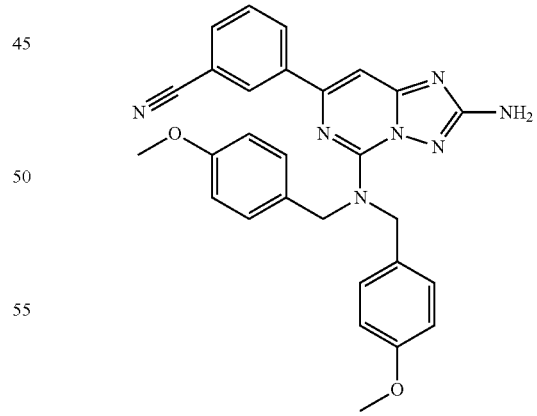

Chloro(2-dicyclohexylphosphino-2',4',6'-tri-i-propyl-1,1'-biphenyl)(2'-amino-1,1'-biphenyl-2-yl) palladium(II) (330 mg, 0.42 mmol) was added to a mixture of (3-cyanophenyl)boronic acid (460 mg, 3.2 mmol), 7-chloro-N$^5$,N$^5$-bis(4-methoxybenzyl)-[1,2,4]triazolo[1,5-c]pyrimidine-2,5-diamine (890 mg, 2.1 mmol), and sodium carbonate (890 mg, 8.4 mmol) in 1,4-dioxane (8.8 mL) and water (1.8 mL).

The mixture was purged with N₂ and stirred at 95° C. overnight. The reaction mixture was then cooled to r.t., concentrated, and purified by silica gel chromatography eluting with 0% to 50% EtOAc in DCM to afford the desired product. LC-MS calculated for C$_{28}$H$_{26}$N$_7$O$_2$ (M+H)$^+$: 492.2; found 492.2.

Step 4: 3-(2-Amino-5-(bis(4-methoxybenzyl)amino)-8-bromo-[1,2,4]triazolo[1,5-c]pyrimidin-7-yl)benzonitrile

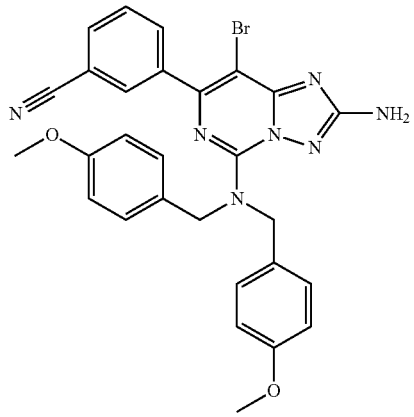 [SMILES: COc1ccc(CN(Cc2ccc(OC)cc2)c2nc(-c3cccc(C#N)c3)c(Br)c3nc(N)nn23)cc1]

To a solution of 3-(2-amino-5-(bis(4-methoxybenzyl)amino)-[1,2,4]triazolo[1,5-c]pyrimidin-7-yl)benzonitrile (330 mg, 0.66 mmol) in DMF (1.4 mL) was slowly added NBS (120 mg, 0.66 mmol) at 0° C. The reaction mixture was then stirred at r.t. for 30 min before water (10 mL) was added. The resulting solid was collected by filtration, and dried to obtain the desired product. LC-MS calculated for C$_{28}$H$_{25}$BrN$_7$O$_2$ (M+H)$^+$: m/z=570.1; found 570.2.

Step 5: 3-(2-Amino-5-(bis(4-methoxybenzyl)amino)-8-(pyrimidin-4-yl)-[1,2,4]triazolo[1,5-c]pyrimidin-7-yl)benzonitrile

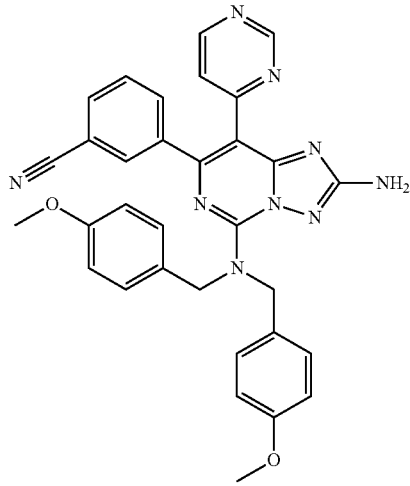 [SMILES: COc1ccc(CN(Cc2ccc(OC)cc2)c2nc(-c3cccc(C#N)c3)c(-c3ccncn3)c3nc(N)nn23)cc1]

A mixture of 3-(2-amino-5-(bis(4-methoxybenzyl)amino)-8-bromo-[1,2,4]triazolo[1,5-c]pyrimidin-7-yl)benzonitrile (350 mg, 0.61 mmol), 4-(tributylstannyl)pyrimidine (210 μL, 0.67 mmol), tetrakis(triphenylphosphine)palladium(0) (70 mg, 0.060 mmol), copper(I) iodide (23 mg, 0.12 mmol) and cesium fluoride (180 mg, 1.2 mmol) in dioxane (4.7 mL) was heated and stirred at 140° C. for 30 min in a microwave reactor. The reaction mixture was then cooled to r.t., filtered through a Celite plug (washed with DCM), and concentrated. The resulting material was purified by silica gel column chromatography eluting with 0-20% MeOH/DCM to give the desired product. LC-MS calculated for C$_{32}$H$_{28}$N$_9$O$_2$ (M+H)$^+$. m/z=570.2; found 570.3.

Step 6: 3-(5-(Bis(4-methoxybenzyl)amino)-2-bromo-8-(pyrimidin-4-yl)-[1,2,4]triazolo[1,5-c]pyrimidin-7-yl)benzonitrile

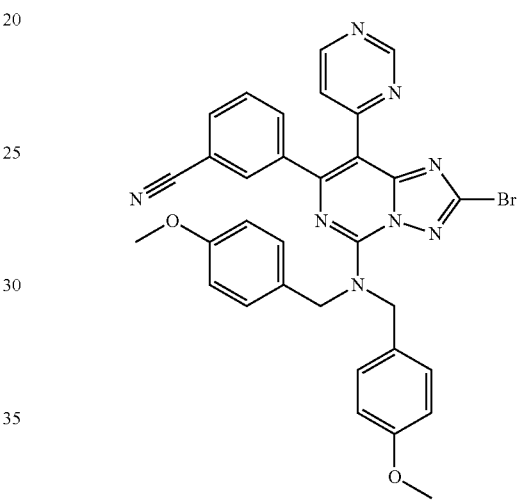

To a mixture of copper(II) bromide (91 mg, 0.407 mmol) and tert-butyl nitrite (0.054 ml, 0.407 mmol) in acetonitrile (3 mL) under nitrogen at 50° C. was added dropwise 3-(2-amino-5-(bis(4-methoxybenzyl)amino)-8-(pyrimidin-4-yl)-[1,2,4]triazolo[1,5-c]pyrimidin-7-yl)benzonitrile (100 mg, 0.203 mmol) in acetonitrile (3 mL). The mixture was stirred at 50° C. for 2 hours. After cooling to room temperature, 1 N aqueous NH$_4$OH solution (20 mL) was added and the mixture was extracted three times with CH$_2$Cl$_2$ (20 mL). The combined organic layers were dried over sodium sulfate, filtered and concentrated. The crude material was purified by silica gel column chromatography eluting with 50-100% ethyl acetate/hexane to give the desired product. LC-MS calculated for C$_{32}$H$_{26}$BrN$_8$O$_2$ (M+H)$^+$: m/z=633.1; found 633.2.

Step 7: 3-(5-Amino-2-((3-methylpyridin-2-yl)methoxy)-8-(pyrimidin-4-yl)-[1,2,4]triazolo[1,5-c]pyrimidin-7-yl)benzonitrile A suspension of sodium hydride (60% in mineral oil, 3.8 mg, 0.095 mmol), 3-(5-(bis(4-methoxybenzyl)amino)-2-bromo-8-(pyrimidin-4-yl)-[1,2,4]triazolo[1,5-c]pyrimidin-7-yl)benzonitrile (20 mg, 0.032 mmol) and (3-methylpyridin-2-yl)methanol (9.1 μL, 0.095 mmol) in 1,4-dioxane (1 mL) was heated and stirred at 110° C. under nitrogen overnight. The reaction mixture was then cooled to rt, concentrated, and added TFA (1.0 mL). The resulting mixture was then stirred at 110° C. for 30 min, cooled to rt, diluted with acetonitrile, filtered and purified by preparative LC-MS (pH 2, acetonitrile/water with TFA) to give desired product as a TFA salt. LC-MS calculated for $C_{23}H_{18}N_9O$ (M+H)$^+$: m/z=436.2; found 436.2. $^1$H NMR (600 MHz, DMSO) δ 8.97 (d, J=1.4 Hz, 1H), 8.88 (d, J=5.2 Hz, 1H), 8.58-8.52 (m, 1H), 7.97 (d, J=7.8 Hz, 1H), 7.88 (dd, J=5.4, 1.4 Hz, 1H), 7.85 (dt, J=7.5, 1.5 Hz, 1H), 7.78 (t, J=1.8 Hz, 1H), 7.60-7.54 (m, 2H), 7.53 (t, J=7.8 Hz, 1H), 5.69 (s, 2H), 2.48 (s, 3H).

Example A5: Synthesis of 3-(5-Amino-2-(hydroxy(phenyl)methyl)-[1,2,4]triazolo[1,5-c]pyrimidin-7-yl)benzonitrile (Compound 5)

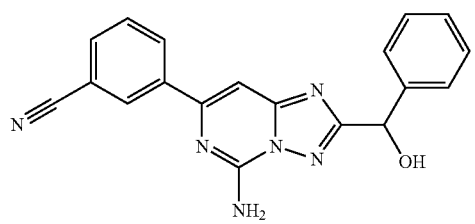 [SMILES: N#Cc1cccc(-c2cc3nc(C(O)c4ccccc4)nn3c(N)n2)c1]

Step 1:
3-(2-Amino-6-chloropyrimidin-4-yl)benzonitrile

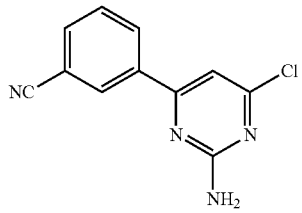 [SMILES: N#Cc1cccc(-c2cc(Cl)nc(N)n2)c1]

A mixture of 4,6-dichloropyrimidin-2-amine (2.5 g, 15.24 mmol), (3-cyanophenyl)boronic acid (2.016 g, 13.72 mmol), tetrakis(triphenylphosphine)palladium(0) (1.057 g, 0.915 mmol) and sodium carbonate (3.23 g, 30.5 mmol) in 1,4-dioxane (60 mL), and water (5 mL) was degassed with nitrogen, then the resulting mixture was heated at 60° C. for two days. After cooled to room temperature (RT), the mixture was concentrated, then diluted with water, and extracted with dichloromethane (DCM, 3×30 mL). The combined organic layers were dried over MgSO$_4$, filtered, and concentrated. The residue was purified by flash chromatography on a silica gel column with 8% ethyl acetate (EtOAc) in dichloromethane to afford the desired product. LCMS calculated for $C_{11}H_8ClN_4$ (M+H)$^+$: 231.0. Found: 231.0.

Step 2: 3-(5-Amino-2-(hydroxy(phenyl)methyl)-[1,2,4]triazolo[1,5-c]pyrimidin-7-yl)benzonitrile A solution of 3-(2-amino-6-chloropyrimidin-4-yl)benzonitrile (100 mg, 0.434 mmol) and 2-hydroxy-2-phenylacetohydrazide (108 mg, 0.650 mmol) in ethanol (2 ml) was heated and stirred at 95° C. for 3 h. After cooling to RT, the reaction mixture was concentrated to dryness, taken into N,O-bis(trimethylsilyl)acetamide (1 mL) and stirred at 120° C. for 7 h. The resulting mixture was cooled to RT, poured onto ice, and stirred for 1 h. The resulting suspension was extracted with DCM three times. The combined organic layers were dried over MgSO$_4$, filtered, and concentrated. The residue was dissolved in methanol (MeOH) and purified by preparative LC-MS (pH 2, acetonitrile/water with TFA) to afford the product as TFA salt. LCMS calculated for $C_{19}H_{15}N_6O$ (M+H)$^+$: 343.1; found 343.1.

Example A6: Synthesis of 3-(5-Amino-2-((2,6-difluorophenyl)(hydroxy)methyl)-[1,2,4]triazolo[1,5-c]pyrimidin-7-yl)-2-fluorobenzonitrile (Compound 6)

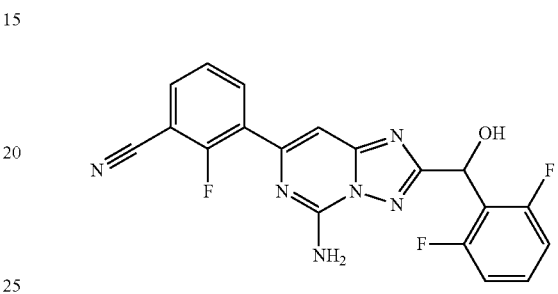

Step 1: 3-(2-Amino-6-chloropyrimidin-4-yl)-2-fluorobenzonitrile

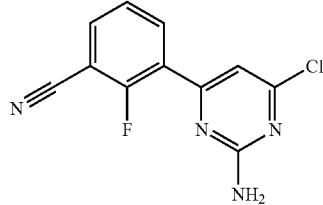 [SMILES: N#Cc1cccc(-c2cc(Cl)nc(N)n2)c1F]

To a solution of 3-bromo-2-fluorobenzonitrile (18.3 g, 91 mmol) in THF (60 mL) cooled to 0° C. was added i-PrMgCl LiCl complex (70.4 mL, 91 mmol) in THF (1.3 M) over 20 min. The mixture was stirred at 0° C. for 50 min, then zinc chloride (48.1 mL, 91 mmol) in 2-MeTHF (1.9 M) was added at 0° C. The reaction was stirred at r.t. for 25 min, at which point 4,6-dichloropyrimidin-2-amine (10 g, 61.0 mmol) was added in one portion. The solution was stirred for 10 min. Tetrakis(triphenylphosphine)palladium (1.41 g, 1.22 mmol) was added to the mixture and the reaction was stirred at r.t. for 16 h. Upon completion, 2,4,6-trimercaptotriazine silica gel (2 g) was added to the reaction solution. The mixture was stirred for 1 h and filtered. The solid was washed with ethyl acetate until the desired product had eluted completely (as detected by LCMS). The filtrate was washed with saturated ammonium chloride solution and water. The organics were concentrated to afford the crude product. Water was added to the crude material and the resulting precipitate was collected by filtration and dried under a stream of nitrogen. The crude material was taken forward without additional purification. LC-MS calculated for $C_{11}H_7ClFN_4$ (M+H)$^+$: m/z=249.0; found 249.0.

Step 2: Methyl 2-(2,6-difluorophenyl)-2-hydroxyacetate

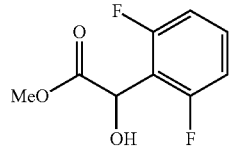 [SMILES: COC(=O)C(O)c1c(F)cccc1F]

Concentrated sulfuric acid (1.4 mL, 27 mmol) was added to a methanol (45 mL) solution of 2,6-difluoromandelic acid (5.0 g, 27 mmol) at 0° C. The mixture was stirred at r.t. for 4 h before being concentrated. To the resulting slurry was added saturated NaHCO₃ solution. The resulting mixture was extracted with DCM. The combined organic layers were washed with water, dried over MgSO₄, filtered, and concentrated to afford the crude product, which was used in the next step without further purification. LC-MS calculated for $C_{11}H_{12}F_2NO_3$ (M+H+MeCN)⁺: m/z=244.1; found 244.2.

Step 3: 2-(2,6-Difluorophenyl)-2-hydroxyacetohydrazide

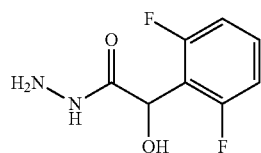 [SMILES: NNC(=O)C(O)c1c(F)cccc1F]

Hydrazine (3.0 mL, 96 mmol) was added to an ethanol (90 mL) solution of methyl 2-(2,6-difluorophenyl)-2-hydroxyacetate (10.8 g, 53 mmol) at RT. The reaction mixture was stirred at 100° C. for 2 h, cooled to RT, concentrated, and used in next step without further purification. LC-MS calculated for $C_8H_9F_2N_2O_2$ (M+H)⁺: 203.1; found 203.2.

Step 4: 3-(5-Amino-2-((2,6-difluorophenyl)(hydroxy)methyl)-[1,2,4]triazolo[1,5-c]pyrimidin-7-yl)-2-fluorobenzonitrile The title compound was prepared using similar procedures as described for Example A5 Step 2, with 3-(2-amino-6-chloropyrimidin-4-yl)-2-fluorobenzonitrile replacing 3-(2-amino-6-chloropyrimidin-4-yl)benzonitrile, and with 2-(2,6-Difluorophenyl)-2-hydroxyacetohydrazide replacing 2-hydroxy-2-phenylacetohydrazide. The two enantiomers were separated by chiral SFC using a Phenomenex (R,R)-Whelk-O1 column (21.2×250 mm, 5 μm particle size) eluting with an isocratic mobile phase 15% MeOH in CO₂ with a flow rate of 85 mL/minute. The retention times of peak one and peak two were 3.8 min and 5.3 min, respectively. Following concentration, peak two was purified by prep-LCMS (pH=2, MeCN/water with TFA) to give the desired product as a TFA salt. LC-MS calculated for $C_{19}H_{12}F_3N_6O$ (M+H)⁺: 397.1; found 397.1.

Example A7: Synthesis of 5-Amino-7-(3-cyano-2-fluorophenyl)-2-((2,6-difluorophenyl)(hydroxy)methyl)-[1,2,4]triazolo[1,5-c]pyrimidine-8-carbonitrile (Compound 7)

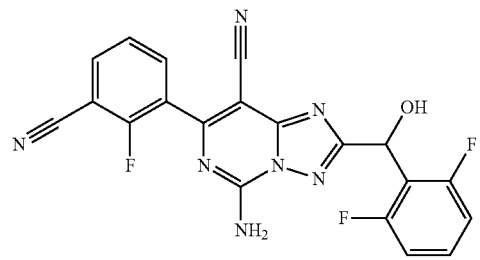 [SMILES: N#Cc1cccc(-c2nc(N)n3nc(C(O)c4c(F)cccc4F)nc3c2C#N)c1F]

Step 1: 3-(5-Amino-8-bromo-2-((2,6-difluorophenyl)(hydroxy)methyl)-[1,2,4]triazolo[1,5-c]pyrimidin-7-yl)-2-fluorobenzonitrile

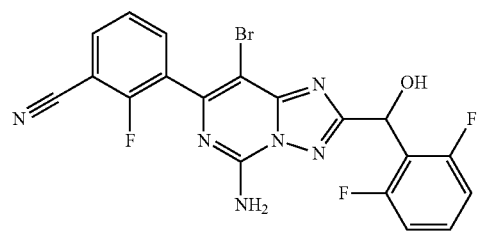 [SMILES: N#Cc1cccc(-c2nc(N)n3nc(C(O)c4c(F)cccc4F)nc3c2Br)c1F]

This compound was prepared using similar procedures as described for Example A1, Step 4, with 3-(5-amino-2-((2,6-difluorophenyl)(hydroxy)methyl)-[1,2,4]triazolo[1,5-c]pyrimidin-7-yl)-2-fluorobenzonitrile (from Example A6) replacing 3-(5-amino-2-(pyridin-2-ylmethyl)-[1,2,4]triazolo[1,5-c]pyrimidin-7-yl)benzonitrile. LCMS calculated for $C_9H_{11}BrF_3N_6O$ (M+H)⁺: 475.0; found 475.0.

Step 2: 5-Amino-7-(3-cyano-2-fluorophenyl)-2-((2,6-difluorophenyl)(hydroxy)methyl)-[1,2,4]triazolo[1,5-c]pyrimidine-8-carbonitrile A mixture of 3-(5-amino-8-bromo-2-((2,6-difluorophenyl)(hydroxy)methyl)-[1,2,4]triazolo[1,5-c]pyrimidin-7-yl)-2-fluorobenzonitrile (0.12 g, 0.25 mmol), ZnCN₂ (0.060 g, 0.51 mmol) and tBuXPhos Pd G3 (0.020 g, 0.025 mmol) in 1,4-dioxane (0.63 mL) and water (0.63 mL) was purged with N₂ and was stirred at 100° C. for 1 h. After cooling to r.t., the reaction was diluted with saturated NaHCO₃ and the organics were extracted with EtOAc (3×). The combined organics were dried over MgSO₄ and concentrated. The two enantiomers were separated by chiral HPLC using a Phenomenex Lux Celluose-4 column (21.2×250 mm, 5 μm particle size) eluting with an isocratic mobile phase 60% EtOH in hexanes with a flow rate of 20 mL/minute. The retention times of peak one and peak two were 4.9 min and 7.2 min, respectively. Following concentration, peak one was purified by preparative LC-MS (pH 2, acetonitrile/water with TFA) to give the desired product as a TFA salt. LC-MS calculated for $C_{20}H_{11}F_3N_7O$ (M+H)⁺: 422.1; found 422.1.

Example A8: Synthesis of 3-(5-Amino-2-((2-fluoro-6-(((1-methyl-2-oxopyrrolidin-3-yl)amino)methyl)phenyl)(hydroxy)methyl)-[1,2,4]triazolo[1,5-c]pyrimidin-7-yl)-2-fluorobenzonitrile (Compound 8)

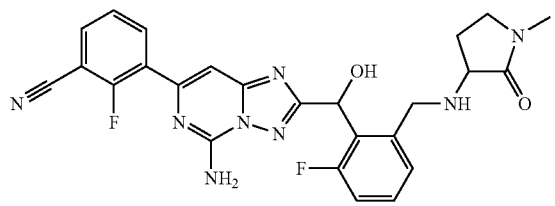 [SMILES: CN1CCC(NCc2cccc(F)c2C(O)c2nc3cc(-c4cccc(C#N)c4F)nc(N)n3n2)C1=O]

Step 1: Methyl 2-(2-fluoro-6-vinylphenyl)acetate

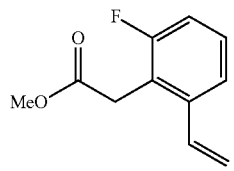

A mixture of methyl 2-(2-bromo-6-fluorophenyl)acetate (6.0 g, 24 mmol), potassium phosphate, tribasic (15.5 g, 73 mmol), palladium(II) acetate (0.55 g, 2.4 mmol), and SPhos (1.0 g, 2.4 mmol) were added to a 500 mL pressure vessel. Next, 4,4,5,5-tetramethyl-2-vinyl-1,3,2-dioxaborolane (6.4 ml, 36 mmol) in dioxane (150 mL) and water (15 mL) was added, the reaction mixture was purged with N2, and stirred at 80° C. for 16 h. The reaction mixture was then cooled to RT, concentrated, and extracted with EtOAc (×3). The combined organic layers were dried over MgSO4, concentrated, and purified by column chromatography (0 to 50% EtOAc in DCM). LC-MS calculated for C11H12FO2 (M+H)+: 195.1; found 195.1.

Step 2: Methyl 2-(2-fluoro-6-vinylphenyl)-2-hydroxyacetate

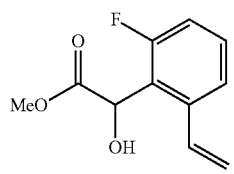

Methyl 2-(2-fluoro-6-vinylphenyl)acetate (2.5 g, 12.9 mmol) was dissolved in THF (130 mL) and cooled to −78° C. LDA (16.7 mL, 16.7 mmol) in THF (1.0 M) was added dropwise, and the resulting solution was stirred at −78° C. for 30 min. Then, 9,9-dimethyltetrahydro-4H-4a,7-methanobenzo[c][1,2]oxazireno[2,3-b]isothiazole 3,3-dioxide (4.7 g, 20.6 mmol) was added dropwise in THF (0.5 M). After 30 min at −78° C., the reaction mixture was warmed to 0° C. and stirred for 1 h. The reaction was quenched with saturated NH4Cl. The aqueous layer was extracted with DCM (3×). The combined organics were dried over anhydrous Na2SO4, filtered, and concentrated under reduced pressure. The crude product was purified by column chromatography eluting with 0 to 50% ethyl acetate in hexanes to afford the desired product. LCMS calculated for $C_{11}H_{11}FO_3Na$ (M+Na)+: 233.1; found 233.1.

Step 3: 2-(2-Fluoro-6-vinylphenyl)-2-hydroxyacetohydrazide

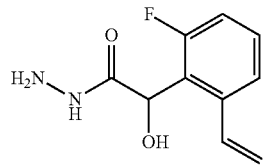

This compound was prepared using similar procedures as described for Example A6, Step 3, with methyl 2-(2-fluoro-6-vinylphenyl)-2-hydroxyacetate replacing methyl 2-(2,6-difluorophenyl)-2-hydroxyacetate. LCMS calculated for $C_{10}H_{12}FN_2O_2$ (M+H)+: 211.1; found 211.1.

Step 4: 3-(5-Amino-2-((2-fluoro-6-vinylphenyl)(hydroxy)methyl)-[1,2,4]triazolo[1,5-c]pyrimidin-7-yl)-2-fluorobenzonitrile

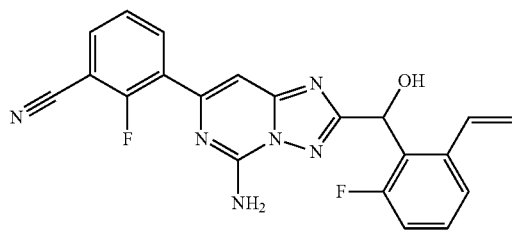 [SMILES: C=Cc1cccc(F)c1C(O)c1nc2cc(-c3cccc(C#N)c3F)nc(N)n2n1]

This compound was prepare using similar procedures as described for Example A6 Step 4, with 2-(2-fluoro-6-vinylphenyl)-2-hydroxyacetohydrazide replacing 2-(2,6-difluorophenyl)-2-hydroxyacetohydrazide. LCMS calculated for C21H15F2N6O (M+H)+: 405.1; found 405.1.

Step 5: 3-(5-Amino-2-((2-fluoro-6-formylphenyl)(hydroxy)methyl)-[1,2,4]triazolo[1,5-c]pyrimidin-7-yl)-2-fluorobenzonitrile

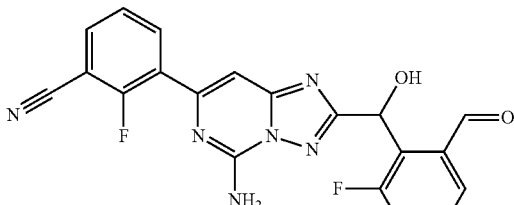

Osmium tetroxide in water (4% w/w, 0.36 mL, 0.12 mmol) was added to a THF (18 mL) and water (4.6 mL) solution of 3-(5-amino-2-((2-fluoro-6-vinylphenyl)(hydroxy)methyl)-[1,2,4]triazolo[1,5-c]pyrimidin-7-yl)-2-fluorobenzonitrile (930 mg, 2.30 mmol). The reaction mixture was stirred for 5 min at RT and then sodium periodate (2.5 g, 11.5 mmol) was added. After stirring for 1 h, the mixture was diluted with sodium metabisulfite in saturated aq. NaHCO3 (5% w/w, 20 mL) and extracted with EtOAc (×3). The combined organic layers were dried over MgSO4 and concentrated under reduced pressure. The crude material was purified by column chromatography eluting with 0 to 100% ethyl acetate in hexanes to afford the desired product. LCMS calculated for C20H13F2N6O2 (M+H)+: 407.1; found 407.1.

Step 6: 3-(5-Amino-2-((2-fluoro-6-(((1-methyl-2-oxopyrrolidin-3-yl)amino)methyl)phenyl)(hydroxy)methyl)-[1,2,4]triazolo[1,5-c]pyrimidin-7-yl)-2-fluorobenzonitrile A solution of 3-amino-1-methylpyrrolidin-2-one (63 mg, 0.55 mmol) and 3-(5-amino-2-((2-fluoro-6-formylphenyl)(hydroxy)methyl)-[1,2,4]triazolo[1,5-c]pyrimidin-7-yl)-2-fluorobenzonitrile (150 mg, 0.37 mmol) was stirred at 40° C. for 2 h in 1,2-dichloroethane (1.9 mL). Then sodium triacetoxyborohydride (160 mg, 0.74 mmol) was added and the reaction mixture was stirred at room temperature for 16 h. The reaction was diluted with saturated NaHCO$_3$ and the organics were extracted with EtOAc (3×). The combined organics were dried over MgSO$_4$ and concentrated. The diastereomers were separated by chiral HPLC using a Phenomenex Lux Celluose-4 column (21.2×250 mm, 5 µm particle size) eluting with an isocratic mobile phase 45% EtOH in hexanes with a flow rate of 20 mL/minute. The retention times of peak one and peak two were 14.9 min and 17.5 min, respectively. Following concentration, peak two was further separated by chiral HPLC using a Phenomenex Lux Celluose-1 column (21.2×250 mm, 5 µm particle size) eluting with an isocratic mobile phase 30% EtOH in hexanes with a flow rate of 20 mL/minute. The retention times of peak one and peak two were 11.0 min and 15.5 min, respectively. Following concentration, peak one was purified by preparative LC-MS (pH=2, MeCN/water with TFA) to give the desired product as a TFA salt. LC-MS calculated for C$_{25}$H$_{23}$F$_2$N$_8$O$_2$ (M+H)$^+$. 505.2; found 505.2.

Example A9: Synthesis of 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile (Compound 9)

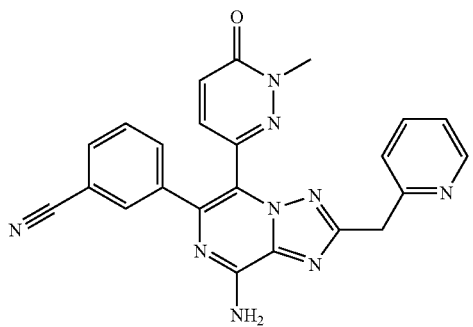 [SMILES: Cn1nc(-c2c(-c3cccc(C#N)c3)nc(N)c3nc(Cc4ccccn4)nn23)ccc1=O]

Step 1: Methyl 3-bromo-1-(2-(3-cyanophenyl-2-oxoethyl)-1H-1,2,4-triazole-5-carboxylate

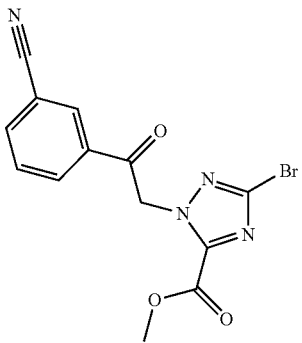 [SMILES: COC(=O)c1nc(Br)nn1CC(=O)c1cccc(C#N)c1]

To a solution of methyl 3-bromo-1H-1,2,4-triazole-5-carboxylate (5.0 g, 24.3 mmol), 3-(2-bromoacetyl)benzonitrile (5.44 g, 24.3 mmol) in DMF (100 mL) was added potassium carbonate (3.35 g, 24.3 mmol). The reaction mixture was stirred at ambient temperature for 2 h. The reaction mixture was then diluted with water and DCM. The organic layer was separated, washed with brine, dried over Na$_2$SO$_4$, filtered and concentrated. The resulting residue was purified via flash chromatography to give the desired product as a white solid (5.2 g, 61%). LC-MS calculated for C$_{13}$H$_{10}$BrN$_4$O$_3$ (M+H)$^+$: m/z=349.0; found 349.0.

Step 2: 3-(2-Bromo-8-oxo-7,8-dihydro-[1,2,4]triazolo[1,5-a]pyrazin-6-yl)benzonitrile

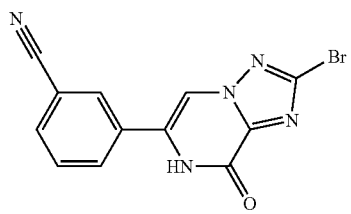 [SMILES: N#Cc1cccc(-c2cn3nc(Br)nc3c(=O)[nH]2)c1]

Methyl 3-bromo-1-(2-(3-cyanophenyl)-2-oxoethyl)-1H-1,2,4-triazole-5-carboxylate (10.5 g, 30.1 mmol) was dissolved in acetic acid (100 mL), and ammonium acetate (23.18 g, 301 mmol) was added. The mixture was stirred at 110° C. for 12 h. After cooling to room temperature, the reaction mixture was diluted with water. The resulting precipitate was collected via filtration, washed with water, and dried under vacuum to afford the product (8.4 g, 88%). LC-MS calculated for C$_{12}$H$_7$BrN$_5$O (M+H)$^+$: m/z=316.0; found 316.0.

Step 3: 3-(2-Bromo-8-chloro-[1,2,4]triazolo[1,5-a]pyrazin-6-yl)benzonitrile

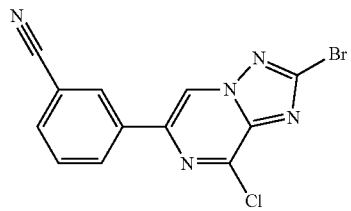 [SMILES: N#Cc1cccc(-c2cn3nc(Br)nc3c(Cl)n2)c1]

A mixture of 3-(2-bromo-8-oxo-7,8-dihydro-[1,2,4]triazolo[1,5-a]pyrazin-6-yl)benzonitrile (8.4 g, 26.6 mmol) and POCl$_3$ (49.5 mL, 531 mmol) was stirred at 110° C. overnight. After cooling to room temperature, the reaction mixture was slowly added to a flask containing ice and sodium bicarbonate. The resulting precipitate was collected, washed with water, and dried to afford the product (8.8 g, 99%). LC-MS calculated for C$_{12}$H$_6$BrClN$_5$ (M+H)$^+$: m/z=333.9; found 334.0.

Step 4. 3-(8-(Bis(4-methoxybenzyl)amino)-2-bromo-[1,2,4]triazolo[1,5-a]pyrazin-6-yl)benzonitrile

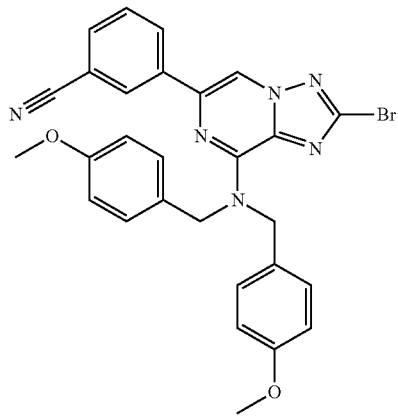 [SMILES: COc1ccc(CN(Cc2ccc(OC)cc2)c2nc(-c3cccc(C#N)c3)cn3nc(Br)nc23)cc1]

A mixture of 3-(2-bromo-8-chloro-[1,2,4]triazolo[1,5-a]pyrazin-6-yl)benzonitrile (8.99 g, 26.9 mmol), bis(4-methoxybenzyl)amine (10.37 g, 40.3 mmol), and DIPEA (9.4 mL, 53.7 mmol) in DMF (134 mL) was stirred at 85° C. overnight. The reaction mixture was cooled to room temperature, and diluted with water. The resulting precipitate was collected via filtration, and dried to afford the product (14.1 g, 94%). LC-MS calculated for C$_{28}$H$_{24}$BrN$_6$O$_2$ (M+H)$^+$: m/z=555.1; found 555.1.

Step 5: 3-(8-(Bis(4-methoxybenzyl)amino)-2-(pyridin-2-ylmethyl)-[1,2,4]triazolo[1,5-a]pyrazin-6-yl)benzonitrile

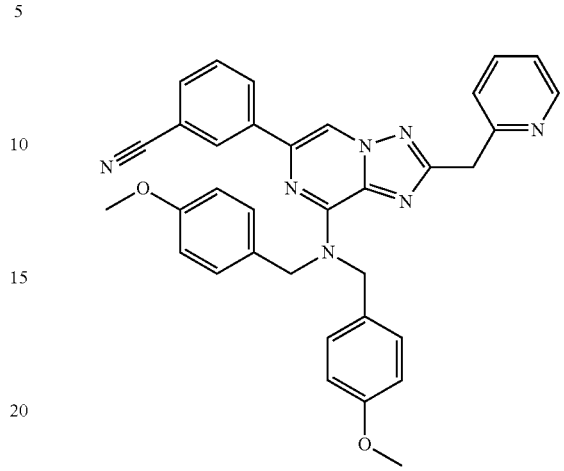

To a solution of 2-methylpyridine (0.050 g, 0.540 mmol) in THF (0.5 mL) was added 2.5 M n-butyllithium (0.216 mL, 0.540 mmol) at −78° C. The resulting solution was stirred at the same temperature for 1 h, before 1.9 M zinc chloride in 2-methyltetrahydrofuran (0.284 mL, 0.540 mmol) was added, and the resulting mixture was stirred at room temperature for 10 min.

A microwave vial charge with 3-(8-(bis(4-methoxybenzyl)amino)-2-bromo-[1,2,4]triazolo[1,5-a]pyrazin-6-yl)benzonitrile (0.15 g, 0.270 mmol), palladium acetate (1.1 mg, 4.7 µmol), and 2'-(dicyclohexylphosphino)-N,N,N',N'-tetramethylbiphenyl-2,6-diamine (4.1 mg, 9.5 µmol) was evacuated under high vacuum and backfilled with nitrogen. THF (2.0 mL) and toluene (0.5 mL) was then added to the reaction vial. The mixture was cooled to 0° C. and the zinc reagent prepared from previous step was added slowly via a syringe. The reaction mixture was then stirred at 60° C. overnight, cooled to room temperature, and partitioned between ethylacetate and saturated NH$_4$Cl solution. The layers were separated and the aqueous layer was extracted with ethylacetate. The combined organic layers were washed with water and brine, dried over MgSO$_4$, and concentrated. The resulting residue was purified via flash chromatography to afford the product (0.11 g, 71%). LC-MS calculated for C$_{34}$H$_{30}$N$_7$O$_2$ (M+H)$^+$: m/z=568.2; found 568.3.

Step 6. 3-(8-Amino-2-(pyridin-2-ylmethyl)-[1,2,4]triazolo[1,5-a]pyrazin-6-yl)benzonitrile

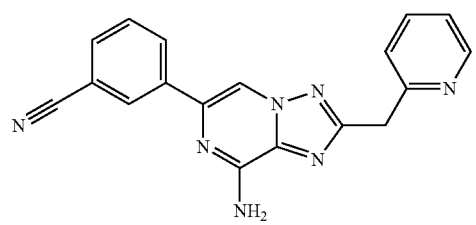 [SMILES: N#Cc1cccc(-c2cn3nc(Cc4ccccn4)nc3c(N)n2)c1]

A mixture of 3-(8-(bis(4-methoxybenzyl)amino)-2-(pyridin-2-ylmethyl)-[1,2,4]triazolo[1,5-a]pyrazin-6-yl)benzonitrile (110 mg, 0.194 mmol) and TFA (746 μL, 9.69 mmol) was stirred at 80° C. for 30 min, cooled to room temperature, and concentrated. The resulting residue was purified via prep-LCMS (pH 2) to give the product as a white solid (TFA salt) (57 mg, 90%). LC-MS calculated for C18H$_{14}$N$_7$ (M+H)$^+$: m/z=328.1; found 328.1.

Step 7. 3-(8-Amino-5-bromo-2-(pyridin-2-ylmethyl)-[1,2,4]triazolo[1,5-a]pyrazin-6-yl)benzonitrile

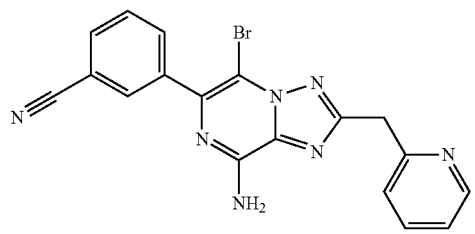 [SMILES: N#Cc1cccc(-c2nc(N)c3nc(Cc4ccccn4)nn3c2Br)c1]

To a solution of 3-(8-amino-2-(pyridin-2-ylmethyl)-[1,2,4]triazolo[1,5-a]pyrazin-6-yl)benzonitrile (TFA salt) (35 mg, 0.079 mmol) in DMF (0.5 mL)/DCM (0.5 mL) was added NBS (14.1 mg, 0.079 mmol). The reaction mixture was then stirred at room temperature for 1 h, and concentrated to afford the crude product, which was used in the next step without further purification. LC-MS calculated for C$_{18}$H13BrN$_7$ (M+H)$^+$: m/z=406.0; found 406.0.

Step 8. 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile A mixture of 6-chloro-2-methylpyridazin-3(2H)-one (30 mg, 0.21 mmol), bis(pinacolato)diboron (53 mg, 0.21 mmol), chloro(2-dicyclohexylphosphino-2',4',6'-triisopropyl-1,1'-biphenyl)[2-(2'-amino-1,1'-biphenyl)]palladium(II) (15.7 mg, 0.02 mmol) (XPhos Pd G2) and potassium acetate (61.7 mg, 0.63 mmol) in 1,4-dioxane (1 mL) was stirred at 100° C. for 1 h. 3-(8-Amino-5-bromo-2-(pyridin-2-ylmethyl)-[1,2,4]triazolo[1,5-a]pyrazin-6-yl)benzonitrile (10 mg, 0.025 mmol), cesium carbonate (37.6 mg, 0.116 mmol) and water (0.2 mL) were then added to the reaction mixture. The resulting mixture was heated at 90° C. for 1 h. The mixture was concentrated and purified by preparative LCMS (pH 2, acetonitrile/water with TFA) to afford the desired product as TFA salt. LCMS calculated for C$_{23}$H$_{18}$N$_9$O (M+H)$^+$: 436.2; found 436.2.

$^1$H NMR (500 MHz, DMSO) δ 8.66-8.62 (d, J=5.1 Hz, 1H), 8.09-8.02 (d, J=1.8 Hz, 1H), 7.88-7.85 (t, J=1.8 Hz, 1H), 7.85-7.81 (m, 3H), 7.78-7.72 (d, J=9.6 Hz, 1H), 7.66-7.51 (m, 4H), 7.10-7.06 (d, J=9.6 Hz, 1H), 4.59-4.48 (s, 2H), 3.53-3.43 (s, 3H).

Example A10: Synthesis of 3-(8-Amino-2-((2,6-difluorophenyl)(hydroxy)methyl)-5-(pyrimidin-4-yl)-[1,2,4]triazolo[1,5-a]pyrazin-6-yl)benzonitrile (Compound 10)

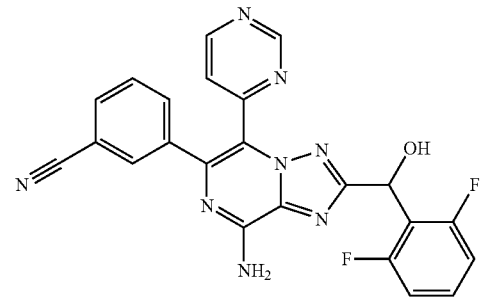 [SMILES: N#Cc1cccc(-c2nc(N)c3nc(C(O)c4c(F)cccc4F)nn3c2-c2ccncn2)c1]

Step 1: Methyl 3-bromo-1-(2 (3-cyanophenyl)-2-oxoethyl)-1H-1,2,4-triazole-5-carboxylate

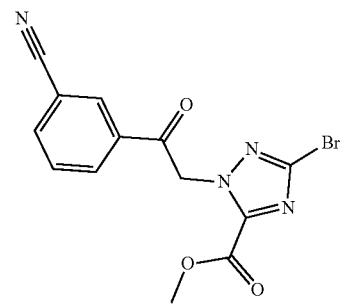 [SMILES: COC(=O)c1nc(Br)nn1CC(=O)c1cccc(C#N)c1]

To a solution of methyl 3-bromo-1H-1,2,4-triazole-5-carboxylate (5.0 g, 24.3 mmol), 3-(2-bromoacetyl)benzonitrile (5.44 g, 24.3 mmol) in DMF (100 mL) was added potassium carbonate (3.35 g, 24.3 mmol). The reaction mixture was stirred at ambient temperature for 2 h. The reaction mixture was then diluted with water and DCM. The organic layer was separated, washed with brine, dried over Na$_2$SO$_4$, filtered and concentrated. The resulting residue was purified via flash chromatography to give the desired product as a white solid (5.2 g, 61%). LC-MS calculated for C$_{13}$H$_{10}$BrN$_4$O$_3$ (M+H)$^+$: m/z=349.0; found 349.0.

Step 2: 3-(2-Bromo-8-oxo-7,8-dihydro-[1,2,4]triazolo[1,5-a]pyrazin-6-yl)benzonitrile

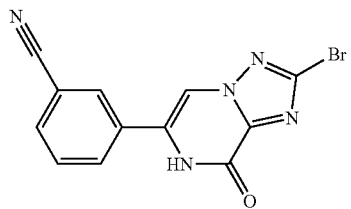

Methyl 3-bromo-1-(2-(3-cyanophenyl)-2-oxoethyl)-1H-1,2,4-triazole-5-carboxylate (10.5 g, 30.1 mmol) was dissolved in acetic acid (100 mL), and ammonium acetate (23.18 g, 301 mmol) was added. The mixture was stirred at 110° C. for 12 h. After cooling to room temperature, the reaction mixture was diluted with water. The resulting precipitate was collected via filtration, washed with water, and dried under vacuum to afford the product (8.4 g, 88%). LC-MS calculated for $C_{12}H_7BrN_5O$ $(M+H)^+$: m/z=316.0; found 316.0.

Step 3: 3-(2-Bromo-8-chloro-[1,2,4]triazolo[1,5-a]pyrazin-6-yl)benzonitrile

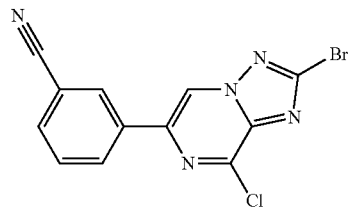 [SMILES: N#Cc1cccc(-c2cn3nc(Br)nc3c(Cl)n2)c1]

A mixture of 3-(2-bromo-8-oxo-7,8-dihydro-[1,2,4]triazolo[1,5-a]pyrazin-6-yl)benzonitrile (8.4 g, 26.6 mmol) and $POCl_3$ (49.5 mL, 531 mmol) was stirred at 110° C. overnight. After cooling to room temperature, the reaction mixture was slowly added to a flask containing ice and sodium bicarbonate. The resulting precipitate was collected via filtration, washed with water, and dried to afford the product (8.8 g, 99%). LC-MS calculated for $C_{12}H_6BrClN_5$ $(M+H)^+$: m/z=336.0; found 336.0.

Step 4: 3-(8-(Bis(4-methoxybenzyl)amino)-2-bromo-[1,2,4]triazolo[1,5-a]pyrazin-6-yl)benzonitrile

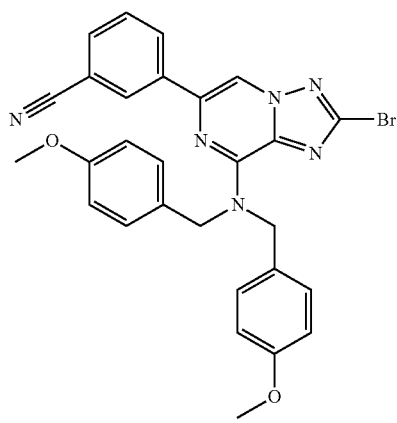 [SMILES: COc1ccc(CN(Cc2ccc(OC)cc2)c2nc(-c3cccc(C#N)c3)cn3nc(Br)nc23)cc1]

A mixture of 3-(2-bromo-8-chloro-[1,2,4]triazolo[1,5-a]pyrazin-6-yl)benzonitrile (8.99 g, 26.9 mmol), bis(4-methoxybenzyl)amine (10.37 g, 40.3 mmol), and DIPEA (9.4 mL, 53.7 mmol) in DMF (134 mL) was stirred at 65° C. overnight. The reaction mixture was cooled to room temperature, and diluted with water. The resulting precipitate was collected via filtration, and dried to afford the product (14.1 g, 94%). LC-MS calculated for $C_{28}H_{24}BrN_6O_2$ $(M+H)^+$: m/z=555.1; found 555.1.

Step 5: 3-(8-(Bis(4-methoxybenzyl)amino)-2-vinyl-[1,2,4]triazolo[1,5-a]pyrazin-6-yl)benzonitrile

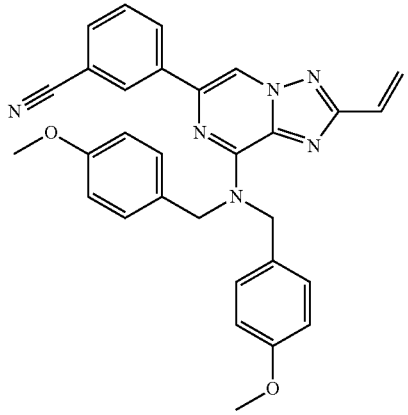 [SMILES: C=Cc1nc2c(N(Cc3ccc(OC)cc3)Cc3ccc(OC)cc3)nc(-c3cccc(C#N)c3)cn2n1]

A mixture of 3-(8-(bis(4-methoxybenzyl)amino)-2-bromo-[1,2,4]triazolo[1,5-a]pyrazin-6-yl)benzonitrile (10.0 g, 18.0 mmol), 4,4,5,5-tetramethyl-2-vinyl-1,3,2-dioxaborolane (3.88 g, 25.2 mmol), potassium phosphate tribasic (9.55 g, 45.0 mmol) and chloro(2-dicyclohexylphosphino-2',4',6'-triisopropyl-1,1'-biphenyl)[2-(2'-amino-1,1'-biphenyl)]palladium(II) (567 mg, 0.72 mmol) in 1,4-dioxane (200 mL) and water (50 mL) was stirred at 85° C. for 2 hrs. The reaction mixture was cooled to room temperature, and most of 1, 4-dioxane was removed. The resulting precipitate was collected via filtration, washed with water and dried to afford the crude product (9.1 g), which was used in the next step directly. LC-MS calculated for $C_{30}H_{27}N_6O_2$ $(M+H)^+$: m/z=503.2; found 503.1.

Step 6. 3-(8-(Bis(4-methoxybenzyl)amino)-5-bromo-2-vinyl-[1,2,4]triazolo[1,5-a]pyrazin-6-yl)benzonitrile

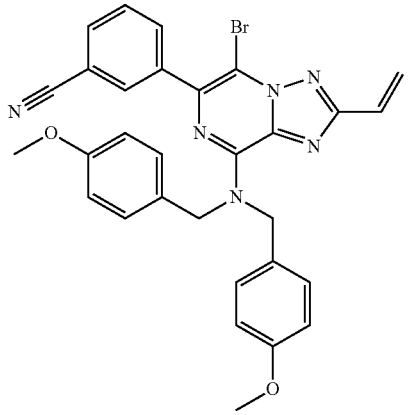 [SMILES: C=Cc1nc2c(N(Cc3ccc(OC)cc3)Cc3ccc(OC)cc3)nc(-c3cccc(C#N)c3)c(Br)n2n1]

To a solution of 3-(8-(bis(4-methoxybenzyl)amino)-2-vinyl-[1,2,4]triazolo[1,5-a]pyrazin-6-yl)benzonitrile (717 mg, 1.43 mmol) in 10 mL of dichloromethane, 1-bromopyrrolidine-2,5-dione (254 mg, 1.43 mmol) was added at 0° C. The resulting mixture was stirred for 4 hrs, and directly purified by a silica gel column to afford the desired product (780 mg, 94%). LC-MS calculated for $C_{30}H_{26}BrN_6O_2$ (M+H)$^+$: m/z=581.1; found 581.2.

Step 7: 3-(8-(Bis(4-methoxybenzyl)amino)-5-(pyrimidin-4-yl)-2-vinyl-[1,2,4]triazolo[1,5-a]pyrazin-6-yl)benzonitrile

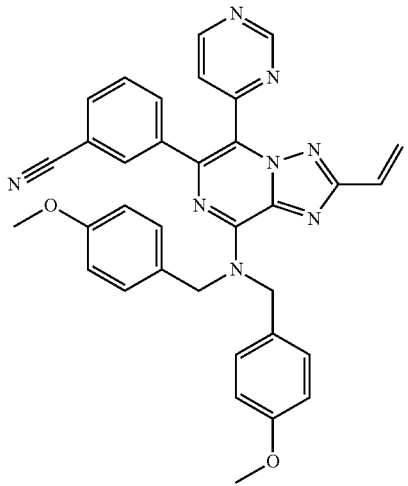 [SMILES: COc1ccc(CN(Cc2ccc(OC)cc2)c2nc(-c3cccc(C#N)c3)c(-c3ccncn3)n3nc(C=O)nc23)cc1]

A mixture of 3-(8-(bis(4-methoxybenzyl)amino)-5-bromo-2-vinyl-[1,2,4]triazolo[1,5-a]pyrazin-6-yl)benzonitrile (260 mg, 0.45 mmol), 4-(tributylstannyl)pyrimidine (215 mg, 0.58 mmol), lithium chloride (28.4 mg, 0.67 mmol), copper(I) chloride (67 mg, 0.67 mmol), and Tetrakis(triphenylphosphine)palladium(0) (52 mg, 0.045 mmol) in THF (5 mL) was stirred at 90° C. for 45 mins. The reaction mixture was quenched with water and extracted with dichloromethane. The combined organic layers were concentrated, and purified by a silica gel column to afford the desired product (176 mg, 67%). LC-MS calculated for $C_{34}H_{29}N_8O_2$ (M+H)$^+$: m/z=581.2; found 581.1.

Step 8: 3-(8-(Bis(4-methoxybenzyl)amino)-2-formyl-5-(pyrimidin-4-yl)-[1,2,4]triazolo[1,5-a]pyrazin-6-yl)benzonitrile

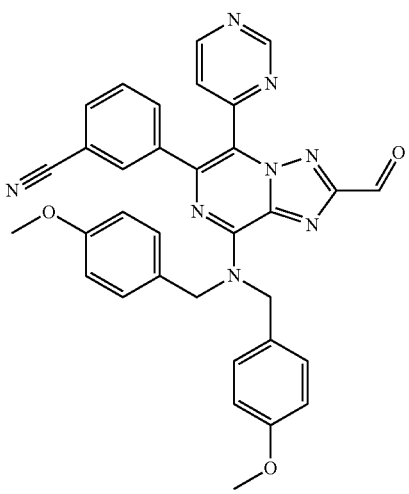

A mixture of 3-(8-(bis(4-methoxybenzyl)amino)-5-(pyrimidin-4-yl)-2-vinyl-[1,2,4]triazolo[1,5-a]pyrazin-6-yl)benzonitrile (176 mg, 0.3 mmol), osmium(VIII) oxide (3 mg in 0.3 mL water, 0.015 mmol), and sodium periodate (292 mg, 1.36 mmol) in THF/water (1:1, 6 mL) was stirred at 65° C. for 1 h. The reaction mixture was cooled to room temperature, and extracted with dichloromethane. The combined organic layers were concentrated, and purified by silica gel column to afford the desired product (130 mg, 74%). LC-MS calculated for $C_{33}H_{27}N_8O_3$ (M+H)$^+$: m/z=583.2; found 583.2.

Step 9: 3-(8-Amino-2-((2,6-difluorophenyl)(hydroxy)methyl)-5-(pyrimidin-4-yl)-[1,2,4]triazolo[1,5-a]pyrazin-6-yl)benzonitrile Preparation of the Grignard reagent: To a solution of 1,3-difluoro-2-iodobenzene (142 mg, 0.6 mmol) in tetrahydrofuran (1 mL), isopropylmagnesium chloride solution (296 µl, 2 M) was added at −10° C. The resulting mixture was stirred for 1 h, and used directly in the following step.

To a solution of 3-(8-(bis(4-methoxybenzyl)amino)-2-formyl-5-(pyrimidin-4-yl)-[1,2,4]triazolo[1,5-a]pyrazin-6-yl)benzonitrile (120 mg, 0.2 mmol) in THF (2 mL), the freshly prepared Grignard reagent from previous step was added at −10° C. The reaction mixture was stirred for 30 min, quenched with ammonium chloride solution (4 mL), and extracted with dichloromethane. The combined organic layers were concentrated under vacuum. The resulting material was dissolved in TFA (5 mL), and stirred at 80° C. for 20 min. The reaction mixture was then cooled to room temperature, concentrated, and basified by adding aqueous NaHCO$_3$ solution.

The crude material was directly purified by a silica gel column to afford the desired product (60 mg, 64%) as a racemic mixture. The product was then separated with chiral HPLC using a chiral column (Phenomenex Lux 5 um Cellulose-4, 21.2×250 mm) and 75% EtOH in hexanes (20 mL/min) solvent system.

Peak 2 was isolated, and further purified via preparative LC/MS (pH=2, acetonitrile/water with TFA) to give the desired product as a TFA salt. LC-MS calculated for $C_{23}H_{15}F_2N_8O$ (M+H)$^+$: m/z=457.1; found 457.0.

$^1$H NMR (600 MHz, DMSO-d6) δ 9.14 (d, J=1.3 Hz, 1H), 8.95 (d, J=5.2 Hz, 1H), 7.90 (dd, J=5.2, 1.4 Hz, 1H), 7.88 (s, 1H), 7.78 (dt, J=7.6, 1.4 Hz, 1H), 7.74 (t, J=1.4 Hz, 1H), 7.54 (dt, J=7.9, 1.3 Hz, 1H), 7.51-7.40 (m, 2H), 7.09 (t, J=8.4 Hz, 2H), 6.27 (s, 1H).

Example A11: Synthesis of 3-(8-amino-2-(amino(2,6-difluorophenyl)methyl)-5-(4-methyloxazol-5-yl)-[1,2,4]triazolo[1,5-a]pyrazin-6-yl)benzonitrile (Compound 11)

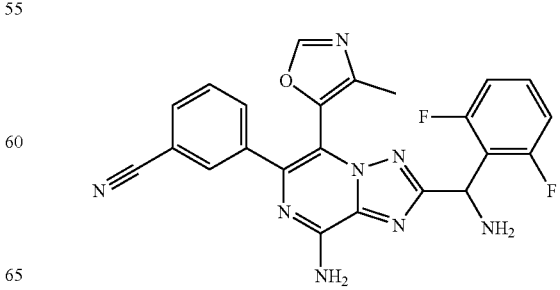

Step 1: 3-(8-(Bis(4-methoxybenzyl)amino)-5-bromo-2-vinyl-[1,2,4]triazolo[1,5-a]pyrazin-6-yl)benzonitrile Step 3: 3-(8-(bis(4-methoxybenzyl)amino)-5-bromo-2-((2,6-difluorophenyl)(hydroxy)methyl)-[1,2,4]triazolo[1,5-a]pyrazin-6-yl)benzonitrile

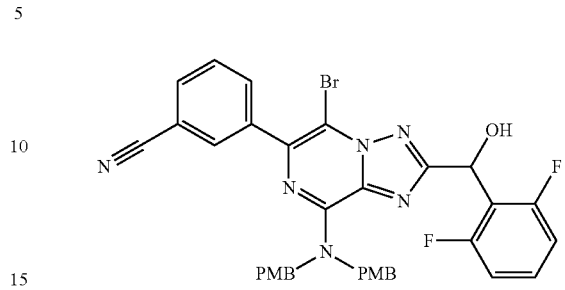

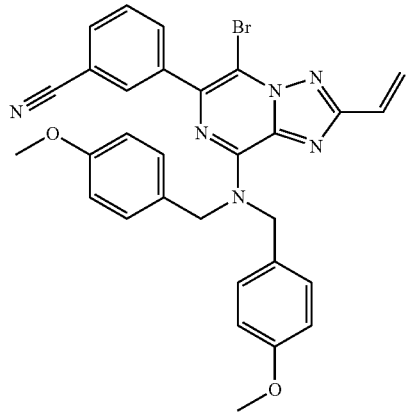 [SMILES: C=Cc1nc2c(N(Cc3ccc(OC)cc3)Cc3ccc(OC)cc3)nc(-c3cccc(C#N)c3)c(Br)n2n1]

Preparation of the Grignard reagent: To a solution of 1,3-difluoro-2-iodobenzene (142 mg, 0.6 mmol) in tetrahydrofuran (1 mL), isopropylmagnesium chloride solution (296 µl, 2 M) was added at −10° C. The resulting mixture was stirred for 1 h, and used directly in the following step.

To a solution of 3-(8-(bis(4-methoxybenzyl)amino)-5-bromo-2-formyl-[1,2,4]triazolo[1,5-a]pyrazin-6-yl)benzonitrile (120 mg, 0.2 mmol) in THF (2 mL), the freshly prepared Grignard reagent from previous step was added at −10° C. The reaction mixture was stirred for 30 min, quenched with ammonium chloride solution (4 mL), and extracted with dichloromethane. The combined organic layers were concentrated under vacuum and purified by a silica gel column to afford the desired product as a racemic mixture. LC-MS calculated for $C_{35}H_{28}N_6O_3BrF_2$ (M+H)$^+$: m/z=697.1; found 697.1.

To a solution of 3-(8-(bis(4-methoxybenzyl)amino)-2-vinyl-[1,2,4]triazolo[1,5-a]pyrazin-6-yl)benzonitrile (Example A10, Step 5; 241 mg, 0.48 mmol) in DCM (5 mL) was added NBS (84.6 mg, 0.48 mmol). The reaction mixture was then stirred at room temperature for 1 h, and concentrated to afford the crude product, which was used in the next step without further purification. LC-MS calculated for $C_{30}H_{26}BrN_6O_2$ (M+H)$^+$: m/z=581.1; found 581.1.

Step 4: 3-(8-(bis(4-methoxybenzyl)amino)-2-((2,6-difluorophenyl)(hydroxy)methyl)-5-(4-methyloxazol-5-yl)-[1,2,4]triazolo[1,5-a]pyrazin-6-yl)benzonitrile Step 2: 3-(8-(bis(4-methoxybenzyl)amino)-5-bromo-2-formyl-[1,2,4]triazolo[1,5-a]pyrazin-6-yl)benzonitrile

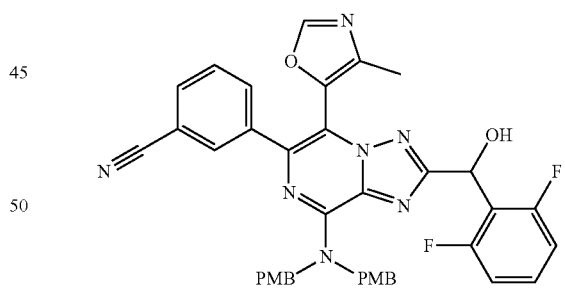

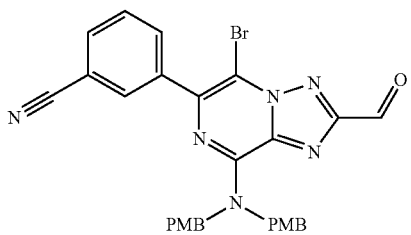

A mixture of 3-(8-(bis(4-methoxybenzyl)amino)-5-bromo-2-vinyl-[1,2,4]triazolo[1,5-a]pyrazin-6-yl)benzonitrile (174 mg, 0.3 mmol), osmium(VIII) oxide (3 mg in 0.3 mL water, 0.015 mmol), and sodium periodate (292 mg, 1.36 mmol) in THF/water (1:1, 6 mL) was stirred at 65° C. for 1 h. The reaction mixture was cooled to room temperature, and extracted with dichloromethane. The combined organic layers were concentrated, and purified by silica gel column to afford the desired product. LC-MS calculated for $C_{29}H_{24}N_6O_3Br$ (M+H)$^+$: m/z=583.1; found 583.1.

A mixture of 3-(8-(bis(4-methoxybenzyl)amino)-5-bromo-2-((2,6-difluorophenyl)(hydroxy)methyl)-[1,2,4]triazolo[1,5-a]pyrazin-6-yl)benzonitrile (382 mg, 0.55 mmol), 4-methyl-5-(4,4,5,5-tetramethyl-1,3,2-dioxaborolan-2-yl)oxazole (137 mg, 0.65 mmol), dicyclohexyl(2',4',6'-triisopropylbiphenyl-2-yl)phosphine-(2'-aminobiphenyl-2-yl)(chloro)palladium (1:1) (17 mg, 21.6 µmol) and $Cs_2CO_3$ (356 mg, 1.09 mmol) in 1,4-dioxane (2 mL) and water (200 µl) was purged with $N_2$ and heated at 95° C. for 7 h. The mixture was concentrated and purified via flash chromatography to afford the desired product as a colorless oil. LCMS calculated for $C_{39}H_{32}N_7O_4F_2$ (M+H)$^+$: 700.2; found 700.2.

Step 5: 3-(8-(bis(4-methoxybenzyl)amino)-2-(chloro(2,6-difluorophenyl)methyl)-5-(4-methyloxazol-5-yl)-[1,2,4]triazolo[1,5-a]pyrazin-6-yl)benzonitrile

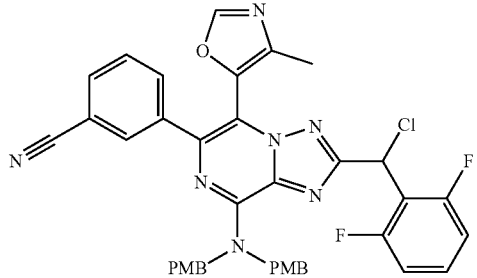

To a solution of 3-(8-(bis(4-methoxybenzyl)amino)-2-((2,6-difluorophenyl)(hydroxy)methyl)-5-(4-methyloxazol-5-yl)-[1,2,4]triazolo[1,5-a]pyrazin-6-yl)benzonitrile (201 mg, 0.29 mmol) in 2 mL of dichloromethane, thionyl chloride (105 μl, 1.435 mmol) was added at rt. The resulting mixture was stirred for 4 h, concentrated and used in next step without any further purification. LC-MS calculated for $C_{39}H_{31}N_7O_3ClF_2$ (M+H)$^+$: m/z=718.2; found 718.2.

Step 6: 3-(8-amino-2-(amino(2,6-difluorophenyl)methyl)-5-(4-methyloxazol-5-yl)-[1,2,4]triazolo[1,5-a]pyrazin-6-yl)benzonitrile To a solution of 3-(8-(bis(4-methoxybenzyl)amino)-2-(chloro(2,6-difluorophenyl)methyl)-5-(4-methyloxazol-5-yl)-[1,2,4]triazolo[1,5-a]pyrazin-6-yl)benzonitrile (40 mg, 0.084 mmol) in 1 mL of DMSO was added ammonia solution (1 mL). The mixture was heated with microwave condition at 100° C. for 10 h before diluted with water and extracted with EtOAc. The combined organic layers were washed with water and brine, dried over MgSO$_4$, and concentrated. The resulting residue was dissolved in TFA (1 mL), and stirred at 80° C. for 20 min. The reaction mixture was then cooled to room temperature, concentrated, and basified by adding aq. NaHCO$_3$ solution. The crude material was directly purified by a silica gel column to afford the desired product as a racemic mixture. The product was then separated with chiral HPLC using a chiral column (AM-1) and 45% EtOH in hexanes (20 mL/min) solvent system. Peak 1 was isolated, and further purified via preparative LC/MS (pH=2, acetonitrile/water with TFA) to give the desired product as a TFA salt. LC-MS calculated for $C_{23}H_{17}F_2N_8O$ (M+H)$^+$: m/z=459.1; found 459.0.

Example A12: Synthesis of 3-(8-amino-2-((2,6-difluorophenyl)(hydroxy)methyl)-5-(2,6-dimethylpyridin-4-yl)-[1,2,4]triazolo[1,5-a]pyrazin-6-yl)benzonitrile (Compound 12)

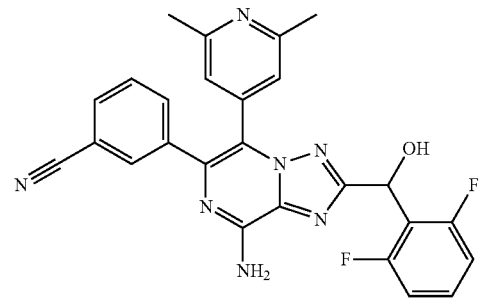 [SMILES: Cc1cc(-c2c(-c3cccc(C#N)c3)nc(N)c3nc(C(O)c4c(F)cccc4F)nn23)cc(C)n1]

To a solution of 3-(8-(bis(4-methoxybenzyl)amino)-5-bromo-2-((2,6-difluorophenyl)(hydroxy)methyl)-[1,2,4]triazolo[1,5-a]pyrazin-6-yl)benzonitrile (Example A11, Step 3; 0.518 g, 0.638 mmol), 2,6-dimethyl-4-(4,4,5,5-tetramethyl-1,3,2-dioxaborolan-2-yl)pyridine (0.346 g, 1.48 mmol), and dicyclohexyl(2',4',6'-triisopropylbiphenyl-2-yl)phosphine-(2'-aminobiphenyl-2-yl)(chloro)palladium (1:1) (0.058 g, 0.074 mmol) in dioxane (3.0 mL) and water (0.60 mL) was added potassium phosphate tribasic (0.472 g, 2.23 mmol). The reaction mixture was stirred at 90° C. for 1 h. The reaction mixture was then diluted with water and DCM. The layers were separated, the aqueous layer was extracted with DCM, and the combined organic fractions were dried over MgSO$_4$, filtered and concentrated. The crude material was dissolved in TFA (5 mL) and heated to 80° C. for 20 minutes. The reaction mixture was then cooled to room temperature, concentrated, and basified by adding aqueous NaHCO$_3$ solution. The crude material was directly purified by a silica gel column to afford the desired product (257 mg, 72%) as a racemic mixture.

The product was then separated with chiral HPLC using a chiral column (Phenomenex Lux 5 um Cellulose-2, 21.1× 250 mm) and 35% EtOH in Hexanes (20 mL/min) solvent system. Peak 2 was isolated, and further purified using preparative LC/MS (pH=2, acetonitrile/water with TFA) to give the desired product as a TFA salt. LC-MS calculated for $C_{26}H_2F_2N_7O$ (M+H)$^+$: m/z=484.2; found 484.2. $^1$H NMR (500 MHz, DMSO-d$_6$) δ 7.92 (s, 2H), 7.85 (s, 1H), 7.83 (d, J=7.6 Hz, 1H), 7.56 (d, J=8.0 Hz, 1H), 7.53-7.40 (m, 4H), 7.10 (t, J=8.4 Hz, 2H), 6.27 (s, 1H), 2.51 (s, 6H).

Example A13: Synthesis of 3-(4-amino-2-(pyridin-2-ylmethyl)-7-(pyrimidin-4-yl)-2H-[1,2,3]triazolo[4,5-c]pyridin-6-yl)benzonitrile (Compound 13)

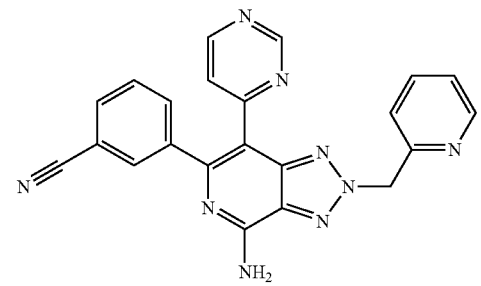 [SMILES: N#Cc1cccc(-c2nc(N)c3nn(Cc4ccccn4)nc3c2-c2ccncn2)c1]

131

Step 1. 4,6-dichloro-3H-[1,2,3]triazolo[4,5-c]pyridine

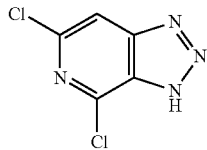 [SMILES: Clc1cc2nn[nH]c2c(Cl)n1]

A solution of $NaNO_2$ (3.88 g, 56.2 mmol) in water (3 mL) was added to a solution of 2,6-dichloropyridine-3,4-diamine (10 g, 56 mmol) in hydrochloric Acid, 37% (5 mL) at 0° C. The solution was stirred for 30 min. Water (20 mL) was added and the white precipitate was filtered, washed with water, and dried to give the desired product. LC-MS calculated for $C_5H_3C_2N_4$: 189.0 (M+H)$^+$; found: 189.0 (M+H)$^+$.

Step 2. 6-chloro-N-(2,4-dimethoxybenzyl)-3H-[1,2,3]triazolo[4,5-c]pyridin-4-amine

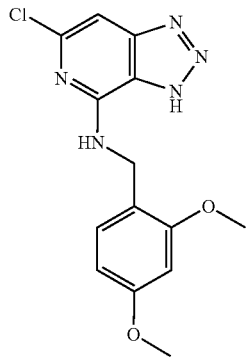 [SMILES: COc1ccc(CNc2nc(Cl)cc3nn[nH]c23)c(OC)c1]

The mixture of 4,6-dichloro-3H-[1,2,3]triazolo[4,5-c]pyridine (600 mg, 3.17 mmol), (2,4-dimethoxyphenyl)methanamine (0.53 mL, 3.49 mmol) and triethylamine (0.53 mL, 3.81 mmol) in 1,4-dioxane (10 mL) was stirred at 110° C. for 3 days. Direct purification on silica gel column afforded the desired product (875 mg, 86%). LC-MS calculated for $C_{14}H_{15}ClN_5O_2$: 320.1 (M+H)$^+$; found: 320.3 (M+H)$^+$.

Step 3. 6-chloro-N-(2,4-dimethoxybenzyl)-2-(pyridin-2-ylmethyl)-2H-[1,2,3]triazolo[4,5-c]pyridin-4-amine

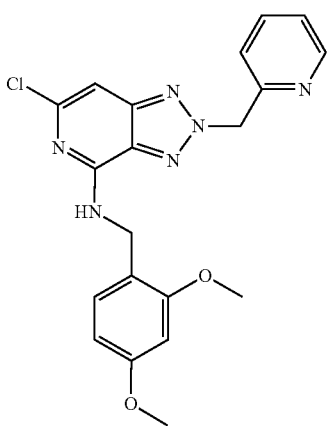 [SMILES: COc1ccc(CNc2nc(Cl)cc3nn(Cc4ccccn4)nc23)c(OC)c1]

132

The mixture of 6-chloro-N-(2,4-dimethoxybenzyl)-3H-[1,2,3]triazolo[4,5-c]pyridin-4-amine (875 mg, 2.74 mmol), pyridin-2-ylmethanol (0.317 mL, 3.28 mmol) and triphenylphosphine (1436 mg, 5.47 mmol) in DCM (20 mL) was added diisopropyl azodicarboxylate (0.647 mL, 3.28 mmol) at 0° C. The resulting mixture was stirred at 0° C. for 1 h. Direct purification on silica gel column afforded the desired product (375 mg, 33.4% yield). LC-MS calculated for $C_{20}H_{20}ClN_6O_2$: 411.1 (M+H)$^+$; found: 411.2 (M+H)$^+$.

Step 4. 3-(4-((2,4-dimethoxybenzyl)amino)-2-(pyridin-2-ylmethyl)-2H-[1,2,3]triazolo[4,5-c]pyridin-6-yl)benzonitrile

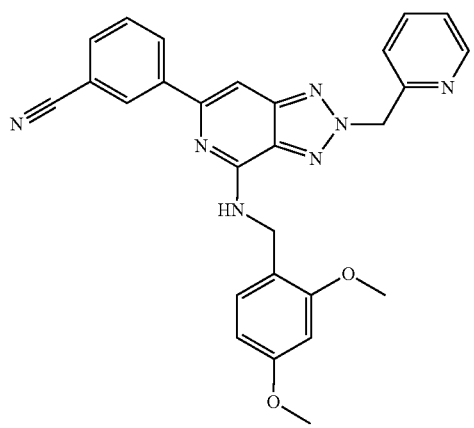 [SMILES: COc1ccc(CNc2nc(-c3cccc(C#N)c3)cc3nn(Cc4ccccn4)nc23)c(OC)c1]

To the mixture of 6-chloro-N-(2,4-dimethoxybenzyl)-2-(pyridin-2-ylmethyl)-2H-[1,2,3]triazolo[4,5-c]pyridin-4-amine (375 mg, 0.913 mmol) and (3-cyanophenyl)boronic acid (268 mg, 1.825 mmol) in 1,4-dioxane (10 mL) and water (1.00 mL) was added cesium carbonate (595 mg, 1.825 mmol). The resulting mixture was purged with $N_2$ and then chloro(2-dicyclohexylphosphino-2',4',6'-triisopropyl-1,1'-biphenyl)[2-(2'-amino-1,1'-biphenyl)]palladium(II) (71.8 mg, 0.091 mmol) was added. The reaction mixture was stirred at 120° C. under microwave irradiation for 90 min. The reaction was quenched with 20 mL of ethyl acetate and 20 mL of water. The organic phase was separated and the aqueous solution was extracted with ethyl acetate twice. The combined extracts were dried over $Na_2SO_4$, filtered and evaporated under reduced pressure. The residue was purified on silica gel column to afford the desired product (300 mg, 68.9%). LC-MS calculated for $C_{27}H_{24}N_7O_2$: 478.2 (M+H)$^+$; found: 478.3 (M+H)$^+$.

Step 5. 3-(4-amino-2-(pyridin-2-ylmethyl)-2H-[1,2,3]triazolo[4,5-c]pyridin-6-yl)benzonitrile

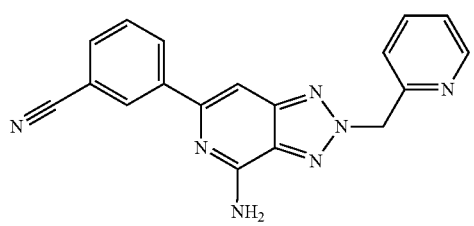 [SMILES: N#Cc1cccc(-c2cc3nn(Cc4ccccn4)nc3c(N)n2)c1]

The solution of 3-(4-((2,4-dimethoxybenzyl)amino)-2-(pyridin-2-ylmethyl)-2H-[1,2,3]triazolo[4,5-c]pyridin-6-yl)benzonitrile (300.3 mg, 0.629 mmol) in TFA (5 mL) was stirred at 100° C. for 30 min. TFA was evaporated under reduced pressure and then 20 mL of saturated NaHCO₃ aqueous solution and 20 mL of ethyl acetate were added. The organic phase was separated and the aqueous solution was extracted with ethyl acetate twice. The combined extracts were dried over Na₂SO₄, filtered and evaporated under reduced pressure. The residue was purified on silica gel column to afford the desired product (175 mg, 85%). LC-MS calculated for $C_{18}H_{14}N_7$: 328.1 (M+H)⁺; found: 328.2 (M+H)⁺.

Step 6. 3-(4-amino-7-bromo-2-(pyridin-2-ylmethyl)-2H-[1,2,3]triazolo[4,5-c]pyridin-6-yl)benzonitrile

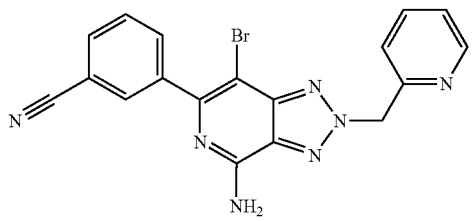 [SMILES: N#Cc1cccc(-c2nc(N)c3nn(Cc4ccccn4)nc3c2Br)c1]

The mixture of 3-(4-amino-2-(pyridin-2-ylmethyl)-2H-[1,2,3]triazolo[4,5-c]pyridin-6-yl)benzonitrile (175 mg, 0.535 mmol) and 1-bromopyrrolidine-2,5-dione (100 mg, 0.561 mmol) in THF (10 mL) was stirred at 0° C. for 30 min and then quenched with saturated NaHCO₃ aqueous solution. The organic phase was separated, dried over Na₂SO₄, filtered and evaporated under reduced pressure. The resulting residue was purified on silica gel column to afforded the desired product (135 mg, 62.2%). LC-MS calculated for $C_{18}H_{13}BrN_7$: 406.0 (M+H)⁺ and 408.0 (M+H)⁺; found: 406.1 (M+H)⁺ and 408.2 (M+H)⁺.

Step 7. 3-(4-amino-2-(pyridin-2-ylmethyl)-7-(pyrimidin-4-yl)-2H-[1,2,3]triazolo[4,5-c]pyridin-6-yl)benzonitrile

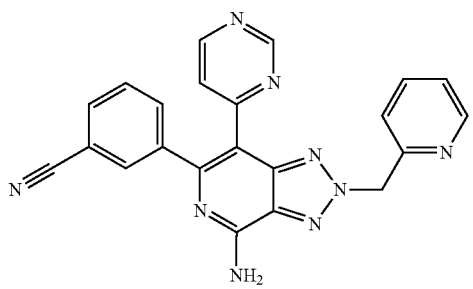 [SMILES: N#Cc1cccc(-c2nc(N)c3nn(Cc4ccccn4)nc3c2-c2ccncn2)c1]

A mixture of 3-(4-amino-7-bromo-2-(pyridin-2-ylmethyl)-2H-[1,2,3]triazolo[4,5-c]pyridin-6-yl)benzonitrile (182 mg, 0.448 mmol), 4-(tributylstannyl)pyrimidine (496 mg, 1.344 mmol), and copper(I) chloride (53.2 mg, 0.538 mmol), lithium chloride (22.79 mg, 0.538 mmol) and tetrakis(triphenylphosphine)palladium(0) (51.8 mg, 0.045 mmol) in THF (1 ml) was first purged with N₂, and then heated and stirred at 90° C. for 2 h. The reaction was diluted with methanol and purified with prep-LCMS (pH=2) to give the desired product. LC-MS calculated for $C_{22}H_{16}N_9$: 406.2 (M+H)⁺; found: 406.2 (M+H)⁺.

Example A14: Synthesis of 3-(4-amino-2-((3-fluoropyridin-2-yl)methyl)-7-(pyrimidin-4-yl)-2H-[1,2,3]triazolo[4,5-c]pyridin-6-yl)benzonitrile (Compound 14)

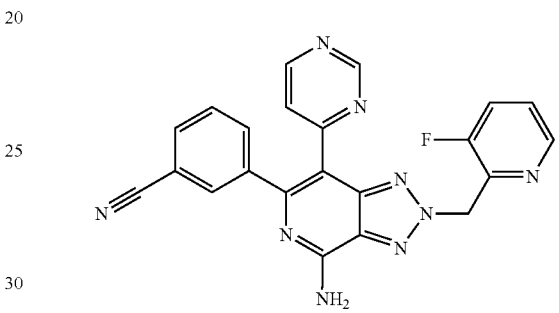

Step 1. 6-chloro-N-(2,4-dimethoxybenzyl)-2-((3-fluoropyridin-2-yl)methyl)-2H-[1,2,3]triazolo[4,5-c]pyridin-4-amine

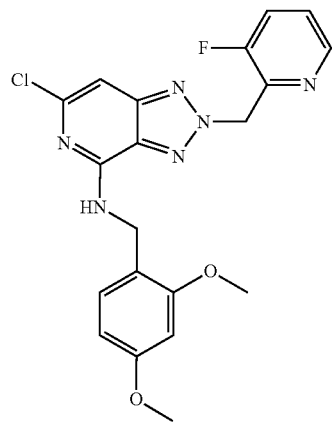 [SMILES: COc1ccc(CNc2nc(Cl)cc3nn(Cc4ncccc4F)nc23)c(OC)c1]

To the mixture of 6-chloro-N-(2,4-dimethoxybenzyl)-3H-[1,2,3]triazolo[4,5-c]pyridin-4-amine (Example A13, Step 2; 1000 mg, 3.13 mmol), (3-fluoropyridin-2-yl)methanol (477 mg, 3.75 mmol) and triphenylphosphine (1641 mg, 6.25 mmol) in DCM (1.7 mL) was added diisopropyl azodicarboxylate (739 μl, 3.75 mmol) at 0° C. The reaction mixture was stirred at 0° C. for 1 h. Direct purification on silica gel column afforded the desired product (433 mg, 32%). LC-MS calculated for $C_{20}H_{19}ClFN_6O_2$: 429.1 (M+H)⁺; found: 429.3 (M+H)⁺.

Step 2. 3-(4-((2,4-dimethoxybenzyl)amino)-2-((3-fluoropyridin-2-yl)methyl)-2H-[1,2,3]triazolo[4,5-c]pyridin-6-yl)benzonitrile

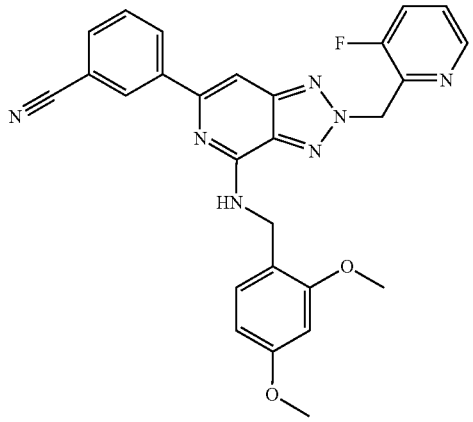 [SMILES: COc1ccc(CNc2nc(-c3cccc(C#N)c3)cc3nn(Cc4ncccc4F)nc23)c(OC)c1]

Cesium carbonate (658 mg, 2.019 mmol) was added to the mixture of 6-chloro-N-(2,4-dimethoxybenzyl)-2-((3-fluoropyridin-2-yl)methyl)-2H-[1,2,3]triazolo[4,5-c]pyridin-4-amine (433 mg, 1.010 mmol) and (3-cyanophenyl)boronic acid (297 mg, 2.019 mmol) in 1,4-dioxane (10.0 mL) and water (1.0 mL). The resulting mixture was sparged with $N_2$ for 2 min and (SP-4-4)-[2'-Amino[1,1'-biphenyl]-2-yl]chloro[dicyclohexyl[2',4',6'-tris(1-methylethyl)[1,1'-biphenyl]-2-yl]phosphine]palladium (79 mg, 0.101 mmol) was added. The reaction mixture was stirred at 120° C. for 1.5 h under microwave irradiation. The reaction was quenched with 20 mL of ethyl acetate and 20 mL of water. The organic phase was separated and the aqueous solution was extracted with ethyl acetate twice. The combined extracts were dried over $Na_2SO_4$, filtered and evaporated under reduced pressure. The residue was purified on silica gel column to afford the desired product (357 mg, 71%). LC-MS calculated for $C_{27}H_{23}FN_7O_2$: 496.2 (M+H)$^+$; found: 496.3 (M+H)$^+$.

Step 3. 3-(4-amino-2-((3-fluoropyridin-2-yl)methyl)-2H-[1,2,3]triazolo[4,5-c]pyridin-6-yl)benzonitrile

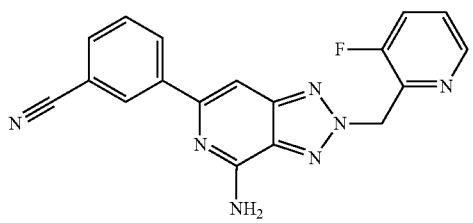 [SMILES: N#Cc1cccc(-c2cc3nn(Cc4ncccc4F)nc3c(N)n2)c1]

The solution of 3-(4-((2,4-dimethoxybenzyl)amino)-2-((3-fluoropyridin-2-yl)methyl)-2H-[1,2,3]triazolo[4,5-c]pyridin-6-yl)benzonitrile (357.3 mg, 0.721 mmol) in TFA (5 mL) was stirred at 100° C. for 1 h. TFA was evaporated under reduced pressure and then 20 mL of saturated NaHCO$_3$ aqueous solution and 20 mL of ethyl acetate were added. The organic phase was separated and the aqueous solution was extracted with ethyl acetate twice. The combined extracts were dried over $Na_2SO_4$, filtered and evaporated under reduced pressure. The residue was purified on silica gel column to afford the desired product (213 mg, 61%). LC-MS m/z calculated for $C_{18}H_{13}FN_7$: 346.1 (M+H)$^+$; found: 346.3 (M+H)$^+$.

Step 4. 3-(4-amino-7-bromo-2-((3-fluoropyridin-2-yl)methyl)-2H-[1,2,3]triazolo[4,5-c]pyridin-6-yl)benzonitrile

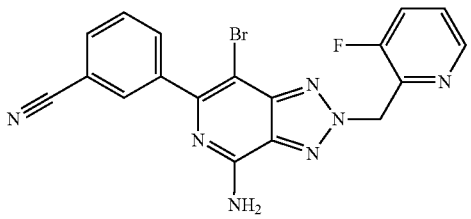 [SMILES: N#Cc1cccc(-c2nc(N)c3nn(Cc4ncccc4F)nc3c2Br)c1]

The mixture of 3-(4-amino-2-((3-fluoropyridin-2-yl)methyl)-2H-[1,2,3]triazolo[4,5-c]pyridin-6-yl)benzonitrile (213 mg, 0.617 mmol) and 1-bromopyrrolidine-2,5-dione (220 mg, 1.234 mmol) in THF (5 mL) was stirred at 0° C. for 1 h. Direct purification on silica gel afforded the desired product (175 mg, 67%). LC-MS calculated for $C_{18}H_{12}BrFN_7$: 424.0 (M+H)$^+$ and 426.0 (M+H)$^+$; found: 424.3 (M+H)$^+$ and 426.3 (M+H)$^+$.

Step 5. 3-(4-amino-2-((3-fluoropyridin-2-yl)methyl)-7-(pyrimidin-4-yl)-2H-[1,2,3]triazolo[4,5-c]pyridin-6-yl)benzonitrile

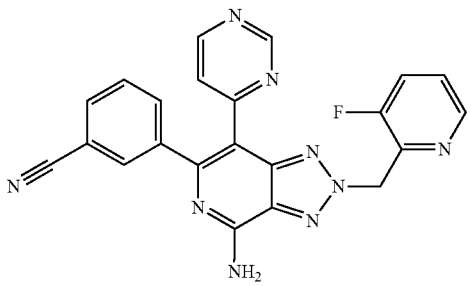 [SMILES: N#Cc1cccc(-c2nc(N)c3nn(Cc4ncccc4F)nc3c2-c2ccncn2)c1]

The mixture of 3-(4-amino-7-bromo-2-((3-fluoropyridin-2-yl)methyl)-2H-[1,2,3]triazolo[4,5-c]pyridin-6-yl)benzonitrile (220 mg, 0.519 mmol), 4-(tributylstannyl)pyrimidine (383 mg, 1.037 mmol), and copper(I) chloride (61.6 mg, 0.622 mmol), lithium chloride (26.4 mg, 0.622 mmol) and tetrakis(triphenylphosphine)palladium(0) (59.9 mg, 0.052 mmol) in THF (1 ml) was first purged with $N_2$, and then heated and stirred at 90° C. for 2 h. The reaction was diluted with methanol and purified with prep-LCMS (pH=2) to give the desired product. LC-MS calculated for $C_{22}H_{15}FN_9$: 424.1 (M+H)$^+$; found: 424.3 (M+H)$^+$. $^1$H NMR (500 MHz, DMSO-d$_6$) ppm 8.98 (s, 1H), 8.77 (d, J=5.02 Hz, 1H), 8.38 (dd, J$_1$=4.60 Hz, J$_2$=1.32 Hz, 1H), 7.90-8.30 (bs, 2H), 7.76-7.89 (m, 3H), 7.66 (dd, J$_1$=5.25 Hz, J$_2$=1.25 Hz, 1H), 7.45-7.58 (m, 3H), 6.25 (s, 2H).

137

Example A15: Synthesis of 3-(4-amino-2-((3-fluoropyridin-2-yl)methyl)-7-(pyridin-4-yl)-2H-[1,2,3]triazolo[4,5-c]pyridin-6-yl)benzonitrile (Compound 15)

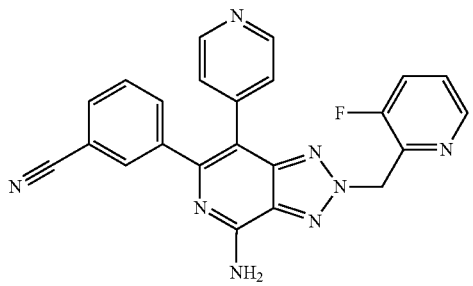

Cesium carbonate (46.1 mg, 0.141 mmol) was added to a mixture of 3-(4-amino-7-bromo-2-((3-fluoropyridin-2-yl)methyl)-2H-[1,2,3]triazolo[4,5-c]pyridin-6-yl)benzonitrile (30 mg, 0.071 mmol) and pyridin-4-ylboronic acid (17.38 mg, 0.141 mmol) in 1,4-dioxane (2 mL) and water (0.2 mL). The resulting mixture was sparged with $N_2$ for 2 min and chloro(2-dicyclohexylphosphino-2',4',6'-triisopropyl-1,1'-biphenyl)[2-(2'-amino-1,1'-biphenyl)]palladium(II) (5.56 mg, 7.07 μmol) was added. The reaction mixture was stirred at 120° C. for 1.5 h under microwave irradiation. The reaction mixture was diluted with methanol. Direct purification on prep. HPLC afforded the desired product. LC-MS calculated for $C_{23}H_{16}FN_8$: 423.1 $(M+H)^+$; found: 423.3 $(M+H)^+$.

Example A16: Synthesis of 3-(4-amino-7-(1-methyl-1H-pyrazol-5-yl)-2-(pyridin-2-ylmethyl)-2H-[1,2,3]triazolo[4,5-c]pyridin-6-yl)-2-fluorobenzonitrile (Compound 16)

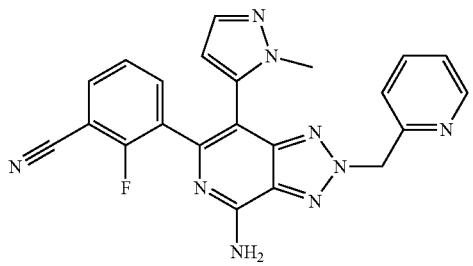 [SMILES: Cn1nccc1-c1c(-c2cccc(C#N)c2F)nc(N)c2nn(Cc3ccccn3)nc12]

Step 1. 3-(4-amino-7-bromo-2-(pyridin-2-ylmethyl)-2H-[1,2,3]triazolo[4,5-c]pyridin-6-yl)-2-fluorobenzonitrile

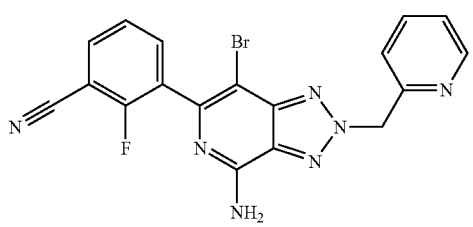 [SMILES: N#Cc1cccc(-c2nc(N)c3nn(Cc4ccccn4)nc3c2Br)c1F]

138

This compound was prepare by following a similar procedure rom Example A13, Step 1 to Step 6, with (3-cyano-2-fluorophenyl)boronic acid replacing (3-cyanophenyl)boronic acid in Step 4. LC-MS calculated for $C_{18}H_{12}BrFN_7$: 424.0 $(M+H)^+$ and 426.0 $(M+H)^+$; found: 424.3 $(M+H)^+$ and 426.3 $(M+H)^+$.

Step 2. 3-(4-amino-7-(1-methyl-1H-pyrazol-5-yl)-2-(pyridin-2-ylmethyl)-2H-[1,2,3]triazolo[4,5-c]pyridin-6-yl)-2-fluorobenzonitrile

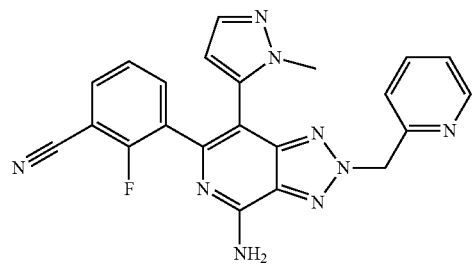 [SMILES: Cn1nccc1-c1c(-c2cccc(C#N)c2F)nc(N)c2nn(Cc3ccccn3)nc12]

This compound was prepared by following a similar procedure in Example A15, with (1-methyl-1H-pyrazol-5-yl)boronic acid replacing pyridin-4-ylboronic acid, and with 3-(4-amino-7-bromo-2-(pyridin-2-ylmethyl)-2H-[1,2,3]triazolo[4,5-c]pyridin-6-yl)-2-fluorobenzonitrile replacing 3-(4-amino-7-bromo-2-((3-fluoropyridin-2-yl)methyl)-2H-[1,2,3]triazolo[4,5-c]pyridin-6-yl)benzonitrile. LC-MS calculated for $C_{22}H_{17}FN_9$: 426.2 $(M+H)^+$; found: 426.3 $(M+H)^+$.

Example A17: Synthesis of 7-(1-((5-Chloropyridin-3-yl)methyl)-1H-pyrazol-4-yl)-3-methyl-9-pentyl-6,9-dihydro-5H-pyrrolo[3,2-d][1,2,4]triazolo[4,3-a]pyrimidin-5-one (Compound 17)

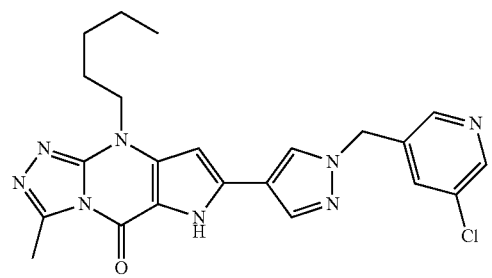 [SMILES: CCCCCn1c2cc(-c3cnn(Cc4cncc(Cl)c4)c3)[nH]c2c(=O)n2c(C)nnc12]

Step 1: Ethyl 3-(pentylamino)-1H-pyrrole-2-carboxylate

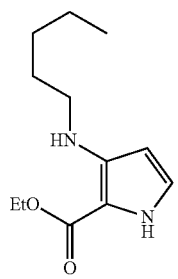 [SMILES: CCCCCNc1cc[nH]c1C(=O)OCC]

Ethyl 3-amino-1H-pyrrole-2-carboxylate (5 g, 32.4 mmol), pentanal (3.79 ml, 35.7 mmol), and sodium cyanoborohydride (2.038 g, 32.4 mmol) were mixed in methanol (64.9 ml) at room temperature overnight. The reaction mixture was concentrated under reduced pressure. The crude residue was purified by flash chromatography (0 to 100% EtOAc in hexanes) to give the desired product (4.4 g, 61%). LCMS calculated for $C_{12}H_{21}N_2O_2$ (M+H): 225.2. Found: 225.1.

Step 2: Ethyl 3-(3-(ethoxycarbonyl)-1-pentylthioureido)-1H-pyrrole-2-carboxylate

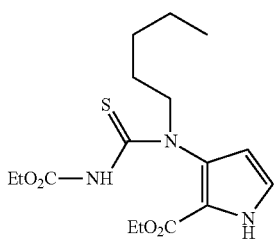 [SMILES: CCCCCN(C(=S)NC(=O)OCC)c1cc[nH]c1C(=O)OCC]

A vial was charged with ethyl 3-(pentylamino)-1H-pyrrole-2-carboxylate (4.4 g, 19.62 mmol), dichloromethane (39.2 ml), and ethoxycarbonyl isothiocyanate (2.78 ml, 23.54 mmol). The reaction mixture was stirred at room temperature overnight. The reaction mixture was quenched with water (40 ml), and the layers were separated. The aqueous layer was extracted with dichloromethane (3×40 mL) and the combined organic fractions were dried over MgSO₄, filtered, and concentrated. The crude material was used in the next step without further purification (7.3 g, quant.). LCMS calculated for $C_{16}H_{26}N_3O_4S$ (M+H): 356.2. Found: 356.1.

Step 3: 1-Pentyl-2-thioxo-2,3-dihydro-1H-pyrrolo[3,2-d]pyrimidin-4(5H)-one

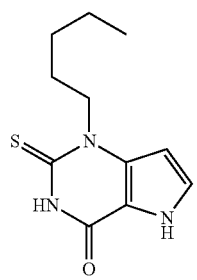 [SMILES: CCCCCn1c(=S)[nH]c(=O)c2[nH]ccc21]

A microwave vial was charged with ethyl 3-(3-(ethoxycarbonyl)-1-pentylthioureido)-1H-pyrrole-2-carboxylate (7.31 g, 20.57 mmol) and sodium ethoxide (21% w/w, 8.45 ml, 22.62 mmol) solution. The vial was capped and heated in a microwave reactor for 10 minutes at 120 degrees Celsius. The reaction mixture was brought to neutral pH on addition of 1M HCl solution and the solid product was filtered and dried (3.1 g, 64%). LCMS calculated for $C_{11}H_{16}N_3OS$ (M+H): 238.1. Found: 238.1.

Step 4: 2-Hydrazono-1-pentyl-2,3-dihydro-1H-pyrrolo[3,2-d]pyrimidin-4(5H)-one

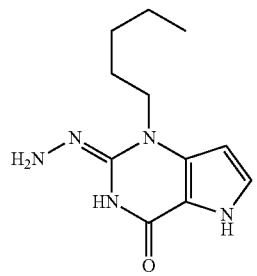 [SMILES: CCCCCn1/c(=N/N)[nH]c(=O)c2[nH]ccc21]

A vial was charged with 1-pentyl-2-thioxo-2,3-dihydro-1H-pyrrolo[3,2-d]pyrimidin-4(5H)-one (3.13 g, 13.19 mmol) and hydrazine hydrate (20 mL). The reaction mixture was stirred at 100 degrees Celsius overnight. The solid formed was filtered and washed with water to give the desired product (2.2 g, 70%). LCMS calculated for $C_{11}H_{18}N_5O$ (M+H): 236.1. Found: 236.1.

Step 5: 3-Methyl-9-pentyl-6,9-dihydro-5H-pyrrolo[3,2-d][1,2,4]triazolo[4,3-a]pyrimidin-5-one

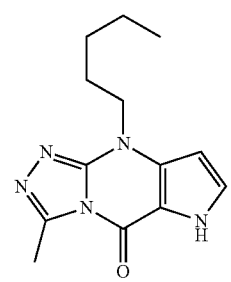 [SMILES: CCCCCn1c2cc[nH]c2c(=O)n2c(C)nnc12]

A vial was charged with (E)-2-hydrazono-1-pentyl-2,3-dihydro-1H-pyrrolo[3,2-d]pyrimidin-4(5H)-one (4.8 g, 20.40 mmol), a drop of trifluoroacetic acid, and triethyl orthoacetate (20 mL). The reaction mixture was heated to 110 degrees Celsius for three hours. The suspension was filtered, washed with hexanes, and dried (4.0 g, 76%). LCMS calculated for $C_{13}H_{18}N_5O$ (M+H): 260.1. Found: 260.2.

Step 6: 3-Methyl-9-pentyl-6-(phenylsulfonyl)-6,9-dihydro-5H-pyrrolo[3,2-d][1,2,4]triazolo[4,3-a]pyrimidin-5-one

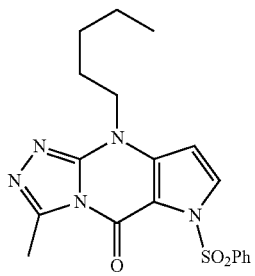

A vial was charged with 3-methyl-9-pentyl-6,9-dihydro-5H-pyrrolo[3,2-d][1,2,4]triazolo[4,3-a]pyrimidin-5-one (from Step 1) (4 g, 15.43 mmol), dichloromethane (40 mL), dimethylaminopyridine (0.188 g, 1.543 mmol), triethylamine (3.23 ml, 23.14 mmol), and benzenesulfonyl chloride (2.187 ml, 16.97 mmol). The reaction mixture was stirred at room temperature for one hour. The reaction mixture was quenched with water, and the layers were separated. The aqueous layer was extracted with dichloromethane (3×40 mL) and the combined organic fractions were dried over MgSO$_4$, filtered, and concentrated. The crude material was used in the next step without further purification (6.1 g, quant.). LCMS calculated for $C_{19}H_{22}N_5O_3S$ (M+H): 400.1. Found: 400.1.

Step 7: 7-Bromo-3-methyl-9-pentyl-6-(phenylsulfonyl)-6,9-dihydro-5H-pyrrolo[3,2-d][1,2,4]triazolo[4,3-a]pyrimidin-5-one

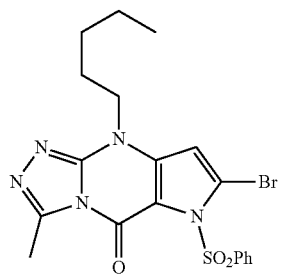

A vial was charged with 3-methyl-9-pentyl-6-(phenylsulfonyl)-6,9-dihydro-5H-pyrrolo[3,2-d][1,2,4]triazolo[4,3-a]pyrimidin-5-one (1 g, 2.503 mmol), dry THF (30 mL) and the mixture was cooled to −78 degrees Celsius. Lithium diisopropylamide solution (1M in hexanes/THF, 3.13 ml, 3.13 mmol) was added dropwise. The reaction mixture was maintained at −78° C. for 1.5 hours. A solution of 1,2-dibromo-1,1,2,2-tetrachloroethane (1.223 g, 3.75 mmol) in dry THF (3 ml) was added dropwise to the reaction mixture and the reaction mixture was maintained at −78° C. for a further 1.5 hours. The reaction mixture was quenched with sat. aq. NH$_4$Cl solution (30 mL) and diluted with dichloromethane (30 mL). The layers were separated and the aqueous layer was extracted with DCM (3×30 mL). The combined organic fractions were dried over MgSO$_4$, filtered, and concentrated. The crude residue was purified by automated flash chromatography (0 to 100% EtOAc in DCM) to give the desired product (0.84 g, 70%). LCMS calculated for $C_{19}H_{21}BrN_5O_3S$ (M+H): 478.1. Found: 478.1.

Step 8: 3-Chloro-5-((4-(4,4,5,5-tetramethyl-1,3,2-dioxaborolan-2-yl)-1H-pyrazol-1-yl)methyl)pyridine

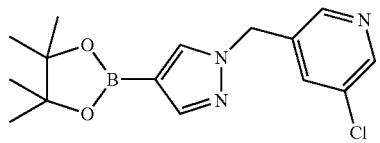 [SMILES: CC1(C)OB(c2cnn(Cc3cncc(Cl)c3)c2)OC1(C)C]

A vial was charged with 4-(4,4,5,5-tetramethyl-1,3,2-dioxaborolan-2-yl)-1H-pyrazole (0.5 g, 2.58 mmol), 3-(bromomethyl)-5-chloropyridine hydrobromide (0.741 g, 2.58 mmol), cesium carbonate (2.52 g, 7.73 mmol), and DMF (6.44 ml). The reaction mixture was stirred at 60 degrees Celsius for one hour. The reaction mixture was quenched with water (10 ml) and diluted with dichloromethane (10 ml). The layers were separated, and the aqueous layer was extracted with dichloromethane (3×10 mL). The combined dichloromethane extracts were dried over MgSO$_4$, filtered, and concentrated. Purification by automated flash chromatography (0 to 100% EtOAc in DCM) afforded the product (0.548 g, 67%). LCMS calculated for $C_{15}H_{20}BCN_3O_2$ (M+H): 320.1, 322.1. Found: 320.1, 322.1.

Step 9: 7-(1-((5-Chloropyridin-3-yl)methyl)-1H-pyrazol-4-yl)-3-methyl-9-pentyl-6,9-dihydro-5H-pyrrolo[3,2-d][1,2,4]triazolo[4,3-a]pyrimidin-5-one A vial was charged with 7-bromo-3-methyl-9-pentyl-6-(phenylsulfonyl)-6,9-dihydro-5H-pyrrolo[3,2-d][1,2,4]triazolo[4,3-a]pyrimidin-5-one (0.01 g, 0.021 mmol), 3-chloro-5-((4-(4,4,5,5-tetramethyl-1,3,2-dioxaborolan-2-yl)-1H-pyrazol-1-yl)methyl)pyridine (0.013 g, 0.042 mmol), Chloro(2-dicyclohexylphosphino-2',4',6'-triisopropyl-1,1'-biphenyl)[2-(2'-amino-1,1'-biphenyl)]palladium(II) (5.00 mg, 0.006 mmol) and potassium phosphate tribasic (0.016 g, 0.074 mmol). 1,4-dioxane (0.35 ml) and water (0.07 ml) were added and the reaction mixture was sparged with nitrogen gas for 5 minutes then stirred at 90° C. for two hours. The reaction mixture was cooled to room temperature and sodium hydroxide (10 mg) was added. The reaction mixture was stirred at 40 degrees Celsius for 60 minutes. The reaction mixture was cooled to room temperature and diluted with DMF (5 ml). Purification by preparative HPLC (pH 2, acetonitrile/water with TFA) afforded the product as a TFA salt (2 mg, 21%). LCMS calculated for $C_{22}H_{24}ClN_8O$ (M+H): 451.2, 453.2. Found: 451.2, 453.2.

Example A18: Synthesis of 3-Methyl-7-(1-((5-methylpyridin-3-yl)methyl)-1H-pyrazol-4-yl)-9-pentyl-6,9-dihydro-5H-pyrrolo[3,2-d][1,2,4]triazolo[4,3-a]pyrimidin-5-one (Compound 18)

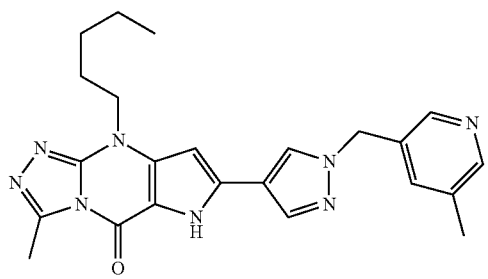 [SMILES: CCCCCn1c2cc(-c3cnn(Cc4cncc(C)c4)c3)[nH]c2c(=O)n2c(C)nnc12]

This compound was prepared using similar procedures as described in Example A17 using 3-(bromomethyl)-5-methylpyridine in place of 3-(bromomethyl)-5-chloropyridine hydrobromide in Step 8. LCMS calculated for $C_{23}H_{27}N_8O$ (M+H): 431.2. Found: 431.3.

Example A19: Synthesis of 3-Methyl-9-pentyl-7-(1-(thieno[3,2-b]pyridin-6-ylmethyl)-1H-pyrazol-4-yl)-6,9-dihydro-5H-pyrrolo[3,2-d][1,2,4]triazolo[4,3-a]pyrimidin-5-one (Compound 19)

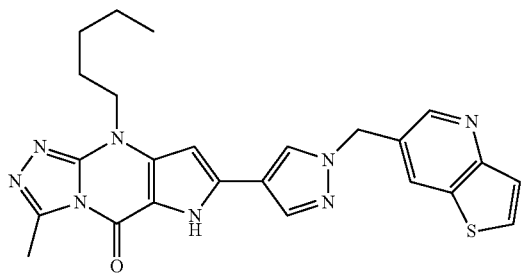 [SMILES: CCCCCn1c2cc(-c3cnn(Cc4cnc5ccsc5c4)c3)[nH]c2c(=O)n2c(C)nnc12]

This compound was prepared using similar procedures as described in Example A17 using 6-(bromomethyl)thieno[3,2-b]pyridine in place of 3-(bromomethyl)-5-chloropyridine hydrobromide in Step 8. LCMS calculated for $C_{24}H_{25}N_8OS$ (M+H): 473.2. Found: 473.3.

Example A20: 7-(1-((2-(2-(Dimethylamino)acetyl)-1,2,3,4-tetrahydroisoquinolin-6-yl)methyl)-1H-pyrazol-4-yl)-3-methyl-9-pentyl-6,9-dihydro-5H-pyrrolo[3,2-d][1,2,4]triazolo[4,3-a]pyrimidin-5-one (Compound 20)

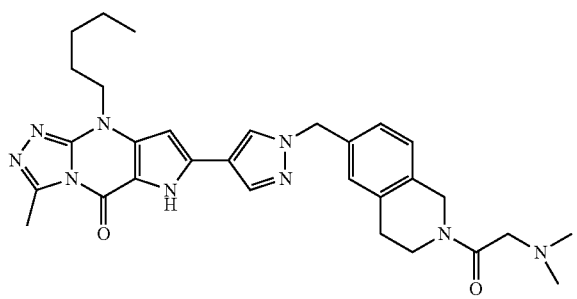 [SMILES: CCCCCn1c2cc(-c3cnn(Cc4ccc5c(c4)CCN(C(=O)CN(C)C)C5)c3)[nH]c2c(=O)n2c(C)nnc12]

Step 1: Tert-Butyl 6-((4-(4,4,5,5-tetramethyl-1,3,2-dioxaborolan-2-yl)-1H-pyrazol-1-yl)methyl)-3,4-dihydroisoquinoline-2(1H)-carboxylate

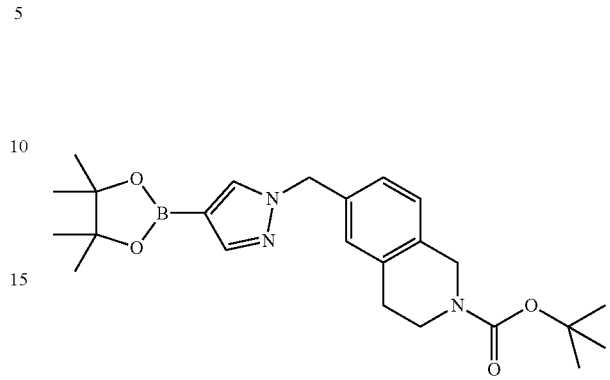

A flask was charged with 4-(4,4,5,5-tetramethyl-1,3,2-dioxaborolan-2-yl)-1H-pyrazole (0.5 g, 2.58 mmol), tert-butyl 6-(hydroxymethyl)-3,4-dihydroisoquinoline-2(1H)-carboxylate (0.339 g, 1.288 mmol), triphenylphosphine (0.743 g, 2.83 mmol), and THF (12 ml). The solution was cooled to 0° C. and DIAD (0.601 ml, 3.09 mmol) was added dropwise. The reaction mixture was stirred overnight at room temperature. The mixture was diluted with ethyl acetate and washed with water, dried and concentrated. The product was purified by column chromatography eluting with Hexane/EtOAc (max. EtOAc 60%) to afford the product. LCMS calculated for $C_{24}H_{35}BN_3O_4$ $(M+H)^+$: m/z=440.3; found 440.3.

Step 2: 7-bromo-3-methyl-9-pentyl-6,9-dihydro-5H-pyrrolo[3,2-d][,2,4]triazolo[4,3-a]pyrimidin-5-one

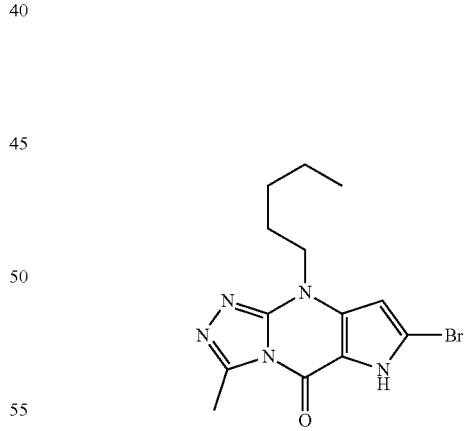

TBAF (1.0 M in THF) (2.0 ml, 2.0 mmol) was added to a solution of 7-bromo-3-methyl-9-pentyl-6-(phenylsulfonyl)-6,9-dihydro-5H-pyrrolo [3,2-d][1,2,4]triazolo[4,3-a]pyrimidin-5-one (0.360 g, 0.753 mmol) in THF (4.0 ml), and then the reaction was stirred at 50° C. for 1 h. The solvent was removed and the product was purified by column chromatography eluting with $CH_2Cl_2$/MeOH (max. MeOH 10%). LCMS calculated for $C_{13}H_{17}BrN_5O$ $(M+H)^+$: m/z=338.1; found 338.1.

Step 3: Tert-Butyl 6-((4-(3-methyl-5-oxo-9-pentyl-6,9-dihydro-5H-pyrrolo[3,2-d][1,2,4]triazolo[4,3-a]pyrimidin-7-yl)-1H-pyrazol-1-yl)methyl)-3,4-dihydroisoquinoline-2(1H)-carboxylate

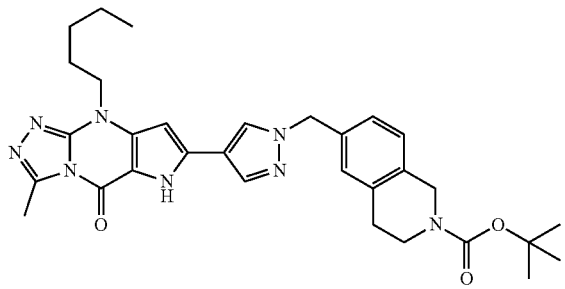 [SMILES: CCCCCn1c2cc(-c3cnn(Cc4ccc5c(c4)CCN(C(=O)OC(C)(C)C)C5)c3)[nH]c2c(=O)n2c(C)nnc12]

A mixture of 7-bromo-3-methyl-9-pentyl-6,9-dihydro-5H-pyrrolo[3,2-d][1,2,4]triazolo[4,3-a]pyrimidin-5-one (from Example A20, Step 2) (0.040 g, 0.118 mmol), tert-butyl 6-((4-(4,4,5,5-tetramethyl-1,3,2-dioxaborolan-2-yl)-1H-pyrazol-1-yl)methyl)-3,4-dihydroisoquinoline-2(1H)-carboxylate (0.062 g, 0.142 mmol), dichloro[1,1'-bis(dicyclohexylphosphino)ferrocene]palladium(II), dichloromethane adduct (Pd-127) (8.94 mg, 0.012 mmol) and cesium fluoride (0.090 g, 0.591 mmol) in t-BuOH (1.5 ml)/Water (0.6 ml) was vacuumed and replaced with $N_2$ for 3 times. The reaction was then stirred at 105° C. for 2 h, cooled to rt, diluted with ethyl acetate, washed with water, dried and concentrated. The product was purified by column eluting with $CH_2Cl_2$/MeOH (max. MeOH 10%). LCMS calculated for $C_{31}H_{39}N_8O_3$ (M+H)$^+$: m/z=571.3; found 571.5.

Step 4: 3-Methyl-9-pentyl-7-(1-((1,2,3,4-tetrahydroisoquinolin-6-yl)methyl)-1H-pyrazol-4-yl)-6,9-dihydro-5H-pyrrolo[3,2-d][1,2,4]triazolo[4,3-a]pyrimidin-5-one

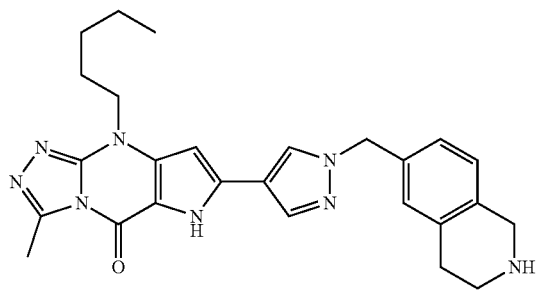 [SMILES: CCCCCn1c2cc(-c3cnn(Cc4ccc5c(c4)CCNC5)c3)[nH]c2c(=O)n2c(C)nnc12]

TFA (0.5 ml, 6.49 mmol) was added to a solution of tert-butyl 6-((4-(3-methyl-5-oxo-9-pentyl-6,9-dihydro-5H-pyrrolo[3,2-d][1,2,4]triazolo[4,3-a]pyrimidin-7-yl)-1H-pyrazol-1-yl)methyl)-3,4-dihydroisoquinoline-2(1H)-carboxylate (50.0 mg, 0.088 mmol) in $CH_2Cl_2$ (0.5 ml), and then the reaction was stirred at room temperature for 30 min. The solvent was then removed to provide the crude product as TFA salt. LCMS calculated for $C_{26}H_{31}N_8O$ (M+H)$^+$: m/z=471.3; found 471.2.

Step 5: 7-(1-((2-(2-(Dimethylamino)acetyl)-1,2,3,4-tetrahydroisoquinolin-6-yl)methyl)-1H-pyrazol-4-yl)-3-methyl-9-pentyl-6,9-dihydro-5H-pyrrolo[3,2-d][1,2,4]triazolo[4,3-a]pyrimidin-5-one Dimethylglycinoyl chloride (3.10 mg, 0.026 mmol) was added to a solution of 3-methyl-9-pentyl-7-(1-((1,2,3,4-tetrahydroisoquinolin-6-yl)methyl)-1H-pyrazol-4-yl)-6,9-dihydro-5H-pyrrolo[3,2-d][1,2,4]triazolo[4,3-a]pyrimidin-5-one (6.0 mg, 0.013 mmol) and triethylamine (8.89 µl, 0.064 mmol) in $CH_2Cl_2$ (0.8 ml) at room temperature and stirred for 30 min. The solvent was removed, and the mixture was diluted with acetonitrile/water and purified by prep HPLC (pH 2, acetonitrile/water with TFA) to provide the desired compound as its TFA salt. LC-MS calculated for $C_3H_{38}N_9O_2$ (M+H)$^+$: m/z=556.3; found 556.3.

Example A21. 3-(2-((5-(1H-pyrazol-1-yl)-2H-tetrazol-2-yl)methyl)-5-amino-8-(pyrimidin-4-yl)-[1,2,4]triazolo[1,5-c]pyrimidin-7-yl)benzonitrile (Compound 21A) and 3-(2-((5-(1H-Pyrazol-1-yl)-1H-tetrazol-1-yl)methyl)-5-amino-8-(pyrimidin-4-yl)-[1,2,4]triazolo[1,5-c]pyrimidin-7-yl)benzonitrile (Compound 21B)

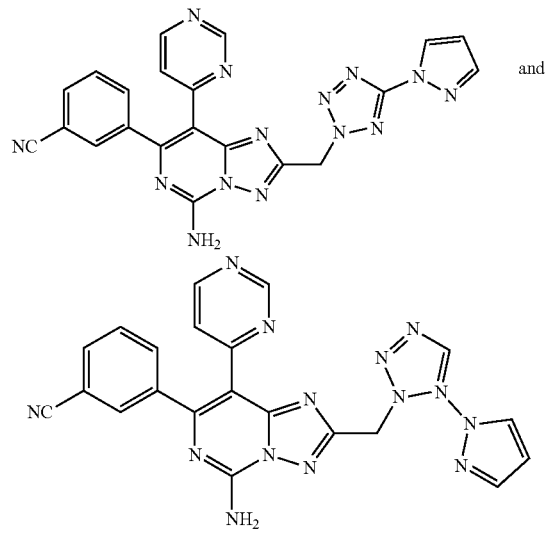

The mixture of title compounds was prepared using similar procedures as described for Example A3, with 5-(1H-pyrazol-1-yl)-1H-tetrazole replacing 2-(1H-tetrazol-5-yl)pyridine. Compound 21A was purified by preparative LC-MS (pH 2, acetonitrile/water with TFA) to afford the product as a TFA salt. LCMS calculated for $C_{21}H_{15}N_{14}$ (M+H)$^+$: 463.2; found 463.2.

Example 1: Generation of Anti-Human CD73 Monoclonal Antibodies

To generate anti-human CD73 monoclonal antibodies, mice were immunized with recombinant human CD73 (SEQ ID NO:70) protein comprising a C-terminal HIS-tag and B cells were isolated from the mouse spleen and lymph nodes. Antibody sequences of the B cells were determined using 10× Genomics VH/VL paired B cell sequencing. The murine VH/VL pairs were expressed as chimeras with huIgG1 Fc (SEQ ID NOs: 73 and 74) and tested for binding and functionality. An antibody designated CL25 was produced by this process. Table 1, above, shows the amino acid sequences of the CL25 CDRs according to IMGT, Chothia, AbM, Kabat, and Contact numbering and the mature VH, VL, heavy chain, and light chain.

Chimeric antibody CL25 (comprising the murine VH of SEQ ID NO:26 and murine VL of SEQ ID NO:27) was humanized to minimize the immunogenicity of the antibody frameworks while maintaining specific activity. Humanization was conducted by aligning the VH and VL sequences to a database of human VH and VK genes. The CDRs (Table 1) from the murine CL25 antibody were grafted into several top human VH and VK genes. The VH and VL sequences of exemplary humanized CL25 antibodies are depicted in FIG. 1A-FIG. 1C. Alignments of the VH and VL of CL25 and exemplary humanized CL25 antibodies are depicted in FIG. 1D and FIG. 1E, respectively. Several framework mutations present in the murine CL25 were also tested along with the murine CDRs (FIG. 1A-FIG. 1E). The humanized version of CL25 having a VH of SEQ ID NO:22 and a VL of SEQ ID NO:23, referred to herein as "HzCL25", was selected for further studies. Table 2, above, shows the amino acid sequences of the HzCL25 CDRs according to IMGT, Chothia, AbM, Kabat, and Contact numbering and the mature VH, VL, heavy chain, and light chain.

Example 2: Binding of Anti-Human CD73 Monoclonal Antibodies to Cell Surface CD73

To test the binding of humanized and non-humanized CL25 clones to cell surface CD73, MDA-MB-231 or A375 cells were washed and added to 96-well plates at $5 \times 10^4$ cells/well. The cells were stained with the indicated concentration of antibodies for 30 minutes on ice (FIG. 2A and FIG. 2B). Next, the cells were washed and stained using goat anti-mouse secondary conjugated to phycoerythrin (PE) for 30 minutes on ice. The cells were then washed and analyzed by flow cytometry. Geometric mean fluorescence intensity (GMFI) of CD73 staining was graphed (FIG. 2A and FIG. 2B). Both CL25 and HzCL25 displayed high potency binding to cells with high levels of surface CD73 (MDA-MB-231 cells) and moderate levels of surface CD73 (as tested in A375 cells).

Figure 3A:
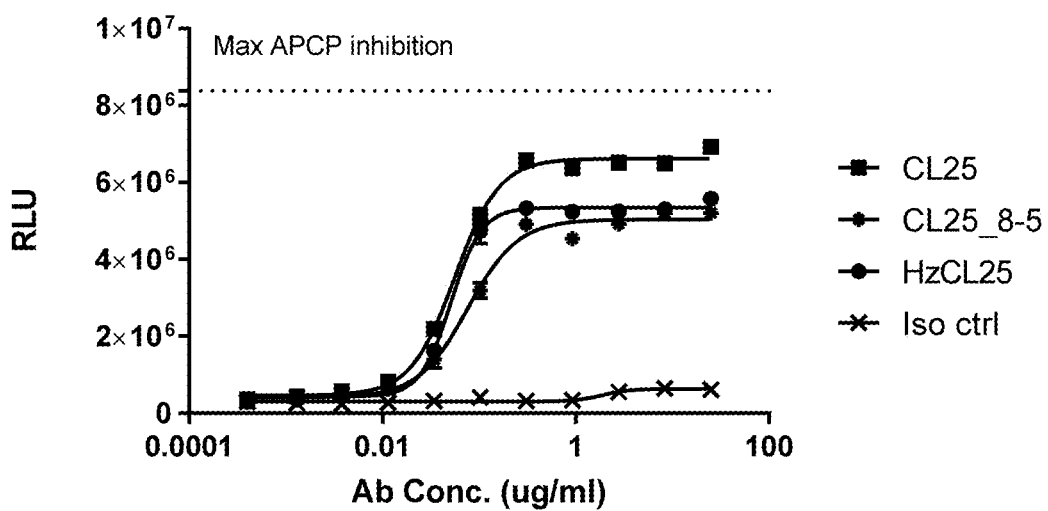
FIG. 3A is a graph depicting the cellular CD73 inhibition on A375 cells treated with the indicated antibodies or isotype control (iso ctrl) at the indicated concentrations.
Figure 3B:
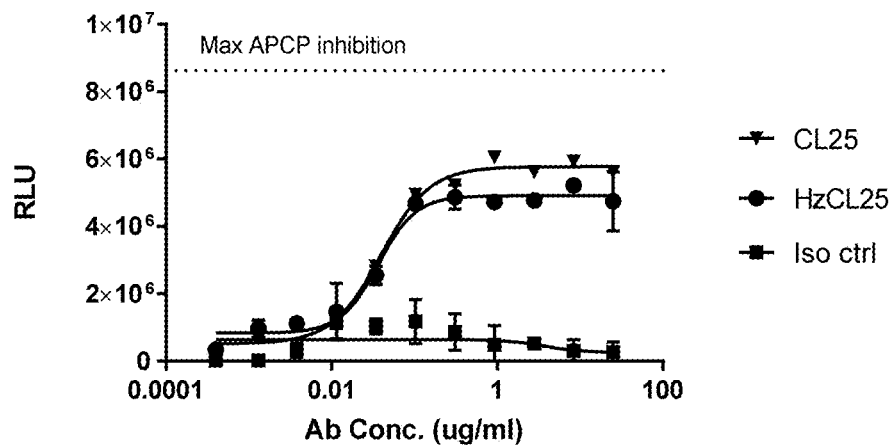
FIG. 3B is a graph depicting the cellular CD73 inhibition on MDA-MB-231 cells treated with the indicated antibodies or isotype control (iso ctrl) at the indicated concentrations.
Figure 3C:
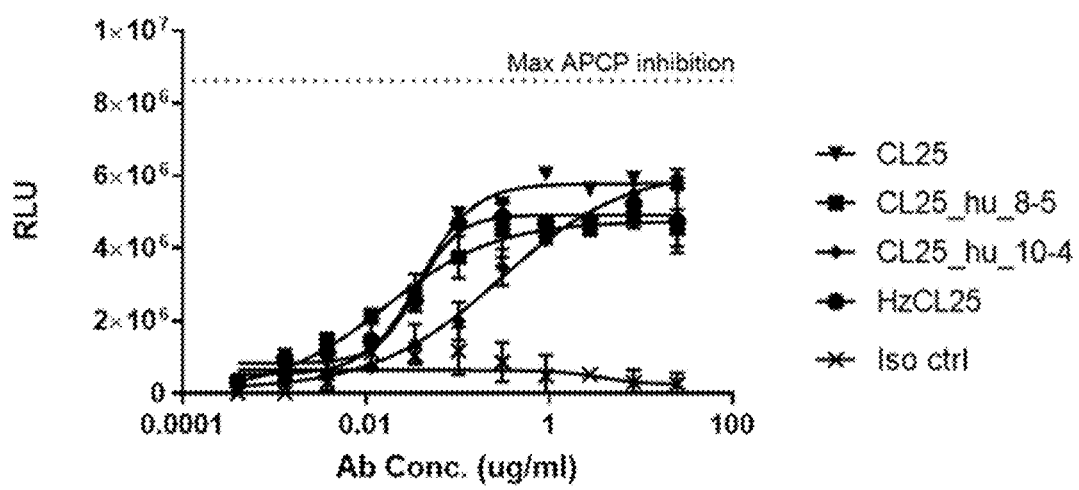
FIG. 3C is a graph depicting the cellular CD73 inhibition on MDA-MB-231 cells treated with the indicated antibodies or isotype control (iso ctrl) at the indicated concentrations.

Example 3: Anti-Human CD73 Monoclonal Antibody-Mediated Cellular CD73 Inhibition To measure ability of anti-CD73 antibody to inhibit CD73 activity on cells, A375 and MDA-MB-231 cells were washed with serum free RPMI media (ThermoFisher) and plated in 96-well plates at a concentration of $8 \times 10^4$ cells/well for A375 or $1 \times 10^4$ cells/well for MDA-MB-231. The cells were incubated with the indicated concentration of antibodies or APCP at 37° C. 5% C02 for 30 minutes (FIG. 3A, FIG. 3B, and FIG. 3C). Next, adenosine monophosphate (AMP) was added to a final concentration of 100 μM and cells were incubated an additional 3 hours at 37° C. 5% $CO_2$. Plates were centrifuged for 1-2 minutes at 300 g and 25 μL of supernatant was transferred into a new 96-well plates. AMP-Glo Assay was used according to the manufacturer's instructions (Promega). Relative luminescence unit (RLU) is directly correlated with the AMP concentration in this assay. Results are depicted in FIG. 3A, FIG. 3B, and FIG. 3C.

Both CL25 and HzCL25 had good potency in inhibiting cellular CD73 in both tested cell types (FIG. 3A, FIG. 3B, and FIG. 3C). HzCL25 had a similar ability as CL25 to inhibit cellular CD73 (FIG. 3A, FIG. 3B, and FIG. 3C).

Example 4: Anti-Human CD73 Monoclonal Antibody-Mediated Soluble CD73 Inhibition

Figure 4:
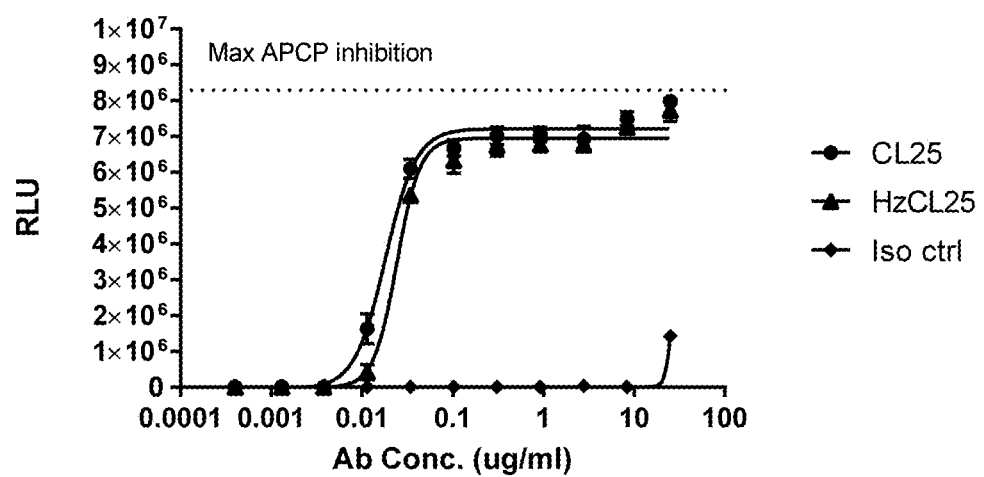
FIG. 4 is a graph depicting inhibition of recombinant CD73 treated with the indicated antibodies or isotype control (iso ctrl) at the indicated concentrations.

To measure the ability of the CD73 antibodies to inhibit CD73 activity of recombinant protein, recombinant human CD73 (rhuCD73) (SEQ ID NO:70) was added to 96-well plates at a final concentration of 0.008 μg/mL with the indicated concentration of antibodies (FIG. 4) or adenosine 5'-[α,β-methylene]diphosphate (APCP) and incubated at 37° C. 5% $CO_2$ for 30 minutes. After the 30 minute incubation, AMP was added to a final concentration of 100 μM and the reactions were incubated an additional 3 hours at 37° C. 5% $CO_2$. 25 μL of supernatant was transferred into new 96-well plates. The AMP-Glo Assay was used according to the manufacturer's instructions. RLU is a directly correlated with the AMP concentration in this assay. Results are depicted in FIG. 4. Both CL25 and HzCL25 showed high potency and no hook-effect (FIG. 4). HzCL25 had a similar ability as CL25 to inhibit cellular CD73 (FIG. 4).

Example 5: Binding Affinity

CD73 enzymatic activity requires substrate binding in the open conformation. After substrate binding, CD73 has to go through a large conformational change from open to closed conformation to convert AMP to adenosine. Antibody binding that inhibits or modulates this conformational change will potentially decrease the rate of AMP to adenosine conversion.

To assess the binding affinity of HzCL25, surface plasmon resonance (SPR) was performed using a Biacore 8K instrument (GE Healthcare) at 25° C. The SPR running buffer (10 mM HEPES, 150 mM NaCl, 3 mM EDTA and 0.05% v/v Surfactant P20, pH 7.4) was prepared from 10xHBS-EP Buffer (GE Healthcare). Anti-human Fc antibodies (GE Healthcare) were immobilized via amine coupling on all sixteen flow cells of an S series sensor chip CM5 (GE Healthcare). The immobilization levels were ~9000 RU for all flow cells. The desired capturing level of anti-CD73 antibody was achieved by flowing appropriate concentration of anti-CD73 antibody through the active flow cell of each channel. The non-cleavable ADP analogue APCP (adenosine-5'-(α,β-methylene) diphosphate) with the presence of $Zn^{2+}$ can be used to shift the CD73 conformational equilibrium from open towards closed. Therefore, recombinant CD73 was incubated with SPR running buffer in the presence of 100 μM APCP and 10 μM $ZnCl_2$ (closed SPR running buffer) to study the binding of anti-CD73 antibody to the CD73 in the closed conformation. To achieve this, the ABA injection feature in Biacore 8K was used. For open conformation, the ABA injection sequence started with 60 seconds injection of running buffer. Then, CD73 3-fold serial dilution concentration series prepared from CD73 stock (BPS Bioscience) and running buffer were injected for 180 seconds immediately followed by running buffer for 240 seconds. For closed conformation, the normal SPR running buffer was replaced by closed SPR running buffer. Surface was regenerated with 30 seconds injection of 3 M $MgCl_2$. Binding kinetics and affinity parameters were obtained from a global fit of the data to 1 to 1 binding model. Binding affinities and kinetic association and dissociation rate constants to human, cynomolgus, and mouse CD73 in either open or closed conformations are shown in Table 8 below.

The results in Table 8 ensure cynomolgus pharmacokinetic data will reflect human pharmacokinetic data.

TABLE 8

Binding affinities and kinetic association and dissociation rate constants to human (SEQ ID NO: 70), cynomolgus (SEQ ID NO: 72), and mouse (SEQ ID NO: 71) CD73 in either open or closed conformations for the indicated antibodies (Ab).

| Ab | CD73 | Open | | | Closed | | |
|---|---|---|---|---|---|---|---|
| | | $k_a$ (1/Ms) | $k_d$ (1/s) | $K_D$ (M) | $k_a$ (1/Ms) | $k_d$ (1/s) | $K_D$ (M) |
| CL25 | human | >1E+06 | 3.94E−04 | <3.94E−10 | 9.03E+05 | 3.44E−04 | 3.81E−10 |
| | Cyno-molgus | >1E+06 | 6.58E−04 | <6.58E−10 | 9.36E+05 | 4.95E−04 | 5.29E−10 |
| | Murine | | No Binding | | | No Binding | |
| HzCL25 | Human | >1E+06 | 4.49E−04 | <4.49E−10 | | Not performed | |
| | Cyno-molgus | >1E+06 | 4.68E−04 | <4.68E−10 | | Not performed | |
| | Murine | | No binding | | | Not performed | |
| CL25_hu_8-4 | Human | 7.70E+05 | 1.76E−03 | 2.29E−09 | | Not performed | |
| CL25_hu_8-5 | Human | >1E+06 | 9.49E−04 | 7.18E−10 | | Not performed | |
| CL25_hu_8-6 | Human | 7.15E+05 | 1.11E−03 | 1.55E−09 | | Not performed | |
| CL25_hu_9-4 | Human | 3.82E+05 | 2.64E−03 | 6.90E−09 | | Not performed | |
| CL25_hu_9-5 | Human | 5.65E+05 | 1.14E−03 | 2.02E−09 | | Not performed | |
| CL25_hu_9-6 | Human | 4.24E+05 | 9.53E−04 | 2.25E−09 | | Not performed | |
| CL25_hu_10-4 | Human | 8.87E+05 | 1.07E−03 | 1.20E−09 | | Not performed | |
| CL25_hu_10-6 | Human | 5.24E+05 | 9.20E−04 | 1.75E−09 | | Not performed | |
| CL25_hu_11-4 | Human | 6.24E+05 | 1.55E−03 | 2.48E−09 | | Not performed | |
| CL25_hu_11-5 | Human | 7.99E+05 | 1.17E−03 | 1.46E−09 | | Not performed | |
| CL25_hu_11-6 | Human | 5.50E+05 | 1.01E−03 | 1.84E−09 | | Not performed | |

Example 6: Epitope Mapping

Figure 5:
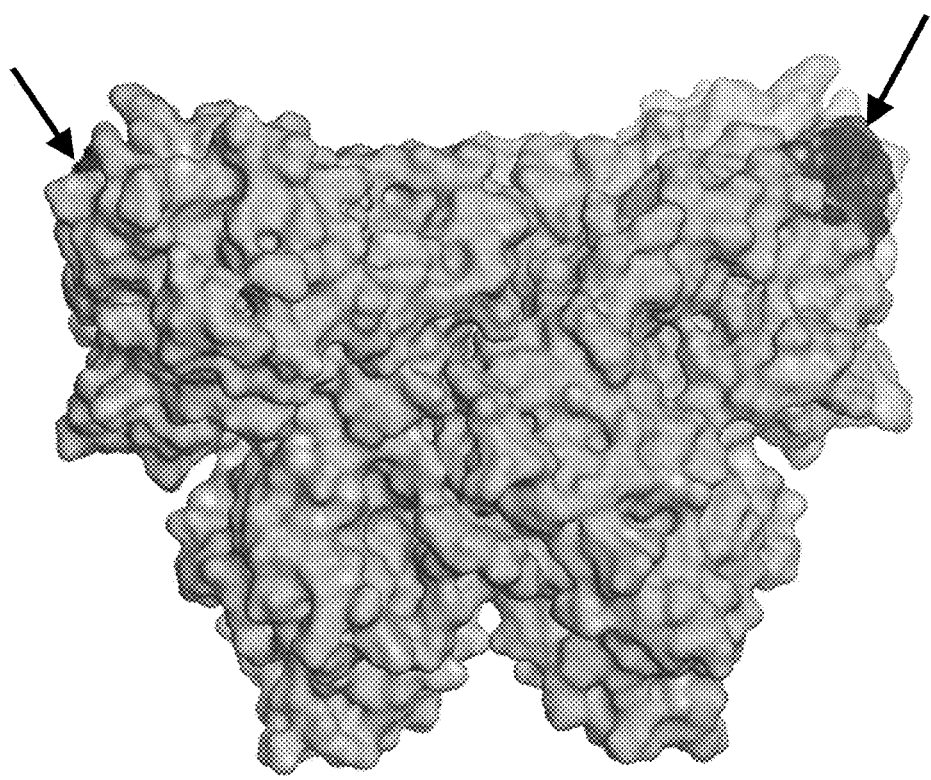
FIG. 5 is a map of the crystal structure of human CD73 (4H2F·pdb) with the CL25 antibody epitope indicated in dark grey (with arrows).

To map the epitope of CL25, Hydrogen-deuterium exchange mass spectrometry (HDX) was performed. CD73 was incubated in deuterium oxide either alone or in complex with CL25 Fab. The deuterium exchange was carried out at 20° C. for 0 seconds, 60 seconds, 600 seconds, or 3600 seconds. The exchange reaction was quenched by low pH and the proteins were digested with pepsin/protease VIII. The deuterium levels at the identified peptides were monitored from the mass shift on LC-MS. The deuterium buildup curves over exchange time for all the peptides were plotted vs time. Peptides with significant reduction in deuterium uptakes upon binding to Fab were assigned as the epitopes for each antibody. The epitope determined by HDX-MS for CL25 is mapped onto the crystal structure of human CD73 (4H2F·pdb) (FIG. 5) and is TKVQQIRRAEPNVL (SEQ ID NO:76) (i.e., amino acids 40-53 of SEQ ID NO:70).

Example 7: CD73 Cell Surface Levels

Figure 6:
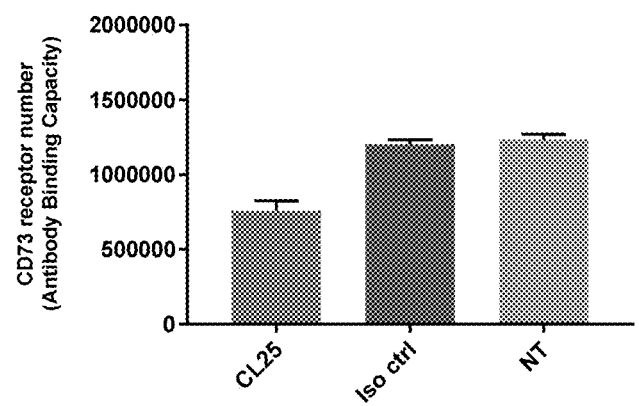
FIG. 6 is a graph depicting surface CD73 levels after 24 hour incubation with the indicated antibody or isotype control (iso ctrl), or without treatment (NT), as measured with a directly conjugated non-competing antibody.

To measure the amount of CD73 on the cell surface after antibody treatment, MDA-MB-231 cells were re-suspended in media (10% FBS RPMI-1640) and plated in 96-well plates at $1\times10^5$ cells/well. Indicated antibodies were added at a final concentration of 10 μg/mL and plates were incubated at 37° C. 5% $CO_2$ for 24 hours. Cells were recovered using Versene and transferred to new 96-well plates. Cells were washed and stained for 30 minutes on ice with 10 μg/mL of non-competing antibody directly conjugated to Dy650. Cells were washed and analyzed by flow cytometry. CD73 cell surface receptor density was determined by Antibody Binding Capacity (ABC) using Quantum Simply Cellular beads. Treatment of cells with CL25 for 24 hours decreased the levels of cell surface CD73 (FIG. 6).

Example 8: Generation of Anti-Human CD73 Monoclonal Antibody 3-F03

To generate additional anti-human CD73 monoclonal antibodies, multiple selection rounds of single donor library were performed. The library of approximately 1.5E12 phage particles was enriched over three rounds of panning using 200 nM biotinylated human CD73 (SEQ ID NO:70). The scFv cassettes from this pool were then recombined into a yeast display vector and a library of approximately 5.4E7 was created. This library was selected by FACS for three rounds using 100 nM biotinylated murine CD73 (SEQ ID NO:71). Unique sequences were obtained from the final sorting output by Sanger sequencing of yeast colonies. The yeast 3-F03 scFv sequence was identified from this pool and contained a VH of the amino acid sequence set forth in SEQ ID NO:77 and a VL of the amino acid sequence set forth in SEQ ID NO:65.

To construct a full-length human 3-F03 antibody, the yeast 3-F03 scFv sequences were modified prior to cloning into a human IgG1 scaffold comprising the human IgG1 constant region set forth in SEQ ID NO:75 and the human kappa light chain constant region set forth in SEQ ID NO:74. For the VH, the N-terminal glutamate (E) of SEQ ID NO:77 was removed and the threonine (T) at Kabat position H77 of SEQ ID NO:77 (i.e., position 78 of SEQ ID NO:77) was substituted with an alanine (A). For the VL, the N-terminal alanine (A) of SEQ ID NO:65 was removed. The resulting full-length human 3-F03 antibody contains the VH and VL set forth in the amino acid sequences of SEQ ID NOs:60 and 61, respectively. The resulting full-length human 3-F03 antibody contains the heavy chain and light chain set forth in the amino acid sequences of SEQ ID NOs: 66 and 31, respectively. This antibody is referred to herein as "3-F03". Table 3, above, shows the amino acid sequences of the 3-F03 CDRs according to IMGT, Chothia, AbM, Kabat, and Contact numbering and of the mature VH, VL, heavy chain, and light chain.

Example 9: Binding of 3-F03 to Cell Surface CD73

Figure 7A:
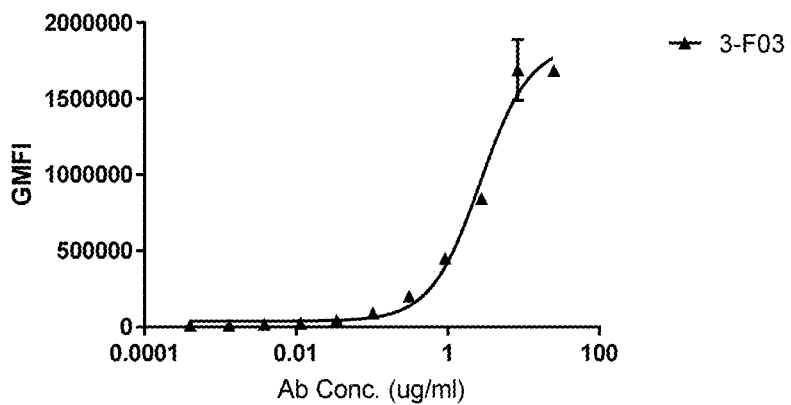
FIG. 7A is a graph depicting the cell binding (GMFI) for antibody 3-F03 at the indicated concentrations on MDA-MB-231 cells.
Figure 7B:
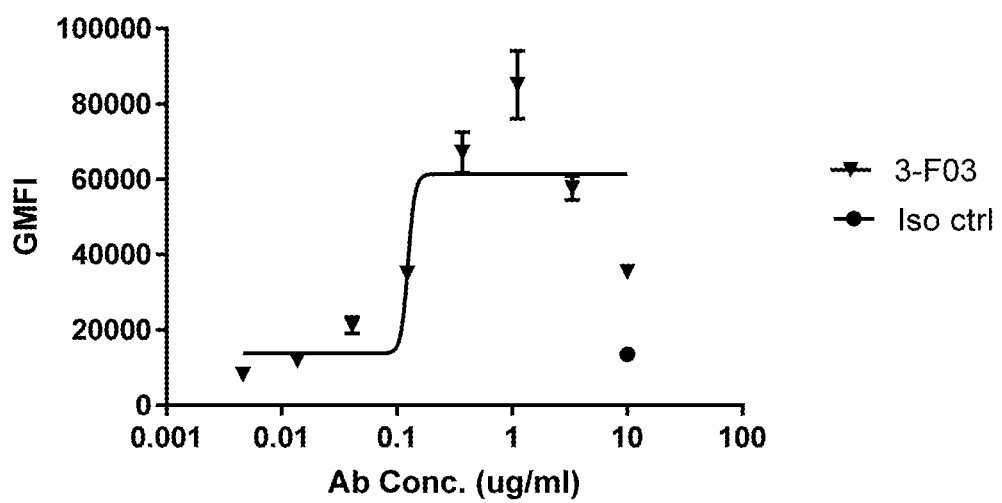
FIG. 7B is a graph depicting the cell binding (measured by GMFI) for 3-F03 or isotype control (Iso ctrl) at the indicated concentrations on A375 cells.

The binding of 3-F03 to cell surface CD73 was performed as described in Example 2, above. 3-F03 displays high potency binding to cells with high levels of surface CD73 (MDA-MB-231), and moderate levels of CD73 (A375 cells) (FIG. 7A and FIG. 7B).

Example 10: 3-F03-Mediated Cellular CD73 Inhibition

The ability of 3-F03 to inhibit CD73 activity on cells was evaluated as described in Example 3, above. Results are depicted in FIG. 8A and FIG. 8B.

Figure 8A:
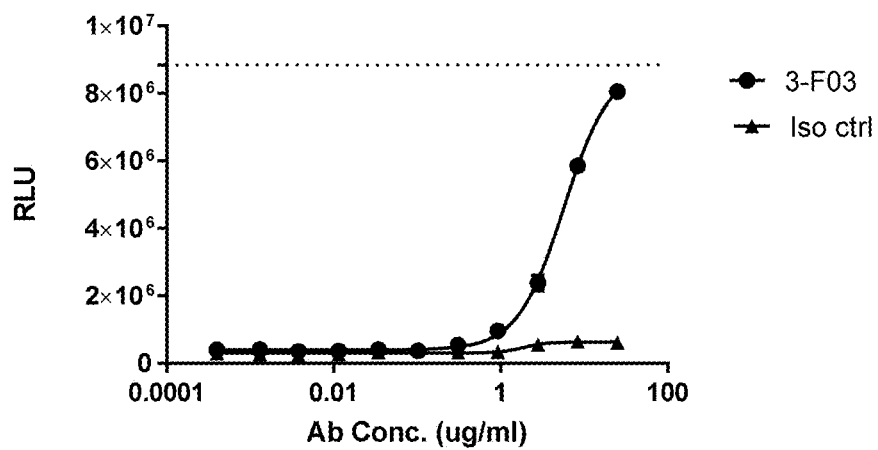
FIG. 8A is a graph depicting the cellular CD73 inhibition on A375 cells treated with 3-F03 or isotype control (Iso ctrl) at the indicated concentrations.
Figure 8B:
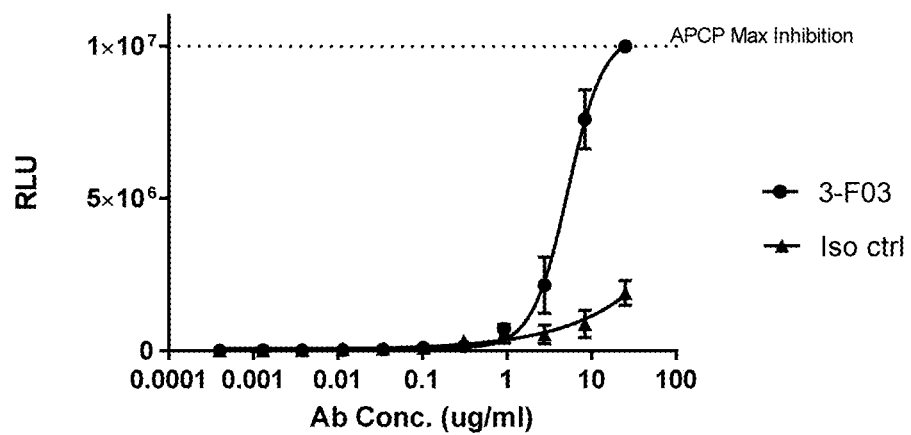
FIG. 8B is a graph depicting the cellular CD73 inhibition on MDA-MB-231 cells treated with 3-F03 or isotype control (Iso ctrl) at the indicated concentrations.

Clone 3-F03 showed maximum inhibition of cellular CD73 in both tested cell types as compared to the small molecule inhibitor of CD73, APCP (FIG. 8A and FIG. 8B).

Example 11: 3-F03-Mediated Soluble CD73 Inhibition

Figure 9:
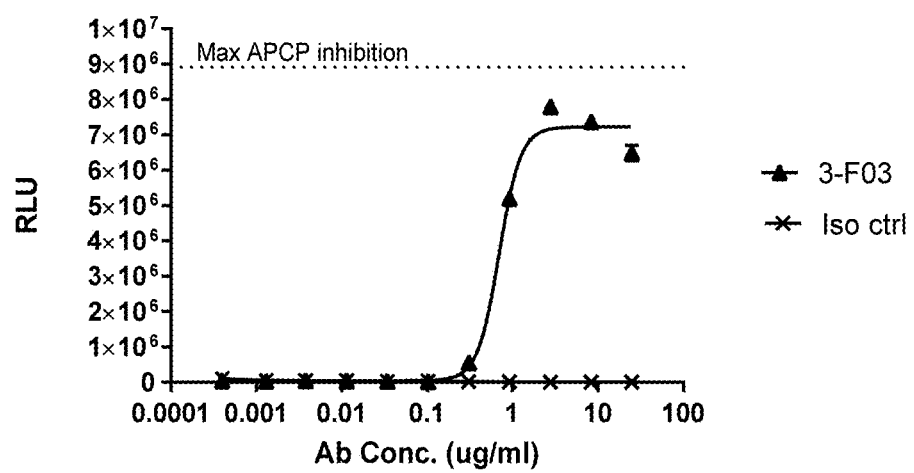
FIG. 9 is a graph depicting inhibition of recombinant CD73 treated with 3-F03 or isotype control (Iso control) at the indicated concentrations.

The ability of 3-F03 to inhibit CD73 activity of recombinant protein was evaluated as described in Example 4, above, except that 0.025 ug/mL of rhuCD73 was used. Results are depicted in FIG. 9. Antibody 3-F03 had good potency (FIG. 9). Antibody 3-F03 did not exhibit any hook-effect.

Example 12: Binding Affinity of Anti-CD73 Antibody

The binding affinity of 3-F03 was evaluated as described in Example 5, above. Binding affinities and kinetic association and dissociation rate constants to human, cynomolgus, and mouse CD73 in either open or closed conformations are shown in Table 9 below.

TABLE 9

Binding affinities and kinetic association and dissociation rate constants to human, cynomolgus, and mouse CD73 in either open or closed conformations.

| Sample | | Open | | | Closed | | |
|---|---|---|---|---|---|---|---|
| Name | CD73 | $k_a$ (1/Ms) | $k_d$ (1/s) | $K_D$ (M) | $k_a$ (1/Ms) | $k_d$ (1/s) | $K_D$ (M) |
| 3-F03 | human | 2.15E+05 | 7.96E−05 | 3.70E−10 | No Binding | | |
| | Cynomolgus | 3.01E+05 | 2.21E−04 | 7.34E−10 | No Binding | | |
| | Murine | 2.17E+05 | 3.60E−04 | 1.66E−09 | No Binding | | |

Example 13: Epitope Mapping of 3-F03

Figure 10:
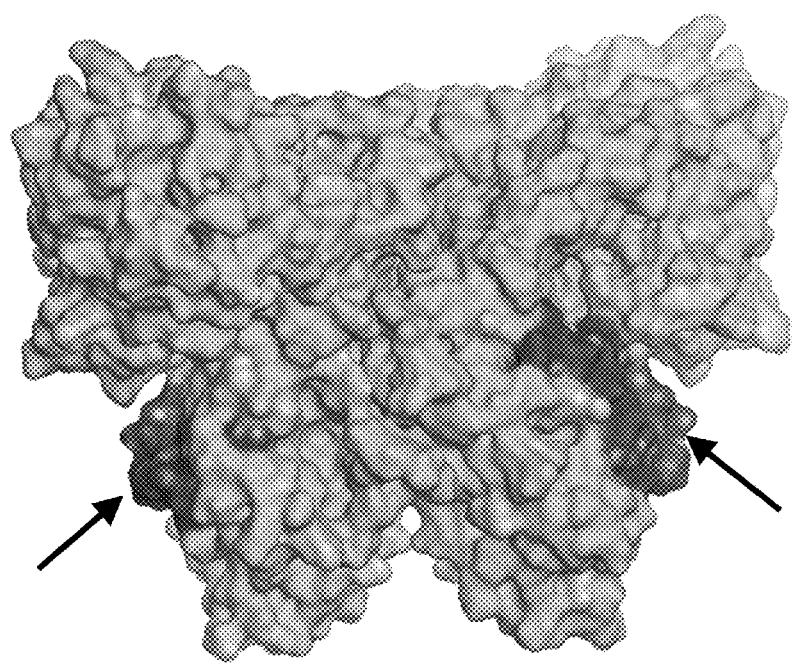
FIG. 10 is a map of the crystal structure of human CD73 (4H2F·pdb) with the 3-F03 antibody epitope indicated in dark grey (with arrows).

The epitope of 3-F03 was mapped as described in Example 6, above. The epitopes determined by HDX-MS for 3-F03 are mapped onto the crystal structure of human CD73 (4H2F·pdb) (FIG. 10) and are AAVLPFGGTFDLVQ (SEQ ID NO:78) (i.e., amino acids 386-399 of SEQ ID NO:70) and ILPNFLANGGDGFQMIKDEL (SEQ ID NO:79) (i.e., amino acids 470-489 of SEQ ID NO:70).

Example 14: Effect of 3-F03 on CD73 Cell Surface Levels

Figure 11:
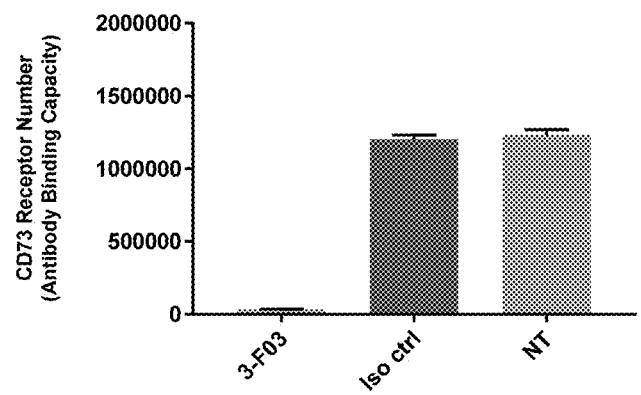
FIG. 11 is a graph depicting CD73 surface levels after 24 hour incubation with 3-F03, isotype control (iso ctrl), or not treated (NT) as measured with a directly conjugated non-competing antibody, CL43-Dy650.

The amount of CD73 on the cell surface after treatment with 3-F03 was evaluated as described in Example 7, above. 3-F03 dramatically decreased the level of detectable CD73 on the cell surface compared to an isotype control antibody or non-treated cells (FIG. 11).

Example 15: 3-F03 Variants

Sequences of the 3-F03 light chain (LC, SEQ ID NO:66) and heavy chain (HC, SEQ ID NO:31) were used to construct a homology model. FIG. 12A-FIG. 12J provide the amino acid sequences of the VH and VL of exemplary 3-F03 variants. Antibodies comprising these VH and VL sequences contained the heavy chain constant region set forth in SEQ ID NO:73 and light chain constant region set forth in SEQ ID NO:74. Table 10 provides the binding affinity and kinetics of the exemplary 3-F03 variants. None of the mutations tested dramatically impacted binding to CD73 by Biacore. All tested mutations had affinities within tenfold of the 3-1F03 antibody, with the majority within two fold of 3-103.

TABLE 10

Biacore binding affinity and kinetics of 3-F03 variants. — = absent

| Sample Name | VH1 (E or —) | VH53 (D, E, or S) | VH77 (A or T) | VL1 (A, D, or —) | $k_a$ (1/Ms) | $k_d$ (1/s) | $K_D$ (M) |
|---|---|---|---|---|---|---|---|
| 3-F03_396 | E | D | T | A | 1.39E+05 | 1.78E−04 | 1.28E−09 |
| 3-F03_408 | E | D | T | — | 1.40E+05 | 1.86E−04 | 1.33E−09 |
| 3-F03_402 | — | D | T | A | 1.32E+05 | 1.84E−04 | 1.39E−09 |
| 3-F03_384 | E | D | T | D | 1.40E+05 | 1.98E−04 | 1.41E−09 |
| 3-F03_399 | E | D | A | A | 1.38E+05 | 1.97E−04 | 1.43E−09 |
| 3-F03_411 | E | D | A | — | 1.39E+05 | 2.04E−04 | 1.47E−09 |
| 3-F03_414 | — | D | T | — | 1.31E+05 | 1.98E−04 | 1.51E−09 |
| 3-F03_390 | — | D | T | D | 1.29E+05 | 2.12E−04 | 1.64E−09 |
| 3-F03_398 | E | E | T | A | 9.26E+04 | 1.59E−04 | 1.71E−09 |
| 3-F03_387 | E | D | A | D | 1.37E+05 | 2.38E−04 | 1.74E−09 |
| 3-F03_386 | E | E | T | D | 9.23E+04 | 1.64E−04 | 1.78E−09 |
| 3-F03_401 | E | E | A | A | 9.15E+04 | 1.67E−04 | 1.82E−09 |
| 3-F03_413 | E | E | A | — | 9.13E+04 | 1.71E−04 | 1.88E−09 |
| 3-F03_405 | — | D | A | A | 1.26E+05 | 2.39E−04 | 1.90E−09 |
| 3-F03_410 | E | E | T | — | 9.01E+04 | 1.76E−04 | 1.95E−09 |
| 3-F03_389 | E | E | A | D | 9.17E+04 | 1.89E−04 | 2.06E−09 |
| 3-F03_393 | — | D | A | D | 1.14E+05 | 2.39E−04 | 2.09E−09 |
| 3-F03_417 | — | D | A | — | 1.34E+05 | 2.84E−04 | 2.12E−09 |
| 3-F03_392 | — | E | T | D | 8.08E+04 | 1.80E−04 | 2.23E−09 |
| 3-F03_404 | — | E | T | A | 8.35E+04 | 1.89E−04 | 2.26E−09 |
| 3-F03_419 | — | E | A | — | 8.28E+04 | 2.00E−04 | 2.41E−09 |
| 3-F03_416 | — | E | T | — | 9.01E+04 | 2.21E−04 | 2.45E−09 |
| 3-F03_407 | — | E | A | A | 8.74E+04 | 2.35E−04 | 2.69E−09 |
| 3-F03_395 | — | E | A | D | 7.12E+04 | 2.10E−04 | 2.94E−09 |
| 3-F03_388 | E | S | A | D | 1.15E+05 | 8.68E−04 | 7.56E−09 |
| 3-F03_397 | E | S | T | A | 6.07E+04 | 4.89E−04 | 8.04E−09 |
| 3-F03_385 | E | S | T | D | 6.33E+04 | 5.38E−04 | 8.50E−09 |
| 3-F03_400 | E | S | A | A | 6.15E+04 | 5.29E−04 | 8.60E−09 |
| 3-F03_409 | E | S | T | — | 6.02E+04 | 5.46E−04 | 9.06E−09 |
| 3-F03_403 | — | S | T | A | 5.79E+04 | 5.41E−04 | 9.34E−09 |
| 3-F03_415 | — | S | T | — | 5.99E+04 | 6.06E−04 | 1.01E−08 |
| 3-F03_391 | — | S | T | D | 5.69E+04 | 5.84E−04 | 1.03E−08 |
| 3-F03_406 | — | S | A | A | 7.41E+04 | 7.65E−04 | 1.03E−08 |
| 3-F03_412 | E | S | A | — | 5.27E+04 | 6.38E−04 | 1.21E−08 |
| 3-F03_394 | — | S | A | D | 4.84E+04 | 6.30E−04 | 1.30E−08 |
| 3-F03_418 | — | S | A | — | 5.55E+04 | 7.99E−04 | 1.44E−08 |

Figure 13:
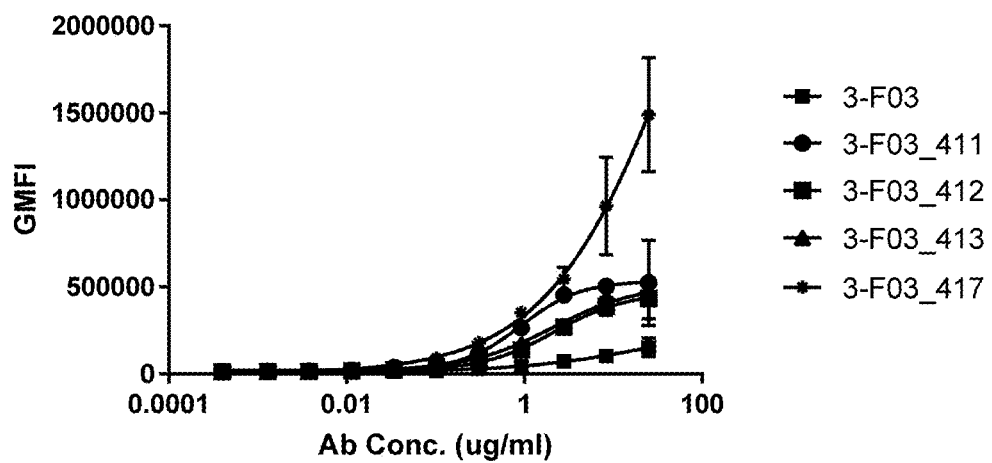
FIG. 13 is a graph depicting cell binding (GMFI) for the indicated antibodies at the indicated concentrations on MDA-MB-231 cells.

To test the binding of engineered 3-F03 variants to cell surface CD73, MDA-MB-231 cells were washed and added to 96-well plates at 5×10⁴ cells/well. Cells were stained with the indicated concentration of antibodies for 1 hour on ice. Cells were then washed and stained goat anti-mouse secondary conjugated to PE for 30 minute on ice. Cells were then washed and analyzed by flow cytometry. The GMFI of CD73 staining is graphed (FIG. 13). Each of the 3-F03 variants had a similar binding profile, except for 3-F03_417, which showed a slightly higher Ymax (FIG. 13). These data confirm the Biacore studies (Table 10): these mutations did not dramatically alter human CD73 binding for these variant clones.

Figure 14:
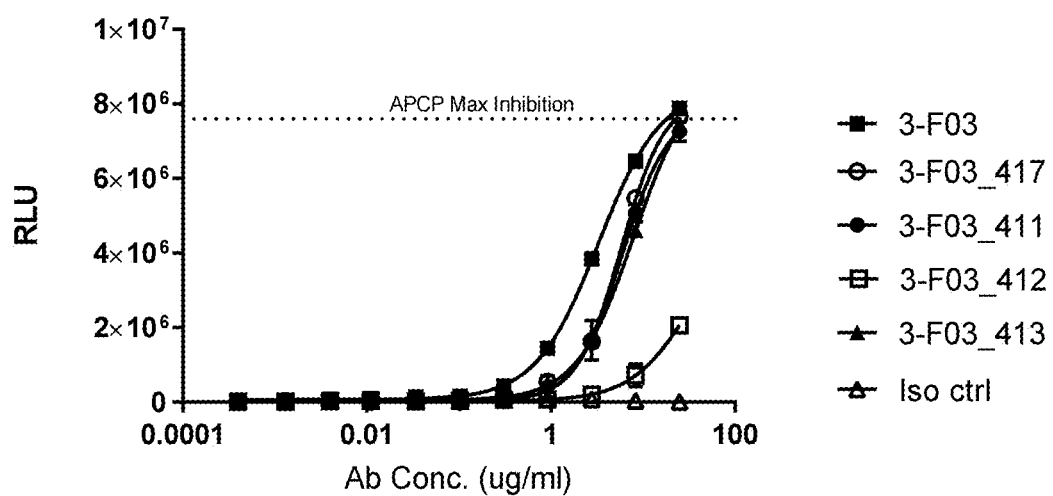
FIG. 14 is a graph depicting the cellular CD73 inhibition on MDA-MB-231 cells treated with the indicated antibodies or isotype control at the indicated concentrations.
Figure 16A:
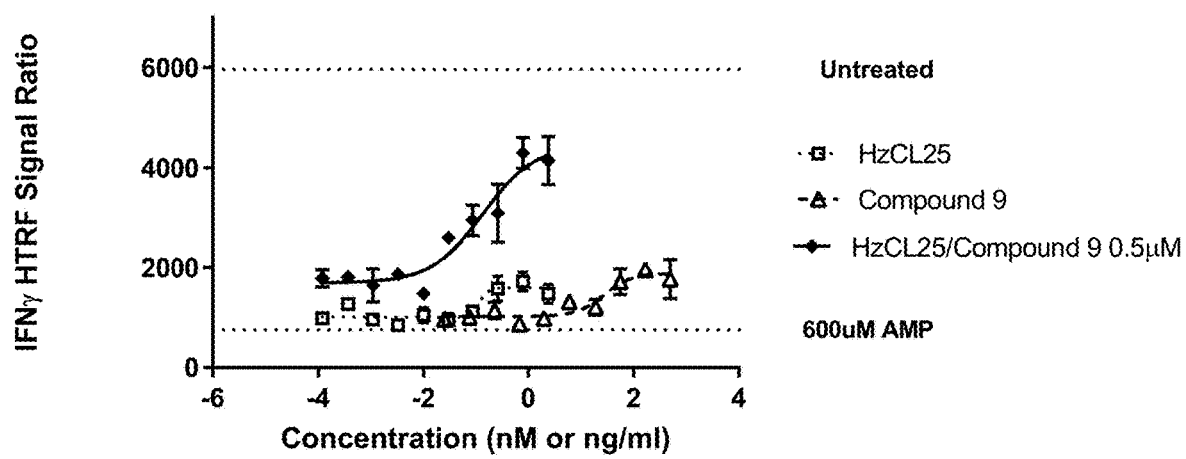
FIG. 16A is a graph showing the IFNγ homogeneous time-resolved fluorescence (HTRF) signal ratio in CD4+ T cells treated with (i) titrated HzCL25, (ii) titrated Compound 9, or (iii) titrated HzCL25 and 0.5 µM of Compound 9.
Figure 16B:
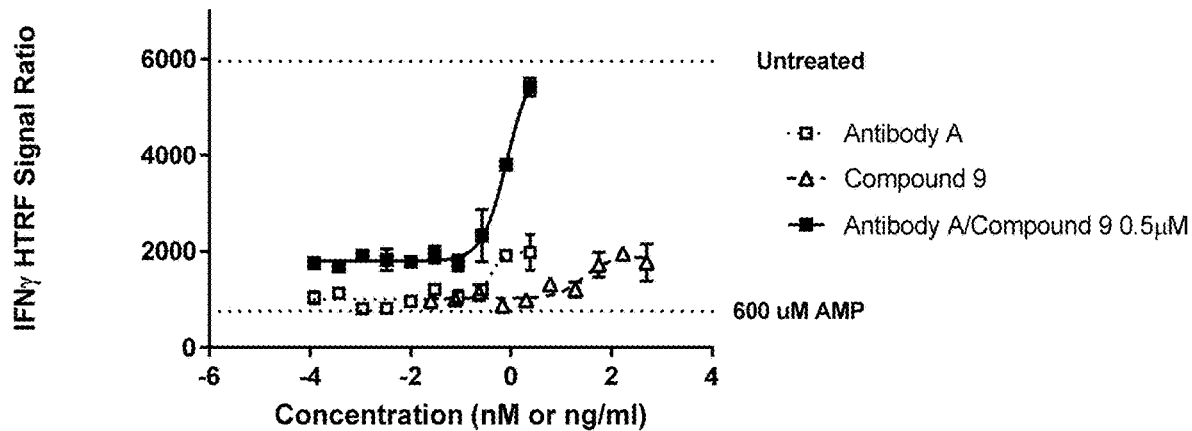
FIG. 16B is a graph showing the IFNγ HTRF signal ratio in CD4+ T cells treated with (i) titrated Antibody A, (ii) titrated Compound 9, or (iii) titrated Antibody A and 0.5 µM of Compound 9.
Figure 16C:
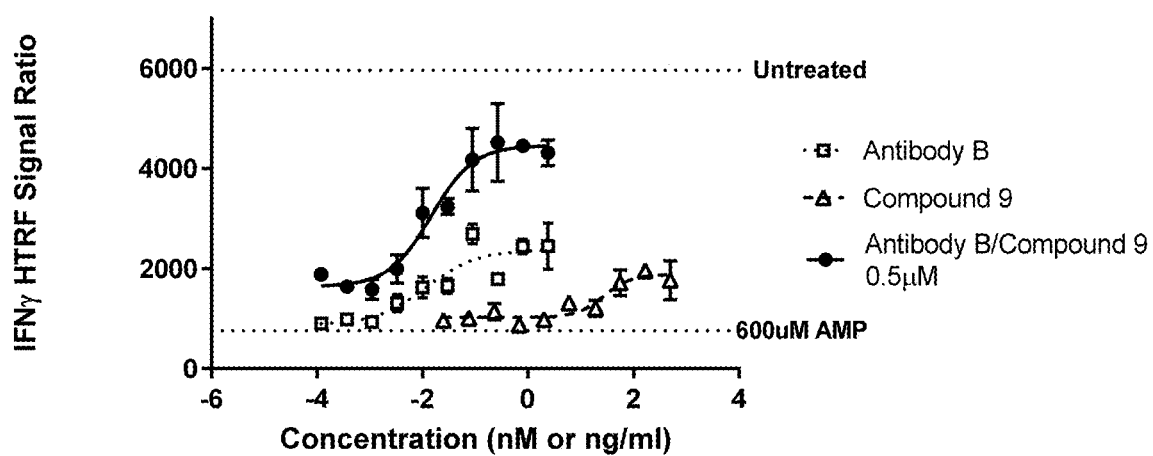
FIG. 16C is a graph showing the IFNγ HTRF signal ratio in CD4+ T cells treated with (i) titrated Antibody B, (ii) titrated Compound 9, or (iii) titrated Antibody B and 0.5 µM of Compound 9.

To test the ability of 3-F03 variants to inhibit CD73 activity on cells, MDA-MB-231 cells were washed with serum free RPMI media and plated 1×10⁴ cells/well in 96-well plates. Cells were incubated with the indicated concentration of antibodies or APCP at 37° C. 5% CO₂ for 30 minutes. Next, AMP was added to a final concentration of 100 µM and cells were incubated an additional 3 hours at 37° C. 5% CO₂. Plates were centrifuged for 1-2 minutes at 300 g and 25 µL of supernatant was transferred into a new 96-well plates. AMP-Glo Assay was used according to the manufacturer's instructions. RLU is a directly correlated with the AMP concentration in this assay. 3-F03 showed maximum inhibition among the 3-F03 variants (FIG. 14). Variants 3-F03_417, 3-F03_411 and 3-F03_413 displayed slightly lower potency compared to 3-F03 (FIG. 14). Variant 3-F03_412 did not inhibit membrane bound CD73 on MDA-MB-231 cells (FIG. 14).

Example 16: Anti-CD73 Antibody Synergizes with A2A Inhibitor

Figure 17A:
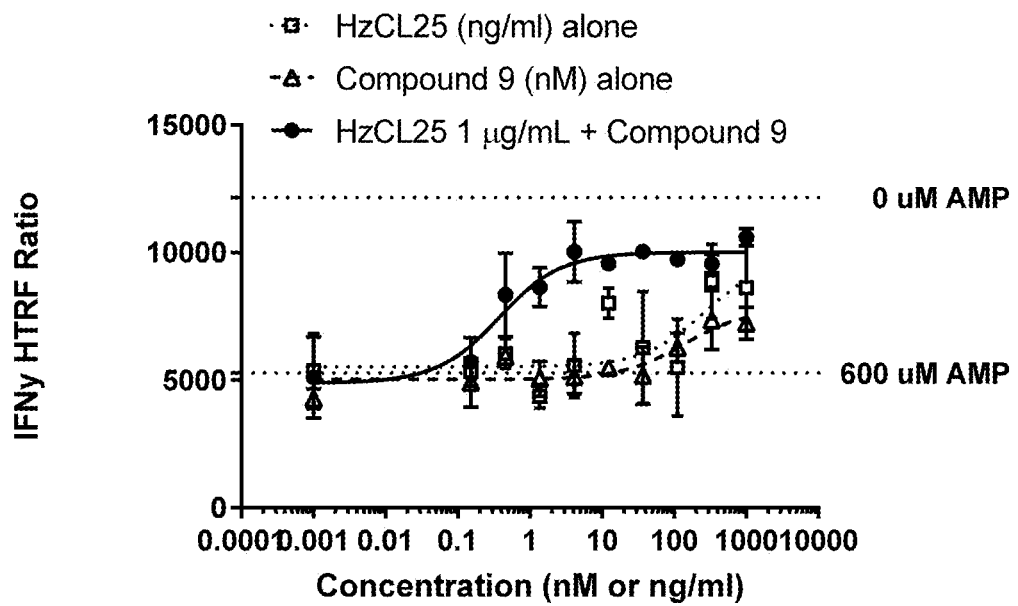
FIG. 17A is a graph showing the IFNγ HTRF signal ratio in CD4+ T cells treated with (i) titrated HzCL25, (ii) titrated Compound 9, or (iii) titrated Compound 9 and 1 µg/mL of HzCL25.
Figure 17B:
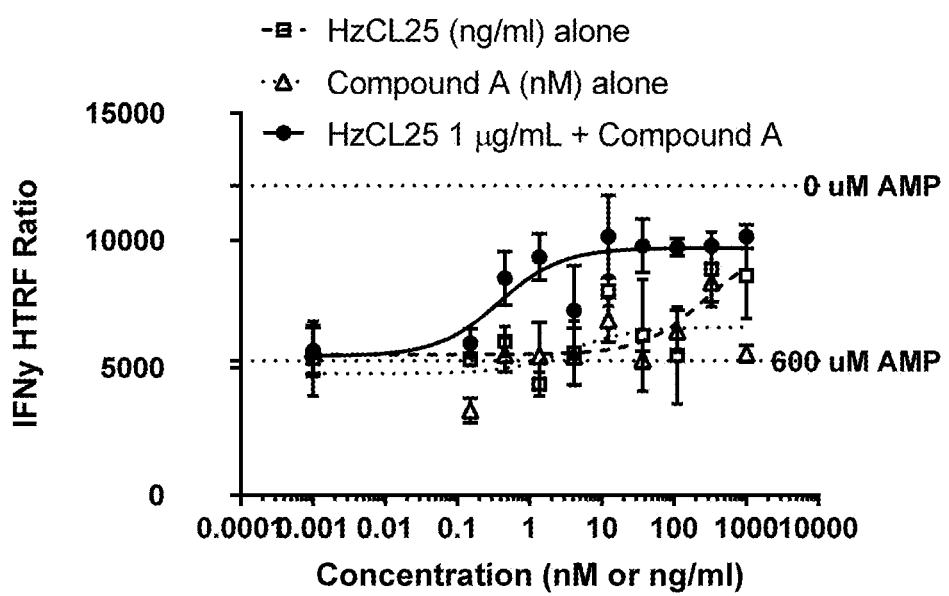
FIG. 17B is a graph showing the IFNγ HTRF signal ratio in CD4+ T cells treated with (i) titrated HzCL25, (ii) titrated Compound A, or (iii) titrated Compound A and 1 µg/mL of HzCL25.
Figure 17C:
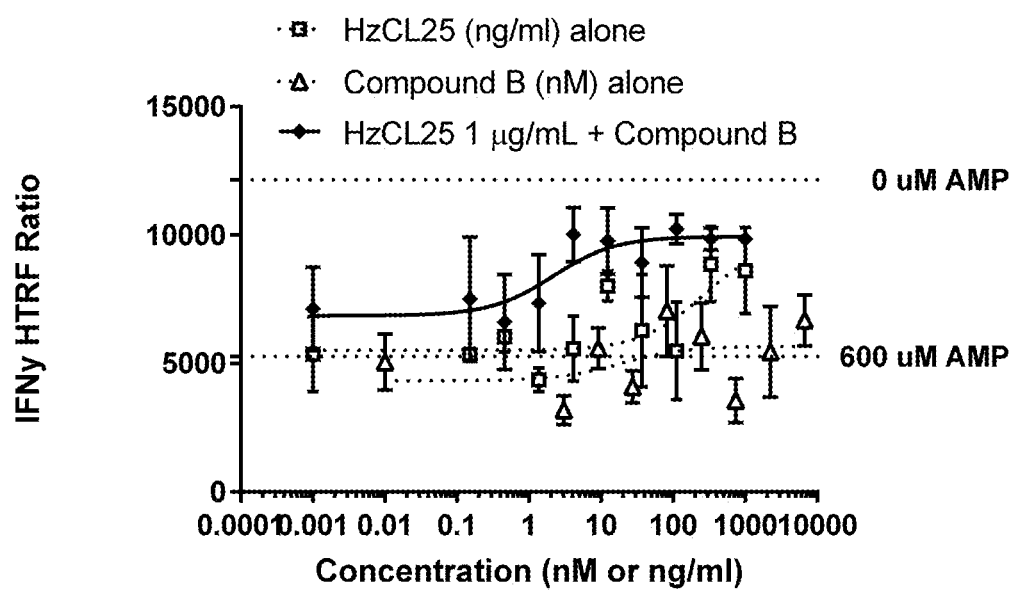
FIG. 17C is a graph showing the IFNγ HTRF signal ratio in CD4+ T cells treated with (i) titrated HzCL25, (ii) titrated Compound B, or (iii) titrated Compound B and 1 µg/mL of HzCL25.
Figure 18A:
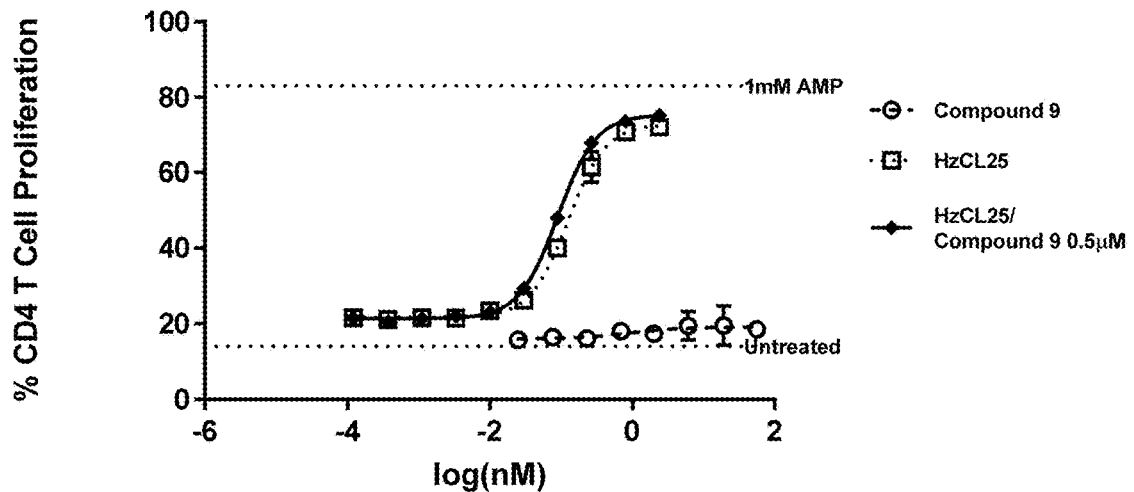
FIG. 18A is a graph showing the percent CD4+ T cell proliferation in donor cells treated with: (i) titrated Compound 9, (ii) titrated HzCL25, or (iii) titrated HzCL25 and 0.5 µM of Compound 9.
Figure 18B:
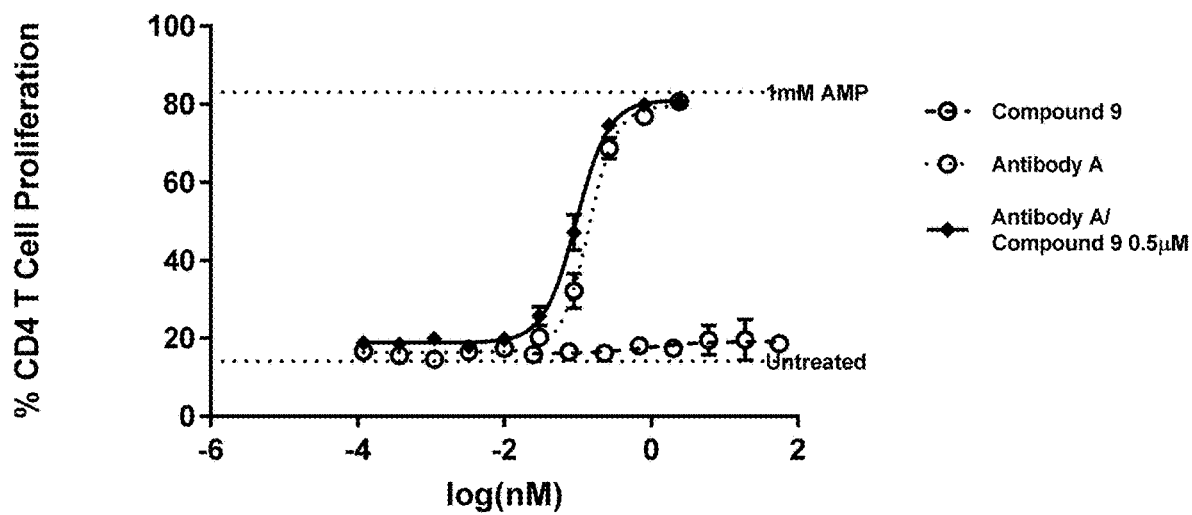
FIG. 18B is a graph showing the percent CD4+ T cell proliferation in donor cells treated with: (i) titrated Compound 9, (ii) titrated Antibody A, or (iii) titrated Antibody A and 0.5 µM of Compound 9.
Figure 18C:
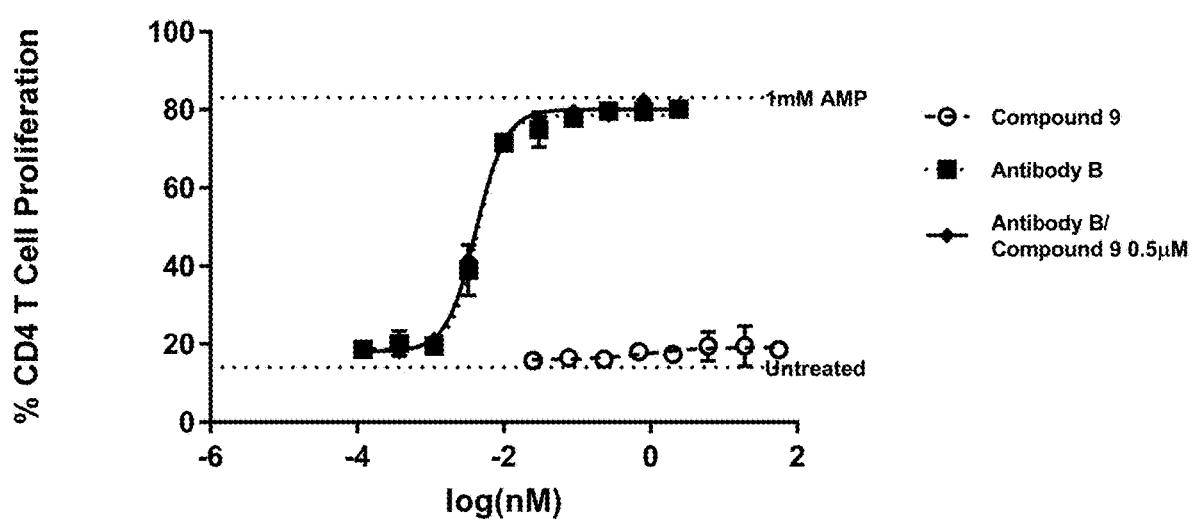
FIG. 18C is a graph showing the percent CD4+ T cell proliferation in donor cells treated with: (i) titrated Compound 9, (ii) titrated Antibody B, or (iii) titrated Antibody B and 0.5 µM of Compound 9.

To measure the ability of anti-CD73 antibody and an inhibitor of A2A to reverse AMP-mediated suppression of T cell proliferation, primary human CD4⁺ T cells were purified from peripheral blood mononuclear cells (PBMCs) using a human CD4⁺ T-cell isolation kit (Miltenyi Biotec). Isolated CD4⁺ T cells were labeled with 1 µM of carboxyfluorescein succinimidyl ester (CFSE) (BD Biosciences) according to the manufacturer's protocol. CFSE labeled cells were resuspended in RPMI containing 10% fetal bovine serum. Approximately 50,000 cells/well were added in round bottom 96-well plate. Dynabeads human T activator CD3/CD28 beads were added to cell suspension at bead:cell ratio 1:1 and incubated for 1 hour at 37° C. Serial dilutions of anti-CD73 antibody (HzCL25, Antibody A, or Antibody B) in the presence or absence of 0.5 µM of an A2A inhibitor (Compound 9) were added into the designated wells and incubated for 30 minutes at 37° C.; serial dilutions of the A2A inhibitor were added into the designated wells as controls (FIG. 16A-FIG. 16C and FIG. 18A-FIG. 18C). Alternatively, serial dilutions of A2A inhibitor (Compound 9, Compound A, or Compound B) in the presence or absence of 1 μg/mL anti-CD73 antibody (HzCL25) were added into the designated wells and incubated for 30 minutes at 37° C.; serial dilutions of the CD73 antibody were added to the indicated wells as controls (FIG. 17A-FIG. 17C). Finally AMP was added at a final concentration of 600 μM and the whole culture was incubated for 4 days at 37° C. in the incubator. After 4 days, IFNγ production was measured (FIG. 16A-FIG. 16C and FIG. 17A-FIG. 17C) and CD4+ T cell proliferation was determined by CFSE based flow cytometry analysis using LSRFORTESSA X-20 analyzer (BD Biosciences) (FIG. 18A-FIG. 18C).

```
Antibody A Heavy Chain (VH italicized):
                                    (SEQ ID NO: 102)
EIQLQQSGPELVKPGASVKVSCKASGYAFTSYNMYWVKQSHGKSLEWIGY

IDPYNGGTSYNQKFKGKATLTVDKSSSTAYMHLNSLTSEDSAVYYCARGY

GNYKAWFAYWGQGTLVTVSAASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYA

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPG

Antibody A Light Chain (VL italicized):
                                    (SEQ ID NO: 103)
DAVMTQTPKFLLVSAGDRVTITCKASQSVTNDVAWYQQKPGQSPKLLIYY

ASNRYTGVPDRFTGSGYGTDFTFTISTVQAEDLAVYFCQQDYSSLTFGAG

TKLELKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC

Antibody B Heavy Chain (VH italicized):
                                    (SEQ ID NO: 98)
EVQLLESGGGLVQPGGSLRLSCAASGFTFSSYAYSWVRQAPGKGLEWVSA

ISGSGGRTYYADSVKGRFTISRDNSKNTLYLQMNSLRAEDTAVYYCARLG

YGRVDEWGRGTLVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTCPPCPAPELLGGPSVFLFPPKPKDT

LMISRTPEVTCVVVDVSHEDPEVKFNWYVDGVEVHNAKTKPREEQYASTY

RVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPG

Antibody B Light Chain (VL italicized):
                                    (SEQ ID NO: 99)
QSVLTQPPSASGTPGQRVTISCSGSLSNIGRNPVNWYQQLPGTAPKLLIY

LDNLRLSGVPDRFSGSKSGTSASLAISGLQSEDEADYYCATWDDSHPGWT

FGGGTKLTVLGQPKANPTVTLFPPSSEELQANKATLVCLISDFYPGAVTV

AWKADGSPVKAGVETTKPSKQSNNKYAASSYLSLTPEQWKSHRSYSCQVT

HEGSTVEKTVAPTECS
```

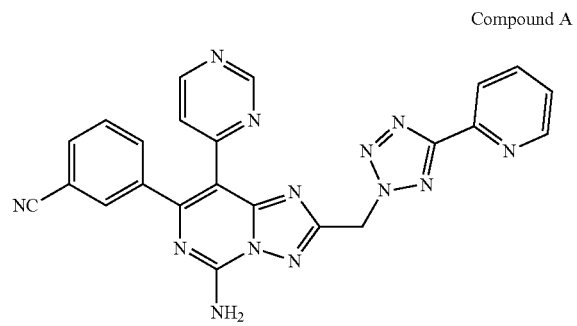 [SMILES: N#Cc1cccc(-c2nc(N)n3nc(Cn4nnc(-c5ccccn5)n4)nc3c2-c2ccncn2)c1]

Compound A (3-(5-Amino-2-((5-(pyridin-2-yl)-2H-tetrazol-2-yl)methyl)-8-(pyrimidin-4-yl)-[1,2,4]triazolo[1,5-c]pyrimidin-7-yl)benzonitrile)

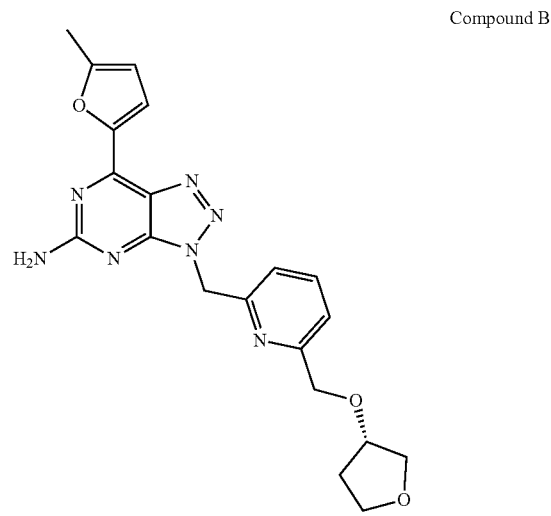 [SMILES: Cc1ccc(-c2nc(N)nc3c2nnn3Cc2cccc(CO[C@H]3CCOC3)n2)o1]

Compound B (7-(5-methylfuran-2-yl)-3-[[6-[[(3S)-oxolan-3-yl]oxymethyl]pyridin-2-yl]methyl]triazolo[4,5-d]pyrimidin-5-amine)

When combined with anti-CD73 antibody, A2A inhibitor increased IFNγ production significantly (FIG. 16A-FIG. 16C and FIG. 17A-FIG. 17C).

When combined with anti-CD73 antibody, A2A/A2B inhibitor reversed AMP-mediated suppression of CD4+ T cell proliferation in a concentration dependent manner in multiple different human donors (FIG. 18A-FIG. 18C).

Example 17: In Vivo Combination of Anti-CD73 Antibody and A2A Inhibitor Reduces Tumor Volume The in vivo efficacy of anti-CD73 antibody in combination with an A2A inhibitor was tested. Anti-CD73 antibody HzCL25 or 3-F03_413 was suspended in 1× phosphate buffered saline (PBS) (Life Technologies) for intraperitoneal dosing of hu-CD34 NSG mice (Jackson laboratories). 1×PBS and Fc disabled human IgG1 suspended in 1×PBS was included in this study as a control. Mice with humanized immune systems were purchased from Jackson Labs (Bar Harbor, Me.). Briefly, 3 week old female NSG/NOD SCID mice received a single dose of irradiation toxic to immune cell precursors and were then "rescued" by injection of human cord blood, CD34$^+$ selected cells. The mice comprised recipients of three distinct human immune donors to better represent individual variations in immune response.

The left flank of the mice were shaved the day prior to inoculation with 5×10$^6$ cells of the human breast cancer line MDA-MB-231 (ATCC, Manassas Va.) suspended in matrigel (Corning Life Sciences, Tewksbury, Mass.). On day 7, tumor dimensions were measured by Vernier calipers, and volume estimated by the formula Volume=[L (long dimension)×W2 (short dimension)]/2. Mice were randomized into 4 groups of 5 or 6 mice of approximate mean volume (~200 mm$^3$) and donor representation. Tumors were measured every 5 days for the duration of the study.

Every five days, from day 8, mice were dosed intraperitoneally with (i) 10 mg/kg of human IgG1 and 10 mg/kg of vehicle; (ii) 10 mg/kg of HzCL25; or (iii) 10 mg/kg of 3-F03_413. For treatment groups (ii) and (iii), mice were dosed twice a day (BID) with Compound 9. A total of 8 doses of antibody were given (i.e., antibody was dosed on days 8 13, 18, 23, 29, 34, 39, and 44 and Compound 9 was dosed twice a day, with 8 and 16 hour intervals) starting on day 8 through the last day).

Figure 19A:
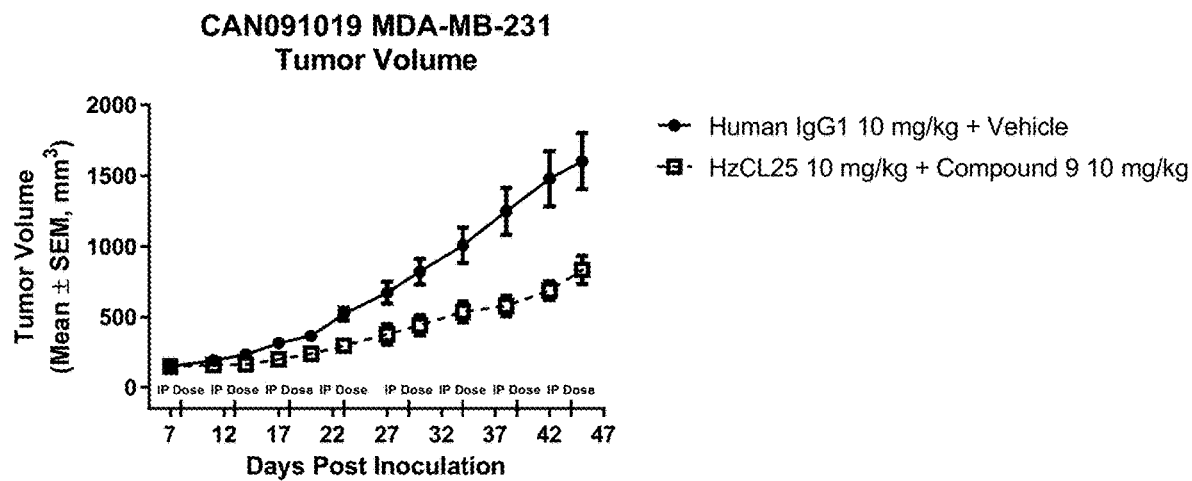
FIG. 19A is a graph depicting the tumor volume in mice administered (i) human IgG1 and vehicle (circles), or (ii) HzCL25 and Compound 9 (squares).
Figure 19B:
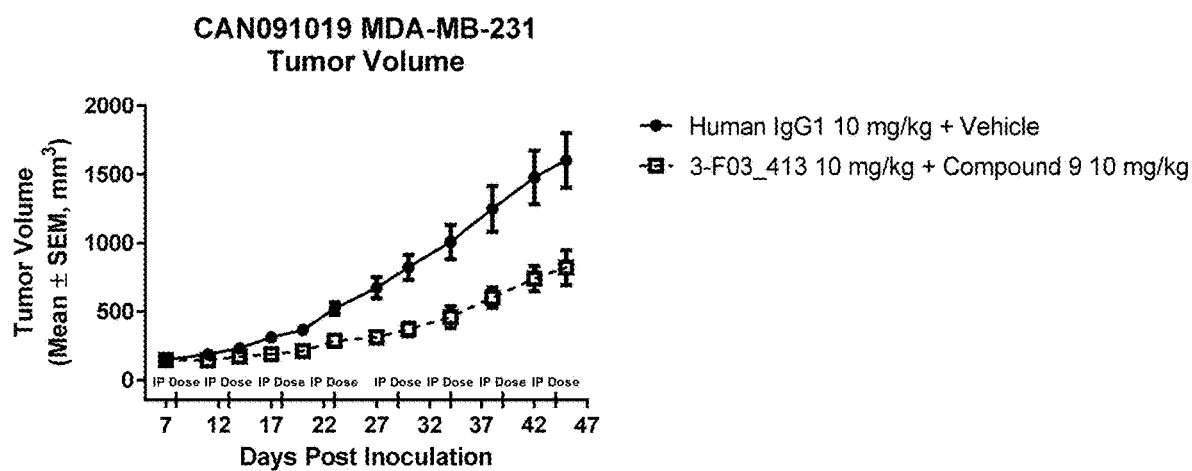
FIG. 19B is a graph depicting the tumor volume in mice administered (i) human IgG1 and vehicle (circles), or (ii) 3-F03_413 and Compound 9 (squares).

Mice administered anti-CD73 antibody in combination with an A2A inhibitor exhibited statistically significantly slowed tumor growth (FIG. 19A and FIG. 19B).

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method for treating a cancer in a human subject in need thereof, comprising administering to the human subject an effective amount of an inhibitor of human CD73 and an inhibitor of A2A adenosine receptor and/or A2B adenosine receptor, wherein:
(1) the inhibitor of human CD73 comprises:
(a) an antibody comprising a variable heavy (VH) domain comprising VH complementarity determining region (CDR)1, VH CDR2, and VH CDR3, wherein:
the VH CDR1 comprises the amino acid sequence GYTFTSYG (SEQ ID NO:1);
the VH CDR2 comprises the amino acid sequence IYPGSGNT (SEQ ID NO:2); and
the VH CDR3 comprises the amino acid sequence ARYDYLGSSYGFDY (SEQ ID NO:3); and
comprising a variable light (VL) domain comprising VL CDR1, VL CDR2, and VL CDR3, wherein:
the VL CDR1 comprises the amino acid sequence QDVSTA (SEQ ID NO:4);
the VL CDR2 comprises the amino acid sequence SAS (SEQ ID NO:5); and
the VL CDR3 comprises the amino acid sequence QQHYNTPYT (SEQ ID NO:6);
(b) an antibody comprising a VH domain comprising VH CDR1, VH CDR2, and VH CDR3, wherein:
the VH CDR1 comprises the amino acid sequence GFTFSSYD (SEQ ID NO:34);
the VH CDR2 comprises the amino acid sequence MSYDGSNK (SEQ ID NO:35) or MSYEGSNK (SEQ ID NO:40); and
the VH CDR3 comprises the amino acid sequence ATEIAAKGDY (SEQ ID NO:36); and
an antibody comprising a VL domain comprising VL CDR1, VL CDR2, and VL CDR3, wherein:
the VL CDR1 comprises the amino acid sequence QGISNY (SEQ ID NO:37);
the VL CDR2 comprises the amino acid sequence AAS (SEQ ID NO:38); and
the VL CDR3 comprises the amino acid sequence QQSYSTPH (SEQ ID NO:39);
(2) the inhibitor of A2A adenosine receptor and/or A2B adenosine receptor (A2A/A2B) comprises a compound of:
(a) Formula (I):

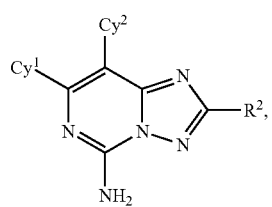

(I)

or a pharmaceutically acceptable salt thereof, wherein $Cy^1$ is phenyl which is substituted by 1 or 2 substituents independently selected from halo and CN;

$Cy^2$ is 5-6 membered heteroaryl or 4-7 membered heterocycloalkyl, wherein the 5-6 membered heteroaryl or 4-7 membered heterocycloalkyl of $Cy^2$ are each optionally substituted with 1, 2, or 3 groups each independently selected from $C_{1-3}$ alkyl, $C_{1-3}$ alkoxy, $NH_2$, $NH(C_{1-3}$ alkyl) and $N(C_{1-3}$ alkyl)$_2$;

$R^2$ is selected from phenyl-$C_{1-3}$ alkyl-, $C_{3-7}$ cycloalkyl-$C_{1-3}$ alkyl-, (5-7 membered heteroaryl)-$C_{1-3}$ alkyl-, (4-7 membered heterocycloalkyl)-$C_{1-3}$ alkyl-, and $OR^{a2}$, wherein the phenyl-$C_{1-3}$ alkyl-, $C_{3-7}$ cycloalkyl-$C_{1-3}$ alkyl-, (5-7 membered heteroaryl)-$C_{1-3}$ alkyl-, and (4-7 membered heterocycloalkyl)-$C_{1-3}$ alkyl- of $R^2$ are each optionally substituted with 1, 2, or 3 independently selected $R^C$ substituents;

$R^{a2}$ is (5-7 membered heteroaryl)-$C_{1-3}$ alkyl- optionally substituted with 1 or 2 independently selected $R^C$ substituents;

each $R^C$ is independently selected from halo, $C_{1-6}$ alkyl, $C_6$ aryl, 5-7 membered heteroaryl, (4-7 membered heterocycloalkyl)-$C_{1-3}$ alkyl-, $OR^{a4}$, and $NR^{c4}R^{d4}$; and each $R^{a4}$, $R^{c4}$, and $R^{d4}$ are independently selected from H and $C_{1-6}$ alkyl;

(b) Formula (II):

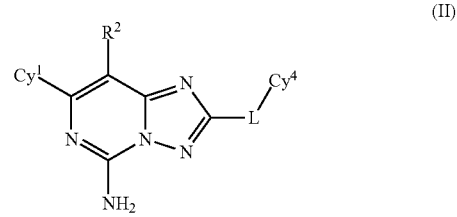

(II)

or a pharmaceutically acceptable salt thereof, wherein $R^2$ is selected from H and CN;

$Cy^1$ is phenyl which is substituted by 1 or 2 substituents independently selected from halo and CN;

L is $C_{1-3}$ alkylene, wherein said alkylene is optionally substituted with 1, 2, or 3 independently selected $R^{8D}$ substituents;

$Cy^4$ is selected from phenyl, cyclohexyl, pyridyl, pyrrolidinonyl, and imidazolyl, wherein the phenyl, cyclohexyl, pyridyl, pyrrolidinonyl, and imidazolyl are each optionally substituted with 1, 2, or 3 substituents independently selected from $R^{8D}$ and $R^8$;

each $R^8$ is independently selected from halo, $C_{1-6}$ alkyl, $C_{1-6}$ haloalkyl, $C_{2-4}$ alkenyl, $C_{2-4}$ alkynyl, phenyl, $C_{3-7}$ cycloalkyl, 5-6 membered heteroaryl, 4-7 membered heterocycloalkyl, phenyl-$C_{1-3}$ alkyl, $C_{3-7}$ cycloalkyl-$C_{1-3}$ alkyl, (5-6 membered heteroaryl)-$C_{1-3}$ alkyl, and (4-7 membered heterocycloalkyl)-$C_{1-3}$ alkyl, wherein the $C_{1-6}$ alkyl, $C_{2-4}$ alkenyl, $C_{2-4}$ alkynyl, phenyl, $C_{3-7}$ cycloalkyl, 5-6 membered heteroaryl, 4-7 membered heterocycloalkyl, phenyl-$C_{1-3}$ alkyl, $C_{3-7}$ cycloalkyl-$C_{1-3}$ alkyl, (5-6 membered heteroaryl)-$C_{1-3}$ alkyl, and (4-7 membered heterocycloalkyl)-$C_{1-3}$ alkyl of $R^8$ are each optionally substituted with 1, 2, or 3 independently selected $R^{8A}$ substituents;

each $R^{8A}$ is independently selected from halo, $C_{1-6}$ alkyl, 5-6 membered heteroaryl, 4-7 membered heterocycloalkyl, CN, $OR^{a81}$, and $NR^{c81}R^{d81}$, wherein the $C_{1-3}$ alkyl, 5-6 membered heteroaryl, and 4-7 membered heterocycloalkyl of $R^{8A}$ are each optionally substituted with 1, 2, or 3 independently selected $R^{8B}$ substituents;

each $R^{a81}$, $R^{c81}$ and $R^{d81}$ is independently selected from H, $C_{1-6}$ alkyl, and 4-7 membered heterocycloalkyl, wherein the $C_{1-6}$ alkyl and 4-7 membered heterocycloalkyl of $R^{a81}$, $R^{c81}$, and $R^{d81}$ are each optionally substituted with 1, 2, or 3 independently selected $R^{8B}$ substituents;

each $R^{8B}$ is independently selected from halo and $C_{1-3}$ alkyl; and each $R^{8D}$ is independently selected from OH, CN, halo, $C_{1-6}$ alkyl, and $C_{1-6}$ haloalkyl;

(c) Formula (III):

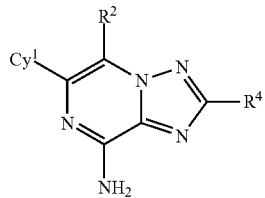

(III)

or a pharmaceutically acceptable salt thereof, wherein $Cy^1$ is phenyl which is substituted by 1 or 2 substituents independently selected from halo and CN;

$R^2$ is selected from 5-6 membered heteroaryl and 4-7 membered heterocycloalkyl, wherein the 5-6 membered heteroaryl and 4-7 membered heterocycloalkyl of $R^2$ are each optionally substituted with 1, 2, or 3 independently selected $R^{2A}$ substituents;

each $R^{2A}$ is independently selected from D, halo, $C_{1-6}$ alkyl, and $C_{1-6}$ haloalkyl;

$R^4$ is selected from phenyl-$C_{1-3}$ alkyl-, $C_{3-7}$ cycloalkyl-$C_{1-3}$ alkyl-, (5-6 membered heteroaryl)-$C_{1-3}$ alkyl-, and (4-7 membered heterocycloalkyl)-$C_{1-3}$ alkyl wherein the phenyl-$C_{1-3}$ alkyl-, $C_{3-7}$ cycloalkyl-$C_{1-3}$ alkyl-, (5-6 membered heteroaryl)-$C_{1-3}$ alkyl-, and (4-7 membered heterocycloalkyl)-$C_{1-3}$ alkyl- of $R^4$ are each optionally substituted with 1, 2, or 3 independently selected $R^{4A}$ substituents;

each $R^{4A}$ is independently selected from halo, $C_{1-6}$ alkyl, $C_{1-6}$ haloalkyl, CN, $OR^{a1}$, and $NR^{c41}R^{d41}$; and each $R^{a41}$, $R^{c41}$, and $R^{d41}$ is independently selected from H and $C_{1-6}$ alkyl; or (d) Formula (IV):

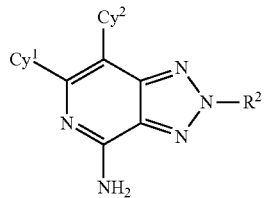

(IV)

or a pharmaceutically acceptable salt thereof, wherein $Cy^1$ is phenyl which is substituted by 1 or 2 substituents independently selected from halo and CN;

$Cy^2$ is selected from 5-6 membered heteroaryl and 4-7 membered heterocycloalkyl, wherein the 5-6 membered heteroaryl and 4-7 membered heterocycloalkyl of $Cy^2$ are each optionally substituted with 1, 2, or 3 independently selected $R^6$ substituents;

each $R^6$ is independently selected from halo, $C_{1-6}$ alkyl, and $C_{1-6}$ haloalkyl;

$R^2$ is phenyl-$C_{1-3}$ alkyl- or (5-6 membered heteroaryl)-$C_{1-3}$ alkyl-, wherein the phenyl-$C_{1-3}$ alkyl- and (5-6 membered heteroaryl)-$C_{1-3}$ alkyl- of $R^2$ are each optionally substituted with 1, 2, or 3 independently selected $R^{2A}$ substituents; and each $R^{2A}$ is independently selected from halo, $C_{1-6}$ alkyl, and $C_{1-6}$ haloalkyl;

or a pharmaceutically acceptable salt thereof.

2. The method of claim 1, wherein the inhibitor of A2A/A2B is a compound of Formula (I):

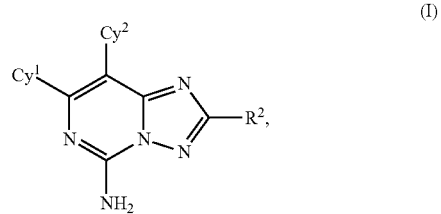

(I)

or a pharmaceutically acceptable salt thereof, wherein $Cy^1$ is phenyl which is substituted by 1 or 2 substituents independently selected from halo and CN;

$Cy^2$ is 5-6 membered heteroaryl or 4-7 membered heterocycloalkyl, wherein the 5-6 membered heteroaryl or 4-7 membered heterocycloalkyl of $Cy^2$ are each optionally substituted with 1, 2, or 3 groups each independently selected from $C_{1-3}$ alkyl, $C_{1-3}$ alkoxy, $NH_2$, $NH(C_{1-3}$ alkyl) and $N(C_{1-3}$ alkyl)$_2$;

$R^2$ is selected from phenyl-$C_{1-3}$ alkyl-, $C_{3-7}$ cycloalkyl-$C_{1-3}$ alkyl-, (5-7 membered heteroaryl)-$C_{1-3}$ alkyl-, (4-7 membered heterocycloalkyl)-$C_{1-3}$ alkyl-, and $OR^1$, wherein the phenyl-$C_{1-3}$ alkyl-, $C_{3-7}$ cycloalkyl-$C_{1-3}$ alkyl-, (5-7 membered heteroaryl)-$C_{1-3}$ alkyl-, and (4-7 membered heterocycloalkyl)-$C_{1-3}$ alkyl- of $R^2$ are each optionally substituted with 1, 2, or 3 independently selected $R^C$ substituents;

$R^{a2}$ is (5-7 membered heteroaryl)-$C_{1-3}$ alkyl- optionally substituted with 1 or 2 independently selected $R^C$ substituents;

each $R^C$ is independently selected from halo, $C_{1-6}$ alkyl, $C_6$ aryl, 5-7 membered heteroaryl, (4-7 membered heterocycloalkyl)-$C_{1-3}$ alkyl-, $OR^{a4}$, and $NR^{c4}R^{d4}$; and each $R^{a1}$, $R^{c4}$, and $R^{d4}$ are independently selected from H and $C_{1-6}$ alkyl.

3. The method of claim 2, wherein the inhibitor of A2A/A2B is selected from:

3-(5-Amino-2-(pyridin-2-ylmethyl)-8-(pyrimidin-4-yl)-[1,2,4]triazolo[1,5-c]pyrimidin-7-yl)benzonitrile, or a pharmaceutically acceptable salt thereof;

3-(5-Amino-2-(2,6-difluorophenyl)(hydroxy)methyl)-8-(pyrimidin-4-yl)-[1,2,4]triazolo[1,5-c]pyrimidin-7-yl) benzonitrile, or a pharmaceutically acceptable salt thereof;

3-(5-Amino-2-((5-(pyridin-2-yl)-2H-tetrazol-2-yl) methyl)-8-(pyrimidin-4-yl)-[1,2,4]triazolo[1,5-c]pyrimidin-7-yl)benzonitrile, or a pharmaceutically acceptable salt thereof;

3-(5-Amino-2-(3-methylpyridin-2-yl)methoxy)-8-(pyrimidin-4-yl)-[1,2,4]triazolo[1,5-c]pyrimidin-7-yl)benzonitrile, or a pharmaceutically acceptable salt thereof; and 3-(2-((5-(1H-Pyrazol-1-yl)-1H-tetrazol-1-yl)methyl)-5-amino-8-(pyrimidin-4-yl)-[1,2,4]triazolo[1,5-c]pyrimidin-7-yl)benzonitrile, or a pharmaceutically acceptable salt thereof.

4. The method of claim 1, wherein the inhibitor of A2A/A2B is a compound of Formula (II):

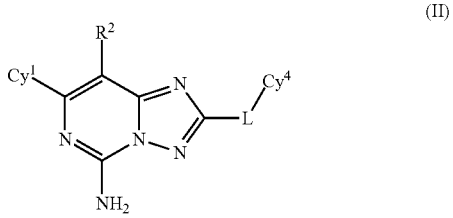

(II)

or a pharmaceutically acceptable salt thereof, wherein
$R^2$ is selected from H and CN;
$Cy^1$ is phenyl which is substituted by 1 or 2 substituents independently selected from halo and CN;
L is $C_{1-3}$ alkylene, wherein said alkylene is optionally substituted with 1, 2, or 3 independently selected $R^{8D}$ substituents;
$Cy^4$ is selected from phenyl, cyclohexyl, pyridyl, pyrrolidinonyl, and imidazolyl, wherein the phenyl, cyclohexyl, pyridyl, pyrrolidinonyl, and imidazolyl are each optionally substituted with 1, 2, or 3 substituents independently selected from $R^{8D}$ and $R^8$;
each $R^8$ is independently selected from halo, $C_{1-6}$ alkyl, $C_{1-6}$ haloalkyl, $C_{2-4}$ alkenyl, $C_{2-4}$ alkynyl, phenyl, $C_{3-7}$ cycloalkyl, 5-6 membered heteroaryl, 4-7 membered heterocycloalkyl, phenyl-$C_{1-3}$ alkyl, $C_{3-7}$ cycloalkyl-$C_{1-3}$ alkyl, (5-6 membered heteroaryl)-$C_{1-3}$ alkyl, and (4-7 membered heterocycloalkyl)-$C_{1-3}$ alkyl, wherein the $C_{1-6}$ alkyl, $C_{2-4}$ alkenyl, $C_{2-4}$ alkynyl, phenyl, $C_{3-7}$ cycloalkyl, 5-6 membered heteroaryl, 4-7 membered heterocycloalkyl, phenyl-$C_{1-3}$ alkyl, $C_{3-7}$ cycloalkyl-$C_{1-3}$ alkyl, (5-6 membered heteroaryl)-$C_{1-3}$ alkyl, and (4-7 membered heterocycloalkyl)-$C_{1-3}$ alkyl of $R^8$ are each optionally substituted with 1, 2, or 3 independently selected $R^{8A}$ substituents;
each $R^{8A}$ is independently selected from halo, $C_{1-6}$ alkyl, 5-6 membered heteroaryl, 4-7 membered heterocycloalkyl, CN, $OR^{a81}$, and $NR^{c81}R^{d81}$, wherein the $C_{1-3}$ alkyl, 5-6 membered heteroaryl, and 4-7 membered heterocycloalkyl of $R^{8A}$ are each optionally substituted with 1, 2, or 3 independently selected $R^{8B}$ substituents;
each $R^{a81}$, $R^{c81}$ and $R^{d81}$ is independently selected from H, $C_{1-6}$ alkyl, and 4-7 membered heterocycloalkyl, wherein the $C_{1-6}$ alkyl and 4-7 membered heterocycloalkyl of $R^{a81}$, $R^{c81}$, and $R^{d81}$ are each optionally substituted with 1, 2, or 3 independently selected $R^{8B}$ substituents;
each $R^{8B}$ is independently selected from halo and $C_{1-3}$ alkyl; and
each $R^{8D}$ is independently selected from OH, CN, halo, $C_{1-6}$ alkyl, and $C_{1-6}$ haloalkyl.

5. The method of claim 4, wherein the inhibitor of A2A/A2B is selected from:

3-(5-Amino-2-(hydroxy(phenyl)methyl)-[1,2,4]triazolo[1,5-c]pyrimidin-7-yl)benzonitrile, or a pharmaceutically acceptable salt thereof;

3-(5-Amino-2-(2,6-difluorophenyl)(hydroxy)methyl)-[1,2,4]triazolo[1,5-c]pyrimidin-7-yl)-2-fluorobenzonitrile, or a pharmaceutically acceptable salt thereof;

1-Amino-7-(3-cyano-2-fluorophenyl)-2-(2,6-difluorophenyl)(hydroxy)methyl)-[1,2,4]triazolo[1,5-c]pyrimidine-8-carbonitrile, or a pharmaceutically acceptable salt thereof; and 3-(5-Amino-2-((2-fluoro-6-(((1-methyl-2-oxopyrrolidin-3-yl)amino)methyl)phenyl)(hydroxy)methyl)-[1,2,4]triazolo[1,5-c]pyrimidin-7-yl)-2-fluorobenzonitrile, or a pharmaceutically acceptable salt thereof.

6. The method of claim 1, wherein the inhibitor of A2A/A2B is a compound of Formula (III):

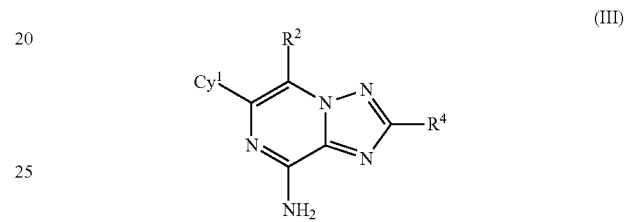

(III)

or a pharmaceutically acceptable salt thereof, wherein
$Cy^1$ is phenyl which is substituted by 1 or 2 substituents independently selected from halo and CN;
$R^2$ is selected from 5-6 membered heteroaryl and 4-7 membered heterocycloalkyl, wherein the 5-6 membered heteroaryl and 4-7 membered heterocycloalkyl of $R^2$ are each optionally substituted with 1, 2, or 3 independently selected $R^{2A}$ substituents;
each $R^{2A}$ is independently selected from D, halo, $C_{1-6}$ alkyl, and $C_{1-6}$ haloalkyl;
$R^4$ is selected from phenyl-$C_{1-3}$ alkyl-, $C_{3-7}$ cycloalkyl-$C_{1-3}$ alkyl-, (5-6 membered heteroaryl)-$C_{1-3}$ alkyl-, and (4-7 membered heterocycloalkyl)-$C_{1-3}$ alkyl wherein the phenyl-$C_{1-3}$ alkyl-, $C_{3-7}$ cycloalkyl-$C_{1-3}$ alkyl-, (5-6 membered heteroaryl)-$C_{1-3}$ alkyl-, and (4-7 membered heterocycloalkyl)-$C_{1-3}$ alkyl- of $R^4$ are each optionally substituted with 1, 2, or 3 independently selected $R^{4A}$ substituents;
each $R^{4A}$ is independently selected from halo, $C_{1-6}$ alkyl, $C_{1-6}$ haloalkyl, CN, $OR^1$, and $NR^{c41}R^{d41}$; and
each $R^{a41}$, $R^{c41}$, and $R^{d41}$ is independently selected from H and $C_{1-6}$ alkyl.

7. The method of claim 6, wherein the inhibitor of A2A/A2B is selected from:

3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile;

3-(8-Amino-2-(2,6-difluorophenyl)(hydroxy)methyl)-5-(pyrimidin-4-yl)[1,2,4]triazolo[1,5-a]pyrazin-6-yl)benzonitrile, or a pharmaceutically acceptable salt thereof;

3-(8-amino-2-(amino(2,6-difluorophenyl)methyl)-5-(4-methyloxazol-5-yl)-[1,2,4]triazolo[1,5-a]pyrazin-6-yl)benzonitrile, or a pharmaceutically acceptable salt thereof; and 3-(8-amino-2-(2,6-difluorophenyl)(hydroxy)methyl)-5-(2,6-dimethylpyridin-4-yl)-[1,2,4]triazolo[1,5-a]pyrazin-6-yl)benzonitrile, or a pharmaceutically acceptable salt thereof.

8. The method of claim 1, wherein the inhibitor of A2A/A2B is a compound of Formula (IV):

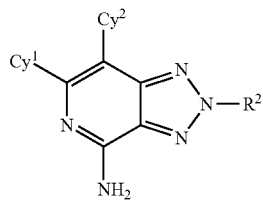

(IV)

or a pharmaceutically acceptable salt thereof, wherein
Cy$^1$ is phenyl which is substituted by 1 or 2 substituents independently selected from halo and CN;
Cy$^2$ is selected from 5-6 membered heteroaryl and 4-7 membered heterocycloalkyl, wherein the 5-6 membered heteroaryl and 4-7 membered heterocycloalkyl of Cy$^2$ are each optionally substituted with 1, 2, or 3 independently selected R$^6$ substituents;
each R$^6$ is independently selected from halo, C$_{1-6}$ alkyl, and C$_{1-6}$ haloalkyl;
R$^2$ is phenyl-C$_{1-3}$ alkyl- or (5-6 membered heteroaryl)-C$_{1-3}$ alkyl-, wherein the phenyl-C$_{1-3}$ alkyl- and (5-6 membered heteroaryl)-C$_{1-3}$ alkyl- of R$^2$ are each optionally substituted with 1, 2, or 3 independently selected R$^{2A}$ substituents; and
each R$^{2A}$ is independently selected from halo, C$_{1-6}$ alkyl, and C$_{1-6}$ haloalkyl;
or a pharmaceutically acceptable salt thereof.

9. The method of claim 8, wherein the inhibitor of A2A/A2B is selected from:
3-(4-amino-2-(pyridin-2-ylmethyl)-7-(pyrimidin-4-yl)-2H-[1,2,3]triazolo[4,5-c]pyridin-6-yl)benzonitrile, or a pharmaceutically acceptable salt thereof;
3-(4-amino-2-((3-fluoropyridin-2-yl)methyl)-7-(pyrimidin-4-yl)-2H-[1,2,3]triazolo[4,5-c]pyridin-6-yl)benzonitrile, or a pharmaceutically acceptable salt thereof;
3-(4-amino-2-((3-fluoropyridin-2-yl)methyl)-7-(pyridin-4-yl)-2H-[1,2,3]triazolo[4,5-c]pyridin-6-yl)benzonitrile, or a pharmaceutically acceptable salt thereof; and
3-(4-amino-7-(1-methyl-1H-pyrazol-5-yl)-2-(pyridin-2-ylmethyl)-2H-[1,2,3]triazolo[4,5-c]pyridin-6-yl)-2-fluorobenzonitrile, or a pharmaceutically acceptable salt thereof.

10. The method of claim 1, wherein the inhibitor of A2A/A2B is 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile, or a pharmaceutically acceptable salt thereof.

11. The method of claim 1, wherein the inhibitor of A2A/A2B is 3-(5-Amino-2-((5-(pyridin-2-yl)-2H-tetrazol-2-yl)methyl)-8-(pyrimidin-4-yl)-[1,2,4]triazolo[1,5-c]pyrimidin-7-yl)benzonitrile, or a pharmaceutically acceptable salt thereof.

12. The method of claim 1, wherein the inhibitor of human CD73 comprises an antibody comprising:
a VH domain comprising VH CDR1, VH CDR2, and VH CDR3, wherein:
the VH CDR1 comprises the amino acid sequence GYTFTSYG (SEQ ID NO:1);
the VH CDR2 comprises the amino acid sequence IYPGSGNT (SEQ ID NO:2); and
the VH CDR3 comprises the amino acid sequence ARYDYLGSSYGFDY (SEQ ID NO:3); and
a VL domain comprising VL CDR1, VL CDR2, and VL CDR3, wherein:
the VL CDR1 comprises the amino acid sequence QDVSTA (SEQ ID NO:4);
the VL CDR2 comprises the amino acid sequence SAS (SEQ ID NO:5); and
the VL CDR3 comprises the amino acid sequence QQHYNTPYT (SEQ ID NO:6).

13. The method of claim 1, wherein the inhibitor of human CD73 comprises an antibody comprising:
a VH domain comprising VH CDR1, VH CDR2, and VH CDR3, wherein:
the VH CDR1 comprises the amino acid sequence GFTFSSYD (SEQ ID NO:34);
the VH CDR2 comprises the amino acid sequence MSYDGSNK (SEQ ID NO:35) or MSYEGSNK (SEQ ID NO:40); and
the VH CDR3 comprises the amino acid sequence ATEIAAKGDY (SEQ ID NO:36); and
a VL domain comprising VL CDR1, VL CDR2, and VL CDR3, wherein:
the VL CDR1 comprises the amino acid sequence QGISNY (SEQ ID NO:37);
the VL CDR2 comprises the amino acid sequence AAS (SEQ ID NO:38); and
the VL CDR3 comprises the amino acid sequence QQSYSTPH (SEQ ID NO:39).

14. The method of claim 12, wherein the VH domain comprises the amino acid sequence set forth in SEQ ID NO:22 and the VL domain comprises the amino acid sequence set forth in SEQ ID NO:23, and wherein the compound comprises 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile.

15. The method of claim 12, wherein the antibody comprises a heavy chain and a light chain, and wherein the heavy chain comprises the amino acid sequence set forth in SEQ ID NO:24 and the light chain comprises the amino acid sequence set forth in SEQ ID NO:25, and wherein the compound comprises 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile.

16. The method of claim 13, wherein the VH domain comprises the amino acid sequence set forth in SEQ ID NO:62 and the VL domain comprises the amino acid sequence set forth in SEQ ID NO:61, and wherein the compound comprises 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile.

17. The method of claim 13, wherein the antibody comprises a heavy chain and a light chain, and wherein the heavy chain comprises the amino acid sequence set forth in SEQ ID NO:30 and the light chain comprises the amino acid sequence set forth in SEQ ID NO:31, and wherein the compound comprises 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile.

18. The method of claim 13, wherein the VH domain comprises the amino acid sequence set forth in SEQ ID NO:63 and the VL domain comprises the amino acid sequence set forth in SEQ ID NO:61, and wherein the compound comprises 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile.

19. The method of claim 13, wherein the antibody comprises a heavy chain and a light chain, and wherein the heavy chain comprises the amino acid sequence set forth in SEQ ID NO:33 and the light chain comprises the amino acid sequence set forth in SEQ ID NO:31, and wherein the compound comprises 3-(8-Amino-5-(1-methyl-6-oxo-1,6-dihydropyridazin-3-yl)-2-(pyridin-2-ylmethyl)-[1,2,4]triazolo[1,5-a]pyrazin-6-yl)benzonitrile.

20. A method for treating a cancer in a human subject in need thereof, comprising administering to the human subject an effective amount of an antibody that binds to human CD73 and an inhibitor of A2A adenosine receptor and/or A2B adenosine receptor, wherein the antibody:
 (a) comprises a variable heavy (VH) domain comprising VH complementarity determining region (CDR)1, VH CDR2, and VH CDR3, wherein:
  the VH CDR1 comprises the amino acid sequence GYTFTSYG (SEQ ID NO:1);
  the VH CDR2 comprises the amino acid sequence IYPGSGNT (SEQ ID NO:2); and
  the VH CDR3 comprises the amino acid sequence ARYDYLGSSYGFDY (SEQ ID NO:3); and
 comprises a variable light (VL) domain comprising VL CDR1, VL CDR2, and VL CDR3, wherein:
  the VL CDR1 comprises the amino acid sequence QDVSTA (SEQ ID NO:4);
  the VL CDR2 comprises the amino acid sequence SAS (SEQ ID NO:5); and
  the VL CDR3 comprises the amino acid sequence QQHYNTPYT (SEQ ID NO:6); or
 (b) comprises a VH domain comprising VH CDR1, VH CDR2, and VH CDR3, wherein:
  the VH CDR1 comprises the amino acid sequence GFTFSSYD (SEQ ID NO:34);
  the VH CDR2 comprises the amino acid sequence MSYDGSNK (SEQ ID NO:35) or MSYEGSNK (SEQ ID NO:40); and
  the VH CDR3 comprises the amino acid sequence ATE-IAAKGDY (SEQ ID NO:36); and
 wherein the antibody comprises a VL domain comprising VL CDR1, VL CDR2, and VL CDR3, wherein:
  the VL CDR1 comprises the amino acid sequence QGISNY (SEQ ID NO:37);
  the VL CDR2 comprises the amino acid sequence AAS (SEQ ID NO:38); and
  the VL CDR3 comprises the amino acid sequence QQSYSTPH (SEQ ID NO:39).

21. The method of claim 20, wherein the inhibitor is selected from the group consisting of:
 7-(5-methylfuran-2-yl)-3-[[6-[[(3S)-oxolan-3-yl]oxymethyl]pyridin-2-yl]methyl]triazolo[4,5-d]pyrimidin-5-amine,
 3-(5-Amino-2-((5-(pyridin-2-yl)-2H-tetrazol-2-yl)methyl)-8-(pyrimidin-4-yl)[1,2,4]triazolo[1,5-c]pyrimidin-7-yl)benzonitrile,
 3-[2-Amino-6-[1-[[6-(2-hydroxypropan-2-yl)pyridin-2-yl]methyl]triazol-4-yl]pyrimidin-4-yl]-2-methylbenzonitrile,
 6-(2-Chloro-6-methylpyridin-4-yl)-5-(4-fluorophenyl)-1,2,4-triazin-3-amine, 5-Bromo-2,6-di(1H-pyrazol-1-yl)pyrimidin-4-amine, and
 EOS100850.

22. The method of claim 1, wherein the cancer has a high adenosine signature.

23. The method of claim 1, wherein the cancer is head and neck cancer, colorectal cancer, lung cancer, melanoma, ovarian, bladder, liver cancer, or renal cell carcinoma.

24. The method of claim 20, wherein the cancer has a high adenosine signature.

25. The method of claim 20, wherein the cancer is head and neck cancer, colorectal cancer, lung cancer, melanoma, ovarian, bladder, liver cancer, or renal cell carcinoma.

26. The method of claim 20, wherein the antibody comprises a VH domain comprising VH CDR1, VH CDR2, and VH CDR3, wherein:
 the VH CDR1 comprises the amino acid sequence GYTFTSYG (SEQ ID NO:1);
 the VH CDR2 comprises the amino acid sequence IYPGSGNT (SEQ ID NO:2); and
 the VH CDR3 comprises the amino acid sequence ARYDYLGSSYGFDY (SEQ ID NO:3); and
comprises a VL domain comprising VL CDR1, VL CDR2, and VL CDR3, wherein:
 the VL CDR1 comprises the amino acid sequence QDVSTA (SEQ ID NO:4);
 the VL CDR2 comprises the amino acid sequence SAS (SEQ ID NO:5); and
 the VL CDR3 comprises the amino acid sequence QQHYNTPYT (SEQ ID NO:6).

27. The method of claim 20, wherein the antibody comprises a VH domain comprising VH CDR1, VH CDR2, and VH CDR3, wherein:
 the VH CDR1 comprises the amino acid sequence GFTFSSYD (SEQ ID NO:34);
 the VH CDR2 comprises the amino acid sequence MSYDGSNK (SEQ ID NO:35) or MSYEGSNK (SEQ ID NO:40); and
 the VH CDR3 comprises the amino acid sequence ATE-IAAKGDY (SEQ ID NO:36); and
wherein the antibody comprises a VL domain comprising VL CDR1, VL CDR2, and VL CDR3, wherein:
 the VL CDR1 comprises the amino acid sequence QGISNY (SEQ ID NO:37);
 the VL CDR2 comprises the amino acid sequence AAS (SEQ ID NO:38); and
 the VL CDR3 comprises the amino acid sequence QQSYSTPH (SEQ ID NO:39).

28. The method of claim 12, wherein the VH domain comprises the amino acid sequence set forth in SEQ ID NO:22 and the VL domain comprises the amino acid sequence set forth in SEQ ID NO:23.

29. The method of claim 12, wherein the antibody comprises a heavy chain and a light chain, and wherein the heavy chain comprises the amino acid sequence set forth in SEQ ID NO:24 and the light chain comprises the amino acid sequence set forth in SEQ ID NO:25.

30. The method of claim 13, wherein the VH domain comprises the amino acid sequence set forth in SEQ ID NO:62 and the VL domain comprises the amino acid sequence set forth in SEQ ID NO:61.

31. The method of claim 13, wherein the antibody comprises a heavy chain and a light chain, and wherein the heavy chain comprises the amino acid sequence set forth in SEQ ID NO:30 and the light chain comprises the amino acid sequence set forth in SEQ ID NO:31.

32. The method of claim 13, wherein the VH domain comprises the amino acid sequence set forth in SEQ ID NO:63 and the VL domain comprises the amino acid sequence set forth in SEQ ID NO:61.

33. The method of claim 13, wherein the antibody comprises a heavy chain and a light chain, and wherein the heavy chain comprises the amino acid sequence set forth in SEQ ID NO:33 and the light chain comprises the amino acid sequence set forth in SEQ ID NO:31.

34. The method of claim 26, wherein the VH domain comprises the amino acid sequence set forth in SEQ ID NO:22 and the VL domain comprises the amino acid sequence set forth in SEQ ID NO:23.

35. The method of claim 26, wherein the antibody comprises a heavy chain and a light chain, and wherein the heavy chain comprises the amino acid sequence set forth in SEQ ID NO:24 and the light chain comprises the amino acid sequence set forth in SEQ ID NO:25.

36. The method of claim 27, wherein the VH domain comprises the amino acid sequence set forth in SEQ ID NO:62 and the VL domain comprises the amino acid sequence set forth in SEQ ID NO:61.

37. The method of claim 27, wherein the antibody comprises a heavy chain and a light chain, and wherein the heavy chain comprises the amino acid sequence set forth in SEQ ID NO:30 and the light chain comprises the amino acid sequence set forth in SEQ ID NO:31.

38. The method of claim 27, wherein the VH domain comprises the amino acid sequence set forth in SEQ ID NO:63 and the VL domain comprises the amino acid sequence set forth in SEQ ID NO:61.

39. The method of claim 27, wherein the antibody comprises a heavy chain and a light chain, and wherein the heavy chain comprises the amino acid sequence set forth in SEQ ID NO:33 and the light chain comprises the amino acid sequence set forth in SEQ ID NO:31.

* * * * *

UNITED STATES PATENT AND TRADEMARK OFFICE
CERTIFICATE OF CORRECTION

PATENT NO. : 12,060,433 B2
APPLICATION NO. : 17/138306
DATED : August 13, 2024
INVENTOR(S) : Nastri et al.

Page 1 of 2

It is certified that error appears in the above-identified patent and that said Letters Patent is hereby corrected as shown below:

On the Title Page

Column 2 (Other Publications), Line 14: Delete "microorganisms, "" and insert
-- microorganisms," --.

In the Claims

Column 247, Line 7: In Claim 1, delete "$R^{c81}$" and insert -- $R^{c81}$, --.

Column 247, Line 49 (approx.): In Claim 1, delete "$OR^{a1}$," and insert -- $OR^{a41}$, --.

Column 247, Line 49 (approx.): In Claim 1, delete "$NR^{c41}, R^{d41}$;" and insert -- $NR^{c41}R^{d41}$; --.

Column 248, Line 41: In Claim 2, delete "$OR^1$," and insert -- $OR^{a2}$, --.

Column 248, Line 53: In Claim 2, delete "$R^{a1}$," and insert -- $R^{a4}$, --.

Column 248, Line 60: In Claim 3, delete "3-(5-Amino-2-(2,6-difluorophenyl)" and insert
-- 3-(5-Amino-2-((2,6-difluorophenyl) --.

Column 249, Line 1: In Claim 3, delete "3-(5-Amino-2-(3-methylpyridin-2-yl)" and insert
-- 3-(5-Amino-2-((3-methylpyridin-2-yl) --.

Column 249, Line 56: In Claim 4, delete "$R^{c81}$" and insert -- $R^{c81}$, --.

Column 250, Line 4: In Claim 5, delete "3-(5-Amino-2-(2,6-difluorophenyl)" and insert
-- 3-(5-Amino-2-((2,6-difluorophenyl) --.

Column 250, Line 7: In Claim 5, delete "1-Amino" and insert -- 5-Amino --.

Signed and Sealed this
Thirty-first Day of December, 2024

Derrick Brent
*Acting Director of the United States Patent and Trademark Office*

Column 250, Lines 7-8: In Claim 5, delete "2-(2,6-difluorophenyl)" and insert -- 2-((2,6-difluorophenyl) --.

Column 250, Line 48: In Claim 6, delete "$OR^1$," and insert -- $OR^{a41}$, --.

Column 250, Line 48: In Claim 6, delete "$NR^{c41}$, $R^{d41}$;" and insert -- $NR^{c41}R^{d41}$; --.

Column 250, Line 56: In Claim 7, delete "2-(2,6-difluorophenyl)" and insert -- 2-((2,6-difluorophenyl) --.

Column 250, Line 64: In Claim 7, delete "2-(2,6-difluorophenyl)" and insert -- 2-((2,6-difluorophenyl) --.

SEQUENCE LISTING

```
<160> NUMBER OF SEQ ID NOS: 103

<210> SEQ ID NO 1
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Tyr Thr Phe Thr Ser Tyr Gly
1               5

<210> SEQ ID NO 2
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ile Tyr Pro Gly Ser Gly Asn Thr
1               5

<210> SEQ ID NO 3
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Ala Arg Tyr Asp Tyr Leu Gly Ser Ser Tyr Gly Phe Asp Tyr
1               5                   10

<210> SEQ ID NO 4
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                           Synthetic peptide"

<400> SEQUENCE: 4

Gln Asp Val Ser Thr Ala
1               5

<210> SEQ ID NO 5
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Ser Ala Ser
1

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gln Gln His Tyr Asn Thr Pro Tyr Thr
1               5

<210> SEQ ID NO 7
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Tyr Thr Phe Thr Ser Tyr
1               5

<210> SEQ ID NO 8
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Tyr Pro Gly Ser Gly Asn
1               5

<210> SEQ ID NO 9
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9
```

```
Tyr Asp Tyr Leu Gly Ser Ser Tyr Gly Phe Asp Tyr
1               5                   10
```

```
<210> SEQ ID NO 10
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Lys Ala Ser Gln Asp Val Ser Thr Ala Val Ala
1               5                   10
```

```
<210> SEQ ID NO 11
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ser Ala Ser Tyr Arg Tyr Ser
1               5
```

```
<210> SEQ ID NO 12
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Tyr Thr Phe Thr Ser Tyr Gly Leu Ser
1               5                   10
```

```
<210> SEQ ID NO 13
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Glu Ile Tyr Pro Gly Ser Gly Asn Thr Tyr
1               5                   10
```

```
<210> SEQ ID NO 14
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ser Tyr Gly Leu Ser
1               5
```

```
<210> SEQ ID NO 15
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Glu Ile Tyr Pro Gly Ser Gly Asn Thr Tyr Tyr Asn Glu Lys Phe Lys
1               5                   10                  15
Gly

<210> SEQ ID NO 16
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Thr Ser Tyr Gly Leu Ser
1               5

<210> SEQ ID NO 17
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Trp Met Gly Glu Ile Tyr Pro Gly Ser Gly Asn Thr Tyr
1               5                   10

<210> SEQ ID NO 18
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Ala Arg Tyr Asp Tyr Leu Gly Ser Ser Tyr Gly Phe Asp
1               5                   10

<210> SEQ ID NO 19
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Ser Thr Ala Val Ala Trp Tyr
1               5

<210> SEQ ID NO 20
<211> LENGTH: 10
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Leu Leu Ile Tyr Ser Ala Ser Tyr Arg Tyr
1               5                   10

<210> SEQ ID NO 21
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Gln Gln His Tyr Asn Thr Pro Tyr
1               5

<210> SEQ ID NO 22
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Ser Tyr
            20                  25                  30

Gly Leu Ser Trp Val Arg Gln Met Pro Gly Lys Gly Leu Glu Trp Met
        35                  40                  45

Gly Glu Ile Tyr Pro Gly Ser Gly Asn Thr Tyr Tyr Asn Glu Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Asp Tyr Leu Gly Ser Ser Tyr Gly Phe Asp Tyr Trp Gly
            100                 105                 110

Ala Gly Thr Thr Val Thr Val Ser Ser
        115                 120

<210> SEQ ID NO 23
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ser Thr Ala
```

```
                    20                  25                  30
Val Ala Trp Tyr Gln Gln Lys Pro Gly Gln Pro Pro Lys Leu Leu Ile
            35                  40                  45

Tyr Ser Ala Ser Tyr Arg Tyr Ser Gly Val Pro Asp Arg Phe Ser Gly
        50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His Tyr Asn Thr Pro Tyr
                85                  90                  95

Thr Phe Gly Gly Gly Thr Lys Leu Glu Ile Lys
            100                 105

<210> SEQ ID NO 24
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Ser Tyr
            20                  25                  30

Gly Leu Ser Trp Val Arg Gln Met Pro Gly Lys Gly Leu Glu Trp Met
        35                  40                  45

Gly Glu Ile Tyr Pro Gly Ser Gly Asn Thr Tyr Tyr Asn Glu Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Asp Tyr Leu Gly Ser Ser Tyr Gly Phe Asp Tyr Trp Gly
            100                 105                 110

Ala Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270
```

-continued

```
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Ala Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Glu Glu Met Thr Lys Asn Gln Val Ser
                355                 360                 365
Leu Thr Cys Leu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
            435                 440                 445
Pro Gly
    450

<210> SEQ ID NO 25
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Asp Ile Val Met Thr Gln Ser Pro Asp Ser Leu Ala Val Ser Leu Gly
1               5                   10                  15
Glu Arg Ala Thr Ile Asn Cys Lys Ala Ser Gln Asp Val Ser Thr Ala
            20                  25                  30
Val Ala Trp Tyr Gln Gln Lys Pro Gly Gln Pro Pro Lys Leu Leu Ile
        35                  40                  45
Tyr Ser Ala Ser Tyr Arg Tyr Ser Gly Val Pro Asp Arg Phe Ser Gly
    50                  55                  60
Ser Gly Ser Gly Thr Asp Phe Thr Leu Thr Ile Ser Ser Leu Gln Ala
65                  70                  75                  80
Glu Asp Val Ala Val Tyr Tyr Cys Gln Gln His Tyr Asn Thr Pro Tyr
                85                  90                  95
Thr Phe Gly Gly Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 26
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

```
Gln Val Gln Leu Gln Gln Ser Gly Ala Glu Leu Ala Arg Pro Gly Ala
1               5                   10                  15

Ser Val Lys Leu Ser Cys Arg Ala Ser Gly Tyr Thr Phe Thr Ser Tyr
            20                  25                  30

Gly Leu Ser Trp Val Lys Gln Arg Thr Gly Gln Gly Leu Glu Trp Ile
        35                  40                  45

Gly Glu Ile Tyr Pro Gly Ser Gly Asn Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Tyr Asp Tyr Leu Gly Ser Ser Tyr Gly Phe Asp Tyr Trp Gly
            100                 105                 110

Gln Gly Thr Thr Leu Thr Val Ser Ser
        115                 120
```

<210> SEQ ID NO 27
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Asn Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Asn Thr Pro Tyr
                85                  90                  95

Thr Phe Gly Gly Gly Thr Lys Leu Glu Ile Lys
```

-continued

<210> SEQ ID NO 28
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Trp Ile Gly Glu Ile Tyr Pro Gly Ser Gly Asn Thr Tyr
1               5                   10

<210> SEQ ID NO 29
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ser Ala Ser Tyr Arg Tyr Asn
1               5

<210> SEQ ID NO 30
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Met Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Ala Leu Tyr
65                  70                  75                  80

Leu Gln Met Asn Ser Leu Arg Ala Glu Asp Thr Ala Val Tyr Tyr Cys
                85                  90                  95

Ala Thr Glu Ile Ala Ala Lys Gly Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

```
Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 31
<211> LENGTH: 212
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Ile Gln Met Thr Gln Ser Pro Ser Ser Leu Ser Ala Ser Val Gly Asp
1               5                   10                  15

Arg Val Thr Ile Thr Cys Arg Ala Ser Gln Gly Ile Ser Asn Tyr Leu
            20                  25                  30

Ala Trp Tyr Gln Gln Lys Pro Gly Lys Ala Pro Lys Leu Leu Ile Tyr
        35                  40                  45

Ala Ala Ser Thr Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Ser Tyr Ser Thr Pro His Phe
                85                  90                  95
```

Gly Gln Gly Thr Arg Leu Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
            165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
            195                 200                 205

Arg Gly Glu Cys
    210

<210> SEQ ID NO 32
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Phe Ser Ser Tyr Asp
            20                  25                  30

Met His Trp Val Arg Gln Ala Pro Gly Lys Gly Leu Glu Trp Val Ala
        35                  40                  45

Val Met Ser Tyr Ser Gly Ser Asn Lys Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Thr Glu Ile Ala Ala Lys Gly Asp Tyr Trp Gly Gln Gly Thr Leu Val
            100                 105                 110

Thr Val Ser Ser
        115

<210> SEQ ID NO 33
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val

```
                35                  40                  45
Ala Val Met Ser Tyr Glu Gly Ser Asn Lys Tyr Tyr Ala Asp Ser Val
 50                  55                  60

Lys Gly Arg Phe Thr Ile Ser Arg Asp Asn Ser Lys Asn Ala Leu Tyr
 65                  70                  75                  80

Leu Gln Met Asn Ser Leu Arg Ala Glu Asp Thr Ala Val Tyr Tyr Cys
                 85                  90                  95

Ala Thr Glu Ile Ala Ala Lys Gly Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Ala Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
            435                 440                 445

<210> SEQ ID NO 34
```

```
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Gly Phe Thr Phe Ser Ser Tyr Asp
1               5

<210> SEQ ID NO 35
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Met Ser Tyr Asp Gly Ser Asn Lys
1               5

<210> SEQ ID NO 36
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Ala Thr Glu Ile Ala Ala Lys Gly Asp Tyr
1               5                   10

<210> SEQ ID NO 37
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Gln Gly Ile Ser Asn Tyr
1               5

<210> SEQ ID NO 38
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Ala Ala Ser
1

<210> SEQ ID NO 39
<211> LENGTH: 8
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 39

Gln Gln Ser Tyr Ser Thr Pro His
1               5

<210> SEQ ID NO 40
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Met Ser Tyr Glu Gly Ser Asn Lys
1               5

<210> SEQ ID NO 41
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Gly Phe Thr Phe Ser Ser Tyr
1               5

<210> SEQ ID NO 42
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ser Tyr Asp Gly Ser Asn
1               5

<210> SEQ ID NO 43
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ser Tyr Glu Gly Ser Asn
1               5

<210> SEQ ID NO 44
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 44

Arg Ala Ser Gln Gly Ile Ser Asn Tyr Leu Ala
1               5                   10

<210> SEQ ID NO 45
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Ala Ala Ser Thr Leu Gln Ser
1               5

<210> SEQ ID NO 46
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Gly Phe Thr Phe Ser Ser Tyr Asp Met His
1               5                   10

<210> SEQ ID NO 47
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Val Met Ser Tyr Asp Gly Ser Asn Lys Tyr
1               5                   10

<210> SEQ ID NO 48
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Val Met Ser Tyr Glu Gly Ser Asn Lys Tyr
1               5                   10

<210> SEQ ID NO 49
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Ser Tyr Asp Met His
1               5
```

```
<210> SEQ ID NO 50
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Val Met Ser Tyr Asp Gly Ser Asn Lys Tyr Tyr Ala Asp Ser Val Lys
1               5                   10                  15

Gly

<210> SEQ ID NO 51
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Val Met Ser Tyr Glu Gly Ser Asn Lys Tyr Tyr Ala Asp Ser Val Lys
1               5                   10                  15

Gly

<210> SEQ ID NO 52
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Glu Ile Ala Ala Lys Gly Asp Tyr
1               5

<210> SEQ ID NO 53
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Ser Ser Tyr Asp Met His
1               5

<210> SEQ ID NO 54
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Trp Val Ala Val Met Ser Tyr Asp Gly Ser Asn Lys Tyr
1               5                   10
```

```
<210> SEQ ID NO 55
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Trp Val Ala Val Met Ser Tyr Glu Gly Ser Asn Lys Tyr
1               5                   10

<210> SEQ ID NO 56
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Ala Thr Glu Ile Ala Ala Lys Gly Asp
1               5

<210> SEQ ID NO 57
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Ser Asn Tyr Leu Ala Trp Tyr
1               5

<210> SEQ ID NO 58
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Leu Leu Ile Tyr Ala Ala Ser Thr Leu Gln
1               5                   10

<210> SEQ ID NO 59
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gln Gln Ser Tyr Ser Thr Pro
1               5

<210> SEQ ID NO 60
<211> LENGTH: 116
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Phe Ser Ser Tyr Asp
            20                  25                  30

Met His Trp Val Arg Gln Ala Pro Gly Lys Gly Leu Glu Trp Val Ala
        35                  40                  45

Val Met Ser Tyr Asp Gly Ser Asn Lys Tyr Tyr Ala Asp Ser Val Lys
    50                  55                  60

Gly Arg Phe Thr Ile Ser Arg Asp Asn Ser Lys Asn Ala Leu Tyr Leu
65                  70                  75                  80

Gln Met Asn Ser Leu Arg Ala Glu Asp Thr Ala Val Tyr Tyr Cys Ala
                85                  90                  95

Thr Glu Ile Ala Ala Lys Gly Asp Tyr Trp Gly Gln Gly Thr Leu Val
            100                 105                 110

Thr Val Ser Ser
            115

<210> SEQ ID NO 61
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Ile Gln Met Thr Gln Ser Pro Ser Ser Leu Ser Ala Ser Val Gly Asp
1               5                   10                  15

Arg Val Thr Ile Thr Cys Arg Ala Ser Gln Gly Ile Ser Asn Tyr Leu
            20                  25                  30

Ala Trp Tyr Gln Gln Lys Pro Gly Lys Ala Pro Lys Leu Leu Ile Tyr
        35                  40                  45

Ala Ala Ser Thr Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Ser Tyr Ser Thr Pro His Phe
                85                  90                  95

Gly Gln Gly Thr Arg Leu Glu Ile Lys
            100                 105

<210> SEQ ID NO 62
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Glu Val Gln Leu Val Glu Ser Gly Gly Gly Leu Val Gln Pro Gly Gly
```

```
  1               5                  10                  15
Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
            35                  40                  45

Ala Val Met Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Ala Leu Tyr
 65                  70                  75                  80

Leu Gln Met Asn Ser Leu Arg Ala Glu Asp Thr Ala Val Tyr Tyr Cys
                 85                  90                  95

Ala Thr Glu Ile Ala Ala Lys Gly Asp Tyr Trp Gly Gln Gly Thr Leu
                100                 105                 110

Val Thr Val Ser Ser
            115

<210> SEQ ID NO 63
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
            35                  40                  45

Ala Val Met Ser Tyr Glu Gly Ser Asn Lys Tyr Tyr Ala Asp Ser Val
            50                  55                  60

Lys Gly Arg Phe Thr Ile Ser Arg Asp Asn Ser Lys Asn Ala Leu Tyr
 65                  70                  75                  80

Leu Gln Met Asn Ser Leu Arg Ala Glu Asp Thr Ala Val Tyr Tyr Cys
                 85                  90                  95

Ala Thr Glu Ile Ala Ala Lys Gly Asp Tyr Trp Gly Gln Gly Thr Leu
                100                 105                 110

Val Thr Val Ser Ser
            115

<210> SEQ ID NO 64
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
            35                  40                  45
```

Tyr Ala Ala Ser Thr Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro His
                85                  90                  95

Phe Gly Gln Gly Thr Arg Leu Glu Ile Lys
                100                 105

<210> SEQ ID NO 65
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro His
                85                  90                  95

Phe Gly Gln Gly Thr Arg Leu Glu Ile Lys
                100                 105

<210> SEQ ID NO 66
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Val Gln Leu Val Glu Ser Gly Gly Gly Leu Val Gln Pro Gly Gly Ser
 1               5                  10                  15

Leu Arg Leu Ser Cys Ala Ala Ser Gly Phe Thr Phe Ser Ser Tyr Asp
                20                  25                  30

Met His Trp Val Arg Gln Ala Pro Gly Lys Gly Leu Glu Trp Val Ala
            35                  40                  45

Val Met Ser Tyr Asp Gly Ser Asn Lys Tyr Tyr Ala Asp Ser Val Lys
            50                  55                  60

Gly Arg Phe Thr Ile Ser Arg Asp Asn Ser Lys Asn Ala Leu Tyr Leu
 65                  70                  75                  80

Gln Met Asn Ser Leu Arg Ala Glu Asp Thr Ala Val Tyr Tyr Cys Ala
                85                  90                  95

Thr Glu Ile Ala Ala Lys Gly Asp Tyr Trp Gly Gln Gly Thr Leu Val
                100                 105                 110

```
Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Ala Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 67
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Phe Ser Ser Tyr Asp
```

```
                    20                  25                  30
Met His Trp Val Arg Gln Ala Pro Gly Lys Gly Leu Glu Trp Val Ala
            35                  40                  45

Val Met Ser Tyr Ser Gly Ser Asn Lys Tyr Tyr Ala Asp Ser Val Lys
    50                  55                  60

Gly Arg Phe Thr Ile Ser Arg Asp Asn Ser Lys Asn Ala Leu Tyr Leu
65                  70                  75                  80

Gln Met Asn Ser Leu Arg Ala Glu Asp Thr Ala Val Tyr Tyr Cys Ala
            85                  90                  95

Thr Glu Ile Ala Ala Lys Gly Asp Tyr Trp Gly Gln Gly Thr Leu Val
            100                 105                 110

Thr Val Ser Ser
            115

<210> SEQ ID NO 68
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Met Ser Tyr Ser Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Thr Glu Ile Ala Ala Lys Gly Asp Tyr Trp Gly Gln Gly Thr Leu
            100                 105                 110

Val Thr Val Ser Ser
            115

<210> SEQ ID NO 69
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Met Ser Tyr Ser Gly Ser Asn Lys Tyr Tyr Ala Asp Ser Val
    50                  55                  60
```

```
Lys Gly Arg Phe Thr Ile Ser Arg Asp Asn Ser Lys Asn Ala Leu Tyr
 65                  70                  75                  80

Leu Gln Met Asn Ser Leu Arg Ala Glu Asp Thr Ala Val Tyr Tyr Cys
                 85                  90                  95

Ala Thr Glu Ile Ala Ala Lys Gly Asp Tyr Trp Gly Gln Gly Thr Leu
            100                 105                 110

Val Thr Val Ser Ser
            115

<210> SEQ ID NO 70
<211> LENGTH: 523
<212> TYPE: PRT
<213> ORGANISM: Homo sapiens

<400> SEQUENCE: 70

Trp Glu Leu Thr Ile Leu His Thr Asn Asp Val His Ser Arg Leu Glu
  1               5                  10                  15

Gln Thr Ser Glu Asp Ser Ser Lys Cys Val Asn Ala Ser Arg Cys Met
                 20                  25                  30

Gly Gly Val Ala Arg Leu Phe Thr Lys Val Gln Gln Ile Arg Arg Ala
             35                  40                  45

Glu Pro Asn Val Leu Leu Leu Asp Ala Gly Asp Gln Tyr Gln Gly Thr
 50                  55                  60

Ile Trp Phe Thr Val Tyr Lys Gly Ala Glu Val Ala His Phe Met Asn
 65                  70                  75                  80

Ala Leu Arg Tyr Asp Ala Met Ala Leu Gly Asn His Glu Phe Asp Asn
                 85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
            115                 120                 125

Ser Gly Leu Tyr Leu Pro Tyr Lys Val Leu Pro Val Gly Asp Glu Val
            130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Met Asp Lys Leu Ile Ala Gln Lys Val Arg
            195                 200                 205

Gly Val Asp Val Val Val Gly Gly His Ser Asn Thr Phe Leu Tyr Thr
        210                 215                 220

Gly Asn Pro Pro Ser Lys Glu Val Pro Ala Gly Lys Tyr Pro Phe Ile
225                 230                 235                 240

Val Thr Ser Asp Asp Gly Arg Lys Val Pro Val Val Gln Ala Tyr Ala
                245                 250                 255

Phe Gly Lys Tyr Leu Gly Tyr Leu Lys Ile Glu Phe Asp Glu Arg Gly
            260                 265                 270

Asn Val Ile Ser Ser His Gly Asn Pro Ile Leu Leu Asn Ser Ser Ile
            275                 280                 285

Pro Glu Asp Pro Ser Ile Lys Ala Asp Ile Asn Lys Trp Arg Ile Lys
        290                 295                 300

Leu Asp Asn Tyr Ser Thr Gln Glu Leu Gly Lys Thr Ile Val Tyr Leu
```

```
            305                 310                 315                 320
Asp Gly Ser Ser Gln Ser Cys Arg Phe Arg Glu Cys Asn Met Gly Asn
                325                 330                 335

Leu Ile Cys Asp Ala Met Ile Asn Asn Asn Leu Arg His Thr Asp Glu
                340                 345                 350

Met Phe Trp Asn His Val Ser Met Cys Ile Leu Asn Gly Gly Gly Ile
                355                 360                 365

Arg Ser Pro Ile Asp Glu Arg Asn Asn Gly Thr Ile Thr Trp Glu Asn
            370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
                405                 410                 415

Gly Gln Ser Thr Gly Glu Phe Leu Gln Val Gly Gly Ile His Val Val
                420                 425                 430

Tyr Asp Leu Ser Arg Lys Pro Gly Asp Arg Val Val Lys Leu Asp Val
            435                 440                 445

Leu Cys Thr Lys Cys Arg Val Pro Ser Tyr Asp Pro Leu Lys Met Asp
            450                 455                 460

Glu Val Tyr Lys Val Ile Leu Pro Asn Phe Leu Ala Asn Gly Gly Asp
465                 470                 475                 480

Gly Phe Gln Met Ile Lys Asp Glu Leu Leu Arg His Asp Ser Gly Asp
                485                 490                 495

Gln Asp Ile Asn Val Val Ser Thr Tyr Ile Ser Lys Met Lys Val Ile
                500                 505                 510

Tyr Pro Ala Val Glu Gly Arg Ile Lys Phe Ser
            515                 520

<210> SEQ ID NO 71
<211> LENGTH: 523
<212> TYPE: PRT
<213> ORGANISM: Mus musculus

<400> SEQUENCE: 71

Trp Glu Leu Thr Ile Leu His Thr Asn Asp Val His Ser Arg Leu Glu
1               5                   10                  15

Gln Thr Ser Asp Asp Ser Thr Lys Cys Leu Asn Ala Ser Leu Cys Val
                20                  25                  30

Gly Gly Val Ala Arg Leu Phe Thr Lys Val Gln Gln Ile Arg Lys Glu
            35                  40                  45

Glu Pro Asn Val Leu Phe Leu Asp Ala Gly Asp Gln Tyr Gln Gly Thr
        50                  55                  60

Ile Trp Phe Thr Val Tyr Lys Gly Leu Glu Val Ala His Phe Met Asn
65                  70                  75                  80

Ile Leu Gly Tyr Asp Ala Met Ala Leu Gly Asn His Glu Phe Asp Asn
                85                  90                  95

Gly Val Glu Gly Leu Ile Asp Pro Leu Leu Arg Asn Val Lys Phe Pro
            100                 105                 110

Ile Leu Ser Ala Asn Ile Lys Ala Arg Gly Pro Leu Ala His Gln Ile
            115                 120                 125

Ser Gly Leu Phe Leu Pro Ser Lys Val Leu Ser Val Gly Gly Glu Val
        130                 135                 140

Val Gly Ile Val Gly Tyr Thr Ser Lys Glu Thr Pro Phe Leu Ser Asn
145                 150                 155                 160
```

```
Pro Gly Thr Asn Leu Val Phe Glu Asp Glu Ile Ser Ala Leu Gln Pro
            165                 170                 175

Glu Val Asp Lys Leu Lys Thr Leu Asn Val Asn Lys Ile Ile Ala Leu
        180                 185                 190

Gly His Ser Gly Phe Glu Met Asp Lys Leu Ile Ala Gln Lys Val Arg
    195                 200                 205

Gly Val Asp Ile Val Gly Gly His Ser Asn Thr Phe Leu Tyr Thr
210                 215                 220

Gly Asn Pro Pro Ser Lys Glu Val Pro Ala Gly Lys Tyr Pro Phe Ile
225                 230                 235                 240

Val Thr Ala Asp Asp Gly Arg Gln Val Pro Val Gln Ala Tyr Ala
            245                 250                 255

Phe Gly Lys Tyr Leu Gly Tyr Leu Lys Val Glu Phe Asp Asp Lys Gly
            260                 265                 270

Asn Val Ile Thr Ser Tyr Gly Asn Pro Ile Leu Leu Asn Ser Ser Ile
            275                 280                 285

Pro Glu Asp Ala Thr Ile Lys Ala Asp Ile Asn Gln Trp Arg Ile Lys
            290                 295                 300

Leu Asp Asn Tyr Ser Thr Gln Glu Leu Gly Arg Thr Ile Val Tyr Leu
305                 310                 315                 320

Asp Gly Ser Thr Gln Thr Cys Arg Phe Arg Glu Cys Asn Met Gly Asn
                325                 330                 335

Leu Ile Cys Asp Ala Met Ile Asn Asn Asn Leu Arg His Pro Asp Glu
                340                 345                 350

Met Phe Trp Asn His Val Ser Met Cys Ile Val Asn Gly Gly Gly Ile
            355                 360                 365

Arg Ser Pro Ile Asp Glu Lys Asn Asn Gly Thr Ile Thr Trp Glu Asn
370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
                405                 410                 415

Gly Gln Ser Thr Gly Glu Phe Leu Gln Val Gly Gly Ile His Val Val
            420                 425                 430

Tyr Asp Ile Asn Arg Lys Pro Trp Asn Arg Val Val Gln Leu Glu Val
            435                 440                 445

Leu Cys Thr Lys Cys Arg Val Pro Ile Tyr Glu Pro Leu Glu Met Asp
            450                 455                 460

Lys Val Tyr Lys Val Thr Leu Pro Ser Tyr Leu Ala Asn Gly Gly Asp
465                 470                 475                 480

Gly Phe Gln Met Ile Lys Asp Glu Leu Leu Lys His Asp Ser Gly Asp
                485                 490                 495

Gln Asp Ile Ser Val Val Ser Glu Tyr Ile Ser Lys Met Lys Val Val
            500                 505                 510

Tyr Pro Ala Val Glu Gly Arg Ile Lys Phe Ser
            515                 520

<210> SEQ ID NO 72
<211> LENGTH: 523
<212> TYPE: PRT
<213> ORGANISM: Macaca fascicularis

<400> SEQUENCE: 72

Trp Glu Leu Thr Ile Leu His Thr Asn Asp Val His Ser Arg Leu Glu
1               5                   10                  15
```

-continued

```
Gln Thr Ser Glu Asp Ser Ser Lys Cys Val Asn Ala Ser Arg Cys Met
         20                  25                  30

Gly Gly Val Ala Arg Leu Phe Thr Lys Val Gln Gln Ile Arg Arg Ala
     35                  40                  45

Glu Pro Asn Val Leu Leu Leu Asp Ala Gly Asp Gln Tyr Gln Gly Thr
 50                  55                  60

Ile Trp Phe Thr Val Tyr Lys Gly Ala Glu Val Ala His Phe Met Asn
 65                  70                  75                  80

Ala Leu Arg Tyr Asp Ala Met Ala Leu Gly Asn His Glu Phe Asp Asn
             85                  90                  95

Gly Val Glu Gly Leu Ile Glu Pro Leu Leu Lys Glu Ala Lys Phe Pro
                100                 105                 110

Ile Leu Ser Ala Asn Ile Lys Ala Lys Gly Pro Leu Ala Ser Gln Ile
            115                 120                 125

Ser Gly Leu Tyr Leu Pro Tyr Lys Val Leu Pro Val Gly Asp Glu Val
130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Thr Asp Lys Leu Ile Ala Gln Lys Val Arg
        195                 200                 205

Gly Val Asp Val Val Val Gly His Ser Asn Thr Phe Leu Tyr Thr
        210                 215                 220

Gly Asn Pro Pro Ser Lys Glu Val Pro Ala Gly Lys Tyr Pro Phe Ile
225                 230                 235                 240

Val Thr Ser Asp Asp Gly Arg Lys Val Pro Val Val Gln Ala Tyr Ala
                245                 250                 255

Phe Gly Lys Tyr Leu Gly Tyr Leu Lys Ile Glu Phe Asp Glu Arg Gly
                260                 265                 270

Asn Val Ile Ser Ser His Gly Asn Pro Ile Leu Leu Asn Ser Ser Ile
            275                 280                 285

Pro Glu Asp Pro Ser Ile Lys Ala Asp Ile Asn Lys Trp Arg Ile Lys
    290                 295                 300

Leu Asp Asn Tyr Ser Thr Gln Glu Leu Gly Lys Thr Ile Val Tyr Leu
305                 310                 315                 320

Asp Gly Ser Ser Gln Ser Cys Arg Phe Arg Glu Cys Asn Met Gly Asn
                325                 330                 335

Leu Ile Cys Asp Ala Met Ile Asn Asn Leu Arg His Ala Asp Glu
                340                 345                 350

Met Phe Trp Asn His Val Ser Met Cys Ile Leu Asn Gly Gly Gly Ile
            355                 360                 365

Arg Ser Pro Ile Asp Glu Arg Asn Asn Gly Thr Ile Thr Trp Glu Asn
    370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
                405                 410                 415

Gly Gln Ser Thr Gly Glu Phe Leu Gln Val Gly Ile His Val Val
                420                 425                 430
```

Tyr Asp Leu Ser Arg Lys Pro Gly Asp Arg Val Val Lys Leu Asp Val
            435                 440                 445

Leu Cys Thr Lys Cys Arg Val Pro Ser Tyr Asp Pro Leu Lys Met Asp
450                 455                 460

Glu Ile Tyr Lys Val Ile Leu Pro Asn Phe Leu Ala Asn Gly Gly Asp
465                 470                 475                 480

Gly Phe Gln Met Ile Lys Asp Glu Leu Leu Arg His Asp Ser Gly Asp
            485                 490                 495

Gln Asp Ile Asn Val Val Ser Thr Tyr Ile Ser Lys Met Lys Val Ile
                500                 505                 510

Tyr Pro Ala Val Glu Gly Arg Ile Lys Phe Ser
            515                 520

<210> SEQ ID NO 73
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn

```
                260                 265                 270
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 74
<211> LENGTH: 107
<212> TYPE: PRT
<213> ORGANISM: Homo sapiens

<400> SEQUENCE: 74

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 75
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
        130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Ala Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 76
<211> LENGTH: 14
<212> TYPE: PRT
<213> ORGANISM: Homo sapiens

<400> SEQUENCE: 76

Thr Lys Val Gln Gln Ile Arg Arg Ala Glu Pro Asn Val Leu
1               5                   10

<210> SEQ ID NO 77
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Asp Met His Trp Val Arg Gln Ala Pro Gly Lys Gly Leu Glu Trp Val
        35                  40                  45
Ala Val Met Ser Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
```

```
Ala Thr Glu Ile Ala Ala Lys Gly Asp Tyr Trp Gly Gln Gly Thr Leu
            100                 105                 110

Val Thr Val Ser Ser
        115

<210> SEQ ID NO 78
<211> LENGTH: 14
<212> TYPE: PRT
<213> ORGANISM: Homo sapiens

<400> SEQUENCE: 78

Ala Ala Val Leu Pro Phe Gly Gly Thr Phe Asp Leu Val Gln
1               5                   10

<210> SEQ ID NO 79
<211> LENGTH: 20
<212> TYPE: PRT
<213> ORGANISM: Homo sapiens

<400> SEQUENCE: 79

Ile Leu Pro Asn Phe Leu Ala Asn Gly Gly Asp Gly Phe Gln Met Ile
1               5                   10                  15

Lys Asp Glu Leu
            20

<210> SEQ ID NO 80
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Leu
        35                  40                  45

Tyr Ser Ala Ser Tyr Arg Tyr Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Tyr Asn Thr Pro Tyr
                85                  90                  95

Thr Phe Gly Gly Gly Thr Lys Leu Glu Ile Lys
            100                 105

<210> SEQ ID NO 81
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Ala Ile Arg Met Thr Gln Ser Pro Ser Ser Phe Ser Ala Ser Thr Gly
1               5                   10                  15
```

-continued

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln His Tyr Asn Thr Pro Tyr
                85                  90                  95

Thr Phe Gly Gly Gly Thr Lys Leu Glu Ile Lys
            100                 105

<210> SEQ ID NO 82
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Leu Ser Trp Val Arg Gln Ala Thr Gly Gln Gly Leu Glu Trp Met
        35                  40                  45

Gly Glu Ile Tyr Pro Gly Ser Gly Asn Thr Tyr Tyr Asn Glu Lys Phe
    50                  55                  60

Lys Gly Arg Val Thr Met Thr Ala Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Leu Gly Ser Ser Tyr Gly Phe Asp Tyr Trp Gly
            100                 105                 110

Ala Gly Thr Thr Val Thr Val Ser Ser
        115                 120

<210> SEQ ID NO 83
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Leu Ser Trp Val Arg Gln Ala Thr Gly Gln Gly Leu Glu Trp Met
        35                  40                  45

Gly Glu Ile Tyr Pro Gly Ser Gly Asn Thr Tyr Tyr Asn Glu Lys Phe
    50                  55                  60

Lys Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Leu Gly Ser Ser Tyr Gly Phe Asp Tyr Trp Gly
            100                 105                 110

Ala Gly Thr Thr Val Thr Val Ser Ser
        115                 120

<210> SEQ ID NO 84
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Gly Leu Ser Trp Val Arg Gln Ala Pro Gly Gln Gly Leu Glu Trp Met
        35                  40                  45

Gly Glu Ile Tyr Pro Gly Ser Gly Asn Thr Tyr Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Leu Gly Ser Ser Tyr Gly Phe Asp Tyr Trp Gly
            100                 105                 110

Ala Gly Thr Thr Val Thr Val Ser Ser
        115                 120

<210> SEQ ID NO 85
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Phe Ser Ser Tyr Asp
            20                  25                  30

Met His Trp Val Arg Gln Ala Pro Gly Lys Gly Leu Glu Trp Val Ala
        35                  40                  45

Val Met Ser Tyr Asp Gly Ser Asn Lys Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Thr Glu Ile Ala Ala Lys Gly Asp Tyr Trp Gly Gln Gly Thr Leu Val

Thr Val Ser Ser
        115

<210> SEQ ID NO 86
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Met Ser Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Ile Ala Ala Lys Gly Asp Tyr Trp Gly Gln Gly Thr Leu
            100                 105                 110

Val Thr Val Ser Ser
        115

<210> SEQ ID NO 87
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Phe Ser Ser Tyr Asp
            20                  25                  30

Met His Trp Val Arg Gln Ala Pro Gly Lys Gly Leu Glu Trp Val Ala
        35                  40                  45

Val Met Ser Tyr Glu Gly Ser Asn Lys Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Thr Glu Ile Ala Ala Lys Gly Asp Tyr Trp Gly Gln Gly Thr Leu Val
            100                 105                 110

Thr Val Ser Ser
        115

<210> SEQ ID NO 88

<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 88

Val Gln Leu Val Glu Ser Gly Gly Gly Leu Val Gln Pro Gly Ser
1               5                   10                  15

Leu Arg Leu Ser Cys Ala Ala Ser Gly Phe Thr Phe Ser Ser Tyr Asp
            20                  25                  30

Met His Trp Val Arg Gln Ala Pro Gly Lys Gly Leu Glu Trp Val Ala
        35                  40                  45

Val Met Ser Tyr Glu Gly Ser Asn Lys Tyr Tyr Ala Asp Ser Val Lys
    50                  55                  60

Gly Arg Phe Thr Ile Ser Arg Asp Asn Ser Lys Asn Ala Leu Tyr Leu
65                  70                  75                  80

Gln Met Asn Ser Leu Arg Ala Glu Asp Thr Ala Val Tyr Tyr Cys Ala
                85                  90                  95

Thr Glu Ile Ala Ala Lys Gly Asp Tyr Trp Gly Gln Gly Thr Leu Val
            100                 105                 110

Thr Val Ser Ser
        115

<210> SEQ ID NO 89
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 89
gaagtgcagc tcgtgcagtc cggagccgaa gtgaaaaagc tggagagtc cctgaagatc        60 agctgcaagg gttccggcta cattcacc tcctacgggc tcagctgggt cagacagatg       120
ccgggaaagg gtcttgagtg gatgggagag atctacccgg gctccggcaa cacctactac      180
aacgaaaagt tcaagggcca ggtcaccatt tccgccgaca gtcaatctc accgcttac        240 ctccaatggt cgagcctgaa ggcatcggat accgcgatgt actactgcgc ccgctacgac      300
tacctgggct cgtcatacgg cttcgattac tgggggggcgg gaactaccgt gactgtgtcc    360
tccgcctcca ctaagggacc ctcagtgttc ccccttgccc cgagctccaa gagcacttcg     420
ggcggaaccg ctgccctggg ttgcctcgtg aaggattact cccccgagcc tgtgaccgtg     480
tcctggaact ccggggcctt gaccagcgga gtccacacct tccggccgt gctgcaatca      540 tccggtctgt acagtctgtc ctccgtggtc acggtgccct cgtcctcact ggggactcag     600
acttacatct gtaacgtgaa ccataagcca tcgaacacca agtcgacaa acgggtggaa      660 cctaagtcat gcgacaagac ccacacgtgc ccaccttgcc ccgcccccga gctcctgggg     720
gggccgagcg tgttcctctt cccgccgaaa ccgaaggaca ccctgatgat ctcgaggact     780
cctgaagtca cttgcgtggt cgtggacgtg tcgcacgagg accccgaagt caagttcaat     840
tggtacgtgg acggagtcga agtgcacaac gctaagacca accccgcga ggagcagtac     900 gcaagcacct accgcgttgt cagcgtgctc accgtgctgc atcaggattg gctgaatgga    960
aaggagtaca gtgcaaagt gtccaacaag gccctgcctg caccaattga aaagaccatc    1020

```
tccaaggcca agggccagcc ccgggagccc caagtctaca ctctgccgcc gtcgagagaa   1080
gaaatgacca agaaccaagt gtccctgact tgtctggtca agggcttcta tccttcggac   1140
atcgcggtgg aatgggagag caacggccag ccggagaaca attacaagac tacgccaccc   1200
gtgctggact ctgacggctc cttttttcctg tattccaagc tcaccgtgga caagagccgc   1260
```

```
tccaaggcca agggccagcc ccgggagccc caagtctaca ctctgccgcc gtcgagagaa   1080
gaaatgacca agaaccaagt gtccctgact tgtctggtca agggcttcta tccttcggac   1140
atcgcggtgg aatgggagag caacggccag ccggagaaca attacaagac tacgccaccc   1200
gtgctggact ctgacggctc ctttttcctg tattccaagc tcaccgtgga caagagccgc   1260
tggcaacagg gaaacgtgtt cagctgctcc gtgatgcacg aagccctgca caaccactac   1320
acccagaagt ccctgagctt gtcccctggt                                     1350
```

<210> SEQ ID NO 90  
<211> LENGTH: 642  
<212> TYPE: DNA  
<213> ORGANISM: Artificial Sequence  
<220> FEATURE:  
<221> NAME/KEY: source  
<223> OTHER INFORMATION: /note="Description of Artificial Sequence: Synthetic polynucleotide"

<400> SEQUENCE: 90

```
gacatcgtga tgacccagtc cccggattca ctcgcggtgt ctttggggga gagggcaacc    60
attaactgca aggcctcaca ggatgtgtcc actgctgtcg cctggtacca gcagaagcct   120
gggcagccgc ccaagctgct gatctactcg gcctcctacc gctattccgg agtccccgac   180
cggttctccg gctcgggttc cggaactgat ttcaccctga caatttcgtc gctgcaagcc   240
gaggacgtgg ccgtgtacta ctgccaacag cattacaaca ctccttacac ttttggtggc   300
ggaactaagc tcgagatcaa gcggacggtg gcagctccgt cagtgttcat cttccctcca   360
tcggacgaac agctgaagtc cggcaccgcg tccgtcgtgt gtctgttgaa caacttctac   420
ccgcgggaag ccaaggtcca gtggaaagtc gacaacgcgc tgcagtccgg aaatagccag   480
gaaagcgtga ccgaacagga ctccaaggac agcacctact ccctgagctc aaccctgacc   540
ctgagcaagg ccgactatga gaagcacaaa gtgtacgcct gcgaagtgac ccaccaaggc   600
ctgagcagcc cagtgaccaa gtccttcaac cgcggggagt gt                      642
```

<210> SEQ ID NO 91  
<211> LENGTH: 1338  
<212> TYPE: DNA  
<213> ORGANISM: Artificial Sequence  
<220> FEATURE:  
<221> NAME/KEY: source  
<223> OTHER INFORMATION: /note="Description of Artificial Sequence: Synthetic polynucleotide"

<400> SEQUENCE: 91

```
gaagtgcagt tggtggagag cggggggcgga ctggtgcagc cggggggctc gctgcggctg    60
tcctgcgccg cgtccggttt cacttttttcg agctacgaca tgcactgggt ccgccaagca   120
ccggggaagg gtctggaatg ggtggccgtg atgtcgtacg acggctccaa caagtactac   180
gccgactccg tgaagggacg gttcaccatc tcccgcgaca cagcaagaa cgcccttttac   240 ctccaaatga acagcctgag ggccgaggac acagccgtat actactgcgc gaccgagatc   300
gccgccaagg gggactactg gggtcaaggc actctggtca ccgtgtcctc cgcctccact   360
aagggaccct cagtgttccc ccttgccccg agctccaaga gcacttcggg cggaaccgct   420
gccctgggtt gcctcgtgaa ggattacttc cccgagcctg tgaccgtgtc ctggaactcc   480
ggggccttga ccagcggagt ccacaccttc ccggccgtgc tgcaatcatc cggtctgtac   540
agtctgtcct ccgtggtcac ggtgccctcg tcctcactgg ggactcagac ttacatctgt   600
```

| | |
|---|---|
| aacgtgaacc ataagccatc gaacaccaaa gtcgacaaac gggtggaacc taagtcatgc | 660 |
| gacaagaccc acacgtgccc accttgcccc gcccccgagc tcctgggggg gccgagcgtg | 720 |
| ttcctcttcc cgccgaaacc gaaggacacc ctgatgatct cgaggactcc tgaagtcact | 780 |
| tgcgtggtcg tggacgtgtc gcacgaggac cccgaagtca agttcaattg gtacgtggac | 840 |
| ggagtcgaag tgcacaacgc taagaccaaa ccccgcgagg agcagtacgc aagcacctac | 900 |
| cgcgttgtca gcgtgctcac cgtgctgcat caggattggc tgaatggaaa ggagtacaag | 960 |
| tgcaaagtgt ccaacaaggc cctgcctgca ccaattgaaa agaccatctc caaggccaag | 1020 |
| ggccagcccc gggagcccca agtctacact ctgccgccgt cgagagaaga atgaccaag | 1080 |
| aaccaagtgt ccctgacttg tctggtcaag ggcttctatc cttcggacat cgcggtggaa | 1140 |
| tgggagagca acggccagcc ggagaacaat tacaagacta cgccacccgt gctggactct | 1200 |
| gacggctcct ttttcctgta ttccaagctc accgtggaca agagccgctg gcaacaggga | 1260 |
| aacgtgttca gctgctccgt gatgcacgaa gccctgcaca accactacac ccagaagtcc | 1320 |
| ctgagcttgt cccctggt | 1338 |

<210> SEQ ID NO 92
<211> LENGTH: 636
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 92

| | |
|---|---|
| atccagatga ctcagtcccc ttcctcgttg tccgcttccg tgggtgatcg ggtcacaatc | 60 |
| acttgccggg ccagccaggg aatttccaac tacctcgcct ggtaccagca gaagcccgga | 120 |
| aaggcaccga agctgctgat ctacgccgcg tccactctgc aatccggagt gccttctcgg | 180 |
| ttctcgggct cgggaagcgg caccgacttt accctgacca ttagcagcct gcagcccgag | 240 |
| gacttcgcaa cctactactg tcagcagtcc tactcaaccc ctcacttcgg acagggtact | 300 |
| agactcgaga tcaagaggac tgtggccgcg ccgtcggtgt tcatcttccc accctcggac | 360 |
| gagcagctga agtccggcac cgccagcgtg gtctgcctgc tgaacaactt ctatccgcgc | 420 |
| gaagccaagg tccagtggaa agtggataat gcgctgcaga gcggaactc ccaagagtcc | 480 |
| gtgacggaac aggactccaa agactccacc tactcactgt catccaccct gaccctgtca | 540 |
| aaggccgact acgagaagca taaggtctac gcctgcgaag tgacccacca agggctgagc | 600 |
| tcgcccgtga ccaagtcctt caaccggggc gaatgc | 636 |

<210> SEQ ID NO 93
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 93

| | |
|---|---|
| gaagtgcagt tggtggagag cggggggcgga ctggtgcagc cgggggggctc gctgcggctg | 60 |
| tcctgcgccg cgtccggttt cactttttcg agctacgaca tgcactgggt ccgccaagca | 120 |
| ccggggaagg gtctgaatg ggtggccgtg atgtcgtacg aaggctccaa caagtactac | 180 |
| gccgactccg tgaagggacg gttcaccatc tcccgcgaca acagcaagaa cgcccttac | 240 |

```
ctccaaatga acagcctgag ggccgaggac acagccgtat actactgcgc gaccgagatc    300
gccgccaagg gggactactg gggtcaaggc actctggtca ccgtgtcctc cgcctccact    360
aagggaccct cagtgttccc ccttgccccg agctccaaga gcacttcggg cggaaccgct    420
gccctgggtt gcctcgtgaa ggattacttc cccgagcctg tgaccgtgtc ctggaactcc    480
ggggccttga ccagcggagt ccacaccttc ccggccgtgc tgcaatcatc cggtctgtac    540
agtctgtcct ccgtggtcac ggtgccctcg tcctcactgg ggactcagac ttacatctgt    600
aacgtgaacc ataagccatc gaacaccaaa gtcgacaaac gggtggaacc taagtcatgc    660
gacaagaccc acacgtgccc accttgcccc gcccccgagc tcctgggggg gccgagcgtg    720
ttcctcttcc cgccgaaacc gaaggacacc ctgatgatct cgaggactcc tgaagtcact    780
tgcgtggtcg tggacgtgtc gcacgaggac cccgaagtca agttcaattg gtacgtggac    840
ggagtcgaag tgcacaacgc taagaccaaa ccccgcgagg agcagtacgc aagcacctac    900
cgcgttgtca gcgtgctcac cgtgctgcat caggattggc tgaatggaaa ggagtacaag    960
tgcaaagtgt ccaacaaggc cctgcctgca ccaattgaaa agaccatctc caaggccaag    1020
ggccagcccc gggagcccca gtctacact ctgccgccgt cgagagaaga atgaccaag    1080
aaccaagtgt ccctgacttg tctggtcaag ggcttctatc cttcggacat cgcggtggaa    1140
tgggagagca acggccagcc ggagaacaat tacaagacta cgccaccgt gctggactct    1200
gacggctcct ttttcctgta ttccaagctc accgtggaca gagccgctg caacaggga    1260
aacgtgttca gctgctccgt gatgcacgaa gccctgcaca accactacac ccagaagtcc    1320
ctgagcttgt cccctggt                                                  1338

<210> SEQ ID NO 94
<211> LENGTH: 412
<212> TYPE: PRT
<213> ORGANISM: Homo sapiens

<400> SEQUENCE: 94

Met Pro Ile Met Gly Ser Ser Val Tyr Ile Thr Val Glu Leu Ala Ile
1               5                   10                  15

Ala Val Leu Ala Ile Leu Gly Asn Val Leu Val Cys Trp Ala Val Trp
            20                  25                  30

Leu Asn Ser Asn Leu Gln Asn Val Thr Asn Tyr Phe Val Val Ser Leu
        35                  40                  45

Ala Ala Ala Asp Ile Ala Val Gly Val Leu Ala Ile Pro Phe Ala Ile
    50                  55                  60

Thr Ile Ser Thr Gly Phe Cys Ala Ala Cys His Gly Cys Leu Phe Ile
65                  70                  75                  80

Ala Cys Phe Val Leu Val Leu Thr Gln Ser Ser Ile Phe Ser Leu Leu
                85                  90                  95

Ala Ile Ala Ile Asp Arg Tyr Ile Ala Ile Arg Ile Pro Leu Arg Tyr
            100                 105                 110

Asn Gly Leu Val Thr Gly Thr Arg Ala Lys Gly Ile Ile Ala Ile Cys
        115                 120                 125

Trp Val Leu Ser Phe Ala Ile Gly Leu Thr Pro Met Leu Gly Trp Asn
    130                 135                 140

Asn Cys Gly Gln Pro Lys Glu Gly Lys Asn His Ser Gln Gly Cys Gly
145                 150                 155                 160

Glu Gly Gln Val Ala Cys Leu Phe Glu Asp Val Val Pro Met Asn Tyr
                165                 170                 175
```

```
Met Val Tyr Phe Asn Phe Phe Ala Cys Val Leu Val Pro Leu Leu Leu
                180                 185                 190

Met Leu Gly Val Tyr Leu Arg Ile Phe Leu Ala Ala Arg Arg Gln Leu
            195                 200                 205

Lys Gln Met Glu Ser Gln Pro Leu Pro Gly Glu Arg Ala Arg Ser Thr
        210                 215                 220

Leu Gln Lys Glu Val His Ala Ala Lys Ser Leu Ala Ile Ile Val Gly
225                 230                 235                 240

Leu Phe Ala Leu Cys Trp Leu Pro Leu His Ile Ile Asn Cys Phe Thr
                245                 250                 255

Phe Phe Cys Pro Asp Cys Ser His Ala Pro Leu Trp Leu Met Tyr Leu
            260                 265                 270

Ala Ile Val Leu Ser His Thr Asn Ser Val Val Asn Pro Phe Ile Tyr
        275                 280                 285

Ala Tyr Arg Ile Arg Glu Phe Arg Gln Thr Phe Arg Lys Ile Ile Arg
290                 295                 300

Ser His Val Leu Arg Gln Gln Glu Pro Phe Lys Ala Ala Gly Thr Ser
305                 310                 315                 320

Ala Arg Val Leu Ala Ala His Gly Ser Asp Gly Glu Gln Val Ser Leu
                325                 330                 335

Arg Leu Asn Gly His Pro Pro Gly Val Trp Ala Asn Gly Ser Ala Pro
            340                 345                 350

His Pro Glu Arg Arg Pro Asn Gly Tyr Ala Leu Gly Leu Val Ser Gly
        355                 360                 365

Gly Ser Ala Gln Glu Ser Gln Gly Asn Thr Gly Leu Pro Asp Val Glu
370                 375                 380

Leu Leu Ser His Glu Leu Lys Gly Val Cys Pro Glu Pro Pro Gly Leu
385                 390                 395                 400

Asp Asp Pro Leu Ala Gln Asp Gly Ala Gly Val Ser
                405                 410

<210> SEQ ID NO 95
<211> LENGTH: 332
<212> TYPE: PRT
<213> ORGANISM: Homo sapiens

<400> SEQUENCE: 95

Met Leu Leu Glu Thr Gln Asp Ala Leu Tyr Val Ala Leu Glu Leu Val
1               5                   10                  15

Ile Ala Ala Leu Ser Val Ala Gly Asn Val Leu Val Cys Ala Ala Val
            20                  25                  30

Gly Thr Ala Asn Thr Leu Gln Thr Pro Thr Asn Tyr Phe Leu Val Ser
        35                  40                  45

Leu Ala Ala Ala Asp Val Ala Val Gly Leu Phe Ala Ile Pro Phe Ala
50                  55                  60

Ile Thr Ile Ser Leu Gly Phe Cys Thr Asp Phe Tyr Gly Cys Leu Phe
65                  70                  75                  80

Leu Ala Cys Phe Val Leu Val Leu Thr Gln Ser Ser Ile Phe Ser Leu
                85                  90                  95

Leu Ala Val Ala Val Asp Arg Tyr Leu Ala Ile Cys Val Pro Leu Arg
            100                 105                 110

Tyr Lys Ser Leu Val Thr Gly Thr Arg Ala Arg Gly Val Ile Ala Val
        115                 120                 125

Leu Trp Val Leu Ala Phe Gly Ile Gly Leu Thr Pro Phe Leu Gly Trp
```

```
                    130                 135                 140
Asn Ser Lys Asp Ser Ala Thr Asn Asn Cys Thr Glu Pro Trp Asp Gly
145                 150                 155                 160

Thr Thr Asn Glu Ser Cys Cys Leu Val Lys Cys Leu Phe Glu Asn Val
                    165                 170                 175

Val Pro Met Ser Tyr Met Val Tyr Phe Asn Phe Gly Cys Val Leu
                180                 185                 190

Pro Pro Leu Leu Ile Met Leu Val Ile Tyr Ile Lys Ile Phe Leu Val
                195                 200                 205

Ala Cys Arg Gln Leu Gln Arg Thr Glu Leu Met Asp His Ser Arg Thr
210                 215                 220

Thr Leu Gln Arg Glu Ile His Ala Ala Lys Ser Leu Ala Met Ile Val
225                 230                 235                 240

Gly Ile Phe Ala Leu Cys Trp Leu Pro Val His Ala Val Asn Cys Val
                245                 250                 255

Thr Leu Phe Gln Pro Ala Gln Gly Lys Asn Lys Pro Lys Trp Ala Met
                260                 265                 270

Asn Met Ala Ile Leu Leu Ser His Ala Asn Ser Val Val Asn Pro Ile
                275                 280                 285

Val Tyr Ala Tyr Arg Asn Arg Asp Phe Arg Tyr Thr Phe His Lys Ile
                290                 295                 300

Ile Ser Arg Tyr Leu Leu Cys Gln Ala Asp Val Lys Ser Gly Asn Gly
305                 310                 315                 320

Gln Ala Gly Val Gln Pro Ala Leu Gly Val Gly Leu
                325                 330

<210> SEQ ID NO 96
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Tyr Ser Trp Val Arg Gln Ala Pro Gly Lys Gly Leu Glu Trp Val
        35                  40                  45

Ser Ala Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
            100                 105                 110

Val Thr Val Ser Ser
        115

<210> SEQ ID NO 97
<211> LENGTH: 110
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 97

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Arg Asn
                20                  25                  30

Pro Val Asn Trp Tyr Gln Gln Leu Pro Gly Thr Ala Pro Lys Leu Leu
            35                  40                  45

Ile Tyr Leu Asp Asn Leu Arg Leu Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser His
                85                  90                  95

Pro Gly Trp Thr Phe Gly Gly Gly Thr Lys Leu Thr Val Leu
            100                 105                 110

<210> SEQ ID NO 98
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Tyr Ser Trp Val Arg Gln Ala Pro Gly Lys Gly Leu Glu Trp Val
            35                  40                  45

Ser Ala Ile Ser Gly Ser Gly Gly Arg Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Arg Val Asp Glu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

-continued

```
Thr Lys Val Asp Lys Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
                260                 265                 270
Val Lys Phe Asn Trp Tyr Val Asp Gly Val Glu Val His Asn Ala Lys
            275                 280                 285
Thr Lys Pro Arg Glu Glu Gln Tyr Ala Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly
            435                 440                 445

<210> SEQ ID NO 99
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Gln Ser Val Leu Thr Gln Pro Pro Ser Ala Ser Gly Thr Pro Gly Gln
1               5                   10                  15
Arg Val Thr Ile Ser Cys Ser Gly Ser Leu Ser Asn Ile Gly Arg Asn
            20                  25                  30
Pro Val Asn Trp Tyr Gln Gln Leu Pro Gly Thr Ala Pro Lys Leu Leu
        35                  40                  45
Ile Tyr Leu Asp Asn Leu Arg Leu Ser Gly Val Pro Asp Arg Phe Ser
    50                  55                  60
Gly Ser Lys Ser Gly Thr Ser Ala Ser Leu Ala Ile Ser Gly Leu Gln
65                  70                  75                  80
Ser Glu Asp Glu Ala Asp Tyr Tyr Cys Ala Thr Trp Asp Asp Ser His
                85                  90                  95
Pro Gly Trp Thr Phe Gly Gly Gly Thr Lys Leu Thr Val Leu Gly Gln
                100                 105                 110
Pro Lys Ala Asn Pro Thr Val Thr Leu Phe Pro Pro Ser Ser Glu Glu
```

```
                115                 120                 125
Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
    210                 215

<210> SEQ ID NO 100
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Tyr
                20                  25                  30

Asn Met Tyr Trp Val Lys Gln Ser His Gly Lys Ser Leu Glu Trp Ile
            35                  40                  45

Gly Tyr Ile Asp Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Gly Tyr Gly Asn Tyr Lys Ala Trp Phe Ala Tyr Trp Gly Gln
                100                 105                 110

Gly Thr Leu Val Thr Val Ser Ala
            115                 120

<210> SEQ ID NO 101
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Asp Ala Val Met Thr Gln Thr Pro Lys Phe Leu Leu Val Ser Ala Gly
1               5                   10                  15

Asp Arg Val Thr Ile Thr Cys Lys Ala Ser Gln Ser Val Thr Asn Asp
                20                  25                  30

Val Ala Trp Tyr Gln Gln Lys Pro Gly Gln Ser Pro Lys Leu Leu Ile
            35                  40                  45

Tyr Tyr Ala Ser Asn Arg Tyr Thr Gly Val Pro Asp Arg Phe Thr Gly
    50                  55                  60
```

```
Ser Gly Tyr Gly Thr Asp Phe Thr Phe Thr Ile Ser Thr Val Gln Ala
 65                  70                  75                  80

Glu Asp Leu Ala Val Tyr Phe Cys Gln Gln Asp Tyr Ser Ser Leu Thr
                 85                  90                  95

Phe Gly Ala Gly Thr Lys Leu Glu Leu Lys
            100                 105

<210> SEQ ID NO 102
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

Glu Ile Gln Leu Gln Gln Ser Gly Pro Glu Leu Val Lys Pro Gly Ala
 1               5                  10                  15

Ser Val Lys Val Ser Cys Lys Ala Ser Gly Tyr Ala Phe Thr Ser Tyr
             20                  25                  30

Asn Met Tyr Trp Val Lys Gln Ser His Gly Lys Ser Leu Glu Trp Ile
         35                  40                  45

Gly Tyr Ile Asp Pro Tyr Asn Gly Gly Thr Ser Tyr Asn Gln Lys Phe
 50                  55                  60

Lys Gly Lys Ala Thr Leu Thr Val Asp Lys Ser Ser Thr Ala Tyr
 65                  70                  75                  80

Met His Leu Asn Ser Leu Thr Ser Glu Asp Ser Ala Val Tyr Tyr Cys
                 85                  90                  95

Ala Arg Gly Tyr Gly Asn Tyr Lys Ala Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 103
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Asp Ala Val Met Thr Gln Thr Pro Lys Phe Leu Leu Val Ser Ala Gly
1               5                   10                  15

Asp Arg Val Thr Ile Thr Cys Lys Ala Ser Gln Ser Val Thr Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Leu Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205
```

Asn Arg Gly Glu Cys
    210